United States Patent
Hammer et al.

(10) Patent No.: US 10,654,814 B2
(45) Date of Patent: May 19, 2020

(54) BICYCLIC HYDROXAMIC ACIDS USEFUL AS INHIBITORS OF MAMMALIAN HISTONE DEACETYLASE ACTIVITY

(71) Applicant: KANCERA AB, Solna (SE)

(72) Inventors: Kristin Hammer, Sollentuna (SE); Mattias Jönsson, Knivsta (SE); Lars Krüger, Huddinge (SE)

(73) Assignee: KANCERA AB (SE)

( * ) Notice: Subject to any disclaimer, the term of this patent is extended or adjusted under 35 U.S.C. 154(b) by 0 days.

(21) Appl. No.: 16/063,682

(22) PCT Filed: Nov. 16, 2016

(86) PCT No.: PCT/EP2016/077914
§ 371 (c)(1),
(2) Date: Jun. 18, 2018

(87) PCT Pub. No.: WO2017/108282
PCT Pub. Date: Jun. 29, 2017

(65) Prior Publication Data
US 2019/0284147 A1    Sep. 19, 2019

(30) Foreign Application Priority Data
Dec. 22, 2015  (EP) ..................................... 15201841

(51) Int. Cl.
| | | |
|---|---|---|
| C07D 263/54 | (2006.01) |
| C07D 277/66 | (2006.01) |
| C07D 307/79 | (2006.01) |
| C07D 333/54 | (2006.01) |
| C07D 413/04 | (2006.01) |
| C07D 413/10 | (2006.01) |
| C07D 413/14 | (2006.01) |
| C07D 417/04 | (2006.01) |
| C07D 471/04 | (2006.01) |
| C07D 495/04 | (2006.01) |
| C07D 498/04 | (2006.01) |
| A61K 31/57 | (2006.01) |
| C07D 401/04 | (2006.01) |
| C07D 263/57 | (2006.01) |
| C07D 263/58 | (2006.01) |
| C07D 209/08 | (2006.01) |
| C07D 409/04 | (2006.01) |
| C07D 491/04 | (2006.01) |
| C07D 235/30 | (2006.01) |
| C07D 487/04 | (2006.01) |
| C07D 277/64 | (2006.01) |
| C07D 413/12 | (2006.01) |

(52) U.S. Cl.
CPC ......... *C07D 263/54* (2013.01); *C07D 209/08* (2013.01); *C07D 235/30* (2013.01); *C07D 263/57* (2013.01); *C07D 263/58* (2013.01); *C07D 277/64* (2013.01); *C07D 277/66* (2013.01); *C07D 307/79* (2013.01); *C07D 333/54* (2013.01); *C07D 401/04* (2013.01); *C07D 409/04* (2013.01); *C07D 413/04* (2013.01); *C07D 413/10* (2013.01); *C07D 413/12* (2013.01); *C07D 413/14* (2013.01); *C07D 417/04* (2013.01); *C07D 471/04* (2013.01); *C07D 487/04* (2013.01); *C07D 491/04* (2013.01); *C07D 495/04* (2013.01); *C07D 498/04* (2013.01); *A61K 31/57* (2013.01)

(58) Field of Classification Search
None
See application file for complete search history.

(56) References Cited

FOREIGN PATENT DOCUMENTS

| | | |
|---|---|---|
| RU | 2501787 C2 | 12/2013 |
| WO | 2005/028447 | 3/2005 |
| WO | 2005/066151 | 7/2005 |
| WO | 2008/129276 | 10/2008 |
| WO | 2008/129994 | 10/2008 |
| WO | 2009055917 A1 | 5/2009 |

(Continued)

OTHER PUBLICATIONS

Aldana-Masangkay GI, Sakamoto KM. The role of HDAC6 in cancer. J Biomed Biotechnol 2011, doi:10.1155/2011/875824.
Balasubramanian S, Ramos J, Luo W, Sirisawad M, Verner E, Buggy JJ. A novel histone deacetylase 8 (HDAC8)-specific inhibitor PCI-34051 induces apoptosis in T-cell lymphomas. Leukemia. 2008; 22:1026-1034.
Balasubramanian, S.; Verner, E. V.; Buggy, J. J. Isoform-specific histone deacetylase inhibitors: the next step? Cancer Lett. 2009, 280, 211.

(Continued)

*Primary Examiner* — Alicia L Otton
(74) *Attorney, Agent, or Firm* — Adsero IP

(57) ABSTRACT

A compound of formula (Ia) or (Ib)

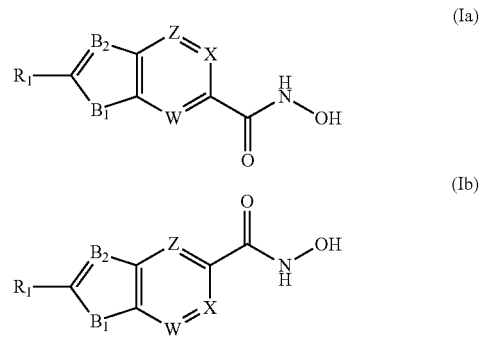

or a pharmaceutically acceptable salt thereof. The compound is an inhibitor of a histone deacetylase, and as such is useful in therapy, e.g. in the treatment of autoimmune disorders, mental disorders, neurodegenerative disorders, and hyperproliferative disorders.

16 Claims, No Drawings

(56) References Cited

FOREIGN PATENT DOCUMENTS

| WO | 2009/071650 | | 6/2009 | |
| WO | 2009129335 | | 10/2009 | |
| WO | 2010/061903 | | 6/2010 | |
| WO | WO 2010/061903 | * | 6/2010 | ........... C07D 401/14 |
| WO | 2014/015088 | | 1/2014 | |
| WO | 2015/031613 | | 3/2015 | |
| WO | 2015137750 A1 | | 9/2015 | |
| WO | 2015/188015 | | 12/2015 | |
| WO | 2016/180472 | | 11/2016 | |

OTHER PUBLICATIONS

Bazzaro M, Lin Z, Santillan A et al., "Ubiquitin proteasome system stress underlies synergistic killing of ovarian cancer cells by bortezomib and a novel HDAC6 inhibitor," *Clinical Cancer Research*, 2008, vol. 14, No. 22, pp. 7340-7347.

Best, J. D.; Carey, N. Epigenetic therapies for non-oncology indications. Drug Discovery Today 2010, 15, 1008-1014.

Bradner JE, West N, Grachan ML, Greenberg EF, Haggarty SJ, Warnow T et al. Chemical phylogenetics of histone deacetylases. Nat Chem Biol 2010, 6, 238-243.

Brana I, Taberno J. Cardiotoxicity, Annals of Oncology 2010, 21, Supplement 7: vii173-vii179.

Chen, Y.; He, R.; D'Annibale, M. A.; Langley, B.; Kozikowski, A.P. Studies of benzamide- and thiol-based histone deacetylase inhibitorsin models of oxidative-stress-induced neuronal death: identification of some HDAC3-selective inhibitors. ChemMedChem 2009, 4, 842-852.

Choudhary C, Kumar C, Gnad F, Nielsen ML, Rehman M,Walther TC et al. Lysine acetylation targets protein complexes and co-regulates major cellular functions. Science 2009, 325, 834-840.

Cook C, Gendron TF, Scheffel K, Carlomagno Y, Dunmore J, DeTure M, Petrucelli L. Loss of HDAC6, a novel CHIP substrate, alleviates abnormal tau accumulation. Hum Mol Genet 2012, 21, 2936-2945.

Cook C, Petrucelli L. 2013. Tau triage decisions mediated by the chaperone network. J Alzheimers Dis 33 Suppl 1:S145-S151.

Database Registry RN 1463893-08-4, Entered STN Oct. 25, 2013, XP-002754571, C:\EPODATA\SEA\eplogf\ep152018.log.

International Preliminary Report on Patentability for PCT/EP2016/077914, dated Dec. 5, 2017, 26 pages.

International Search Report for PCT/EP2016/077914, dated Dec. 8, 2016, 3 pages.

de Zoeten, E. F.; Wang, L.; Butler, K.; Beier, U. H.; Akimova, T.; Sal, H.; Bradner, J. E.; Mazitschek, R.; Kozikowski, A. P.; Matthias, P.; Hancock, W. W. Histone deacetylase 6 and heat shock protein 90 control the functions of Foxp3(+) T-regulatory cells. Mol. Cell. Biol. 2011, 31, 2066-2078.

D'Ydewalle C, Krishnan J, Chiheb DM, Van Damme P, Irobi J, Kozikowski AP, Vanden Berghe P, Timmerman V, Robberecht W, Van Den Bosch L: HDAC6 inhibitors reverse axonal loss in a mouse model of mutant HSPB1—induced Charcot-Marie-Tooth disease. Nat Med 2011, 17:968-974.

Espallergues J, Teegarden SL, Veerakumar A, Boulden J, Challis C, Jochems J, Chan M, Petersen T, Deneris E, Matthias P, Hahn CG, Lucki I, Beck SG, Berton O. HDAC6 regulates glucocorticoid receptor signaling in serotonin pathways with critical impact on stress resilience. J Neurosci 2012, 32, 4400-4416.

Fukada M, Hanai A, Nakayama A, Suzuki T, Miyata N, Rodriguiz RM, Wetsel WC, Yao TP, Kawaguchi Y. Loss of deacetylation activity of HDAC6 affects emotional behavior in mice. PLoS One 2012, 7, e30924.

George, P., Bali, P., Annavarapu, S., Scuto, A., Fiskus, W., Guo, F., Sigua, C., Sondarva, G., Moscinski, L., Atadja, P. et al. Combination of the histone deacetylase inhibitor LBH589 and the hsp90 inhibitor 17-AAG is highly active against human CML-BC cells and AML cells with activating mutation of FLT-3. Blood, 2005, 105, 1768-1776.

Govindarajan N, Rao P, Burkhardt S, Sananbenesi F, Schluter OM, Bradke F, Lu J, Fischer A: Reducing HDAC6 ameliorates cognitive deficits in a mouse model for Alzheimer's disease. EMBO Mol Med 2013, 5:52-63.

Greer J. M.; McCombe, P. A. The role of epigenetic mechanisms and processes in autoimmune disorders. Biologics 2012, 6, 307-327.

Gregoretti, I.V., Lee, Y.M. & Goodson, H.V. Molecular evolution of the histone deacetylase family: functional implications of phylogenetic analysis. J. Mol. Biol. 2004, 338, 17-31.

Hauser AT, Jung M, Jung M. Assays for histone deacetylases. Curr Top Med Chem 2009, 9, 227-234.

Hideshima, T.; Bradner, J. E.;, Wong J. et al., Small-molecule inhibition of proteasome and aggresome function induces synergistic antitumor activity in multiple myeloma, Proc. Natl. Acad. Sci. U.S.A., 2005, 102, 8567-8572.

Jochems J, Boulden J, Lee BG, Blendy JA, Jarpe M, Mazitschek R, Van Duzer JH, Jones S and Berton O. Antidepressant-Like Properties of Novel HDAC6-Selective Inhibitors with Improved Brain Bioavailability. Neuropsychopharmacology 2014, 39, 389-400.

Kalin JH, Bergman JA. Development and therapeutic implications of selective histone deacetylase 6 inhibitors. J Med Chem 2013, 56, 6297-6313.

Karberg, S. Switching on epigenetic therapy. Cell 2009, 139, 1029-1031.

Kawaguchi Y. Loss of deacetylation activity of Hdac6 affects emotional behavior in mice. PloSone 2012, 7, e30924.

Kim, C.; Choi, H.; Jung, E. S.; Lee, W.; Oh, S.; Jeon, N. L.; Mook-Jung, I. HDAC6 inhibitor blocks amyloid beta-induced impairment of mitochondrial transport in hippocampal neurons. PLoS One 2012, 7, e42983.

Kim, D.; Frank, C. L.; Dobbin, M. M.; Tsunemoto, R. K.; Tu, W.; Peng, P. L.; Guan, J. S.; Lee, B. H.; Moy, L. Y.; Giusti, P.; Broodie, N.; Mazitschek, R.; Delalle, I.; Haggarty, S. J.; Neve, R. L.; Lu, Y.; Tsai, L. H. Deregulation of HDAC1 by p25/Cdk5 in neurotoxicity. Neuron 2008, 60, 803-817.

Kouzarides, T. Chromatin modifications and their function. Cell 2007, 128, 693-705.

Lee J.K.; Zheng B. Role of myelin-associated inhibitors in axonal repair after spinal cord injury. Exp Neurol 2012, 235:33-42.

Lee, Y. S.; Lim, K. H.; Guo, X.; Kawaguchi, Y.; Gao, Y.; Barrientos, T.; Ordentlich, P., Wang, X. F.; Counter, C. M.; Yao, T. P. The cytoplasmic deacetylase HDAC6 is required for efficient oncogenic tumorigenesis. Cancer Res. 2008, 68, 7561-7569.

Morris MJ, Karra AS, Monteggia LM. Histone deacetylates govern cellular mechanisms underlying behavioral and synaptic plasticity in the developing and adult brain. Behav Pharmacol. 2010, 21, 409-419.

Parmigiani, R. B.; Xu, W. S.; Venta-Perez, G.; Erdjument-Bromage, H.; Yaneva, M.; Tempst, P.; Marks, P. A. HDAC6 is a specific deacetylase of peroxiredoxins and is involved in redox regulation. Proc. Natl. Acad. Sci. U.S.A. 2008, 105, 9633-9638.

Prince HM, Bishton MJ, Harrison SJ. Clinical studies of histone deacetylase inhibitors. Clin Cancer Res 2009; 15, 3958-3969.

Raje N, Vogl DT, Hari PN, Jagannath S, Jones SS, Supko JG, Leone G, Wheeler C, Orlowski RZ, Richardson PG, and Lonial S. ACY-1215, a Selective Histone Deacetylase (HDAC) 6 Inhibitor: Interim Results of Combination Therapy With Bortezomib in Patients With Multiple Myeloma (MM). ASH 2013 Annual Meeting Abstract 759.

Rao, R., Fiskus, W., Yang, Y., Lee, P., Joshi, R., Fernandez, P., Mandawat, A., Atadja, P., Bradner, J.E. and Bhalla, K. HDAC6 inhibition enhances 17-AAG—mediated abrogation of hsp90 chaperone function in human leukemia cells. Blood, 2008, 112, 1886-1893.

Santo L, Hideshima T, Kung AL, Tseng J-C, Tamang D, Yang M, Jarpe M, van Duzer JH, Mazitschek R, Ogier WC, Cirstea D, Rodig S, Eda H, Scullen T, Canavese M, Bradner J, Anderson KC, Jones SS, Raje N. Preclinical activity, pharmacodynamic, and pharmacokinetic properties of a selective HDAC6 inhibitor, ACY-1215, in combination with bortezomib in multiple myeloma. Blood 2012, 119:11, 2579-2589.

Simões-Pires C, Zwick V, Nurisso A, Schenker E, Carrupt P-A and Cuendet M. HDAC6 as a target for neurodegenerative diseases:

(56) References Cited

OTHER PUBLICATIONS what makes it different from the other HDACs? Molecular Neurodegeneration 2013, 8:7, 1-16.
Smith, B.C., Hallows, W.C. & Denu, J.M. Mechanisms and molecular probes of sirtuins. Chem. Biol. 2008, 15, 1002-1013.
Southwood CM, Peppi M, Dryden S, Tainsky MA, Gow A. Microtubule deacetylases, SirT2 and HDAC6, in the nervous system. Neurochem Res 2007, 32,187-195.
Ververis, K., Hiong, A., Karagiannis, T.C., and Licciardi, P.V. "Histone deacetylase inhibitors (HDACIs): multitargeted anticancer agents", Biologics: Targets and Therapy 2013, 7 47-60.
Witt, O.; Deubzer, H. E.; Milde, T.; Oehme, I. HDAC family: What are the cancer relevant targets? Cancer Lett. 2009, 277, 8-21.
Xu X, Kozikowski AP, Pozzo-Miller L. A selective histone deacetylase-6 inhibitor improves BDNF trafficking in hippocampal neurons from Mecp2 knockout mice: implications for Rett syndrome. Frontiers in Cellular Neuroscience 2014, 8:68, 1-9.
Zhang, Y.; Kwon, S.; Yamaguchi, T.; Cubizolles, F.; Rousseaux, S.; Kneissel, M.; Cao, C.; Li, N.; Cheng, H. L.; Chua, K.; Lombard, D.; Mizeracki, A.; Matthias, G.; Alt, F. W.; Khochbin, S.; Matthias, P. Mice lacking histone deacetylase 6 have hyperacetylated tubulin but are viable and develop normally. Mol. Cell. Biol. 2008, 28, 1688-1701.
Zhao, S. et al. Regulation of cellular metabolism by protein lysine acetylation. Science 2010, 327, 1000-1004.
Belikov V. G., Pharmacevticheskaja khimija. Moskva, "MEDpress-inform", 2007, pp. 27-29 with English translation.
Office Action for Russian application 2018126815/04, dated Jan. 31, 2020, with English translation, 20 pages.
Search report for Russian application 2018126815/04, dated Jan. 31, 2020, with English translation, 4 pages.

\* cited by examiner

BICYCLIC HYDROXAMIC ACIDS USEFUL AS INHIBITORS OF MAMMALIAN HISTONE DEACETYLASE ACTIVITY

CROSS-REFERENCE TO RELATED APPLICATION

This application claims priority to and is a 35 U.S.C. § 371 national phase application of PCT/EP2016/077914 (WO2017/108282), filed on Nov. 16, 2016 entitled "BICYCLIC HYDROXAMIC ACIDS USEFUL AS INHIBITORS OF MAMMALIAN HISTONE DEACETYLASE ACTIVITY", which application claims priority to and the benefit European Patent Application No. 15201841.2, filed Dec. 22, 2015.

FIELD OF THE INVENTION

The present invention relates to novel bicyclic hydroxamic acid derivatives. More particularly, the invention relates to novel bicyclic hydroxamic acid derivatives useful as inhibitors of a histone deacetylase, and to their use in therapy.

BACKGROUND OF THE INVENTION

Histone deacetylases (HDACs) are a class of enzymes that catalyzes the removal of an acetyl group from an α-N-acetyl lysine amino acid residue from other proteins, mainly histones. The histones are an essential part of how the genome is stored in the cell nucleus and DNA expression is regulated by histone acetylation and de-acetylation. Lysine acetylation is a key post-translational modification of many proteins, and which underlie many aspects of gene transcription, cellular signaling, cellular transport and metabolic changes (Kouzarides et al. 2007, Choudhary et al. 2009, Zhao et al. 2010). HDACs have pivotal roles in the regulation of gene expression, forming complexes with DNA binding proteins and thereby affecting histone acetylation and chromatin accessibility at promoter regions. These enzymes also have non-histone substrates, such as transcription factors and structural proteins whose biological activity is partly regulated by acetylation.

The common classification of human deacetylases is based on molecular phylogenetic analysis of primary structure, subsequently grouped based on homology to yeast enzymes (Gregoretti et al. 2004). This approach yields four distinct classes that vary in size and function. Class I (HDAC1, HDAC2, HDAC3 and HDAC8), class IIa (HDAC4, HDAC5, HDAC7 and HDAC9), class IIb (HDAC6 and HDAC10) and class IV (HDAC11). The HDACs require a divalent ion for catalysis. The class III proteins form a structurally and mechanistically distinct class of hydrolases dependent on nicotinamide adenine dinucleotide (NAD$^+$) (sirtuins, Sirt1-Sirt7) (Smith et al. 2008). The class I HDACs are found primarily in the nucleus, while the class IIa and class IIb HDACs are able to translocate in and out of the nucleus, depending on different signals.

There are numerous diseases that are related to dysregulated HDAC enzymatic function, including cancer, autoimmune and neurodegenerative disorders (Karberg 2009). For example, overexpression of specific HDACs has been identified in a range of human cancers, including HDAC1 in gastric and prostate cancer, HDAC1 and HDAC6 in breast cancer, and HDAC2 and HDAC3 in colorectal cancer (Ververis et al. 2013). Extensive cell-based assays and clinical studies with HDAC inhibitors have been shown to reduce proliferation, induce cell death and apoptosis, cause cell-cycle arrest, and prevent differentiation and migration selectively in malignant and transformed cells with little effect in normal cells (Ververis et al. 2013). Thus, HDAC inhibitors have the potential to be used as mono-therapies in oncology. In addition to their intrinsic cytotoxic properties when tested as a single treatment, HDAC inhibitors have been shown to induce additive cytotoxic effects when used in combination with conventional anticancer therapies, such as chemotherapy (anthracyclines and retinoic acid) and radiotherapy. Furthermore, studies with HDAC inhibitors in combination with ultraviolet radiation and potent iodinated DNA minor groove-binding ligands have been shown to augment photosensitization and cytotoxicity in tumor (Ververis et al. 2013). Currently (2015), there are five HDAC inhibitors that have received approval from the US FDA for the treatment of various cancers: vorinostat (suberoylanilide hydroxamic acid, Zolinza), depsipeptide (romidepsin, Istodax), belinostat (PXD101, Beleodaq), pracinostat (SB939), and panobinostat (LBH-539, Farydak). Many clinical trials assessing the effects of various HDAC inhibitors on hematological and solid cancers are being conducted (Ververis et al. 2013). The five approved inhibitors are active against several members of the HDAC family of enzymes leading to acute toxicities such as gastrointestinal symptoms and myelosuppression as well as severe fatigue (Prince et al. 2009). Also, the risk of significant negative impact on cardiac function is considered to be large (Brana & Tabernero 2010). Several reports show that there are intrinsic toxic side effects associated with inhibition of the HDAC class I isoforms and that this prevents the application of broad spectrum and class I selective inhibitors to areas outside of oncology because of a small therapeutic window. Early clinical trials with the selective HDAC6 inhibitor ACY-1215 appear to largely circumvent undesirable side-effects classically reported with broad-acting or class I-selective inhibitors (Raje et al, 2013). Although it remains to be demonstrated in the clinic, compounds that target specific HDACs with greater selectivity may be beneficial in certain cancers (Balasubramanian et al. 2009). For example, the selective HDAC8 inhibitor PCI-3405, was shown to selectively inhibit HDAC8 and induce apoptosis specifically in T-cell lymphomas and not other tumor or normal cells, showing that HDC8 plays an important role in the pathophysiology of this disease and suggesting that therapy with an HDAC8 specific inhibitor may lead to less side effects (Balasubramanian et al. 2008).

The class IIb enzymes, HDAC6 and HDAC10, differ from the other HDACs in that they primarily localize to the cytoplasm and differ structurally by containing two catalytic sites. HDAC6 is a microtubule-associated enzyme and deacetylases primarily non-histone proteins such as α-tubulin, cortactin, and Hsp90 (Aldana-Masangkay & Sakamoto 2011). α-tubulin is involved in cytoskeletal structural integrity and cellular motility, cortactin plays a role in cell motility, while Hsp90 (heat shock protein) is a molecular chaperone helping client proteins to fold properly and maintain function. The therapeutic areas most susceptible to alterations in HDAC6 activity appear to be cancer, autoimmune disorders, and neurodegenerative diseases. In contrast to other HDACs and especially class I isoforms, the loss of function of HDAC6 does not produce toxicity or major developmental defects in rodents (Govindarajan et al. 2013; Morris et al. 2010; Zhang et al. 2008). Inhibition of HDAC6 does not appear to be associated with the same level of toxicity observed with inhibition of the class I isoforms. The lower level of toxicity associated with HDAC6 inhibition compared to inhibition of the HDAC class I isoforms suggest that selective inhibition may provide a way to circumvent toxicity issues and thereby allow a superior side-effect profile and/or a higher dose with an accompanying superior effect on target. This may permit treatment of a wider range of cancer diseases and also treatment of non-oncology diseases requiring a wider therapeutic window (Best & Carey 2010, Zhang et al. 2008).

Cancer

Oncogenes, such as Ras, deregulate fundamental cellular functions, which can lead to the development of tumors and metastases. The Ras/MAPK signaling pathway is known to be required for tumorigenesis and HDAC6 is required for Ras-induced oncogenic transformation by providing anchorage-independent proliferation (Aldana-Masangkay & Sakamoto 2011). This allows the cancer cell to divide freely without being part of a tissue and is a hallmark of malignant transformation. Further, it has been shown that HDAC6 is required for oncogenes to be able to change the spatial organization of the vimentin fibers of the intracellular cytoskeleton which will induce cell stiffness and promote the invasive capacity of cells (Rathje et al. 2014). Thus, HDAC6 activity contributes to cell changes that lead to both tumor formation and invasion of tumor cells into healthy tissue (metastases).

The antitumor effect observed via HDAC6 inhibition is probably the result of multiple mechanisms involving cell motility/migration, invasion, angiogenesis, induction of apoptosis, and inhibition of DNA repair (Kalin & Bergman 2013). HDAC6 knockout mice demonstrated reduced phosphorylation of AKT and ERK1/2 (signaling pathways involved in tumor growth) and lower levels of activated Ras than those derived from wild-type mice (Lee et al. 2008). HDAC6 knock-down cells from SCID mice subcutaneously injected with HDAC6 specific shRNA showed retarded growth. By reconstitution with wild type HDAC6, but not with catalytically inactive mutant HDAC6, these knock-down cells regained its phenotype indicating that HDAC6 is specifically required for tumorigenic growth (Lee et al. 2008). Another method to combat cancer cells is to target the two major pathways for protein turnover in eukaryotic cells—the Ubiquitin-Proteasome-System (UPS) and the HDAC6-dependent lysosomal pathway. HDAC6 directly interacts with misfolded or poly-ubiquinated proteins to target them for lysosome-mediated protein degradation via aggresome formation and autophagy (Aldana-Masangkay & Sakamoto 2011). If UPS activity is insufficient, this HDAC6 dependent pathway is able to compensate for intracellular protein degradation. Cancer cells accumulate more misfolded proteins compared to nonmalignant cells and depend on efficient disposal of these misfolded proteins for cell survival. Thus, simultaneous inhibition of proteasome and HDAC6 activities has been proposed as a strategy to synergistically induce cancer cell death. Successful examples of this approach have used the proteasome inhibitor bortezomib together with different specific HDAC6 inhibitors such as tubacin on multiple myeloma cells (Hideshima et al. 2005), NK84 on ovarian cancer cells (Bazzaro et al. 2008), and ACY-1215 on cells and animal models of multiple myeloma (Santo et al., 2012). In all cases the two inhibitors showed synergistic effects and high selectivity for cancer cells compared to normal cells.

Autoimmune Disorders

There is strong evidence supporting HDAC6 as a target for the treatment of numerous autoimmune disorders (Greer et al. 2012). In murine models, pan-HDAC inhibitors, such as vorinostat and TSA, were able to alleviate the symptoms and reverse the progression of established colitis (de Zoeten et al. 2011). HDAC6 selective inhibitors such as tubacin and tubastatin A but not class I selective HDAC inhibitors such as entinostat were able to confer protection in these in vivo models. In murine models of allograft rejection tubacin and tubastatin A in combination with low-dose rapamycin, a clinically used immunosuppressant, were able to significantly increase the lifespan of mice from approximately 15 days to more than 60 days in comparison to mice treated with rapamycin alone (de Zoeten et al. 2011). This combination therapy was only administered for 14 days but was able to confer long term protection against allograft rejection.

Mental Disorders

In the mammalian brain, HDAC6 is mainly found in neurons (Southwood et al., 2007) and with the highest levels at the dorsal and median raphe nuclei, parts of the brain that are involved in emotional behaviors. HDAC6-deficient mice exhibit antidepressant-like behavior in behavioral tests, and this was mimicked by administration of NCT-14b, a HDAC6-specific inhibitor, to wild type mice (Fukada et al., 2012). Further, selective knockout of the highly abundant HDAC6 in serotonin neurons reduced acute anxiety caused by administration of the steroid hormone corticosterone, and blocked the expression of social deficits in mice exposed to inescapable traumatic stress (Espallergues et al., 2012). Administration of the selective HDAC6 inhibitors ACY-738 and ACY-775 has been shown to induce dramatic increases in $\alpha$-tubulin acetylation in brain and stimulate mouse exploratory behaviors in novel, but not familiar environments (Jochems et al. 2014). The two compounds share the antidepressant-like properties of pan-HDAC inhibitors, such as SAHA and MS-275, in the tail suspension test and social defeat paradigm without any detectable effect on histone acetylation. These effects of ACY-738 and ACY-775 are directly attributable to the inhibition of HDAC6 expressed centrally, as they are fully abrogated in mice with a neural-specific loss of function of HDAC6. Taken together, these findings suggest that HDAC6-mediated reversible acetylation contribute to maintain proper neuronal activity in serotonergic neurons, and also provide a new therapeutic target for depression. In addition, acute stress, via glucocorticoid receptors (GRs), enhances glutamatergic signalling in the prefrontal cortex, a region responsible for high-order cognitive functions. It has been shown (Lee et al. 2012) that inhibition or knockdown of HDAC6 blocks the enhancement of glutamatergic signalling by acute stress and that inhibition or knockdown of the GR chaperone protein Hsp90 (a HDAC6 substrate) produces a similar blockade of the acute stress-induced enhancement of glutamatergic signalling. This suggests that HDAC6 is a key controller of neuronal adaptations to acute stress and that inhibition of HDAC6 may provide neuroprotective effects against stress-induced mental illness.

Neurodegenerative Disorders

There are numerous reports suggesting that HDAC6 inhibition exert neuroprotection which may benefit patients afflicted with neurodegenerative disorders such as Alzheimer's, Parkinson's and Huntington's diseases as well as patients afflicted by traumatic brain injury (TBI) and inherited neurological disorders such as Charcot-Marie-Tooth disease (CMT) and Rett syndrome (Kalin & Bergman 2013, Simoes-Pires et al. 2013). On the other hand, an induction of HDAC6 would theoretically contribute to the degradation of protein aggregates which characterize various neurodegenerative disorders (Simoes-Pires et al. 2013). HDAC6 has been identified as a potential therapeutic target to modulate Alzheimer's disease (AD) pathogenesis. Specific HDAC6 inhibitors exert neuroprotection by increasing the acetylation levels of α-tubulin with subsequent improvement of the axonal transport, which is usually impaired in neurodegenerative disorders such as AD (Simoes-Pires et al. 2013). The loss of proper axonal transport leads to synaptic degradation through impaired mitochondrial and neurotransmitter trafficking (Kalin & Bergman 2013). It has been demonstrated that treatment of neurons with amyloid beta (Aβ) oligomers significantly attenuated mitochondrial elongation and transport, which was subsequently alleviated by treatment with the HDAC6 inhibitor tubastatin A (Kim et al. 2012). In another report, it was shown that reducing endogenous HDAC6 levels in an AD mouse model restored learning and memory (Govindarajan et al. 2013). These results suggest that HDAC6 inhibition may slow or reverse the neuronal damage associated with Aβ and thus represents a viable drug target for the treatment of AD. Further, HDAC6 together with Hsp90 and the ubiquitin ligase CHIP form a network of chaperone complexes that modulates levels of tau—the microtubule-associated protein that is hyperphosphorylated and forms the pathological hallmark of neurofibrillary tangles in AD (Cook & Petrucelli 2013). It has been demonstrated that HDAC6 levels positively correlate with tau burden, while a decrease in HDAC6 activity or expression promotes tau clearance (Cook et al., 2012). Inhibition or depletion of HDAC6 causes Hsp90 hyperacetylation and the concomitant decreased affinity of Hsp90 for client proteins such as tau, leads to client protein degradation (Kalin & Bergman 2013). In addition, loss of HDAC6 activity augments the efficacy of an Hsp90 inhibitor, opening the possibility to synergistically promoting the degradation of Hsp90 client proteins by co-treatments with both HDAC6 and Hsp90 inhibitors, as has been shown for leukemia cells (Cook et al. 2012; Rao et al. 2008; George et al. 2005).

The neuroprotective effect of HDAC6 inhibition may be beneficial for patients suffering from traumatic brain injuries. For example, it has been reported that HDAC6 inhibition results in the hyperacetylation of peroxiredoxin-1 and -2 leading to increased resistance against oxidative stress such as that observed during ischemic stroke (Parmigiani et al. 2008). HDAC6 inhibition may also be beneficial for patients afflicted by inherited neurological disorders such as Charcot-Marie-Tooth disease (CMT) and Rett syndrome. For example, symptomatic improvement was observed in a transgenic mouse model of CMT after the treatment with specific HDAC6 inhibitors, together with the increase in tubulin acetylation (D'Ydewalle et al. 2011). HDAC6 inhibition by tubastatin A has been shown to restore brain-derived neurotropic factor (BDNF) neurological function in Mecp2 knockout hippocampal neurons showing that HDAC6 is a potential target for Rett syndrome (Xu et al. 2014).

The above described data serve to illustrate the validity of modulating HDAC6 activity for treatment of disorders and diseases that include not only hyperproliferative indications, such as cancer, but also other therapeutic areas such as neurodegenerative disorders, autoimmune disorders, and mental disorders.

SUMMARY OF THE INVENTION

A first aspect is a compound of formula (Ia) or (Ib)

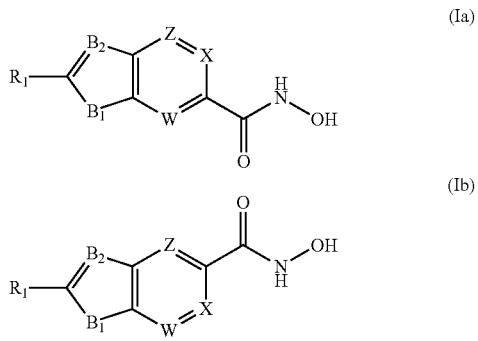

or a pharmaceutically acceptable salt thereof, wherein $R_1$ is

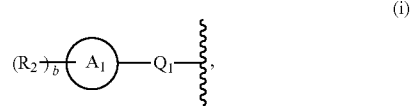

wherein
each $R_2$ is independently selected from C1-C6 alkyl, C3-C6 cycloalkyl, halogen, cyano, $R_3Y_1$-$Q_2$, $R_4R_5N$-$Q_3$, $R_6S(O)_2$-$Q_4$, and

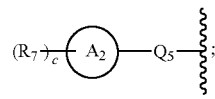

and two $R_2$ attached to adjacent atoms of ring $A_i$, together with the atoms to which they are attached, may form a 5- to 10-membered monocyclic or bicyclic ring, said ring optionally being substituted by one or more moieties selected from C1-C6 alkyl, C1-C6 alkoxy, halogen, and hydroxy;
$R_3$ is selected from H, C1-C6 alkyl, $R_8O$-$Q_6$, and $R_9R_{10}N$-$Q_7$;
$R_4$ and $R_5$ are independently selected from H, C1-C6 alkyl, C3-C8 cycloalkyl and $R_{11}O$-$Q_5$; or $R_4$ and $R_5$, together with the nitrogen atom to which they are both attached, form a 5- or 6-membered ring, which ring is optionally substituted by one or more moieties selected from C1-C6 alkyl and $R_{12}O$-$Q_9$;
$R_6$ is selected from H and C1-C6 alkyl;
each $R_7$ is independently selected from C1-C6 alkyl, halogen, $R_{13}O$-$Q_{10}$, $R_{14}R_{15}N$-$Q_{11}$, and $R_{16}S(O)_2$-$Q_{12}$, and two $R_7$ attached to adjacent atoms of ring $A_2$, together with the atoms to which they are attached, may form a 5- or 6-membered ring;
$R_8$ is selected from H and C1-C6 alkyl,
$R_9$ and $R_{10}$ are independently selected from H and C1-C6 alkyl; or $R_9$ and $R_{10}$, together with the nitrogen atom to which they are both attached, form a 5- or 6-membered ring;
each one of $R_{11}$, $R_{12}$ and $R_{13}$ is selected from H and C1-C6 alkyl,
$R_{14}$ and $R_{15}$ are independently selected from H and C1-C6 alkyl; or $R_{14}$ and $R_{15}$, together with the nitrogen atom to which they are both attached, form a 5- or 6-membered ring;

$R_{16}$ is selected from H and C1-C6 alkyl,
ring $A_1$ and ring $A_2$ are independently selected from phenyl and 5- or 6-membered heteroaryl;
b and c are integers of from 0 to 3;
$Q_1$ is selected from a direct bond, C1-C3 alkylene, C2-C4 alkenylene, and $Q_{13}$-$Y_2$-$Q_{14}$;
$Q_2$ is selected from a direct bond and C1-C3 alkylene;
$Q_3$ is selected from a direct bond, C1-C3 alkylene, and C(O);
$Q_4$ is selected from a direct bond, C1-C3 alkylene, and $NR_{17}$;
$Q_5$ is selected from a direct bond, C1-C3 alkylene, S(O)$_2NR_{18}$, $Q_{15}$-$Y_3$-$Q_{16}$, and

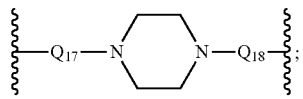

each one of $Q_6$, $Q_7$ and $Q_8$ is independently selected from C1-C3 alkylene;
each one of $Q_9$ and $Q_{10}$ is independently selected from a direct bond and C1-C3 alkylene;
$Q_{11}$ is selected from a direct bond, C1-C3 alkylene, and C(O);
$Q_{12}$ is selected from a direct bond, C1-C3 alkylene, and $NR_{19}$;
$Q_{13}$ is selected from a direct bond, C1-C3 alkylene, and C1-C3 alkylene substituted by $R_{20}$ and $R_{21}$;
each one of $Q_{14}$, $Q_{15}$, $Q_{16}$, $Q_{17}$ and $Q_{18}$ is independently selected from a direct bond and C1-C3 alkylene;
each one of $R_{17}$, $R_{18}$, and $R_{19}$ is independently selected from H and C1-C3 alkyl;
$R_{20}$ and $R_{21}$ are attached to the same carbon atom and form together with the carbon atom to which they are attached a C3-C6 cycloalkyl;
$Y_1$ is selected from O and S;
$Y_2$ is selected from O, and $NR_{22}$;
$Y_3$ is selected from O and $NR_{23}$;
$R_{22}$ is selected from H, phenyl, and C1-C3 alkyl, which alkyl is optionally substituted by a substituent selected from phenyl and $NR_{24}R_{25}$;
$R_{23}$ is H or C1-C3 alkyl; and
$R_{24}$ and $R_{25}$ are independently selected from H and C1-C3 alkyl, or $R_{24}$ and $R_{25}$ form, together with the nitrogen atom to which they are both attached, a 5- or 6-membered ring
(ii) $R_{26}R_{27}N$-$Q_{19}$, wherein
$R_{26}$ and $R_{27}$ are independently selected from H, C1-C6 alkyl and C3-C8 cycloalkyl; or $R_{26}$ and $R_{27}$, together with the nitrogen atom to which they are both attached, form a 5- or 6-membered ring optionally substituted by one or more moieties $R_{28}$;
each $R_{28}$ is independently selected from $R_{29}OC(O)NR_{30}$, and

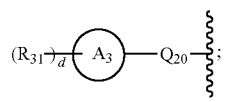

and two $R_{28}$ attached to adjacent atoms of the ring, together with the atoms to which they are attached, may form a 5- or 6-membered ring;
$R_{29}$ and $R_{30}$ are independently selected from H and C1-C6 alkyl;
$R_{31}$ is selected from C1-C6 alkyl and halogen;

d is an integer of from 0 to 3;
ring $A_3$ is selected from 5- to 10-membered aryl or heteroaryl;
$Q_{19}$ is a direct bond or C1-C3 alkylene;
$Q_{20}$ is selected from a direct bond, C1-C3 alkylene and $Q_{21}$-$NR_{32}$-$Q_{22}$;
$Q_{21}$ and $Q_{22}$ are independently selected from a direct bond and C1-C3 alkylene; and
$R_{32}$ is selected from H and C1-C6 alkyl;
(iii) halogen; or
(iv) hydroxy-C1-C6 alkyl;
$B_1$ is O, S or $NR_{33}$;
$B_2$ is N or $CR_{34}$;
W is N or $CR_{35}$;
X is N or $CR_{36}$;
Z is N or $CR_{37}$;
$R_{33}$ is H, or C1-C3 alkyl;
$R_{34}$ is H, C1-C3 alkyl or halogen;
$R_{35}$, $R_{36}$ and $R_{37}$ are independently selected from H and F; and
any alkyl, or cycloalkyl is optionally substituted with one or more F;
provided that when ring $A_1$ is phenyl, $Q_1$ is a direct bond, $B_2$ is N and $B_1$ is $NR_{33}$, b is not 0; and provided that the compound is not selected from:
2-(4-(3,4-dimethoxyphenyl)pyrimidin-2-yl)-N-hydroxy-1H-indole-5-carboxamide and 2-amino-N-hydroxybenzo[d]thiazole-5-carboxamide.

Herein below, unless, a specific regioisomer (Ia) or (Ib) is designated, compounds of formula (Ia) or (Ib) will collectively be referred to as compounds of formula (I). Therefore, it should be clear that a in some embodiments, any mention of a "compound of formula (I)" refers to a compound of formula (Ia), while in some other embodiments, any mention of a "compound of formula (I)" refers to a compound of formula (Ib).

The compounds of formula (I) are useful in therapy. Therefore, one aspect is a compound of formula (I) for use in therapy.

The compounds of formula (I) are histone deacetylase (HDAC) inhibitors. Therefore, one aspect is a compound of formula (I) for use as an HDAC inhibitor.

The compounds of formula (I) have a selectivity for in particular HDAC6. Therefore, one aspect is a compound of formula (I) for use as a selective HDAC6 inhibitor.

Disorders associated with or mediated by HDAC may be treated by use of the compounds of the invention. One aspect therefore is a method of treatment of a mammal suffering from a disorder associated with or mediated by HDAC, in particular HDAC6.

Another aspect is a pharmaceutical composition comprising the compound of formula (I) and optionally a pharmaceutically acceptable excipient.

Another aspect is a pharmaceutical composition comprising the compound of formula (I) and optionally a pharmaceutically acceptable excipient for use in the treatment of a disorder associated with or mediated by HDAC, in particular HDAC6.

Another aspect is a compound of formula (I) for use in the treatment of a disorder associated with or mediated by HDAC, in particular HDAC6.

Another aspect is a compound of formula (I) for use in the treatment of a disorder selected from autoimmune disorders, mental disorders, neurodegenerative disorders and hyperproliferative disorders, in particular cancers.

DETAILED DESCRIPTION

Definitions

Unless otherwise specified, any term used herein is to be given its conventional meaning. For example, the term alkyl either alone or as part of a radical, includes straight or branched chain alkyl of the general formula $C_nH_{2n+1}$.

The term "C1-C6 alkyl" refers to an alkyl as defined herein above, of the general formula $CH_3$, $C_2H_5$, $C_3H_7$, $C_4H_9$, $C_5H_{11}$ or $C_6H_{13}$.

The term "C3-C6 cycloalkyl" refers to a saturated cyclic alkyl moiety containing 2, 4, 5 or 6 carbon atoms in the ring.

The term "halogen" refers to F, Cl, Br or I.

A term of the type RO refers to a moiety of formula

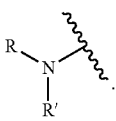

The term "hydroxy" refers to a moiety of the formula RO, i.e. wherein R is H.

The term "heteroatom" preferably refers to N, O or S.

A term of the type RR'N refers to a moiety of formula

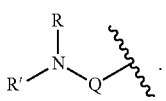

A term of the type RR'N-Q refers to a moiety of formula

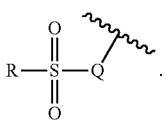

A term of the type RS(O)$_2$-Q refers to a moiety of formula

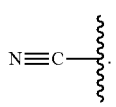

The term CN (or cyano) refers to a moiety of formula $N{\equiv}C{-}$

A "bicyclic ring" is a cyclic moiety having two fused rings, which each may be (hetero)aromatic or non-aromatic.

The term "heteroaryl" refers to an aromatic ring containing at least one heteroatom in the ring, e.g. pyridinyl or thienyl.

The term "bicyclic heteroaryl" refers to a heteroaryl comprising cycles fused to each other, at least one of which is a heteroaryl, the other one being either an aromatic or heteroaromatic ring.

The term "C(O)" refers to a moiety of formula

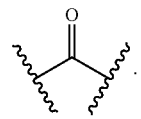 [SMILES: *C(*)=O]

A term of the type NR refers to a moiety of formula

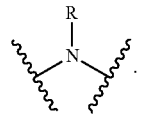

A term of the type (CRR')$_n$ refers to a moiety of formula

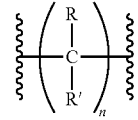

wherein n is 0 or a positive integer, which moiety is a direct bond when n is 0 and which is a chain of n CRR' units when n is a positive integer. As an example, when n is 1 and $R_1$ and $R_1'$ are both H, the moiety is methylene, i.e. —$CH_2$—.

A term of the type (CRR')$_n$NR" refers to a moiety of formula

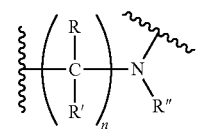

wherein n is 0 or a positive integer, and which is NR" when n is 0.

A term of the type CR=CR' refers to a moiety of formula

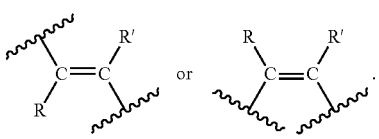

A term of the type S(O)$_2$NR refers to a moiety of formula

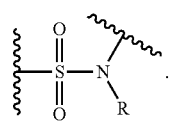

A term of the type $(CR_iR_i')_nO$ refers to a moiety of formula

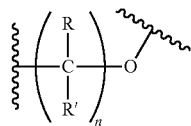

wherein n is 0 or a positive integer, and which is O (i.e. —O—) when n is 0.

The term phenyl refers to the moiety

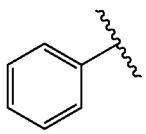

The term benzyl refers to the moiety

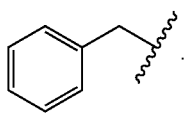 [SMILES: *Cc1ccccc1]

A term of the type ROC(O)NR' refers to a moiety of formula

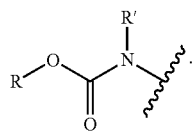

"Optional" or "optionally" means that the subsequently described event or circumstance may but need not occur, and that the description includes instances where the event or circumstance occurs and instances in which it does not.

"Pharmaceutically acceptable" means that which is useful in preparing a pharmaceutical composition that is generally safe, non-toxic, and neither biologically nor otherwise undesirable and includes that which is acceptable for veterinary as well as human pharmaceutical use.

The term "excipient" refers to a pharmaceutically acceptable chemical, such as known to those of ordinary skill in the art of pharmacy to aid in the administration of the medicinal agent. It is a compound that is useful in preparing a pharmaceutical composition, generally safe, non-toxic and neither biologically nor otherwise undesirable, and includes excipients that are acceptable for veterinary use as well as human pharmaceutical use. Exemplary excipients include binders, surfactants, diluents, disintegrants, antiadherents, and lubricants.

"Therapeutically effective amount" means an amount of a compound that, when administered to a subject for treating a disease state, is sufficient to effect such treatment for the disease state. The "therapeutically effective amount" will vary depending on the compound, the disease state being treated, the severity of the disease treated, the age and relative health of the subject, the route and form of administration, the judgment of the attending medical or veterinary practitioner, etc.

As used herein the terms "treatment" or "treating" is an approach for obtaining beneficial or desired results including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total) whether detectable or undetectable. The term can also mean prolonging survival as compared to expected survival without the treatment.

The term "mammal" refers to a human or any mammalian animal, e.g. a primate, a farm animal, a pet animal, or a laboratory animal. Examples of such animals are monkeys, cows, sheep, horses, pigs, dogs, cats, rabbits, mice, rats etc. Preferably, the mammal is a human.

The term "hyperproliferative disorder" refers to a disorder involving undesired and uncontrolled cell proliferation. The hyperproliferative disorder may be benign or malignant (cancer). The term "cancer" thus refers to any malignant growth or tumor caused by abnormal and uncontrolled cell division; it may spread to other parts of the body through the lymphatic system or the blood stream and includes both solid tumors and blood-borne tumors. Exemplary cancers include adrenocortical carcinoma, AIDS-related cancers, AIDS-related lymphoma, anal cancer, anorectal cancer, appendix cancer, childhood cerebellar astrocytoma, childhood cerebral astrocytoma, basal cell carcinoma, biliary cancer, extrahepatic bile duct cancer, intrahepatic bile duct cancer, urinary bladder cancer, bone and joint cancer, osteosarcoma and malignant fibrous histiocytoma, brain tumor, brain stem glioma, cerebellar astrocytoma, cerebral astrocytoma/malignant glioma, ependymoma, medulloblastoma, visual pathway and hypothalamic glioma, breast cancer, bronchial adenomas/carcinoids, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Sezary syndrome, endometrial cancer, esophageal cancer, extracranial germ cell tumor, extragonadal germ cell tumor, eye cancer, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin's lymphoma, hypopharyngeal cancer, ocular cancer, Kaposi's sarcoma, renal cancer, laryngeal cancer, acute lymphoblastic leukemia, acute myeloid leukemia, hairy cell leukemia, lip and oral cavity cancer, lung cancer, non-small cell lung cancer, small cell lung cancer, non-Hodgkin's lymphoma, primary central nervous system lymphoma, Waldenstrom's macroglobulinemia, intraocular (eye) melanoma, Merkel cell carcinoma, malignant mesothelioma, metastatic squamous neck cancer, cancer of the tongue, multiple endocrine neoplasia syndrome, myelodysplastic syndromes, myelodysplastic/myeloproliferative diseases, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pheochromocytoma, pineoblastoma and supratentorial primitive neuroectodermal tumors, pituitary tumor, plasma cell neoplasm/multiple myeloma, pleuropulmonary blastoma, prostate cancer, rhabdomyosarcoma, salivary gland cancer, Ewing's sarcoma family of tumors, soft tissue sarcoma, uterine cancer, uterine sarcoma, skin cancer (non-melanoma), skin cancer (melanoma), small intestine cancer, squamous cell carcinoma, testicular cancer, throat cancer, thymoma, thymoma and thymic carcinoma, thyroid cancer, transitional cell cancer of the renal pelvis and ureter and other urinary organs, gestational trophoblastic tumor, urethral cancer, vaginal cancer, vulvar cancer, and Wilm's tumor.

The term "benign hyperproliferative disorder" refers to disorders such as benign tumors, e.g. hemangiomas, hepatocellular adenoma, cavernous haemangioma, focal nodular hyperplasia, acoustic neuromas, neurofibroma, bile duct adenoma, bile duct cystanoma, fibroma, lipomas, leiomyomas, mesotheliomas, teratomas, myxomas, nodular regenerative hyperplasia, trachomas and pyogenic granulomas. Other types of non-malignant hyperproliferative disorders are abnormal cell proliferation due to insults to body tissue during surgery, proliferative responses associated with organ transplantation, abnormal angiogenesis, e.g. abnormal angiogenesis accompanying rheumatoid arthritis, ischemic-reperfusion related brain edema and injury, cortical ischemia, ovarian hyperplasia and hypervascularity, (polycystic ovary syndrome), endometriosis, psoriasis, diabetic retinopaphy, and other ocular angiogenic diseases such as retinopathy of prematurity (retrolental fibroplastic), macular degeneration, corneal graft rejection, neuroscular glaucoma and Oster Webber syndrome, etc.

The term "autoimmune disorder" (or autoimmune disease) refers to any disorder arising from an inappropriate immune response of the body against substances and tissues normally present in the body (autoimmunity). Such response may be restricted to certain organs or involve a particular tissue in different places. Exemplary autoimmune disorders are acute disseminated encephalomyelitis (ADEM), Addison's disease, agammaglobulinemia, alopecia areata, amyotrophic lateral sclerosis, ankylosing spondylitis, antiphospholipid syndrome, antisynthetase syndrome, atopic allergy, atopic dermatitis, autoimmune aplastic anemia, autoimmune cardiomyopathy, autoimmune enteropathy, autoimmune hemolytic anemia, autoimmune hepatitis, autoimmune inner ear disease, autoimmune lymphoproliferative syndrome, autoimmune peripheral neuropathy, autoimmune pancreatitis, autoimmune polyendocrine syndrome, autoimmune progesterone dermatitis, autoimmune thrombocytopenic purpura, autoimmune urticarial, autoimmune uveitis, Balo disease/Balo concentric sclerosis, Behçet's disease, Berger's disease, Bickerstaffs encephalitis, Blau syndrome, bullous pemphigoid, Castleman's disease, celiac disease, Chagas disease, chronic inflammatory demyelinating polyneuropathy, chronic recurrent multifocal osteomyelitis, chronic obstructive pulmonary disease, Churg-Strauss syndrome, cicatricial pemphigoid, Cogan syndrome, cold agglutinin disease, complement component 2 deficiency, contact dermatitis, cranial arteritis, CREST syndrome, Crohn's disease (one of two types of idiopathic inflammatory bowel disease "IBD"), Cushing's Syndrome, cutaneous leukocytoclastic angiitis, Dego's disease, Dercum's disease, dermatitis herpetiformis, dermatomyositis, diabetes mellitus type 1, diffuse cutaneous systemic sclerosis, Dressler's syndrome, drug-induced lupus, discoid lupus erythematosus, eczema, endometriosis, enthesitis-related arthritis, eosinophilic fasciitis, eosinophilic gastroenteritis, epidermolysis bullosa acquisita, erythema nodosum, erythroblastosis fetalis, essential mixed cryoglobulinemia, Evan's syndrome, fibrodysplasia ossificans progressive, fibrosing alveolitis (or Idiopathic pulmonary fibrosis), gastritis, gastrointestinal pemphigoid, glomerulonephritis, Goodpasture's syndrome, Graves' disease, Guillain-Barré syndrome (GBS), Hashimoto's encephalopathy, Hashimoto's thyroiditis, Henoch-Schonlein purpura, herpes gestationis (aka gestational pemphigoid), Hidradenitis suppurativa, Hughes-Stovin syndrome, hypogammaglobulinemia, idiopathic inflammatory demyelinating diseases, idiopathic pulmonary fibrosis, idiopathic thrombocytopenic purpura, IgA nephropathy, inclusion body myositis, chronic inflammatory demyelinating polyneuropathy, interstitial cystitis, juvenile idiopathic arthritis (aka juvenile rheumatoid arthritis), Kawasaki's disease, Lambert-Eaton myasthenic syndrome, leukocytoclastic vasculitis, lichen planus, lichen sclerosus, linear IgA disease (LAD), lupoid hepatitis (aka autoimmune hepatitis), lupus erythematosus, Majeed syndrome, Ménière's disease, microscopic polyangiitis, mixed connective tissue disease, morphea, Mucha-Habermann disease (aka *pityriasis lichenoides* et *varioliformis acuta*), multiple sclerosis, myasthenia gravis, myositis, narcolepsy, neuromyelitis optica (also Devic's disease), neuromyotonia, occular cicatricial pemphigoid, opsoclonus myoclonus syndrome, Ord's thyroiditis, palindromic rheumatism, PANDAS (pediatric autoimmune neuropsychiatric disorders associated with *streptococcus*), paraneoplastic cerebellar degeneration, paroxysmal nocturnal hemoglobinuria (PNH), Parry Romberg syndrome, Parsonage-Turner syndrome, pars planitis, pemphigus vulgaris, pernicious anaemia, perivenous encephalomyelitis, POEMS syndrome, polyarteritis *nodosa*, polymyalgia rheumatic, polymyositis, primary biliary cirrhosis, primary sclerosing cholangitis, progressive inflammatory neuropathy, psoriasis, psoriatic arthritis, pyoderma gangrenosum, pure red cell aplasia, Rasmussen's encephalitis, Raynaud phenomenon, relapsing polychondritis, Reiter's syndrome, restless leg syndrome, retroperitoneal fibrosis, rheumatoid arthritis, rheumatic fever, sarcoidosis, schizophrenia, Schmidt syndrome another form of APS, Schnitzler syndrome, Scleritis, Scleroderma, Serum Sickness, Sjögren's syndrome, spondyloarthropathy, stiff person syndrome, subacute bacterial endocarditis (SBE), Susac's syndrome, Sweet's syndrome, sympathetic ophthalmia, systemic lupus erythematosis, Takayasu's arteritis, temporal arteritis (also known as "giant cell arteritis"), thrombocytopenia, Tolosa-Hunt syndrome, transverse myelitis, ulcerative colitis (one of two types of idiopathic inflammatory bowel disease "IBD"), undifferentiated connective tissue disease different from mixed connective tissue disease, undifferentiated spondyloarthropathy, urticarial vasculitis, vasculitis, vitiligo, and Wegener's granulomatosis.

The term "neurogenerative disorder" (or neurogenerative disease) refers to disorders associated with a progressive loss of structure or function of neurons affecting the structure or function of the brain, spinal cord or peripheral nervous system. Exemplary neurodegenerative disorders include mitochondrial encephalomyopathies and gut dysmotility syndromes, ataxia syndromes including Friedreich's ataxia and spinocerebellar ataxia (SCA), spinal cord injury, familial and sporadic amyotrophic lateral sclerosis (FALS and ALS, respectively), familial and sporadic Parkinson's disease, familial and sporadic Alzheimer's disease, Huntington's disease, olivopontocerebellar atrophy, multiple system atroph, y, progressive supranuclear palsy, diffuse lewy body disease and synucleinopathies, Down Syndrome, corticodentatonigral degeneration, progressive familial myoclonic epilepsy, strionigral degeneration, torsion dystonia, familial tremor, Gilles de la Tourette syndrome, and Hallervorden-Spatz disease.

The term "mental disorder" refers to a disorder as e.g. referred to in the Diagnostic and Statistical Manual of Mental Disorders (DSM) published by American Psychiatric Publishing Inc. (Arlington, Va.). Examples of mental disorders are psychotic disorders and schizophrenia spectrum disorders such as schizotypal (personality) disorder, delusional disorder, brief psychotic disorder, schizophreniform disorder, schizophrenia, schizoaffective disorder, substance/medication-induced psychotic disorder, and psychotic disorder due to another medical condition; bipolar disorders such as bipolar I disorder, bipolar II disorder, cyclothymic disorder, substance/medication-induced bipolar and related disorder, depressive disorders, such as disruptive mood dysregulation disorder, major depressive disorder, single and recurrent episodes, persistent depressive disorder (dysthymia), premenstrual dysphoric disorder, substance/medication-induced depressive disorder, and depressive disorder due to another medical condition; anxiety disorders, such as separation anxiety disorder, selective mutism, specific phobia, social anxiety disorder (social phobia), panic disorder, agoraphobia, generalized anxiety disorder etc.

The Compound

In a first aspect the present invention relates to a compound of formula (I), i.e. of formula (Ia) or (Ib)

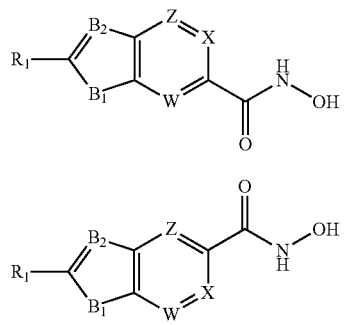

(Ia)

(Ib)

or a pharmaceutically acceptable salt thereof, wherein $R_1$, $B_1$, $B_2$, W, X and Z are as defined herein.

In a compound of formula (I), $R_1$ is a moiety

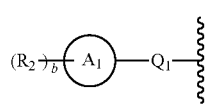

(i)

wherein b, $R_2$, ring $A_1$ and $Q_1$ are as defined herein;

(ii) $R_{26}R_{27}N-Q_{19}$, wherein $R_{26}$, $R_{27}$ and $Q_{19}$ are as defined herein;

(iii) halogen; or (iv) hydroxy-C1-C6 alkyl.

In some embodiments, $R_1$ is a moiety selected from (i), (ii) and (iv). In some other embodiments, $R_1$ is a moiety (i) or (ii). In still other embodiments, $R_1$ is a moiety (i) or (iv). In still other embodiments, $R_1$ is a moiety (ii) or (iv). In some embodiments, $R_1$ is a moiety (i). In other embodiments, $R_1$ is a moiety (ii).

When $R_1$ is a moiety (i), the compound of formula (I) is as represented by any of the formulas (IAa) and (IAb)

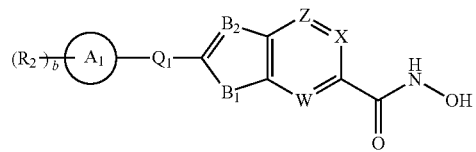

(IAa)

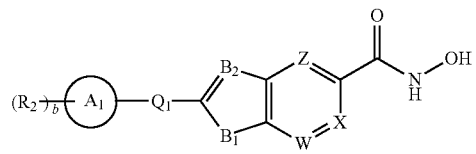

(IAb)

wherein b, $R_2$, ring $A_1$, $Q_1$, $B_1$, $B_2$, W, X and Z are as defined herein.

Herein below, unless the specific regioisomer (IAa) or (IAb) is specifically designated, compounds of formula (IAa) or (IAb) will collectively be referred to as compounds of formula (IA).

In a compound of formula (IA), b represents an integer of from 0 to 3, e.g. from 1 to 3. In some embodiments, b represents an integer of from 0 to 2, e.g. b is 1 or 2. In some embodiments, b is 2. In some other embodiments, b is 0 or 1, e.g. b is 1.

The ring $A_1$ is selected from 5- or 6-membered aryl or heteroaryl, i.e. ring $A_1$ is selected from phenyl and 5- or 6-membered heteroaryl. In some embodiments, ring $A_1$ is selected from phenyl and 5-membered heteroaryl. In some other embodiments, ring $A_1$ is selected from phenyl and 6-membered heteroaryl. In still other embodiments, ring $A_1$ is selected from 5- or 6-membered heteroaryl. In some particular embodiments, ring $A_1$ is phenyl.

In some embodiments, when ring $A_1$ is phenyl, b is not 0.

When ring $A_1$ is heteroaryl, said heteroaryl e.g. may comprise 1, 2, 3 or 4 heteroatoms, e.g. 1-3, or 1 or 2 heterotaoms, or 1 heteroatom, each independently selected from N, O and S. For example, said heteroaryl may be selected from furyl, thienyl, pyrrolyl, pyrazolyl, imidazolyl, (is)oxazolyl, pyridyl, and pyrimidinyl, e.g. from furyl, thienyl, pyrazolyl, (is)oxazolyl, and pyridyl.

In some embodiments, when ring $A_1$ is phenyl or 6-membered heteroaryl, said ring is substituted with $R_2$ in para position, or has a ring heteroatom in para position.

When ring $A_1$ is phenyl, the compound of formula (IA) is as represented by formula (IBa) or (IBb)

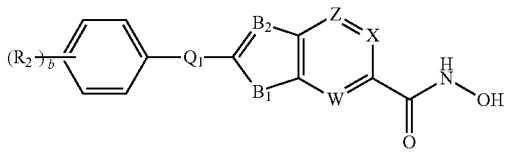

(IBa)

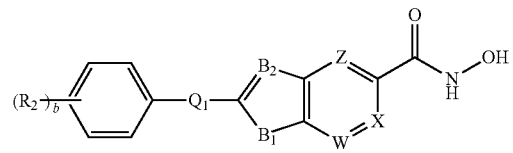

(IBb)

wherein b, $R_2$, $Q_1$, $B_1$, $B_2$, W, X and Z are as defined herein, and which compound may collectively be referred to as a compound of formula (IB).

In some embodiments, when ring $A_1$ is phenyl, and b is at least 1, ring $A_1$ is substituted with a moiety $R_2$ in para position. In such embodiments, a compound of formula (IB) is as represented by formula (ICa) or (ICb)

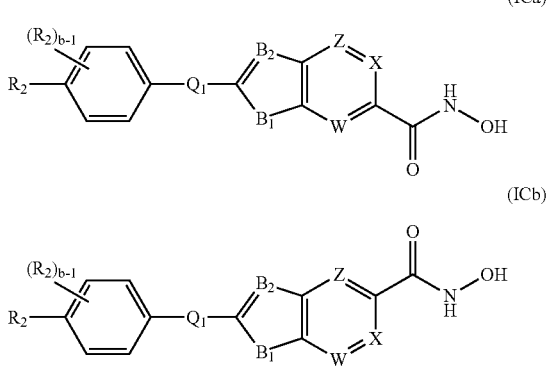

(ICa)

(ICb)

wherein b is at least 1, e.g. b is 1 or 2, or b is 1; and $R_2$, $Q_1$, $B_1$, $B_2$, W, X and Z are as defined herein; which compound may collectively be referred to as a compound of formula (IC).

In a compound of formula (IA), $Q_1$ is a direct bond, C1-C3 alkylene, C2-C4 alkenylene, or $Q_{13}$-$Y_2$-$Q_{14}$. In some embodiments, $Q_1$ is a direct bond, C1-C3 alkylene, or C2-C4 alkenylene. In some other embodiments, $Q_1$ is a direct bond, C1-C3 alkylene, or $Q_{13}$-$Y_2$-$Q_{14}$. In some other embodiments, $Q_1$ is $Q_{13}$-$Y_2$-$Q_{14}$. In still other embodiments, $Q_1$ is a direct bond or C1-C3 alkylene. In some embodiments, $Q_1$ is a direct bond or $Q_{13}$-$Y_2$-$Q_{14}$.

In some embodiments, when $Q_1$ is a direct bond or C1-C3 alkylene, b is not 0. For example, in some embodiments when $Q_1$ is a direct bond or C1-C3 alkylene, and ring $A_1$ is phenyl, b is not 0. In some embodiments, $Q_1$ is a direct bond or $CH_2$. In some preferred embodiments, $Q_1$ is a direct bond.

When $Q_1$ is C1-C3 alkylene, said alkylene more particularly may be C1-C2 alkylene. In some embodiments, when $Q_1$ is C1-C3 alkylene, said alkylene is selected from $CH_2$, $CH(CH_3)$, $CH(CH_2CH_3)$, $C(CH_3)_2$, and $CH_2CH(CH_3)$; e.g. from $CH_2$, $CH(CH_3)$, $C(CH_3)_2$; or from $CH_2$, and $CH(CH_3)$, in particular said alkylene is $CH_2$.

In some embodiments, when $Q_1$ is C2-C4 alkenylene, said alkenylene is of the general formula —$CR_A$=$CR_B$—, wherein $R_A$ and $R_B$ are both independently selected from H and methyl; e.g. both are H. In some embodiments, when $Q_1$ is C2-C4 alkenylene, the double bond is of E configuration. In some other embodiments, when $Q_1$ is C2-C4 alkenylene, the double bond is of Z configuration. In some embodiments, when $Q_1$ is C1-C4 alkenylene, Q1 more particularly is —CH=CH— and is of E configuration.

When $Q_1$ is $Q_{13}$-$Y_2$-$Q_{14}$, $Q_{13}$ is selected from a direct bond, C1-C3 alkylene, and C1-C3 alkylene substituted by $R_{20}$ and $R_{21}$; $Q_{14}$ is selected from a direct bond and C1-C3 alkylene; and $Y_2$ is selected from O and $NR_{22}$. In some of these embodiments, $Q_{13}$ is selected from a direct bond, C1-C2 alkylene, and C1-C2 alkylene substituted by $R_{20}$ and $R_{21}$; and $Q_{14}$ is selected from a direct bond and C1-C2 alkylene; e.g. $Q_{13}$ is selected from a direct bond, methylene, ethylene, and methylene substituted by $R_{20}$ and $R_{21}$; and $Q_{14}$ is selected from a direct bond and methylene; or $Q_{13}$ is selected from a direct bond, methylene, and ethylene; and $Q_{14}$ is selected from a direct bond and methylene; or both $Q_{13}$ and $Q_{14}$ are selected from a direct bond and methylene; or both $Q_{13}$ and $Q_{14}$ are a direct bond.

When $Q_{13}$ is C1-C3 alkylene substituted by $R_{20}$ and $R_{21}$, $R_{20}$ and $R_{21}$ are attached to the same carbon atom and form, together with the carbon atom to which they are attached, a C3-C6 cycloalkyl, e.g. a C5-C6 cycloalkyl, such as cyclohexyl.

In some embodiments, one of $Q_{13}$ and $Q_{14}$ is a direct bond, and the other one is as defined herein above, e.g. the other one is selected from a direct bond, methylene and ethylene, or a direct bond and methylene. In some embodiments, $Q_{13}$ is a direct bond or methylene, and $Q_{14}$ is a direct bond.

It should be realized that the moiety $Q_{13}$-$Y_2$-$Q_{14}$ may be attached either by the "$Q_{13}$ side" or the "$Q_{14}$ side" to the ring $A_1$. In some embodiments, when $Q_1$ is $Q_{13}$-$Y_2$-$Q_{14}$, $Q_{13}$ is attached to the ring $A_1$.

In the moiety, $Q_{13}$-$Y_2$-$Q_{14}$, $Y_2$ is O or $NR_{22}$. In some embodiments, $Y_2$ is O. In some other embodiments, $Y_2$ is $NR_{22}$; wherein $R_{22}$ is selected from H, phenyl, and C1-C6 alkyl, which alkyl is optionally substituted by a substituent selected from phenyl and $NR_{24}R_{25}$; and $R_{24}$ and $R_{25}$ are independently selected from H and C1-C3 alkyl, or $R_{24}$ and $R_{25}$ form, together with the nitrogen atom to which they are both attached, a 5- or 6-membered ring.

In some embodiments, $R_{22}$ is selected from H, phenyl, and C1-C3 alkyl, which alkyl is optionally substituted by a substituent selected from phenyl and $NR_{24}R_{25}$. In some other embodiments, $R_{22}$ is selected from H, phenyl, and C1-C6 alkyl, which alkyl is optionally substituted by a substituent selected from phenyl. In some other embodiments, $R_{22}$ is selected from H and C1-C6 alkyl, e.g. $R_{22}$ is selected from H and C1-C3 alkyl; in particular $R_{22}$ is selected from H and $CH_3$. In some embodiments, $R_{22}$ is H.

In some embodiments, when $Q_1$ is $Q_{13}$-$Y_2$-$Q_{14}$, $Q_{14}$ is a direct bond and $Y_2$ is $NR_{22}$, i.e. the moiety $Q_{13}$-$Y_2$-$Q_{14}$ is a moiety of formula $Q_{13}$-$NR_{22}$, wherein $R_{22}$ is as defined herein above. In some of these embodiments, $R_{22}$ is selected from H, C1-C6 alkyl, phenyl and benzyl. In some of these embodiments, $R_{22}$ is H, C1-C6 alkyl, or phenyl, e.g. H or C1-C6 alkyl, or $R_{22}$ is H. When $R_{22}$ is C1-C6 alkyl, it more particularly may be C1-C3 alkyl, e.g. methyl.

In some embodiments, $Q_{13}$-$NR_{22}$ is

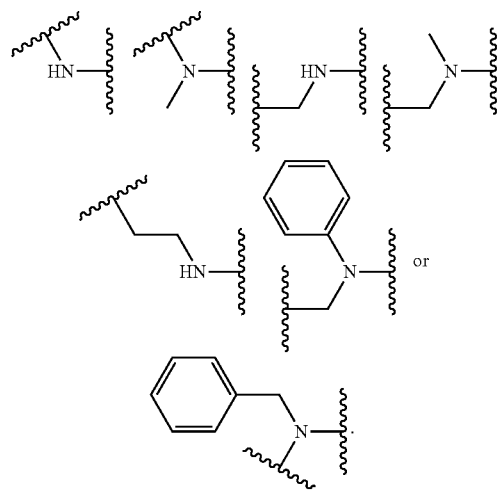

In some preferred embodiments, $Q_1$ is selected from a direct bond, $CH_2$, NH or $N(CH_3)$; e.g. from a direct bond, $CH_2$ or NH; or from a direct bond, NH or $N(CH_3)$, in particular from a direct bond or NH. In some other embodiments, $Q_1$ is selected from a direct bond and $Q_{13}$-$Y_2$-$Q_{14}$, as defined herein above, e.g. from a direct bond and $Q_{13}$-$NR_{22}$-$Q_{14}$ as defined herein above, e.g. from a direct bond and $Q_{13}$-$NR_{22}$.

In some further embodiments, $Q_{13}$-$Y_2$-$Q_{14}$ is selected from

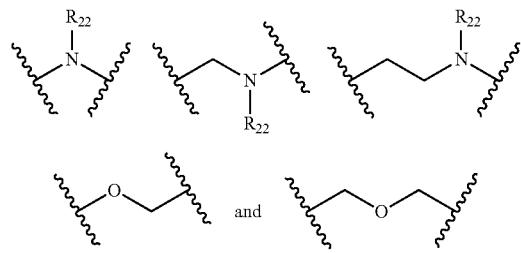

wherein $R_{22}$ is as defined herein above.

In still further embodiments, $Q_{13}$-$Y_2$-$Q_{14}$ is selected from

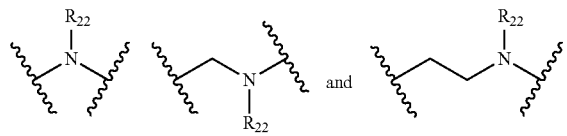

wherein $R_{22}$ is as defined herein above.

In still further embodiments, $Q_{13}$-$Y_2$-$Q_{14}$ is selected from

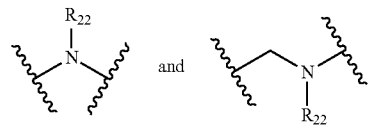

wherein $R_{22}$ is as defined herein above.

In a compound of formula (IA), each $R_2$ is independently selected from C1-C6 alkyl, C3-C6 cycloalkyl, halogen, cyano, $R_3Y_1$-$Q_2$, $R_4R_5N$-$Q_3$, $R_6S(O)_2$-$Q_4$, and

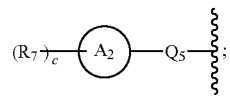

and two $R_2$ attached to adjacent atoms of ring $A_1$, together with the atoms to which they are attached, may form 5- to 10-membered monocyclic or bicyclic ring, said ring optionally being substituted by one or more moieties selected from C1-C6 alkyl, C1-C6 alkoxy, halogen, and hydroxy.

In some embodiments, each $R_2$ is independently selected from C1-C6 alkyl, C3-C6 cycloalkyl, halogen, cyano, $R_3Y_1$-$Q_2$, $R_4R_5N$-$Q_3$, $R_6S(O)_2$-$Q_4$, and

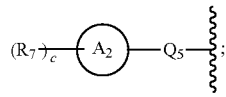

or
two $R_2$ attached to adjacent atoms of ring $A_1$, together with the atoms to which they are attached, form a 5- to 10-membered monocyclic or bicyclic ring, optionally substituted as indicated herein.

In some embodiments, each $R_2$ is independently selected from C1-C6 alkyl, C3-C6 cycloalkyl, halogen, cyano, $R_3Y_1$-$Q_2$, $R_4R_5N$-$Q_3$, $R_6S(O)_2$-$Q_4$, and

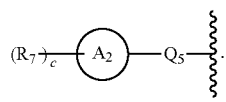

In some other embodiments, each $R_2$ is independently selected from C1-C6 alkyl, C3-C6 cycloalkyl, halogen, $R_3Y_1$-$Q_2$, $R_4R_5N$-$Q_3$, $R_6S(O)_2$-$Q_4$, and

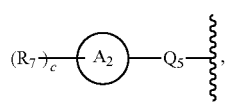

and two $R_2$ attached to adjacent atoms of ring $A_1$, together with the atoms to which they are attached, may form a 5- to 10-membered monocyclic or bicyclic ring, optionally substituted as indicated herein.

In still other embodiments, each $R_2$ is independently selected from C1-C6 alkyl, C3-C6 cycloalkyl, halogen, $R_3Y_1$-$Q_2$, $R_4R_5N$-$Q_3$, $R_6S(O)_2$-$Q_4$, and

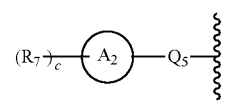

In still other embodiments, each $R_2$ is independently selected from C1-C6 alkyl, C3-C6 cycloalkyl, halogen, $R_3Y_1$-$Q_2$, $R_4R_5N$-$Q_3$, and

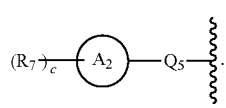

In still other embodiments, each $R_2$ is independently selected from C1-C6 alkyl, C3-C6 cycloalkyl, halogen, cyano, $R_3Y_1$-$Q_2$, $R_4R_5N$-$Q_3$, and $R_6S(O)_2$-$Q_4$.

In still other embodiments, each $R_2$ is independently selected from C1-C6 alkyl, C3-C6 cycloalkyl, halogen, $R_3Y_1$-$Q_2$, $R_4R_5N$-$Q_3$, and $R_6S(O)_2$-$Q_4$.

In still other embodiments, each $R_2$ is independently selected from C1-C6 alkyl, C3-C6 cycloalkyl, halogen, $R_3Y_1$-$Q_2$, and $R_4R_5N$-$Q_3$.

In still other embodiments, each $R_2$ is independently selected from C1-C6 alkyl, C3-C6 cycloalkyl, halogen, and $R_3Y_1$-$Q_2$.

In still other embodiments, each $R_2$ is independently selected from C1-C6 alkyl, halogen, and $R_3Y_1$-$Q_2$.

In still other embodiments, each $R_2$ is independently selected from or from C1-C6 alkyl, C3-C6 cycloalkyl, and halogen.

In still other embodiments, each $R_2$ is independently selected from C1-C6 alkyl and C3-C6 cycloalkyl, e.g. from C1-C6 alkyl.

In still other embodiments, two $R_2$ are attached to adjacent atoms of ring $A_1$ and, together with the atoms to which they are attached, form a 5- to 10-membered monocyclic or bicyclic ring, optionally substituted as indicated herein.

When any $R_2$ is selected from C1-C6 alkyl, it more particularly may be selected from C1-C5 alkyl, or C1-C4 alkyl, or C2-C4 alkyl, or C3-C4 alkyl. In some embodiments, when $R_2$ is C1-C6 alkyl, said alkyl is selected from methyl, ethyl, isopropyl, n-butyl and tert-butyl, and any fluorinated analogues thereof, such as trifluoromethyl. In some embodiments, $R_2$ is isopropyl or tert-butyl, in particular $R_2$ is isopropyl.

When any $R_2$ is selected from C3-C6 cycloalkyl, said cycloalkyl e.g. may be C3-C5 cycloalkyl, or C3-C4 cycloalkyl, e.g. cyclopropyl.

When any $R_2$ is selected from halogen, it more particularly may be selected from F, Cl and Br.

In some embodiments, when b is 2, each $R_2$ is independently selected from C1-C6 alkyl, halogen, and $R_3O$; or the two $R_2$ are attached to adjacent atoms of ring $A_1$, and together with the atoms to which they are attached, form a 5- to 10-membered monocyclic or bicyclic ring, optionally substituted as indicated herein.

In some embodiments, when b is 2, each $R_2$ is independently selected from C1-C6 alkyl, halogen, and $R_3Y_1$-$Q_2$.

When two $R_2$ attached to adjacent atoms of ring $A_1$, together with the atoms to which they are attached, form a 5- to 10-membered monocyclic or bicyclic ring, said ring may be carbocyclic or heterocyclic, and may be aromatic, non-aromatic or—if bicyclic—partly aromatic and partly non-aromatic. In some embodiments, said ring is 5- or 6-membered. In some embodiments, said ring is 5- or 6-membered, non-aromatic and contains one or two ring heteroatoms, e.g. one or two oxygen atoms in the ring. In some other embodiments, two $R_2$ attached to adjacent atoms of ring $A_1$, together with the atoms to which they are attached, form a 5- to 10-membered aromatic or heteroaromatic ring, e.g. a 5- or 6-membered aromatic or heteroaromatic ring. In some embodiments, two $R_2$ attached to adjacent atoms of ring $A_1$, together with the atoms to which they are attached, form a 5- to 10-membered heteroaromatic ring, e.g. a 5- or 6-membered heteroaromatic ring. In some embodiments, two $R_2$ attached to adjacent atoms of ring $A_1$, together with the atoms to which they are attached, form a benzene ring.

Said ring formed by two adjacent $R_2$ is optionally substituted by one or more moieties, e.g. one or two moieties, or one moiety, selected from C1-C6 alkyl, C1-C6 alkoxy, halogen, and hydroxy, e.g. from C1-C6 alkyl and C1-C6 alkoxy, or from C1-C6 alkoxy. In some embodiments, such moieties are selected from C1-C3 alkyl, C1-C3 alkoxy, halogen, and hydroxy; e.g. from methyl, methoxy, halogen and hydroxy, or from methyl, methoxy and hydroxy, e.g. methoxy. In some embodiments, the ring is unsubstituted.

In some embodiments, when two $R_2$ attached to adjacent atoms of ring $A_1$, together with the atoms to which they are attached, form an optionally substituted 5- to 10-membered monocyclic or bicyclic ring, said ring is selected from

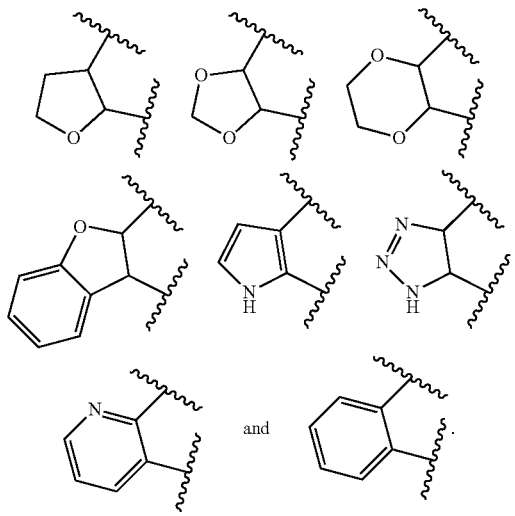

In some embodiments, at least one $R_2$, e.g. one or two $R_2$, is a moiety $R_3Y_1$-$Q_2$.

In a moiety $R_3Y_1$-$Q_2$, $Y_1$ is selected from O and S; e.g. $Y_1$ is O; $Q_2$ is a direct bond or C1-C3 alkylene, e.g. a direct bond or C1-C2 alkylene, or a direct bond and methylene. In some preferred embodiments, $Q_2$ is a direct bond. In some further preferred embodiments, $Y_1$ is O, i.e. the moiety is $R_3O$-$Q_2$. In some particularly preferred embodiments, $Y_1$ is O and $Q_2$ is methylene or a direct bond; more particularly, $Y_1$ is O and $Q_2$ is a direct bond, i.e. $R_3Y_1$-$Q_2$ is a moiety of formula $R_3O$.

The moiety $R_3$ is selected from H, C1-C6 alkyl, $R_8O$-$Q_6$, and $R_9R_{10}N$-$Q_7$. In some embodiments, $R_3$ is selected from H, C1-C6 alkyl, and $R_8O$-$Q_6$, e.g. from C1-C6 alkyl, and $R_8O$-$Q_6$. In some other embodiments, $R_3$ is selected from H and C1-C6 alkyl, e.g. from C1-C6 alkyl. In still other embodiments, $R_3$ is selected from C1-C6 alkyl, $R_8O$-$Q_6$, and $R_9R_{10}N$-$Q_7$.

When $R_3$ is C1-C6 alkyl, it more particularly may be C1-C4 alkyl, or C1-C3 alkyl, such as methyl or isopropyl (including any fluorinated analogue, e.g. difluoromethyl and trifluoromethyl).

When $R_3$ is $R_8O$-$Q_6$, $R_8$ is selected from H and C1-C6 alkyl; and $Q_6$ is C1-C3 alkylene, e.g. $Q_6$ is C2-C3 alkylene, such as $CH_2CH_2$, $CH(CH_3)CH_2$, or $CH_2CH_2CH_2$.

In some embodiments, $R_8$ is selected from H and C1-C4 alkyl, or from H and C1-C3 alkyl, or from H, methyl and ethyl. In some embodiments, $R_8$ is selected from C1-C6 alkyl, e.g. from C1-C4 alkyl, or from C1-C3 alkyl, e.g. $R_8$ is ethyl.

In some embodiments, the moiety $R_8O$-$Q_6$ is $CH_3CH_2OC_2H_4$.

When $R_3$ is $R_9R_{10}N$-$Q_7$, $R_9$ and $R_{10}$ are independently selected from H and C1-C6 alkyl; or $R_9$ and $R_{10}$, together with the nitrogen atom to which they are both attached, form a 5- or 6-membered ring; and $Q_7$ is C1-C3 alkylene, e.g. $Q_7$ is C2-C3 alkylene, such as $CH_2CH_2$, $CH(CH_3)CH_2$, or $CH_2CH_2CH_2$.

In some embodiments, the moiety $R_9R_{10}N$ is a 5- or 6-membered ring, e.g. morpholino. In some particular embodiments, $R_9R_{10}N$-$Q_7$ is moiety

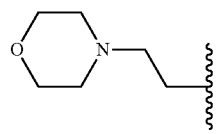

In some embodiments, at least one $R_2$, e.g. one $R_2$, is a moiety $R_4R_5N$-$Q_3$, wherein $R_4$ and $R_5$ are independently selected from H, C1-C6 alkyl, C3-C8 cycloalkyl and $R_{11}O$-$Q_8$; or $R_4$ and $R_5$, together with the nitrogen atom to which they are both attached, form a 5- or 6-membered ring, which ring is optionally substituted by one or more moieties selected from C1-C6 alkyl and $R_{12}O$-$Q_9$; and wherein $Q_3$ is selected from a direct bond, C1-C3 alkylene, and C(O).

In some embodiments, $R_4$ and $R_5$ are independently selected from H, C1-C6 alkyl, and C3-C8 cycloalkyl; or $R_4$ and $R_8$, together with the nitrogen atom to which they are both attached, form a 5- or 6-membered ring. In still further embodiments, $R_4$ and $R_5$ are independently selected from C1-C6 alkyl, C3-C8 cycloalkyl and $R_{10}O$-$Q_5$; or $R_4$ and $R_8$, together with the nitrogen atom to which they are both attached, form a 5- or 6-membered ring, which ring is optionally substituted by one or more moieties selected from C1-C6 alkyl and $R_{12}O$-$Q_9$.

In some embodiments, at least one of $R_4$ and $R_5$ is different from H.

In some embodiments, $R_4$ and $R_5$ are independently selected from H and C1-C6 alkyl; or $R_4$ and $R_5$, together with the nitrogen atom to which they are both attached, form a 5- or 6-membered ring. In some further embodiments, $R_4$ and $R_5$ are independently selected from H and C1-C6 alkyl. In still further embodiments, $R_4$ and $R_5$, together with the nitrogen atom to which they are both attached, form a 5- or 6-membered ring.

When $R_4$ and $R_5$ are independently selected from H and C1-C6 alkyl, they e.g. may be both H, or both may be C1-C6 alkyl, e.g. both may be C1-C4 alkyl, or both may be C1-C3 alkyl, e.g. both may be methyl or ethyl. For example, in some embodiments, when $R_4$ and $R_5$ are independently selected from H and C1-C6 alkyl, $NR_4R_5$ is selected from amino (i.e. $NH_2$), dimethylamino and diethylamino.

In some other embodiments, when $R_4$ and $R_5$ are independently selected from H and C1-C6 alkyl, $NR_4R_5$ is a moiety selected from

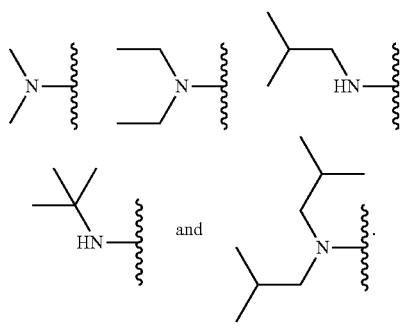

When $R_4$ and $R_5$, together with the nitrogen atom to which they are both attached, form a 5- or 6-membered ring, said ring e.g. may be a non-aromatic, e.g. saturated, ring optionally containing one or more further heteroatoms, e.g. optionally containing one further heteroatom.

In some embodiments, when $R_4$ and $R_8$, together with the nitrogen atom to which they are both attached, form a 5- or 6-membered ring, said ring is a saturated ring optionally containing one further heteroatom, e.g. the ring is pyrrolidinyl, piperidinyl or morpholino; or the ring is pyrrolidinyl or morpholino. In some embodiments, when $R_4$ and $R_5$, together with the nitrogen atom to which they are both attached, form a 5- or 6-membered ring, said ring is substituted by one or more, e.g. 1, 2 or 3, such as 1 or 2, substituents, selected from C1-C6 alkyl and $R_{12}O$-$Q_9$, e.g. from C1-C3 alkyl and $R_{12}O$-$Q_9$, such as from methyl and $R_{12}O$-$Q_9$.

In the moiety $R_{12}O$-$Q_9$, $R_{12}$ is selected from H and C1-C6 alkyl, e.g. from H and C1-C3 alkyl, e.g. $R_{12}$ is H or $CH_3$. In some embodiments, $R_{12}$ is selected from C1-C6 alkyl, e.g. from C1-C3 alkyl, e.g. $R_{12}$ is $CH_3$. The moiety $Q_9$ is a direct bond or C1-C3 alkylene, e.g. $Q_9$ is a direct bond or C1-C2 alkylene, or $Q_9$ is a direct bond or methylene. In some embodiments, $Q_9$ is C1-C3 alkylene, or C1-C2 alkylene, e.g. $Q_9$ is methylene. In some embodiments, $R_{12}O$-$Q_9$ is $CH_3OCH_2$.

In some particular embodiments, when $R_4$ and $R_5$, together with the nitrogen atom to which they are both attached, form a 5- or 6-membered ring, said ring is substituted by one or more, e.g. 1-3, substituents selected from C1-C3 alkoxy and C1-C3 alkyl, e.g. methoxy and methyl. For example, in some embodiments, when $R_4$ and $R_5$, together with the nitrogen atom to which they are both attached, form an optionally substituted 5- or 6-membered ring, $NR_4R_5$ is a moiety selected from

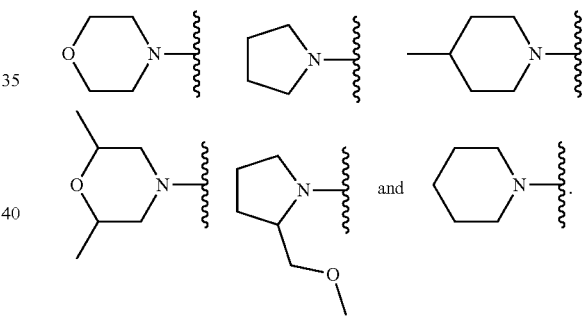

When $R_4$ or $R_5$ is C3-C8 cycloalkyl, said cycloalkyl e.g. may be C5-C8 cycloalkyl, or C6-C8 cycloalkyl, e.g. cyclooctyl. In some embodiments, when one of $R_4$ and $R_5$ is C3-C8 cycloalkyl, the other one is H or C1-C6 alkyl, e.g. H or C1-C3 alkyl, in particular H.

In some embodiments, at least one of $R_4$ and $R_5$ is a moiety $R_{11}O$-$Q_8$. In some embodiments, both R4 and R5 are $R_{11}O$-$Q_8$, i.e. R4R5N is a moiety of formula $(R_{11}O$-$Q_8)_2N$.

In $R_{11}O$-$Q_8$, $R_{11}$ is selected from H and C1-C6 alkyl; and $Q_8$ is C1-C3 alkylene, e.g. $Q_8$ is C2-C3 alkylene, such as $CH_2CH_2$, $CH(CH_3)CH_2$, or $CH_2CH_2CH_2$.

In some embodiments, $R_{11}$ is selected from H and C1-C4 alkyl, or from H and C1-C3 alkyl, or from H, methyl and ethyl. In some embodiments, $R_{11}$ is selected from C1-C6 alkyl, e.g. from C1-C4 alkyl, or from C1-C3 alkyl, e.g. $R_{11}$ is methyl.

In some embodiments, the moiety $R_{11}O$-$Q_5$ is $CH_3OC_2H_4$.

In the moiety $R_4R_5N$-$Q_3$, $Q_3$ is selected from a direct bond, C1-C3 alkylene, and C(O). In some embodiments, $Q_3$ is a direct bond or C1-C3 alkylene. In some other embodiments, $Q_3$ is C(O).

When $Q_3$ is C1-C3 alkylene, said alkylene more particularly may be C1-C2 alkylene. In some embodiments, when $Q_3$ is C1-C3 alkylene, said alkylene is selected from $CH_2$, $CH(CH_3)$, $CH(CH_2CH_3)$, $C(CH_3)_2$, and $CH_2CH(CH_3)$; e.g. from $CH_2$, $CH(CH_3)$, $C(CH_3)_2$; or from $CH_2$, and $CH(CH_3)$, in particular said alkylene is $CH_2$.

In some embodiments, $Q_3$ is selected from a direct bond, $CH_2$ and $C(O)$, in particular from a direct bond and $CH_2$. In some embodiments, $Q_3$ is a direct bond.

In some embodiments, at least one $R_2$, e.g. one $R_2$, is a moiety $R_6S(O)_2$-$Q_4$. In the moiety $R_6S(O)_2$-$Q_4$, $R_6$ is H or C1-C6 alkyl. In some embodiments, $R_6$ is H or C1-C4 alkyl. In some other embodiments, $R_6$ is H or C1-C3 alkyl. In still other embodiments, $R_6$ is H or methyl.

In some embodiments, $R_6$ is selected from C1-C6 alkyl, or from C1-C4 alkyl, or from C1-C3 alkyl. In some embodiments, $R_6$ is methyl.

In the moiety $R_6S(O)_2$-$Q_4$, $Q_4$ is a direct bond, C1-C3 alkylene, or $NR_{17}$. In some embodiments, $Q_4$ is a direct bond or C1-C3 alkylene, e.g. a direct bond or C1-C2 alkylene, or a direct bond or $CH_2$, in particular a direct bond. In some other embodiments, $Q_4$ is $NR_{17}$. In the moiety $NR_{17}$, $R_{17}$ is H or C1-C3 alkyl, e.g. H or methyl, in particular H. In some embodiments, $Q_4$ is a direct bond or NH. In some embodiments, the moiety $R_6S(O)_2$-$Q_4$ is selected from $CH_3S(O)_2$ and $CH_3S(O)NH$.

In some embodiments, at least one $R_2$, e.g. one $R_2$, is a moiety of formula

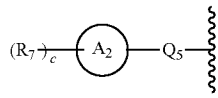

as defined herein.

In the above formula, c represents an integer of from 0 to 3. In some embodiments, c represents an integer of from 0 to 2, e.g. c is 0 or 1. In some embodiments, c is 0. In some other embodiments, c is 1.

The ring $A_2$ is selected from 5- or 6-membered aryl or heteroaryl, i.e. ring $A_2$ is selected from phenyl and 5- or 6-membered heteroaryl. In some embodiments, ring $A_2$ is selected from phenyl and 5-membered heteroaryl. In some other embodiments, ring $A_2$ is selected from phenyl and 6-membered heteroaryl. In still other embodiments, ring $A_2$ is selected from 5- or 6-membered heteroaryl, e.g. ring $A_2$ is 6-membered heteroaryl. When ring $A_2$ is heteroaryl, said heteroaryl e.g. may comprise 1, 2, 3 or 4 heteroatoms, e.g. 1-3, or 1 or 2 heteroatoms, or 1 heteroatom, each selected from N, O and S. When ring $A_2$ is 6-membered heteroaryl, it e.g. may be pyridyl. In some particular embodiments, ring $A_2$ is phenyl.

The moiety $Q_5$ is selected from a direct bond, C1-C3 alkylene, $S(O)_2NR_{18}$, $Q_{15}$-$Y_3$-$Q_{16}$, and

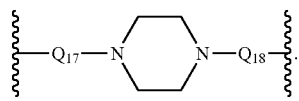

In some embodiments, $Q_5$ is selected from a direct bond, C1-C3 alkylene, $S(O)_2NR_{18}$, and $Q_{15}$-$Y_3$-$Q_{16}$; e.g. $Q_5$ is selected from a direct bond, $S(O)_2NR_{18}$, and $Q_{15}$-$Y_3$-$Q_{16}$; e.g. from a direct bond and $Q_{15}$-$Y_3$-$Q_{16}$. In some embodiments, $Q_5$ is selected from a direct bond and C1-C3 alkylene. In some preferred embodiments, $Q_5$ is a direct bond.

In some further embodiments, $Q_5$ is selected from a direct bond, $S(O)_2NR_{18}$, $Q_{15}$-$Y_3$-$Q_{16}$, and

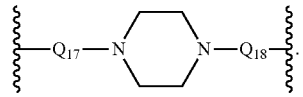

In some embodiments, $Q_5$ is

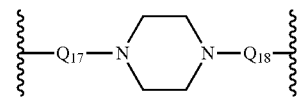

wherein $Q_{17}$ and $Q_{18}$ are as defined herein.

When $Q_5$ is e.g. C1-C3 alkylene, said alkylene e.g. may be methylene, optionally substituted by 1 or 2 methyl groups, or said alkylene may be $CH_2$.

In the moiety $S(O)_2NR_{18}$, $R_{18}$ is selected from H and C1-C3 alkyl, e.g. from H and methyl, in particular $R_{18}$ may be H. The moiety $S(O)_2NR_{18}$ may be attached to ring $A_2$ by a bond either to the S or the N. In some embodiments, the moiety $S(O)_2NR_{18}$ is attached to ring $A_2$ by a bond to the S.

In the moiety $Q_{15}$-$Y_3$-$Q_{16}$, $Q_{15}$ and $Q_{16}$ are independently selected from a direct bond and C1-C3 alkylene; and $Y_3$ is selected from O and $NR_{23}$. When any of $Q_{15}$ and $Q_{16}$ is C1-C3 alkylene, said alkylene e.g. may be methylene, optionally substituted by 1 or 2 methyl groups, or said alkylene may be $CH_2$. In some embodiments, when any of $Q_{15}$ and $Q_{16}$ is C1-C3 alkylene, said alkylene is selected from $CH(CH_3)$ and $CH_2$. In some embodiments, $Q_{16}$ is a direct bond and $Q_{15}$ is C1-C3 alkylene as defined herein above, i.e. $Q_{15}$-$Y_3$-$Q_{16}$ is moiety of formula $Q_{15}$-$Y_3$. In some of those embodiments, $Q_{15}$ is $CH(CH_3)$ or $CH_2$.

In the moiety $Q_{15}$-$Y_3$-$Q_{16}$, $Y_3$ is selected from O and $NR_{23}$. In some embodiments, $Y_3$ is O. In some other embodiments, $Y_3$ is $NR_{23}$. When $Y_3$ is $NR_{23}$, $R_{23}$ is H or C1-C3 alkyl, e.g. $R_{23}$ is H or $CH_3$, or $R_{23}$ is H. In some embodiments, $Y_3$ is selected from O and NH.

The moiety $Q_{15}$-$Y_3$-$Q_{16}$ may be attached to ring $A_2$ at either the $Q_{15}$ side or the $Q_{16}$ side. In some embodiments, $Q_{16}$ is a direct bond, and $Q_{15}$ is C1-C15 alkylene. In some embodiments, $Q_{16}$ is a direct bond, $Q_{15}$ is C1-C13 alkylene, and the moiety $Q_{15}$-$Y_3$ is attached to ring $A_2$ at the $Q_{15}$ side. In some embodiments, $Q_{15}$-$Y_3$-$Q_{16}$ is $CH_2O$ attached to ring $A_2$ via the methylene group. In some further embodiments, $Q_{15}$-$Y_3$-$Q_{16}$ is selected from

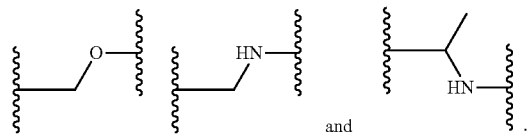

When $Q_5$ is a moiety

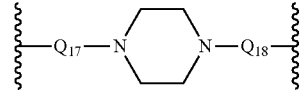

$Q_{17}$ and $Q_{18}$ are independently selected from a direct bond and C1-C3 alkylene. In some embodiments, one of $Q_{17}$ and $Q_{18}$ is a direct bond and the other one is selected from a direct bond and C1-C3 alkylene. In some embodiments, both $Q_{17}$ and $Q_{18}$ are a direct bond.

When either of $Q_{17}$ and $Q_{18}$ is C1-C3 alkylene, said alkylene e.g. may be methylene, optionally substituted by 1 or 2 methyl groups, e.g. said alkylene may be $CH_2$.

In some embodiments, the moiety

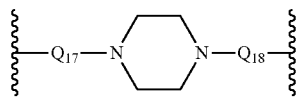

is selected from

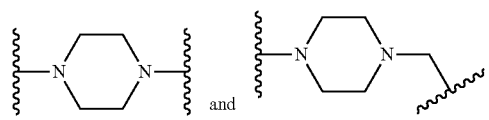

In a moiety of formula

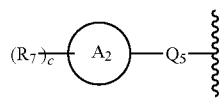

ring $A_2$ may be substituted by one or more moieties $R_7$, which moieties are independently selected from C1-C6 alkyl, halogen, $R_{13}O-Q_{10}$, $R_{14}R_{15}N-Q_{11}$, and $R_{16}S(O)_2-Q_{12}$, and when ring A2 is substituted by at least two moieties $R_7$, attached to adjacent atoms of ring $A_2$, said moieties, together with the atoms to which they are attached, may form a 5- or 6-membered ring.

In some embodiments, each $R_7$ is selected from C1-C6 alkyl, halogen, $R_{13}O-Q_{10}$, and $R_{14}R_{15}N-Q_{11}$, and when ring $A_2$ is substituted by at least two moieties $R_7$, attached to adjacent atoms of ring $A_2$, said moieties, together with the atoms to which they are attached, may form a 5- or 6-membered ring. In some other embodiments, each $R_7$ is selected from C1-C6 alkyl, halogen, $R_{13}O-Q_{10}$, $R_{14}R_{15}N-Q_{11}$, and $R_{16}S(O)_2-Q_{12}$.

In some embodiments, each $R_7$ is selected from halogen, $R_{13}O-Q_{10}$, and $R_{14}R_{15}N-Q_{11}$. In some embodiments, each $R_7$ is selected from halogen and $R_{13}O-Q_{10}$. In some further embodiments, each $R_7$ is selected from $R_{13}O-Q_{10}$. In some still further embodiments, each $R_7$ is selected from halogen and $R_{14}R_{15}N-Q_{11}$, e.g. each $R_7$ is selected from $R_{14}R_{15}N-Q_{11}$.

In some embodiments, each $R_7$ is selected from halogen, $R_{13}O-Q_{10}$, and $R_{14}R_{15}N-Q_{11}$, and when ring $A_2$ is substituted by at least two moieties $R_7$, attached to adjacent atoms of ring $A_2$, said moieties, together with the atoms to which they are attached, may form a 5- or 6-membered ring.

In some embodiments, each $R_7$ is selected from halogen and $R_{13}O-Q_{10}$, or when ring $A_2$ is substituted by at least two moieties $R_7$, attached to adjacent atoms of ring $A_2$, said moieties, together with the atoms to which they are attached, may form a 5- or 6-membered ring.

When $R_7$ is halogen, it e.g. may be F or Cl, in particular F.

In the moiety $R_{13}O-Q_{10}$, $R_{13}$ is H or C1-C6 alkyl, in particular $R_{13}$ is H or C1-C3 alkyl, e.g. $R_{13}$ is H or methyl. In some embodiments, $R_{13}$ is H. In some other embodiments, $R_{13}$ is as defined herein, but is not H.

In the moiety $R_{13}O-Q_{10}$, $Q_{10}$ is a direct bond or C1-C3 alkylene. When $Q_{10}$ is C1-C3 alkylene, said alkylene more particularly may be methylene, optionally substituted by 1 or 2 methyl groups. In some embodiments, when $Q_{10}$ is C1-C3 alkylene, said alkylene is $CH(CH_3)$ or $CH_2$, in particular $CH_2$. In some embodiments, $Q_{10}$ is a direct bond or $CH_2$. In some preferred embodiments, $Q_{10}$ is a direct bond.

When $R_7$ is $R_{14}R_{15}N-Q_{11}$, $R_{14}$ and $R_{15}$ are independently selected from H and C1-C6 alkyl, e.g. H and C1-C3 alkyl; or $R_{14}$ and $R_{15}$, together with the nitrogen atom to which they are both attached, form a 5- or 6-membered ring, e.g. a saturated ring optionally containing one further heteroatom, e.g. piperidinyl; and $Q_{11}$ is a direct bond or C1-C3 alkylene.

$Q_{11}$ is a direct bond or C1-C3 alkylene. When $Q_{11}$ is C1-C3 alkylene, said alkylene more particularly may be methylene, optionally substituted by 1 or 2 methyl groups. In some embodiments, when $Q_{11}$ is C1-C3 alkylene, said alkylene is $CH(CH_3)$ or $CH_2$, in particular $CH_2$. In some embodiments, $Q_{11}$ is a direct bond or $CH_2$.

In some embodiments, two $R_7$ are attached to adjacent atoms of ring $A_2$ and form, together with the atoms to which they are attached a 5- or 6-membered ring. When two $R_7$ attached to adjacent atoms of ring $A_2$, together with the atoms to which they are attached, form a 5- or 6-membered ring, said ring may be carbocyclic or heterocyclic, and may be aromatic or non-aromatic. In some embodiments, said ring is non-aromatic, e.g. saturated. In some embodiments, the ring is heterocyclic. In some embodiment, the ring is a saturated heterocycle, e.g. a saturated heterocycle containing one or two heteroatoms, e.g. one or two oxygen atoms in the ring, for example the ring is tetrahydrofuran, 1,3-dioxolane, tetrahydro-2H-pyran, 1,3-dioxane, or 1,4-dioxane ring. In some embodiments, the ring is tetrahydrofuran or 1,4-dioxane, e.g. the ring is selected from

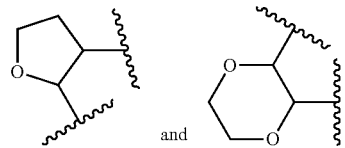 [SMILES: *C1CCOC1* ; *C1OCCOC1*]

In some embodiments, $R_1$ is $R_{26}R_{27}N-Q_{19}$. In those embodiments, the compound of formula (I) is as represented by formula (IDa) or (IDb)

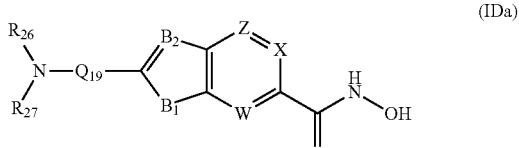

(IDa)

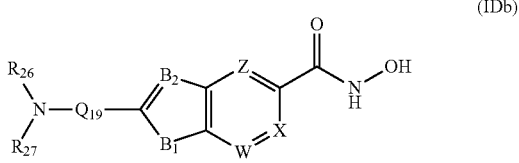

(IDb)

wherein $R_{26}$, $R_{27}$, $Q_{19}$, $B_1$, $B_2$, W, X and Z are as defined herein, which compound may collectively be referred to as a compound of formula (ID).

In a compound of formula (ID), $Q_{19}$ is a direct bond or C1-C3 alkylene. When $Q_{19}$ is C1-C3 alkylene, said alkylene e.g. may be methylene, optionally substituted by 1 or 2 methyl groups, e.g. said alkylene may be $CH(CH_3)$ or $CH_2$, in particular $CH_2$. In some embodiments, $Q_{19}$ is a direct bond or $CH_2$. In some embodiments, $Q_{19}$ is a direct bond.

The moieties $R_{26}$ and $R_{27}$ are independently selected from H, C1-C6 alkyl and C3-C8 cycloalkyl; or $R_{26}$ and $R_{27}$, together with the nitrogen atom to which they are both attached, form a 5- or 6-membered ring optionally substituted by one or more moieties $R_{28}$, as defined herein.

In some embodiments, when $R_{26}$ and $R_{27}$ are independently selected from H and C1-C6 alkyl, $R_{26}$ and $R_{27}$ more particularly are both selected from H and C1-C5 alkyl, e.g. from H and C1-C4 alkyl. In some other embodiments, when $R_{26}$ and $R_{27}$ are independently selected from H and C1-C6 alkyl, $R_{26}$ and $R_{27}$ more particularly are both selected from C1-C6 alkyl, e.g. both are selected from C1-C5 alkyl, or from C1-C4 alkyl.

In some embodiments, when one of $R_{26}$ and $R_{27}$ is C3-C8 cycloalkyl, the other one is H.

In some embodiments, $R_{26}$ and $R_{27}$ are independently selected from H and C1-C6 alkyl; or $R_{26}$ and $R_{27}$, together with the nitrogen atom to which they are both attached, form a 5- or 6-membered ring, optionally substituted by one or more moieties $R_{28}$, as defined herein.

In some embodiments, $R_{26}$ and $R_{27}$ are independently selected from H, C1-C6 alkyl and C3-C8 cycloalkyl, e.g. from H, C1-C5 alkyl and C5-C8 cycloalkyl, or from H, C1-C4 alkyl and C6-C8 cycloalkyl. In some embodiments, $R_{26}$ is selected from H and C1-C6 alkyl, e.g. from H and C1-C4 alkyl, $R_{27}$ is selected from H, C1-C6 alkyl or C3-C8 cycloalkyl, or $R_{26}$ and $R_{27}$, together with the nitrogen atom to which they are both attached, form a 5- or 6-membered ring optionally substituted by one or more moieties $R_{28}$, as defined herein.

In some embodiments, $R_{26}$ and $R_{27}$ are independently selected from H and C1-C6 alkyl, e.g. from H and C1-C4 alkyl, or from H and C1-C3 alkyl. In some embodiments, when $R_{26}$ and $R_{27}$ are independently selected from H and C1-C6 alkyl, said moieties are not H; e.g. $R_{26}$ and $R_{27}$ are independently selected from C1-C4 alkyl, or from C1-C3 alkyl, e.g. $R_{26}$ and $R_{27}$ are both ethyl.

In some further embodiments, $R_{26}$ and $R_{27}$ are selected from C1-C6 alkyl; or $R_{26}$ is H and $R_{27}$ is selected from C3-C8 cycloalkyl; or $R_{26}$ and $R_{27}$, together with the nitrogen atom to which they are both attached, form a 5- or 6-membered ring optionally substituted by one or more moieties $R_{28}$, as defined herein.

In some further embodiments, $R_{26}$ and $R_{27}$ are selected from C1-C4 alkyl; or $R_{26}$ is H and $R_{27}$ is selected from C5-C8 cycloalkyl; or $R_{26}$ and $R_{27}$, together with the nitrogen atom to which they are both attached, form a 5- or 6-membered ring optionally substituted by one or more moieties $R_{28}$, as defined herein.

In some further embodiments, $R_{26}$ and $R_{27}$ are selected from C2-C4 alkyl; or $R_{26}$ is H and $R_{27}$ is selected from C6-C8 cycloalkyl; or $R_{26}$ and $R_{27}$, together with the nitrogen atom to which they are both attached, form a 5- or 6-membered ring optionally substituted by one or more moieties $R_{28}$, as defined herein.

In some embodiments, $R_{26}$ and $R_{27}$, together with the nitrogen atom to which they are both attached, form a 5- or 6-membered ring optionally substituted by one or more moieties $R_{28}$, as defined herein.

When $R_{26}$ and $R_{27}$, together with the nitrogen atom to which they are both attached, form a 5- or 6-membered ring, said ring may optionally contain one or more further heteroatoms, e.g. one or more further heteroatoms selected from N, O and S, e.g. from N and O, or N, and said ring may be heteroaromatic or non-aromatic and saturated or unsaturated. In some embodiments, the ring is non-aromatic. In some embodiments, the ring is saturated. In some embodiments, the ring is saturated and contains no further heteroatom or only one further heteroatom, e.g. one further heteroatom selected from O and N, in particular one further N. In some embodiments, the ring is piperidinyl or piperazinyl, e.g. the ring is piperidinyl.

The ring formed by $R_{26}$, $R_{27}$ and the nitrogen atom to which they are attached is optionally substituted by one or more moieties $R_{28}$, e.g. one or two moieties $R_{28}$, each $R_{28}$ being independently selected from $R_{29}OC(O)NR_{30}$ and

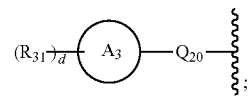

or two moieties $R_{28}$, attached to adjacent atoms of the ring, forming together with the atoms to which they are attached a 5- or 6-membered ring. In some of these embodiments, the ring formed by $R_{26}$, $R_{27}$ and the nitrogen atom to which they are attached, is substituted by one moiety $R_{28}$, selected from $R_{29}OC(O)NR_{30}$ and

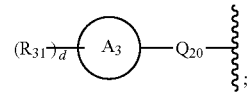

or by two moieties $R_{28}$, attached to adjacent atoms of the ring and forming, together with the atoms to which they are attached, a 5- or 6-membered ring.

In some embodiments, the ring formed by $R_{26}$, $R_{27}$ and the nitrogen atom to which they are attached, is substituted by one moiety $R_{28}$, which is

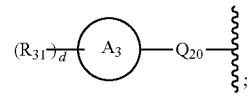

or by two moieties $R_{28}$, attached to adjacent atoms of the ring and forming, together with the atoms to which they are attached, a 5- or 6-membered ring.

In some embodiments, the ring formed by $R_{26}$, $R_{27}$ and the nitrogen atom to which they are attached, is substituted by one moiety $R_{28}$, which is

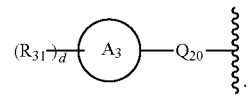

In some embodiments, the ring formed by $R_{26}$, $R_{27}$ and the nitrogen atom to which they are attached, is substituted by two moieties $R_{28}$, attached to adjacent atoms of the ring and forming, together with the atoms to which they are attached, a 5- or 6-membered ring.

In some other embodiments, the ring formed by $R_{26}$, $R_{27}$ and the nitrogen atom to which they are attached, is substituted by one moiety $R_{28}$, which is $R_{29}OC(O)NR_{30}$; or by two moieties $R_{28}$, attached to adjacent atoms of the ring and forming, together with the atoms to which they are attached, a 5- or 6-membered ring.

In still other embodiments, the ring formed by $R_{26}$, $R_{27}$ and the nitrogen atom to which they are attached, is substituted by one moiety $R_{28}$, which is $R_{29}OC(O)NR_{30}$.

When two moieties $R_{28}$ are attached to adjacent atoms of the ring and form, together with the atoms to which they are attached, a 5- or 6-membered ring, said ring is (hetero) aromatic (i.e. heteroaromatic or aromatic) or non-aromatic. In some embodiments, the ring is (hetero)aromatic. In some embodiments, the ring is 6-membered, e.g. 6-membered and (hetero)aromatic. In some embodiments, the ring is benzene.

In the moiety $R_{29}OC(O)NR_{30}$, $R_{29}$ and $R_{30}$ are both independently selected from H and C1-C6 alkyl. In some embodiments, $R_{29}$ is C1-C6 alkyl, e.g. C1-C5 alkyl, or C1-C4 alkyl, e.g. tert-butyl. In some other embodiments, $R_{29}$ is C2-C6 alkyl, e.g. C3-C6 alkyl, or C3-C5 alkyl. In some embodiments, $R_{30}$ is H or C1-C3 alkyl, e.g. H or methyl, or $R_{30}$ is H. In some embodiments, $R_{29}$ is an alkyl group as defined herein above, and $R_{30}$ is H; e.g. $R_{29}$ is tert-butyl and $R_{30}$ is H.

In the moiety

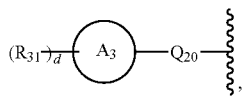

$R_{31}$ is C1-C6 alkyl or halogen;
ring $A_3$ is 5- to 10-membered aryl or heteroaryl;
$Q_{20}$ is selected from a direct bond, C1-C3 alkylene and $Q_{21}$-$NR_{32}$-$Q_{22}$; and
d is an integer of from 0 to 3.

In some embodiments, $R_{31}$ is C1-C6 alkyl or halogen; ring $A_3$ is 5- to 10-membered aryl or heteroaryl; $Q_{20}$ is a direct bond or C1-C3 alkylene; and d is an integer of from 0 to 3.

In some embodiments, $R_{31}$ is C1-C4 alkyl or halogen; or $R_{31}$ is C1-C3 alkyl or halogen, e.g. $R_{31}$ is halogen. In some embodiments, when $R_{31}$ is halogen, it more particularly is F. The number of substituents $R_{31}$ attached to ring $A_3$, denoted by d, is from 0 to 3, e.g. from 0 to 2, in particular d is 0 or 1. In some embodiments, d is 0. In some other embodiments, d is 1.

Ring $A_3$ is a 5- to 10-membered aryl or heteroaryl. In some embodiments, ring $A_3$ is phenyl or 5- or 6-membered heteroaryl. In some embodiments, ring $A_3$ is phenyl.

The moiety $Q_{20}$ is selected from a direct bond, C1-C3 alkylene and $Q_{21}$-$NR_{32}$-$Q_{22}$. In some embodiments, $Q_{20}$ is a direct bond or C1-C3 alkylene. In some other embodiments $Q_{20}$ is C1-C3 alkylene or $Q_{21}$-$NR_{32}$-$Q_{22}$. In still other embodiments, $Q_{20}$ is C1-C3 alkylene. In still other embodiments, $Q_{20}$ is $Q_{21}$-$NR_{32}$-$Q_{22}$. In still further embodiments, $Q_{20}$ is a direct bond.

When $Q_{20}$ is C1-C3 alkylene, said alkylene e.g. may be methylene, optionally substituted by one or two methyl groups, e.g. said alkylene may be $CH(CH_3)$ or $CH_2$, in particular $CH_2$.

In the moiety $Q_{21}$-$NR_{32}$-$Q_{22}$, $Q_{21}$ and $Q_{22}$ are independently selected from a direct bond and C1-C3 alkylene.

When either of $Q_{21}$ and $Q_{22}$ is C1-C3 alkylene, said alkylene e.g. may be methylene, optionally substituted by one or two methyl groups, e.g. said alkylene may be $CH(CH_3)$ or $CH_2$, in particular $CH_2$. In some embodiments, both $Q_{21}$ and $Q_{22}$ are selected from C1-C3 alkylene, e.g. both $Q_{21}$ and $Q_{22}$ are methylene, optionally substituted by one or two methyl groups, e.g. $CH(CH_3)$ or $CH_2$, in particular both $Q_{21}$ and $Q_{22}$ are $CH_2$.

The moiety $R_{32}$, present in $Q_{21}$-$NR_{32}$-$Q_{22}$, is selected from H and C1-C6 alkyl, in particular from H and C1-C3 alkyl, or from H and $CH_3$. In some embodiments, $R_{32}$ is H.

In some embodiments, in $Q_{21}$-$NR_{32}$-$Q_{22}$, $Q_{21}$ and $Q_{22}$ are both C1-C3 alkylene as defined herein above, and $R_{32}$ is $CH_3$ or H, in particular H. In some embodiments, $Q_{21}$-$NR_{32}$-$Q_{22}$ is $CH_2NHCH_2$.

In some particular embodiments, $Q_{20}$ is selected from a direct bond, $CH_2$, and $CH_2NHCH_2$; e.g. $Q_{20}$ is $CH_2$ or $CH_2NHCH_2$.

In some particular embodiments of a compound of formula (ID), $R_{26}$ and $R_{27}$ are independently selected from C1-C6 alkyl; or $R_{26}$ and $R_{27}$, together with the nitrogen atom to which they are both attached, form a 5- or 6-membered ring optionally substituted by one $R_{28}$, selected from $R_{29}OC(O)NR_{30}$, and

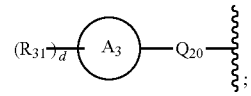

or by two $R_{28}$ attached to adjacent atoms of the ring, and forming together with the atoms to which they are attached, a 6-membered ring;
$R_{29}$ is C1-C6 alkyl;
$R_{30}$ is H;
$R_{31}$ is C1-C6 alkyl or halogen;
ring $A_3$ is phenyl,
$Q_{19}$ is a direct bond or $CH_2$;
$Q_{20}$ is a direct bond or $CH_2$;
d is 0 or 1.

In some particular embodiments of a compound of formula (ID),
$R_{26}$ and $R_{27}$, together with the nitrogen atom to which they are both attached, form a 5- or 6-membered ring optionally substituted by
one $R_{28}$; selected from $R_{29}OC(O)NR_{30}$, and

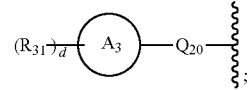

or by two $R_{28}$ attached to adjacent atoms of the ring, and forming together with the atoms to which they are attached, a 6-membered ring;
$R_{29}$ is C1-C6 alkyl;
$R_{30}$ is H;
$R_{31}$ is C1-C6 alkyl or halogen;
ring $A_3$ is phenyl,
$Q_{19}$ is a direct bond or $CH_2$;
$Q_{20}$ is a direct bond or $CH_2$;
d is 0 or 1.

In some further embodiments, of a compound of formula (I), $R_1$ is (iii) halogen, e.g. $R_1$ is Cl, Br or I, or $R_1$ is Cl or Br; in particular $R_1$ is Br.

In still further embodiments of a compound of formula (I), $R_1$ is hydroxy-C1-C6 alkyl, e.g. $R_1$ is hydroxy-C1-C4 alkyl. In some embodiments, when $R_1$ is hydroxy-C1-C6 alkyl, $R_1$ more particularly is a moiety of formula

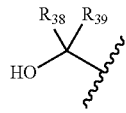

wherein $R_{38}$ is H or an alkyl radical of formula $C_pH_{2p-1}$; $R_{39}$ is H or an alkyl radical of formula $C_qH_{2q-1}$; and p+q is an integer of from 2 to 5, e.g. an integer of from 2 to 4, or an integer of from 2 to 3.

In some embodiments, $R_{38}$ is an alkyl radical of formula $C_pH_{2p-1}$; $R_{39}$ is an alkyl radical of formula $C_qH_{2q-1}$; and p+q is an integer of from 2 to 5, e.g. an integer of from 2 to 4, or an integer of from 2 to 3. In still other embodiments $R_{38}$ and $R_{39}$ are independently selected from H and $CH_3$, e.g. both are H or both are $CH_3$. In some other embodiments, $R_{38}$ and $R_{39}$ are both H.

In a compound of formula (I), $B_1$ is O, S or $NR_{33}$; and $B_2$ is N or $CR_{34}$, wherein $R_{33}$ is H, or C1-C3 alkyl; and $R_{34}$ is H, C1-C3 alkyl or halogen.

In some embodiments, $B_1$ is O or S. In some other embodiments, $B_1$ is O or $NR_{33}$. In some other embodiments, $B_1$ is S or $NR_{33}$.

In still other embodiments, $B_1$ is O. In other embodiments, $B_1$ is S. In some other embodiments, $B_1$ is $NR_{33}$.

In some embodiments of a compound of formula (I), $B_2$ is N, i.e. the compound is as represented by formula (IEa) or (IEb)

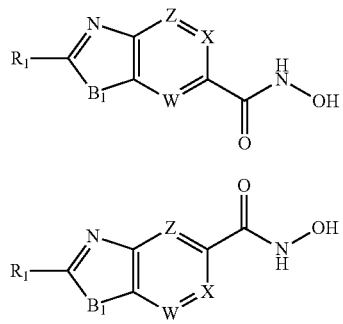

wherein $R_1$, $B_1$, W, X and Z are as defined herein, which compound may collectively be referred to as a compound of formula (IE).

In some embodiments of a compound of formula (IE), $B_1$ is O or S. In some other embodiments of a compound of formula (IE), $B_1$ is O or $NR_{33}$. In still other embodiments, $B_1$ is S or $NR_{33}$. In still other embodiments, $B_1$ is O. In other embodiments, $B_1$ is S. In some other embodiments of a compound of formula (IE), $B_1$ is $NR_{33}$.

In some embodiments, $B_2$ is $CR_{34}$, i.e. the compound of formula (I) is as represented by formula (IFa) or (IFb)

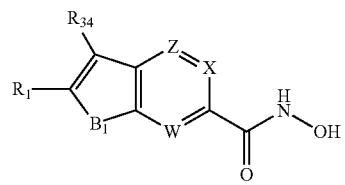

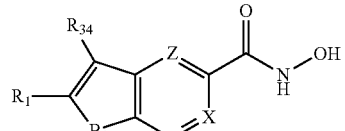

wherein $R_1$, $R_{34}$, $B_1$, W, X and Z are as defined herein, which may collectively be referred to as a compound of formula (IF).

In some embodiments of a compound of formula (IF), $B_1$ is O or S. In some other embodiments, $B_1$ is O or $NR_{33}$. In some other embodiments, $B_1$ is S or $NR_{33}$. In still other embodiments, $B_1$ is O. In other embodiments, $B_1$ is S. In some other embodiments of a compound of formula (IF), $B_1$ is $NR_{33}$.

When $B_1$ is $NR_{33}$, the moiety $R_{33}$ is H or C1-C3 alkyl. In some embodiments, $R_{33}$ is H or methyl. In some particular embodiments, $R_{33}$ is H. In some other embodiments, $R_{33}$ is C1-C3 alkyl, e.g. $R_{33}$ is methyl.

When $B_2$ is $CR_{34}$, the moiety $R_{34}$ is H, C1-C3 alkyl or halogen. In some embodiments, $R_{34}$ is H or C1-C3 alkyl, or $R_{34}$ is H. In some embodiments, $R_{34}$ is H or halogen, e.g. $R_{34}$ is halogen. In still other embodiments, $R_{34}$ is halogen or C1-C3 alkyl. When $R_{34}$ is C1-C3 alkyl, it more particularly may be methyl. When $R_{34}$ is halogen, it e.g. may be F, Cl or Br, in particular Cl.

It goes without saying that a compound of the invention may be part of more than one of the above mentioned embodiments, as far as these are not mutually incompatible of exclusive. Thus, for example, in some embodiments, a compound of formula (IA) also is a compound of formula (IE). In some other embodiments, a compound of formula (IA) also is a compound of formula (IF). Likewise, in some embodiments, a compound of formula (ID) also is a compound of formula (IE). In some other embodiments, a compound of formula (IA) also is a compound of formula (IF).

In some embodiments of a compound of formula (IA) which also is a compound of formula (IE), e.g. in some embodiments wherein $B_1$ is $NR_{33}$, b is not 0.

In a compound of formula (I), W is N or $CR_{35}$; X is N or $CR_{36}$; and Z is N or $CR_{37}$. In some embodiments, at most two of W, X and Z are N. In some embodiments, at most one of W, X and Z is N. In some embodiments, W is $CR_{35}$; X is $CR_{36}$; and Z is $CR_{37}$.

In some embodiments, two of W, X and Z are N, e.g. W and X are N, and Z is $CR_{37}$.

In some embodiments, W is N. In some of these embodiments, X is $CR_{36}$; and Z is $CR_{37}$. In some other embodiments, X is N. In some of these embodiments, W is $CR_{35}$; and Z is $CR_{37}$. In some other embodiments, Z is N. In some of these embodiments, W is $CR_{35}$; and X is $CR_{36}$.

In some other embodiments, W is $CR_{35}$. In some of these embodiments, X is $CR_{36}$; and Z is N or $CR_{37}$. In some others of these embodiments, X is N or $CR_{36}$; and Z is $CR_{37}$. In still others of these embodiments, X and Z are both N.

In some other embodiments, X is $CR_{36}$. In some of these embodiments, W is $CR_{35}$; and Z is N or $CR_{37}$. In some others of these embodiments, W is N or $CR_{35}$; and Z is $CR_{37}$. In still others of these embodiments, W and Z are both N.

In some other embodiments, Z is $CR_{36}$. In some of these embodiments, W is $CR_{35}$; and X is N or $CR_{36}$. In some others of these embodiments, W is N or $CR_{35}$; and X is $CR_{36}$. In still others of these embodiments, W and X are both N.

In a compound of formula (I), each of $R_{35}$, $R_{36}$ and $R_{37}$, when present, is independently selected from H and F. In some embodiments, at least one of $R_{35}$, $R_{36}$ and $R_{37}$, when present, is H. In some embodiments, at least two of $R_{35}$, $R_{36}$ and $R_{37}$, when present, are H. In some embodiments, any $R_{35}$, $R_{36}$ and $R_{37}$, when present, is H.

In some embodiments, the compound of formula (I) is as represented by formula (IGa) or (IGb)

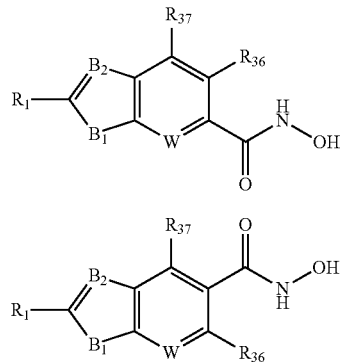

wherein $R_1$, $R_{36}$, $R_{37}$, $B_1$, $B_2$, and W are as defined herein, e.g. $R_{36}$ and $R_{37}$ are H, which compound may collectively be referred to as a compound of formula (IG).

In some embodiments of a compound of formula (IG), the compound also is a compound of formula (IA), in particular of formula (IB), or formula (IC). In some other embodiments of a compound of formula (IG), the compound also is a compound of formula (ID).

In some embodiments, the compound of formula (I) is as represented by formula (IHa) or (IHb)

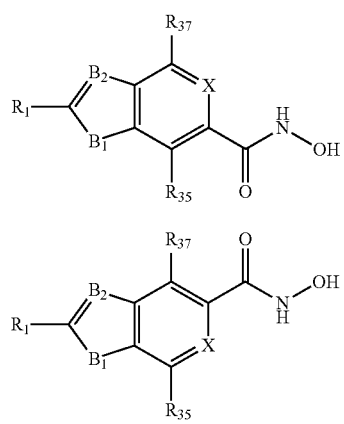

wherein $R_1$, $R_{35}$, $R_{37}$, $B_1$, $B_2$, and X are as defined herein, e.g. $R_{35}$ and $R_{37}$ are H, which may collectively be referred to as a compound of formula (IH).

In some embodiments of a compound of formula (IH), the compound also is a compound of formula (IA), in particular of formula (IB), or formula (IC). In some other embodiments of a compound of formula (IH), the compound also is a compound of formula (ID).

In other embodiments, the compound of formula (I) is as represented by formula (IIa) or (IIb)

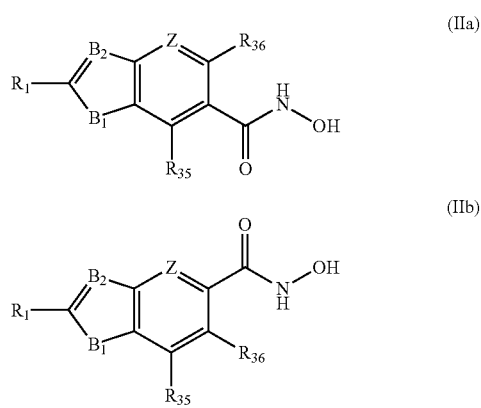

wherein $R_1$, $R_{35}$, $R_{36}$, $B_1$, $B_2$, and Z are as defined herein, e.g. $R_{35}$ and $R_{36}$ are H, which may collectively be referred to as a compound of formula (II).

In some embodiments of a compound of formula (II), the compound also is a compound of formula (IA), in particular of formula (IB), or formula (IC). In some other embodiments of a compound of formula (II), the compound also is a compound of formula (ID).

In other embodiments, the compound of formula (I) is represented by formula (IJa) or (IJb)

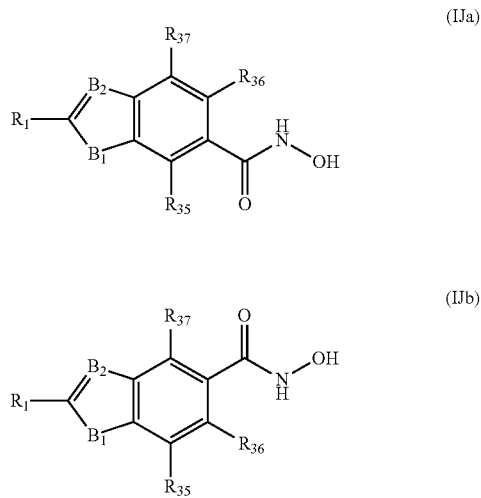

wherein $R_1$, $R_{35}$, $R_{36}$, $R_{37}$, $B_1$, and $B_2$ are as defined herein, e.g. $R_{35}$, $R_{36}$ and $R_{37}$ are H, which compound may collectively be referred to as a compound of formula (IJ).

In some embodiments, a compound of formula (IA) is also a compound of formula (IJ), i.e. a compound as represented by formula (IKa) or (IKb)

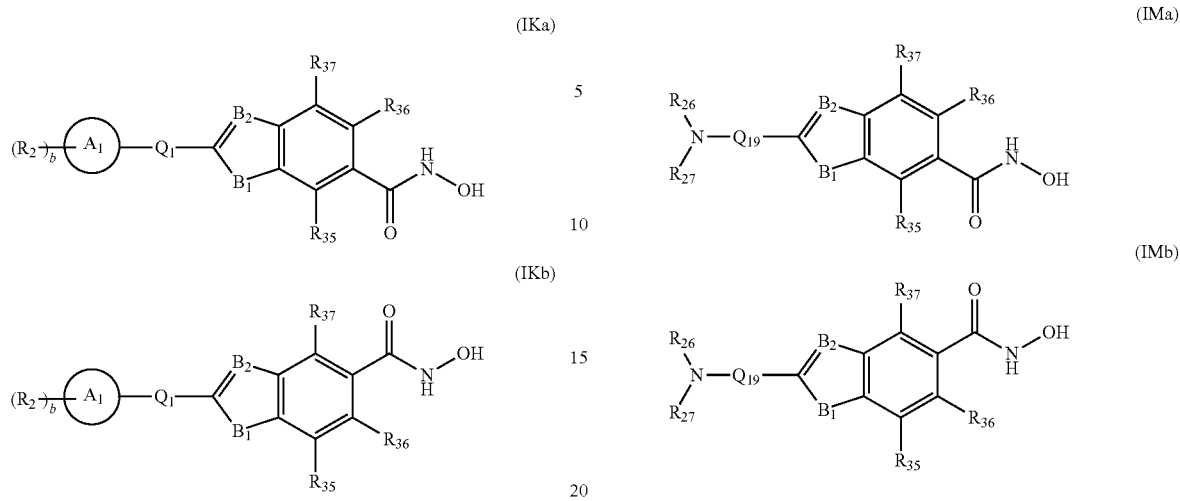

wherein b, $R_2$, ring $A_1$, $Q_1$, $B_1$, $B_2$, $R_{35}$, $R_{36}$, $R_{37}$ are as defined herein, which may collectively be referred to as a compound of formula (IK).

In some embodiments of a compound of formula (IK), the compound also is a compound of formula (IB), and is as represented by formula (ILa) or (ILb)

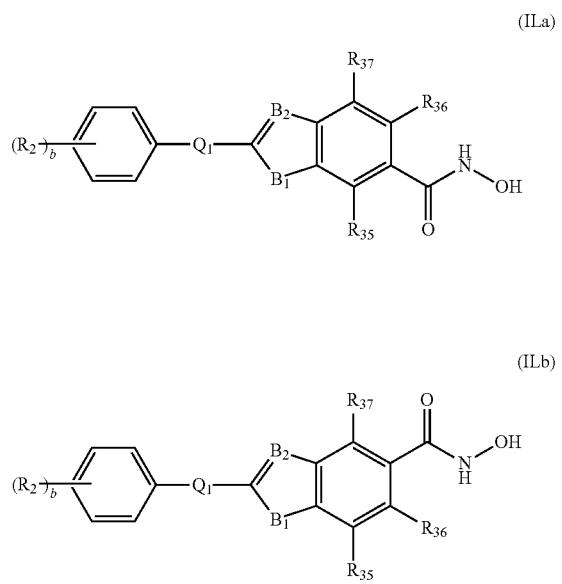

wherein b, $R_2$, $Q_1$, $B_1$, $B_2$, $R_{35}$, $R_{36}$, $R_{37}$ are as defined herein, which compound may collectively be referred to as of formula (IL).

In some embodiments, the compound of formula (IL) also is a compound of (IC) as defined herein above. In some other embodiments, the compound of formula (IL) also is a compound of formula (IE) as defined herein above. In some other embodiments, the compound of formula (IL) also is a compound of formula (IF) as defined herein above.

Likewise, in some embodiments of a compound of formula (IJ), the compound also is a compound of formula (ID), and is as represented by formula (IMa) or (IMb)

wherein $R_{26}$, $R_{27}$, $R_{35}$, $R_{36}$, $R_{37}$, $Q_{19}$, $B_1$, and $B_2$ are as defined herein. In some embodiments of a compound of formula (IM), the compound also is a compound of formula (IE). In some other embodiments of a compound of formula (IM), the compound also is a compound of formula (IF).

In some embodiments the compound of formula (I) more particularly is selected from a compound of formula (IA) and a compound of formula (ID) wherein $R_{26}$ and $R_{27}$, together with the nitrogen atom to which they are both attached, form a 5- or 6-membered ring optionally substituted by one or more moieties $R_{28}$, as defined herein.

In some embodiments, the compound of formula (I) is selected from a compound of formula (IA), e.g. a compound of formula (IB), or a compound of formula (IC), and a compound of formula (ID), wherein $R_{26}$ and $R_{27}$, together with the nitrogen atom to which they are both attached, form a 5- or 6-membered ring, which ring is optionally substituted by one moiety $R_{28}$ of formula

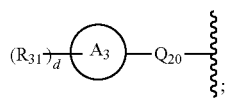;

or by two moieties $R_{28}$ attached to adjacent atoms of the ring formed by $R_{26}$ and $R_{27}$, said moieties $R_{28}$ forming together with the atoms to which they are attached, a 5- or 6-membered ring.

In some other embodiments, the compound of formula (I) is selected from a compound of formula (IA), e.g. a compound of formula (IB), or a compound of formula (IC), and a compound of formula (ID), wherein $R_{26}$ and $R_{27}$, together with the nitrogen atom to which they are both attached, form a 5- or 6-membered ring, which ring is optionally substituted by one moiety $R_{28}$ of formula

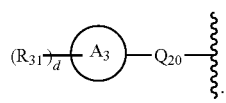.

In some embodiments, the compound of formula (I) is selected from a compound of formula (IA), e.g. a compound of formula (IB), or a compound of formula (IC), and a compound of formula (ID), wherein $R_{26}$ and $R_{27}$, together with the nitrogen atom to which they are both attached, form a 5- or 6-membered ring, which ring is optionally substituted by two moieties $R_{28}$ attached to adjacent atoms of the ring formed by $R_{26}$ and $R_{27}$, said moieties $R_{28}$ forming together with the atoms to which they are attached, a 5- or 6-membered ring.

In some embodiments the compound of formula (I) is a compound as represented by formula (INa) or (INb)

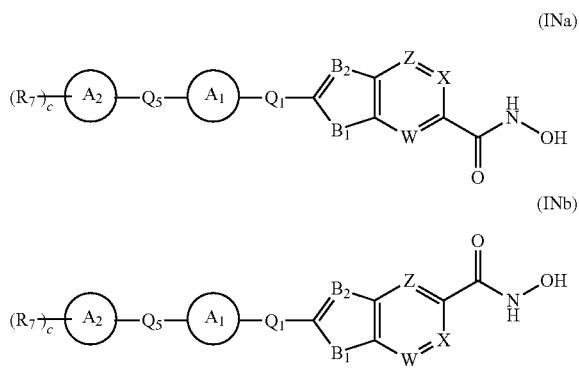

(INa)

(INb)

wherein c, $R_7$, ring $A_1$, ring $A_2$, $Q_1$, $Q_5$, $B_1$, $B_2$, W, X and Z are as defined herein, which compound may collectively be referred to as of formula (IN).

In some embodiments of a compound of formula (IN), both ring $A_1$ and ring $A_2$ are 6-membered, e.g. both are independently selected from phenyl and pyridyl, or both are phenyl; or ring $A_1$ is phenyl and ring $A_2$ is phenyl or pyridyl. In some of those embodiments, ring $A_2$ is attached to ring $A_1$ in meta position or in para position on ring $A_1$, e.g. in para position on ring $A_1$.

In some embodiments of a compound of formula (IN), the compound also is a compound of formula (IE), e.g. a compound of formula (IE) wherein $B_1$ is O or S, or wherein $B_1$ is O. In some embodiments of a compound of formula (IN), the compound also is a compound of formula (IJ). Thus, in some embodiments, the compound of formula (IN) is a compound as represented by formula (IOa) or (IOb)

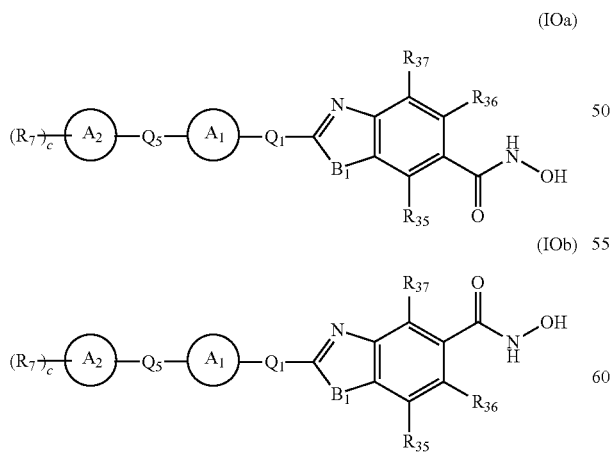

(IOa)

(IOb)

wherein c, $R_7$, ring $A_1$, ring $A_2$, $Q_1$, $Q_5$, $B_1$, $R_{35}$, $R_{36}$ and $R_{37}$ are as defined herein, which compound may collectively be referred to as of formula (IO).

In some embodiments of a compound of formula (IO), ring $A_1$ and ring $A_2$ are both 6-membered, e.g. both are selected from phenyl and pyridyl, or both are phenyl; or ring $A_1$ is phenyl, and ring $A_2$ is phenyl or pyridyl. In some of those embodiments, ring $A_2$ is attached to ring $A_1$ in meta position or in para position on ring $A_1$, e.g. in para position on ring $A_1$. In some embodiments of a compound of formula (IO), $B_1$ is O or S, or $B_1$ is O.

In some other embodiments of a compound of formula (I), viz. in some embodiments of a compound of formula (ID), the compound more particularly is as represented by formula (IPa) or (IPb)

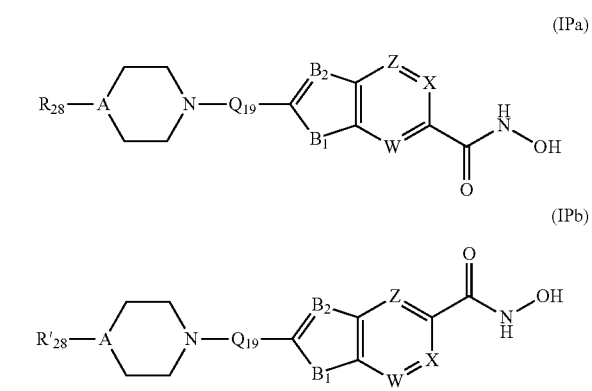

(IPa)

(IPb)

wherein $Q_{19}$, $B_1$, $B_2$, W, X and Z are as defined herein, $R'_{28}$ is H or $R_{28}$ as defined herein, and A is CH or N, which compound may collectively be referred to as a compound of formula (IP).

In some embodiments, the compound of formula (IP) also is a compound of formula (IE). In some other embodiments the compound of formula (IP), also is a compound of formula (IF). In some embodiments, the compound of formula (IP) also is a compound of formula (IG). In some embodiments, the compound of formula (IP) also is a compound of formula (IH). In some embodiments, the compound of formula (IP) also is a compound of formula (II). In some embodiments, the compound of formula (IP) also is a compound of formula (IJ).

In some embodiments of a compound of formula (IP), A is CH. In some of these embodiments, $R'_{28}$ is $R_{28}$. In some embodiments of a compound of formula (IP), $R_{28}$ is

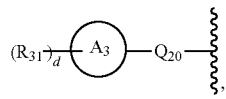

i.e. the compound may be represented by formula (IQa) or (IQb)

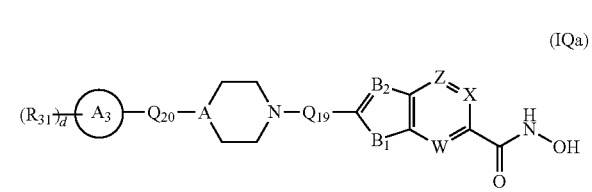

(IQa)

-continued (IQb)

wherein k, $R_{31}$, ring $A_3$, $Q_{20}$, A, $Q_{19}$, $B_1$, $B_2$, W, X and Z are as defined herein, which compound may collectively be referred to as a compound of formula (IQ).

In some embodiments of a compound of formula (IQ), $Q_{19}$ is a direct bond, and $Q_{20}$ is a direct bond or a methylene group. In some embodiments of a compound of formula (IQ), ring $A_3$ is phenyl or 5- or 6-membered heteroaryl, in particular ring $A_3$ is phenyl. In some embodiments, the compound of formula (IQ) also is a compound of formula (IE). In some other embodiments the compound of formula (IQ), also is a compound of formula (IF). In some embodiments, the compound of formula (IQ) also is a compound of formula (IG). In some embodiments, the compound of formula (IQ) also is a compound of formula (IH). In some embodiments, the compound of formula (IQ) also is a compound of formula (II). In some embodiments, the compound of formula (IQ) also is a compound of formula (IJ), i.e. a compound that may be represented by formula (IRa) or (IRb)

(IRa)

(IRb)

wherein k, $R_{31}$, ring $A_3$, $Q_{20}$, A, $Q_{19}$, $B_1$, $B_2$, $R_{35}$, $R_{36}$ and $R_{37}$ are as defined herein, which compound may collectively be referred to as a compound of formula (IR).

In some embodiments of a compound of formula (IR), $Q_{19}$ is a direct bond, and $Q_{20}$ is a direct bond or a methylene group. In some embodiments of a compound of formula (IR), ring $A_3$ is phenyl or 5- or 6-membered heteroaryl, in particular phenyl. In some embodiments, the compound of formula (IR) also is a compound of formula (IE). In some other embodiments the compound of formula (IR), also is a compound of formula (IF).

In some embodiments, the compound of formula (I) more particularly is as represented by formula (IN) or (IQ). In some other embodiments, the compound of formula (I) is as represented by formula (IO) or (IR).

In some embodiments, the compound of any one of the formulas (IA), (IB), (IC), (ID), (IF), (IG), (IH), (II), (IJ), (IK), (IL), (IM), (IN), (IO), (IP), (IQ) or (IR), is a compound of formula (Ia). In some other embodiments, the compound of any one of the formulas (IA), (IB), (IC), (ID), (IF), (IG), (IH), (II), (IJ), (IK), (IL), (IM), (IN), (IO), (IP), (IQ) or (IR) is a compound of formula (Ib).

It should be noted that in a compound of formula (I), any alkyl is optionally substituted with one or more F. For example, any methyl group may be substituted with 1, 2 or 3 F, e.g. 2 or 3 F, in particular 3 F.

In some embodiments, $R_1$ is (i)

wherein
each $R_2$ is independently selected from C1-C6 alkyl, C3-C6 cycloalkyl, halogen, cyano, $R_3O$, $R_4R_5N\text{-}Q_3$, $R_6S(O)_2\text{-}Q_4$, and and two $R_2$ attached to adjacent atoms of ring $A_1$, together with the atoms to which they are attached, may form a 5- to 10-membered monocyclic or bicyclic ring, optionally substituted as indicated herein;
$R_3$ is H or C1-C6 alkyl;
$R_4$ and $R_5$ are independently selected from H and C1-C6 alkyl; or $R_4$ and $R_8$, together with the nitrogen atom to which they are both attached, form a 5- or 6-membered ring;
$R_6$ is H or C1-C6 alkyl;
$R_7$ is halogen, $R_{13}O$, or $R_{14}R_{15}N\text{-}Q_{11}$;
$R_{13}$ is H or C1-C6 alkyl;
$R_{14}$ and $R_{15}$ are independently selected from H and C1-C6 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is a direct bond, C1-C3 alkylene, C2-C4 alkenylene, or $Q_{13}\text{-}NR_{22}$;
$Q_3$ is a direct bond, C1-C3 alkylene, or C(O);
$Q_4$ is a direct bond, C1-C3 alkylene, or $NR_{17}$;
$Q_5$ is a direct bond, C1-C3 alkylene, $S(O)_2NR_{18}$ or $Q_{15}\text{-}O$;
$Q_{11}$ is a direct bond or C1-C3 alkylene;
$Q_{13}$ is a direct bond or C1-C3 alkylene;
$Q_{15}$ is a direct bond or C1-C3 alkylene;
$R_{17}$ and $R_{18}$ are independently selected from H and C1-C3 alkyl;
$R_{22}$ is selected from H, C1-C6 alkyl, phenyl and benzyl;
b is an integer of from 0 to 3; and
c is an integer of from 0 to 3;
(ii) $R_{26}R_{27}N\text{-}Q_{19}$, wherein
$R_{26}$ and $R_{27}$ are independently selected from H and C1-C6 alkyl; or $R_{26}$ and $R_{27}$, together with the nitrogen atom to which they are both attached, form a 5- or 6-membered ring optionally substituted by one or more moieties $R_{28}$;
each $R_{28}$ is independently selected from $R_{29}OC(O)NR_{30}$, and and two $R_{28}$ attached to adjacent atoms of the ring, together with the atoms to which they are attached, may form a 5- or 6-membered ring;
$R_{29}$ is H or C1-C6 alkyl;
$R_{30}$ is H or C1-C6 alkyl;
$R_{31}$ is C1-C6 alkyl or halogen;
ring $A_3$ is 5- to 10-membered aryl or heteroaryl,
$Q_{19}$ is a direct bond or C1-C3 alkylene; and
$Q_{20}$ is a direct bond or C1-C3 alkylene; and
d is an integer of from 0 to 3;
(iii) halogen; or
(iv) hydroxy-C1-C6 alkyl,
wherein any alkyl, or cycloalkyl is optionally substituted with one or more F; any C1-C3 alkylene is preferably methylene, and any C2-C4 alkenylene is preferably ethenylene.

In some further embodiments, $R_1$ is

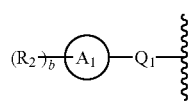

(i)

wherein
each $R_2$ is independently selected from C1-C4 alkyl, C3-C6 cycloalkyl, halogen, cyano, $R_3O$, $R_4R_5N-Q_3$, $R_6S(O)_2-Q_4$, and

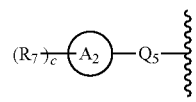

and two $R_2$ attached to adjacent atoms of ring $A_1$, together with the atoms to which they are attached, may form a 5- to 6-membered monocyclic ring, optionally substituted as indicated herein;
$R_3$ is H or C1-C4 alkyl;
$R_4$ and $R_5$ are independently selected from H and C1-C4 alkyl; or $R_4$ and $R_5$, together with the nitrogen atom to which they are both attached, form a 5- or 6-membered ring;
$R_6$ is H or C1-C4 alkyl;
$R_7$ is halogen, $R_{13}O$, or $R_{14}R_{15}N-Q_{11}$;
$R_{13}$ is H or C1-C4 alkyl;
$R_{14}$ and $R_{15}$ are independently selected from H and C1-C4 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is (a direct bond, C1-C3 alkylene, C2-C4 alkenylene, or $Q_{13}$-$NR_{22}$;
$Q_3$ is a direct bond, C1-C3 alkylene or C(O);
$Q_4$ is a direct bond, C1-C3 alkylene or $NR_{17}$;
$Q_5$ is a direct bond, C1-C3 alkylene, S(O)$_2$NR$_{18}$ or $Q_{15}$-O;
$Q_{11}$ is direct bond, C1-C3 alkylene
$R_{17}$ is selected from H and methyl;
$R_{18}$ is selected from H and methyl;
$R_{22}$ is selected from H, C1-C4 alkyl, phenyl and benzyl;
b is an integer of from 0 to 2; and
c is an integer of from 0 to 2;
(ii) $R_{26}R_{27}N-Q_{19}$, wherein
$R_{26}$ and $R_{27}$ are independently selected from C1-C4 alkyl; or $R_{26}$ and $R_{27}$, together with the nitrogen atom to which they are both attached, form a 5- or 6-membered ring optionally substituted by one moiety $R_{28}$ selected from $R_{29}OC(O)NR_{30}$, and

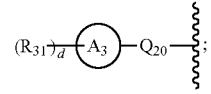

or by two moieties $R_{28}$ attached to adjacent atoms of the ring and forming together with the atoms to which they are attached, a 5- or 6-membered ring;
$R_{29}$ is C1-C6 alkyl;
$R_{30}$ is H or C1-C3 alkyl;
$R_{31}$ is F;
ring $A_3$ is 5- to 6-membered aryl or heteroaryl,
$Q_{19}$ is a direct bond or C1-C3 alkylene;
$Q_{20}$ is a direct bond or C1-C3 alkylene; and
d is an integer of from 0 to 3;
(iii) halogen; or
(iv) hydroxy-C1-C6 alkyl; and
any alkyl, or cycloalkyl is optionally substituted with one or more F; and any C1-C3 alkylene is preferably $CH_2$, and any C2-C4 alkenylene is preferably ethenylene.

In some other embodiments, $R_1$ is

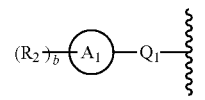

(i)

wherein
each $R_2$ is independently selected from C1-C4 alkyl, C3-C6 cycloalkyl, halogen, cyano, $R_3O$, $R_4R_5N-Q_3$, $R_6S(O)_2-Q_4$, and

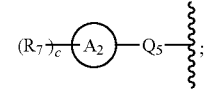

and two $R_2$ attached to adjacent atoms of ring $A_1$, together with the atoms to which they are attached, may form a 5- to 6-membered monocyclic ring, optionally substituted as indicated herein;
$R_3$ is H or C1-C4 alkyl;
$R_4$ and $R_5$ are independently selected from H and C1-C4 alkyl; or $R_4$ and $R_5$, together with the nitrogen atom to which they are both attached, form a 5- or 6-membered ring;
$R_6$ is C1-C4 alkyl;
$R_7$ is halogen, $R_{13}O$, or $R_{14}R_{15}N-Q_{11}$;
$R_{13}$ is C1-C4 alkyl;
$R_{14}$ and $R_{15}$ are independently selected from H and C1-C4 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is a direct bond, C1-C3 alkylene, C2-C4 alkenylene, or $Q_{13}$-$NR_{22}$;
$Q_3$ is a direct bond or C(O);
$Q_4$ is a direct bond or $NR_{17}$;
$Q_5$ is a direct bond, S(O)$_2$NR$_{18}$ or $Q_{15}$-O;
$Q_{11}$ is a direct bond or C1-C3 alkylene;

$R_{17}$ is selected from H and methyl;
$R_{18}$ is selected from H and methyl;
$R_{22}$ is selected from H, C1-C4 alkyl, phenyl and benzyl;
b is an integer of from 0 to 2; and
c is an integer of from 0 to 2;
(ii) $R_{26}R_{27}N\text{-}Q_{19}$, wherein
$R_{26}$ and $R_{27}$ are independently selected from C1-C4 alkyl; or
$R_{26}$ and $R_{27}$, together with the nitrogen atom to which they are both attached, form a 5- or 6-membered ring optionally substituted by one moiety $R_{28}$ selected from $R_{29}OC(O)NR_{30}$, and

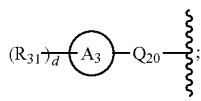

or by two moieties $R_{28}$ attached to adjacent atoms of the ring and forming together with the atoms to which they are attached, a 5- or 6-membered ring;
$R_{29}$ is C1-C6 alkyl;
$R_{30}$ is H or C1-C3 alkyl;
$R_{31}$ is F;
ring $A_3$ is 5- to 6-membered aryl or heteroaryl,
$Q_{19}$ is a direct bond or C1-C3 alkylene;
$Q_{20}$ is a direct bond or C1-C3 alkylene; and
d is 0 or 1;
(iii) halogen; or
(iv) hydroxy-C1-C6 alkyl; and
any alkyl, or cycloalkyl is optionally substituted with one or more F; and any C1-C3 alkylene is preferably $CH_2$, and any C2-C4 alkenylene is preferably ethenylene.

In still other embodiments, $R_1$ is

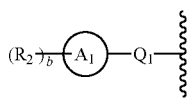

(i)

wherein
each $R_2$ is independently selected from C1-C4 alkyl, C3-C6 cycloalkyl, halogen, cyano, $R_3O$, $R_4R_5N\text{-}Q_3$, $R_6S(O)_2\text{-}Q_4$, and

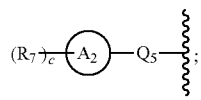

and two $R_2$ attached to adjacent atoms of ring $A_1$, together with the atoms to which they are attached, may form a 5- to 6-membered monocyclic ring, optionally substituted as indicated herein;
$R_3$ is H or C1-C4 alkyl;
$R_4$ and $R_5$ are independently selected from H and C1-C4 alkyl; or $R_4$ and $R_5$, together with the nitrogen atom to which they are both attached, form a 5- or 6-membered ring;
$R_6$ is C1-C4 alkyl;
$R_7$ is halogen, $R_{13}O$, or $R_{14}R_{15}N\text{-}Q_1$;
$R_{13}$ is C1-C4 alkyl;
$R_{14}$ and $R_{15}$ are independently selected from H and C1-C4 alkyl; or $R_{14}$ and $R_{15}$, together with the nitrogen atom to which they are both attached, form a 5- or 6-membered ring;

ring $A_1$ and ring $A_2$ are independently selected from 5- or 6-membered aryl or heteroaryl;
$Q_1$ is a direct bond, $CH_2$, $CH=CH$, $(CH_2)NR_{22}$ or $NR_{22}$;
$Q_3$ is a direct bond or $C(O)$;
$Q_4$ is a direct bond or NH;
$Q_5$ is a direct bond, $S(O)_2NH$ or $(CH_2)O$;
$Q_{11}$ is $CH_2$;
$R_{22}$ is selected from H, C1-C4 alkyl, phenyl and benzyl;
b is an integer of from 0 to 2; and
c is an integer of from 0 to 2;
(ii) $R_{26}R_{27}N\text{-}Q_{19}$, wherein
$R_{26}$ and $R_{27}$ are independently selected from C1-C4 alkyl; or
$R_{26}$ and $R_{27}$, together with the nitrogen atom to which they are both attached, form a 5- or 6-membered ring optionally substituted by one moiety $R_{28}$, selected from $R_{29}OC(O)NR_{30}$, and

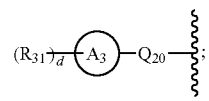

or from two moieties $R_{28}$ attached to adjacent atoms of the ring and forming together with the atoms to which they are attached, a 5- or 6-membered ring;
$R_{29}$ is C1-C6 alkyl;
$R_{30}$ is H or C1-C3 alkyl;
$R_{31}$ is F;
ring $A_3$ is 5- to 6-membered aryl or heteroaryl,
$Q_{19}$ is a direct bond or $CH_2$;
$Q_{20}$ is a direct bond or $CH_2$; and
d is 0 or 1;
(iii) halogen; or
(iv) hydroxy-C1-C6 alkyl; and
any alkyl, or cycloalkyl is optionally substituted with one or more F.

In some of the above embodiments, $R_1$ is selected from (i) and (ii). In some others of the above embodiments, $R_1$ is selected from (i). In some others of the above embodiments, $R_1$ is selected from (ii).

In some further embodiments,
$R_1$ is

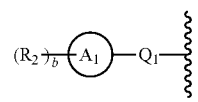

(i)

wherein
b is 1 and $R_2$ is selected from C3-C6 cycloalkyl, $R_4R_5N\text{-}Q_3$, and

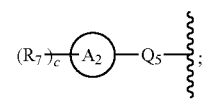

or b is 2 and the two $R_2$ are attached to adjacent atoms of ring $A_1$ and form, together with the atoms to which they are attached, a 5- to 10-membered monocyclic or bicyclic ring, which ring is optionally substituted as indicated herein;
$R_4$ and $R_5$, together with the nitrogen atom to which they are both attached, form a 5- or 6-membered ring;

$R_7$ is halogen, $R_{13}O$, or $R_{14}R_{15}N-Q_{11}$;
$R_{13}$ is H or C1-C6 alkyl;
$R_{14}$ and $R_{15}$ are independently selected from H and C1-C6 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is a direct bond, C1-C3 alkylene, C2-C4 alkenylene, or $NR_{22}$;
$Q_3$ is a direct bond, C1-C3 alkylene or C(O);
$Q_5$ is a direct bond, C1-C3 alkylene, $S(O)_2NR_{18}$ or $Q_{15}$-O;
$Q_{11}$ is a direct bond, C1-C3 alkylene;
each $R_{18}$,
is independently selected from H and C1-C3 alkyl;
$R_{22}$ is selected from H, C1-C6 alkyl, phenyl and benzyl; and
c is an integer of from 0 to 3;
(ii) $R_{26}R_{27}N-Q_{19}$, wherein
$R_{26}$ and $R_{27}$, together with the nitrogen atom to which they are both attached, form a 5- or 6-membered ring substituted by one $R_{28}$, which is

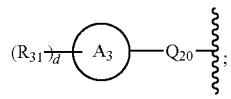

or by two $R_{28}$ attached to adjacent atoms of the ring and forming, together with the atoms to which they are attached, a 5- or 6-membered ring;
$R_{31}$ is C1-C6 alkyl or halogen;
ring $A_3$ is 5- to 10-membered aryl or heteroaryl,
$Q_{19}$ is a direct bond or C1-C3 alkylene;
$Q_{20}$ is a direct bond or C1-C3 alkylene; and
d is an integer of from 0 to 3;
any C1-C3 alkylene is preferably methylene, and any C2-C4 alkenylene is preferably ethenylene.

In some of these embodiments,
$R_1$ is

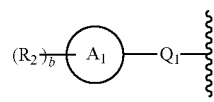 (i)

wherein
b is 1, and $R_2$ is selected from C3-C6 cycloalkyl, $R_4R_5N-Q_3$, and

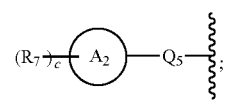

or b is 2 and the two $R_2$ are attached to adjacent atoms of ring $A_1$ and form, together with the atoms to which they are attached, a 5- to 10-membered monocyclic or bicyclic ring;
$R_4$ and $R_5$, together with the nitrogen atom to which they are both attached, form a 5- or 6-membered ring, which ring is optionally substituted as indicated herein;
$R_7$ is halogen, $R_{13}O$, or $R_{14}R_{15}N-Q_{11}$;
$R_{13}$ is H or C1-C6 alkyl;
$R_{14}$ and $R_{15}$ are independently selected from H and C1-C6 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is a direct bond, C1-C3 alkylene, C2-C4 alkenylene, or $Q_{13}-NR_{22}$;
$Q_3$ is a direct bond or C1-C3 alkylene or C(O);
$Q_5$ is a direct bond, C1-C3 alkylene, $S(O)_2NR_{18}$ or $Q_{15}$-O;
$Q_{11}$ is a direct bond or C1-C3 alkylene;
each $R_{18}$, is independently selected from H and methyl;
$R_{22}$ is selected from H, C1-C6 alkyl, phenyl and benzyl; and
c is an integer of from 0 to 3;
(ii) $R_{26}R_{27}N-Q_{19}$, wherein
$R_{26}$ and $R_{27}$, together with the nitrogen atom to which they are both attached, form a 5- or 6-membered ring substituted by one $R_{28}$, which is

or by two $R_{28}$ attached to adjacent atoms of the ring and forming, together with the atoms to which they are attached, a 5- or 6-membered ring;
$R_{31}$ is C1-C6 alkyl or halogen;
ring $A_3$ is 5- to 10-membered aryl or heteroaryl,
$Q_{19}$ is a direct bond or C1-C3 alkylene;
$Q_{20}$ is a direct bond or C1-C3 alkylene; and
d is an integer of from 0 to 3;
any C1-C3 alkylene is preferably methylene, and any C2-C4 alkenylene is preferably ethenylene.

In some of these embodiments,
$R^1$ is (i)

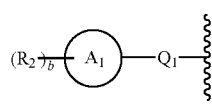

wherein
b is 1, and $R_2$ is selected from C3-C6 cycloalkyl, $R_4R_5N-Q_3$, and

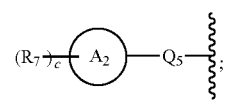

$R_4$ and $R_5$, together with the nitrogen atom to which they are both attached, form a 5- or 6-membered ring;
$R_7$ is halogen, $R_{13}O$, or $R_{14}R_{15}N-Q_{11}$;
$R_{13}$ is H or C1-C6 alkyl;
$R_{14}$ and $R_{15}$ are independently selected from H and C1-C6 alkyl; or $R_{14}$ and $R_{15}$, together with the nitrogen atom to which they are both attached, form a 5- or 6-membered ring;
ring $A_1$ and ring $A_2$ are independently selected from 5- or 6-membered aryl or heteroaryl;
$Q_1$ is a direct bond, C1-C3 alkylene, C2-C4 alkenylene, or $Q_{13}-NR_{22}$;
$Q_3$ is a direct bond, C1-C3 alkylene, or C(O);
$Q_5$ is a direct bond, C1-C3 alkylene, $S(O)_2NR_{18}$ or $Q_{15}$-O;
$Q_{11}$ is a direct bond or C1-C3 alkylene
each $R_{18}$, is independently selected from H and methyl;

$R_{22}$ is selected from H, C1-C6 alkyl, phenyl and benzyl; and
c is an integer of from 0 to 3;
(ii) $R_{26}R_{27}N\text{-}Q_{19}$, wherein
$R_{26}$ and $R_{27}$, together with the nitrogen atom to which they are both attached, form a 5- or 6-membered ring substituted by one $R_{28}$, which is

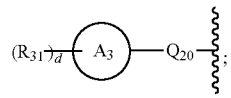

$R_{31}$ is C1-C6 alkyl or halogen;
ring $A_3$ is 5- to 10-membered aryl or heteroaryl,
$Q_{19}$ is a direct bond or C1-C3 alkylene;
$Q_{20}$ is a direct bond or C1-C3 alkylene; and
d is an integer of from 0 to 3;
any C1-C3 alkylene is preferably methylene, and any C2-C4 alkenylene is preferably ethenylene.

In some of the above embodiments, $R_1$ is selected from (i). In some other of the above embodiments, $R_1$ is selected from (ii).

In the above embodiments, $R_1$ is selected from (i), $Q_1$ preferably is a direct bond or methylene, in particular $Q_1$ preferably is a direct bond.

In some of the above embodiments, the compound is a compound of formula (Ia). In some others of the above embodiments, the compound is a compound of formula (Ib). In still others of the above embodiments, the compound is a compound of formula (IE). In others of the above embodiments, the compound is a compound of formula (IF). In some others of the above embodiments, the compound is a compound of formula (IG). In some others of the above embodiments, the compound is a compound of formula (IH). In still others of the above embodiments, the compound is a compound of formula (II). In still others of the above embodiments, the compound is a compound of formula (IJ).

In some embodiments, in a compound of formula (I), any $R_{17}$ and any $R_{18}$, when present, is independently selected from H and methyl. In some particular embodiments, any $R_{17}$ and any $R_{18}$, when present, is H.

Stereoisomers

Whenever a chiral carbon is present in the compound of formula (I), it is intended that all stereoisomers associated with that chiral carbon are encompassed formula (I), unless otherwise specified. Using the Cahn-Ingold-Prelog RS notational system, any asymmetric carbon atom may be present in the (R)- or (S)-configuration, and the compound may be present as a mixture of its stereoisomers, e.g. a racemic (equal) or unequal mixture, or one stereoisomer only. Stereoisomers include enantiomers and diastereomers.

Pharmaceutically Acceptable Salts

A pharmaceutically acceptable salt of the compound of formula (I) may be an acid addition salt or a base addition salt.

In the preparation of acid or base addition salts, such acids or bases are used which form suitable pharmaceutically acceptable salts. Examples of such acids are inorganic acids such as hydrohalogen acids, sulfuric acid, phosphoric acid, nitric acid; organic aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybenzoic acid, embonic acid, methanesulfonic acid, ethanesulfonic acid, hydroxyethanesulfonic acid, halogenbenzenesulfonic acid, toluenesulfonic acid or naphthalenesulfonic acid.

Base addition salts include those derived from inorganic bases, such as ammonium or alkali or alkaline earth metal hydroxides, carbonates, bicarbonates, and the like, and organic bases such as alkoxides, alkyl amides, alkyl and aryl amines, and the like. Examples of bases useful in preparing salts of the present invention include sodium hydroxide, potassium hydroxide, ammonium hydroxide, potassium carbonate, and the like.

Pharmaceutical Formulations

A pharmaceutical composition according to the invention may be for topical (local) or systemic administration, e.g. for enteral administration, such as rectal or oral administration, or for parenteral administration to a mammal (especially a human), and comprises a therapeutically effective amount of a compound according to the invention or a pharmaceutically acceptable salt thereof, as active ingredient, in association with a pharmaceutically acceptable excipient, e.g. a pharmaceutically acceptable carrier. The therapeutically effective amount of the active ingredient is as defined herein above and depends e.g. on the species of mammal, the body weight, the age, the individual condition, individual pharmacokinetic data, the disease to be treated and the mode of administration.

For enteral, e.g. oral, administration, the compounds of the invention may be formulated in a wide variety of dosage forms. The pharmaceutical compositions and dosage forms may comprise a compound or compounds of the present invention or pharmaceutically acceptable salt(s) thereof as the active component. The pharmaceutically acceptable carriers may be either solid or liquid. Solid form preparations include powders, tablets, pills, lozenges, capsules, cachets, suppositories, and dispersible granules. A solid carrier may be one or more substances which may also act as diluents, flavouring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The formulation of the active compound may comprise an encapsulating material as carrier, providing a capsule in which the active component, with or without carriers, is surrounded by a carrier, which is in association with it.

Other forms suitable for oral administration include liquid form preparations including emulsions, syrups, elixirs, aqueous solutions, aqueous suspensions, or solid form preparations which are intended to be converted shortly before use to liquid form preparations. Emulsions may be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and may contain, in addition to the active component, colorants, flavors, stabilizers, buffers, artificial and natural sweeteners, dispersants, thickeners, solubilizing agents, and the like.

Exemplary compositions for rectal administration include suppositories which can contain, for example, a suitable non-irritating excipient, such as cocoa butter, synthetic glyceride esters or polyethylene glycols, which are solid at ordinary temperatures, but liquefy and/or dissolve in the rectal cavity to release the drug.

The compounds of the invention also may be administered parenterally, e.g. by inhalation, injection or infusion, e.g. by intravenous, intraarterial, intraosseous, intramuscular, intracerebral, intracerebroventricular, intrasynovial, intrasternal, intrathecal, intralesional, intracranial, intratumoral, intracutaneous and subcutaneous injection or infusion.

Thus, for parenteral administration, the pharmaceutical compositions of the invention may be in the form of a sterile injectable or infusible preparation, for example, as a sterile aqueous or oleaginous suspension. This suspension may be formulated according to techniques known in the art using suitable dispersing or wetting agents (e.g. Tween 80), and suspending agents. The sterile injectable or infusible preparation may also be a sterile injectable or infusible solution or suspension in a non-toxic parenterally acceptable diluent or solvent. For example, the pharmaceutical composition may be a solution in 1,3-butanediol. Other examples of acceptable vehicles and solvents that may be employed in the compositions of the present invention include, but are not limited to, mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically acceptable oils, such as olive oil or castor oil, especially in their polyoxyethylated versions. These oil solutions or suspensions may also contain a long-chain alcohol diluent or dispersant.

Solutions for parenteral use also may contain suitable stabilizing agents, and if necessary, buffer substances. Suitable stabilizing agents include antioxidizing agents, such as sodium bisulfate, sodium sulfite or ascorbic acid, either alone or combined, citric acid and its salts and sodium EDTA. Parenteral solutions may also contain preservatives, such as benzalkonium chloride, methyl- or propyl-paraben, and chlorobutanol.

For inhalation or nasal administration, suitable pharmaceutical formulations are as particles, aerosols, powders, mists or droplets, e.g. with an average size of about 10 μm in diameter or less. For example, compositions for inhalation may be prepared as solutions in saline, employing benzyl alcohol or other suitable preservatives, absorption promoters to enhance bioavailability, fluorocarbons, and/or other solubilizing or dispersing agents known in the art.

The pharmaceutical compositions of the invention also may be administered topically, to the skin or to a mucous membrane. For topical application, the pharmaceutical composition may be e.g. a lotion, a gel, a paste, a tincture, a transdermal patch, a gel for transmucosal delivery. The composition may be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition may be formulated as a suitable lotion or cream containing the active compound suspended or dissolved in a carrier. Suitable carriers include, but are not limited to, mineral oil, sorbitan monostearate, polysorbate 60, cetyl esters wax, cetaryl alcohol, 2-octyldodecanol, benzyl alcohol and water. The pharmaceutical compositions of this invention may also be topically applied to the lower intestinal tract by rectal suppository formulation or in a suitable enema formulation.

Suitable pharmaceutical excipients, e.g. carriers, and methods of preparing pharmaceutical dosage forms are described in Remington's Pharmaceutical Sciences, Mack Publishing Company, a standard reference text in art of drug formulation.

The pharmaceutical compositions may comprise from approximately 1% to approximately 95%, preferably from approximately 20% to approximately 90% of a compound of formula (I), together with at least one pharmaceutically acceptable excipient. In general, the compounds of the invention will be administered in a therapeutically effective amount by any of the accepted modes of administration for agents that serve similar utilities. Suitable daily dosages typically ranges from 1 to 1000 mg, e.g. 1-500 mg daily, or 1-50 mg daily, depending upon numerous factors such as the severity of the disease to be treated, the age and relative health of the patient, the potency of the compound used, the route and form of administration, and the indication towards which the administration is directed, etc. One of ordinary skill in the art of treating such diseases will be able, without undue experimentation and in reliance upon personal knowledge and the disclosure of this application, to ascertain a therapeutically effective amount of the compounds of the present invention for a given disease. Compounds of the invention may be administered as pharmaceutical formulations including those suitable for enteral or parenteral administration. The preferred manner of administration is generally oral using a convenient daily dosage regimen which can be adjusted according to the degree of affliction.

The compounds of the present invention may also be used or administered in combination with one or more additional therapeutically active agents, e.g. drugs useful in the treatment of a disorder selected from autoimmune disorders, mental disorders, neurodegenerative disorders and cancers. The components may be in the same formulation or in separate formulations for administration simultaneously or sequentially.

In some embodiments, the compounds is used or administered in combination with dexamethasone.

Accordingly, in a further aspect of the invention, there is provided a combination product comprising:
(A) a compound of the invention, as defined herein; and
(B) another therapeutic agent, e.g. one that is useful in the treatment of a disorder selected from autoimmune disorders, mental disorders, neurodegenerative disorders and cancers; whereby (A) and (B) is formulated in admixture with a pharmaceutically acceptable excipient.

In some embodiments, the combination product contains dexamethasone as the other therapeutic agent.

Such combination products provide for the administration of a compound of the invention in conjunction with the other therapeutic agent, and may thus be presented either as separate formulations, wherein at least one of those formulations comprises a compound of the invention, and at least one comprises the other therapeutic agent, or may be presented (i.e. formulated) as a combined preparation (i.e.

presented as a single formulation including a compound of the invention and the other therapeutic agent).

Thus, there is further provided:
(1) a pharmaceutical formulation including a compound of the invention, as hereinbefore defined, another therapeutic agent, and a pharmaceutically acceptable excipient, e.g. an adjuvant, diluent or carrier; and
(2) a kit of parts comprising, as components:
(a) a pharmaceutical formulation including a compound of the invention, as defined herein, in admixture with a pharmaceutically acceptable excipient, e.g. an adjuvant, diluent or carrier; and
(b) a pharmaceutical formulation including another therapeutic agent in admixture with a pharmaceutically acceptable excipient, e.g. an adjuvant, diluent or carrier, which components (a) and (b) are each provided in a form that is suitable for administration in conjunction with the other.

The compounds of the present invention may also be used or administered in combination with other treatment such as irradiation for the treatment of cancer.

Methods of Treatment

According to one aspect, the present invention relates to a method of treatment of a disease that responds to inhibition of histone deacetylase 6, e.g. a disorder selected from autoimmune disorders, neurodegenerative disorders, and hyperproliferative disorders, such as cancers, which method comprises administering a therapeutically effective amount of a compound of formula (I), or pharmaceutically acceptable salt thereof, to a warm-blooded animal, e.g. a mammal, such as a human, in need of such treatment.

While the compounds of the invention may be administered to a subject in need of treatment e.g. by use of a pharmaceutical formulation and administration route as generally outlined herein above, it should be realized that precise treatment regime, e.g. dosage, will normally be determined by the treating physician.

In some embodiments, the disorder to be treated is an autoimmune disorder, such as any of the autoimmune disorders mentioned herein above, e.g. colitis, or allograft rejection.

In some embodiments, the disorder is a neurodegenerative disorder, such as any of the neurodegenerative disorders mentioned herein above, for example Alzheimer's disease, Parkinson's disease or Huntington's disease.

In some embodiments, the disorder is a mental disorder, such as any of the mental disorders referred to herein above, e.g. a depressive disorder or a stress-induced mental disorder.

In some embodiments, the disorder is a hyperproliferative disorder, such as any of the hyperproliferative disorders mentioned herein above, e.g, a malignant hyperproliferative disorder (cancer).

Methods of Preparation

The compounds of formulas (Ia) and (1b) may be prepared by the person of ordinary skill in the art, using conventional methods of chemical synthesis. The preparation of some intermediates and compounds according to the present invention may in particular be illustrated by the following Schemes.

Compounds of formula (1a) or (1b) may for example be prepared according to the route shown in Scheme 1. An acid chloride and methyl 3-amino-4-hydroxybenzoate in dioxane/MeCN is heated at 180° C. to give the benzoxazole of formula (1). (Pelcman, B. et. al. WO 2008129276 A1). Treatment of the ester (1) with hydroxylamine potassium salt in methanol gives the hydoxamic acid (2).

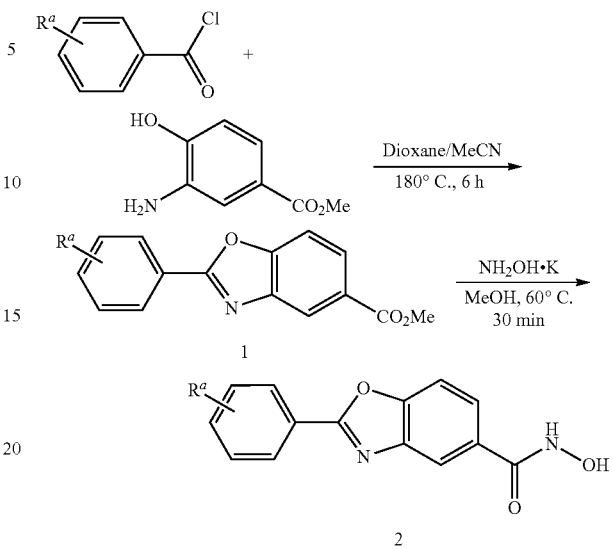

Scheme 1

Compounds of formula (1a) or (1b) may also for example be prepared according to the route shown in Scheme 2. An aldehyde is condensed with methyl 3-amino-4-hydroxybenzoate. The imine intermediate is oxidized to the desired benzoxazole (3) using DDQ (Chang, J. and Pan, S. US 20030148387 A1). The ester (3) is transformed to hydoxamic acid (4) using hydroxylamine potassium salt in methanol.

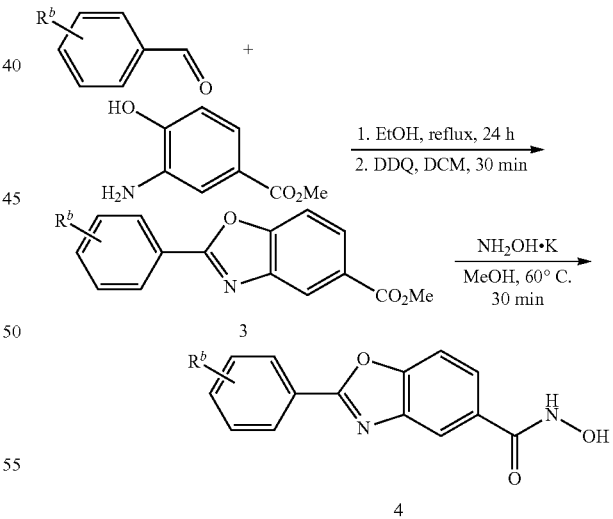

Scheme 2

Compounds of formula (1a) or (1b) may also for example be prepared according to the route shown in Scheme 3. 2-Bromophenyl benzoxazole (5) and an aryl boronic acid is heated in presence of a palladium catalyst, Suzuki coupling conditions (Suzuki, A et. al. Tetrahedron Letters (1979) 20 (36): 3437-3440), to give the biaryl intermediate (6). The ester (6) is transformed to hydoxamic acid (7) using hydroxylamine potassium salt in methanol.

Scheme 3

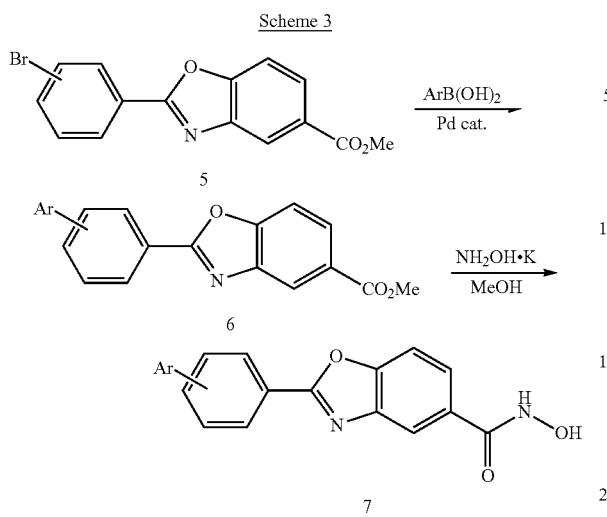

Compounds of formula (1a) or (1b) may also for example be prepared according to the route shown in Scheme 4. Methyl 3-amino-4-hydroxybenzoate is treated with carbondisulfide followed by addition of iodomethane. The 2-methylsulfanylbenzoxazole (8) is formed and used in substitution reactions with amines and anilines to give the 2-aminobenoxazole (9) (Jonckers, T. H. et. al. WO 2009071650 A2). Finally the hydroxamic acid (10) is obtained by treating the ester (9) with hydroxylamine and KOH in methanol.

Scheme 4

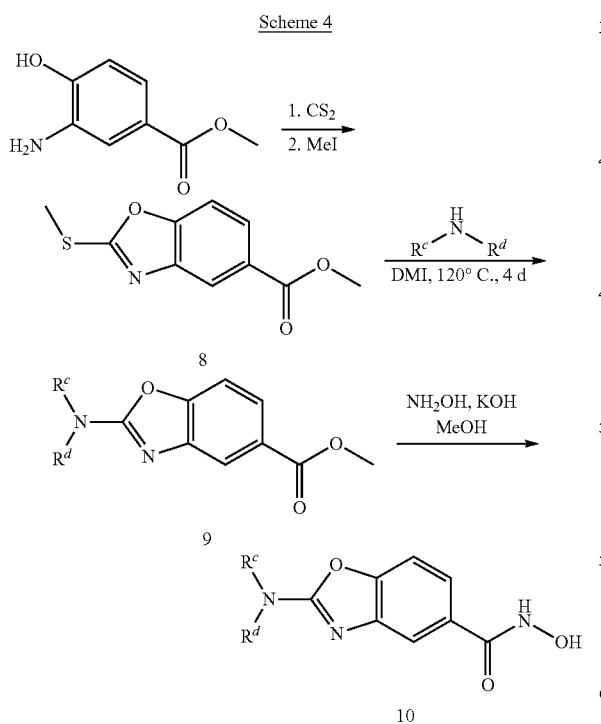

Compounds of formula (1a) or (1b) may also for example be prepared according to the route shown in Scheme 5. Methyl 4,5-diaminopyridine-2-carboxylate is condensed with an aldehyde under acidic catalysis in a vial open to air to give the pyridinoimidazole (11) which is transformed to hydroxamic acid (12) using hydroxylamine and KOH in methanol.

Scheme 5

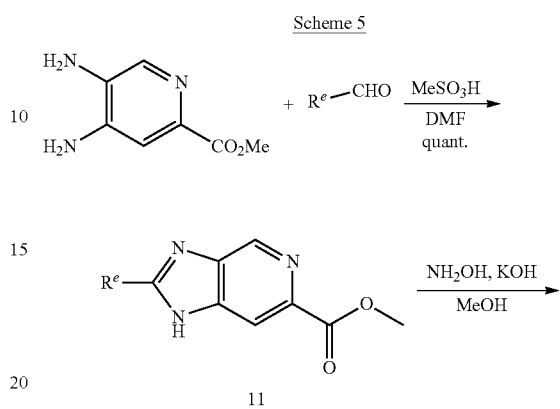

Compounds of formula (1a) or (1b) may also for example be prepared according to the route shown in Scheme 6. Methyl 4-amino-3-iodobenzoate is acylated using trifluoroacetic anhydride to the intermediate (13). The intermediate (13) is used in a coupling reaction using an acetylene under Sonogoshira's conditions (Liu, F. et. al. *J. Org. Chem* (2007), 72(13), 4844-4850). The indole (14) is obtained and converted to hydroxamic acid (15) using hydroxylamine and KOH in methanol.

Scheme 6

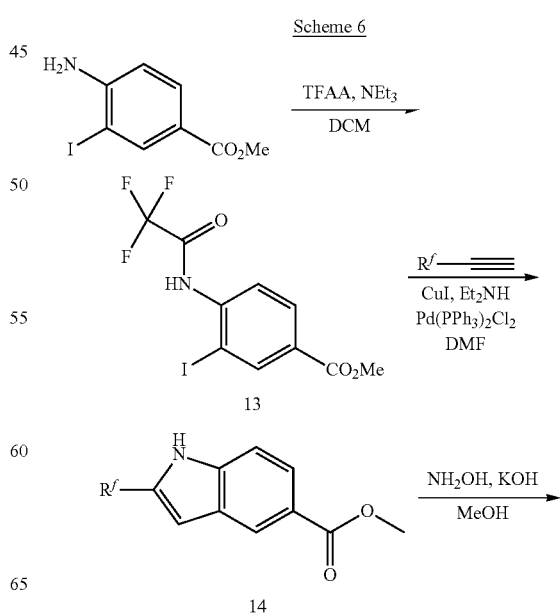

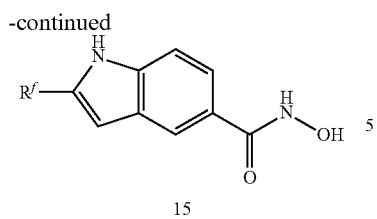

15

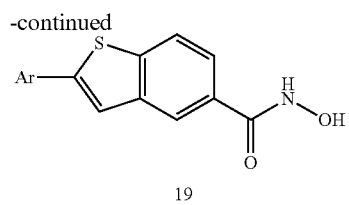

19

Compounds of formula (1a) or (1b) may also for example be prepared according to the route shown in Scheme 7. Methyl 3-amino-4-fluorobenzoate is acylated using an acyl chloride. Treatment with Lawesson's reagent gives the benzothiazole (16) (Finlay, H. et. al. WO 2014015088 A1), which is converted to hydroxamic acid (17) using potassium salt of hydroxylamine in methanol.

Compounds of formula (1a) or (1b) may also for example be prepared according to the route shown in Scheme 9. The 2-position of methyl benzothiophene-5-carboxylate is iodinated using LDA and iodine. The iodo intermediate (20) is used as substrate for Suzuki couplings and the hydroxamate (22) is formed using hydroxylamine and KOH in methanol.

Scheme 7

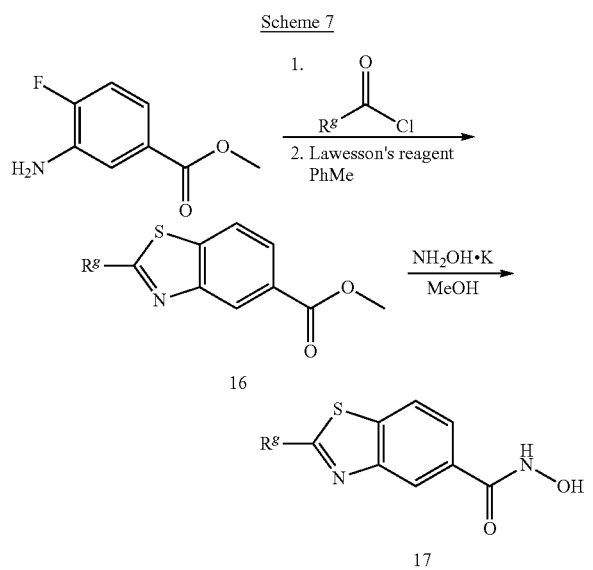

Scheme 9

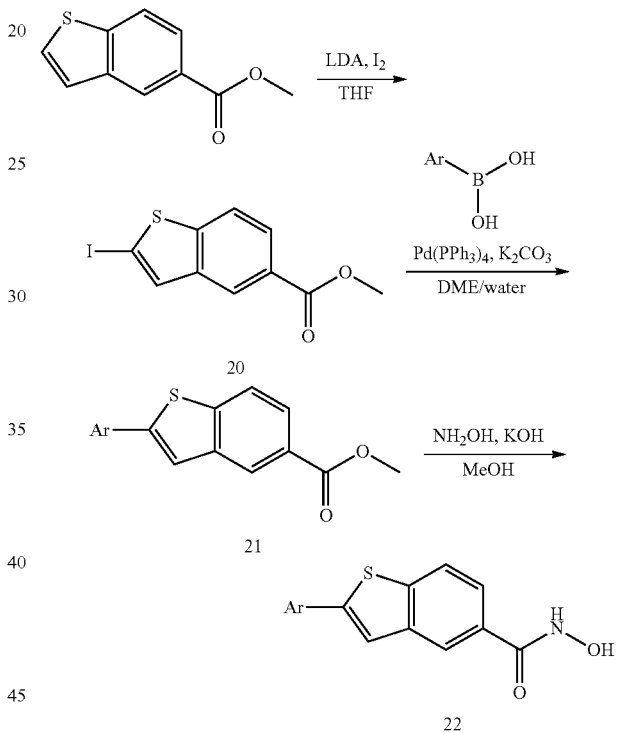

Compounds of formula (1a) or (1b) may also for example be prepared according to the route shown in Scheme 8. Methyl benzothiophene-5-carboxylate is directly arylated in 2-position using arylbromide and palladium catalysis which gives the intermediate (18) (Baghbanzadeh, M. et. el. *Journal of Organic Chemistry* (2011), 76(19), 8138-8142). The ester is converted to hydroxamic acid (19) using potassium salt of hydroxylamine in methanol.

Compounds of formula (1a) or (1b) may also for example be prepared according to the route shown in Scheme 10. 6-Bromobenzothiophene is heated with $Zn(CN)_2$ catalyzed with palladium to give the nitrile (23). This intermediate is directly arylated in 2-position using the method described by Baghbanzadeh, M. et. el. (Baghbanzadeh, M. et. el. *Journal of Organic Chemistry* (2011), 76(19), 8138-8142). The arylated nitrile (24) is hydrolyzed and the carboxylic acid (25) is converted to hydroxamic (26) acid by amide coupling using O-(tetrahydropyran-2-yl)-hydroxylamine followed by TFA deprotection.

Scheme 8

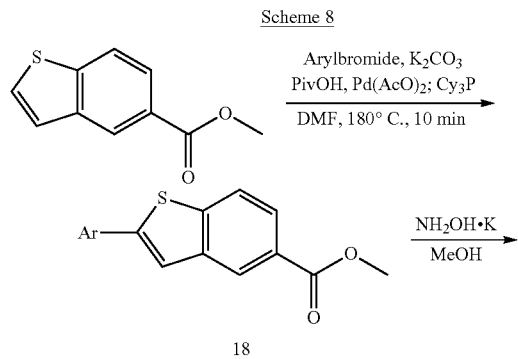

Scheme 10

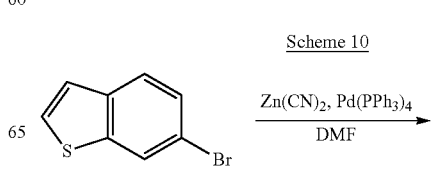

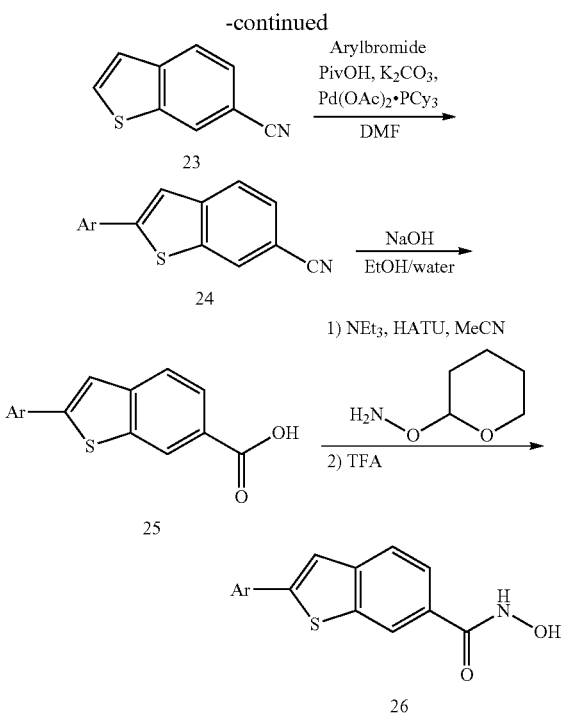

The necessary starting materials for preparation of the compounds of formulas (Ia) and (1b) are either commercially available, or may be prepared by methods known in the art.

The reactions described below in the experimental section may be carried out to give a compound of the invention in the form of a free base or as an acid or base addition salt. The term pharmaceutically acceptable salt of a compound refers to a salt that is pharmaceutically acceptable, as defined herein, and that possesses the desired pharmacological activity of the parent compound. A pharmaceutically acceptable acid addition salt may be obtained by dissolving the free base in a suitable organic solvent and treating the solution with an acid, in accordance with conventional procedures for preparation of acid addition salts from free bases.

The compounds of formula (I) may possess one or more chiral carbon atoms, and may therefore be obtained in the form of optical isomers, e.g. as a pure enantiomer, or as a mixture of enantiomers (racemate) or as a mixture of diastereomers. The separation of mixtures of optical isomers to obtain pure enantiomers is well known in the art and may, for example, be achieved by fractional crystallization of salts with optically active (chiral) acids or by chromatographic separation on chiral columns.

The chemicals used in the synthetic routes described herein may include, for example, solvents, reagents, catalysts, and protecting group and deprotecting group reagents. Examples of protecting groups are t-butoxycarbonyl (Boc), benzyl, trityl (triphenylmethyl) and trimethylsilyl. The methods described above may also additionally include steps, either before or after the steps described specifically herein, to add or to remove suitable protecting groups in order to ultimately allow synthesis of the compounds. In addition, various synthetic steps may be performed in an alternate sequence or order to give the desired compounds. Synthetic chemistry transformations and protecting group methodologies are known in the art and include, for example, those described in R. C. Larock, *Comprehensive Organic Transformations*, VCH Publishers (1989); L. Fieser and M. Fieser, *Fieser and Fieser's Reagents for Organic Synthesis*, John Wiley and Sons (1994); L. A. Paquette, ed., *Encyclopedia of Reagents for Organic Synthesis*, John Wiley and Sons (1995); T. H. Greene and P. G. M. Wuts, *Protective Groups in Organic Synthesis*, 3$^{rd}$ Ed., John Wiley and Sons (1999); and P. J. Kocieński, *Protecting Groups*, Georg Thieme Verlag, (2000) and subsequent editions thereof.

All references cited herein, whether in print, electronic, computer readable storage media or other form, are expressly incorporated by reference in their entirety, including but not limited to abstracts, articles, journals, publications, texts, treatises, technical data sheets, internet web sites, databases, patents, patent applications, and patent publications.

The invention will now be further illustrated by the following non-limiting examples. The specific examples below are to be construed as merely illustrative, and not limitative of the remainder of the disclosure in any way whatsoever. Without further elaboration, it is believed that one skilled in the art can, based on the description herein, utilize the present invention to its fullest extent.

EXAMPLES

The following abbreviations have been used:
AcOH Acetic acid
DABCO 1,4-Diazabicyclo[2.2.2]octane
DCE 1,2-Dichloroethane
DCM Dichloromethane
DDQ 2,3-Dichloro-5,6-dicyano-1,4-benzoquinone
DEAD Diethylazodicarboxylate
DIPEA N,N-diisopropylethylamine
DME 1,2-Dimethoxyethane
DMF N,N-Dimethylformamide
DMI 1,3-Dimethyl-2-imidazolidinone
DMSO Dimethyl sulfoxide
dppf 1,1'-Bis(diphenylphosphino)ferrocene
ESI Electrospray ionization
Et$_3$N Triethylamine
EtOAc Ethyl acetate
HATU (1-[Bis(dimethylamino)methylene]-1H-1,2,3-triazolo[4,5-b]pyridinium-3-oxid hexafluorophosphate)
HPLC High Performance Liquid Chromatography
MeCN Acetonitrile
MeOH Methanol
MS Mass Spectrometry
NMR Nuclear Magnetic Resonance
NMP N-Methyl-2-pyrrolidone
PEPPSI-iPr 1,3-Bis(2,6-Diisopropylphenyl)imidazol-2-ylidene](3-chloropyridyl)-palladium(II) dichloride
rt Room temperature
TBAF Tetrabutylammonium fluoride
THF Tetrahydrofurane
TFA Trifluoroacetic acid
p-TSA p-Toluenesulfonic acid Experimental Methods $^1$H NMR spectra were recorded on a Varian Inova 600 equipped with a triple resonance probe. All spectra were recorded using the residual solvent proton resonance or tetramethylsilane (TMS) as internal standard. Analytical HPLC was carried out on an Agilent Series 1100 system using either an ACE C8 (3 µm, 3.0×50 mm) column with 0.1% TFA in MilliQ H$_2$O/CH$_3$CN as mobile phase (Acidic system) or an XTerra (3.5 µm, 3.0×50 mm) column with 10 mM pH 10 NH$_4$HCO$_3$/CH$_3$CN as mobile phase (Basic system). Electrospray ionization mass spectrometry (ESI-MS) was performed using an Agilent 1100 Series Liquid Chromatograph/Mass Selective Detector (MSD) to obtain the pseudo molecular [M+H]$^+$ ion of the target molecules. Preparative HPLC was performed on a Gilson 306 HPLC system using an ACE C8 (5 μm, 21×50 mm) or Kinetex C18 (5 μm, 21×100 mm) column with 0.1% TFA in MilliQ H$_2$O/CH$_3$CN as mobile phase (Acidic systems) (flow 25 ml/min, gradient over 6 or 12 min), or Gemini-NX C18 (5 μm, 21×50 mm) with 50 mM NH$_4$HCO$_3$ in MilliQ H$_2$O/CH$_3$CN as mobile phase (basic system) (flow 25 ml/min, gradient over 12 min). Fractions were collected based on the UV-signal at 254 nm. Preparative flash chromatography was performed on Merck silica gel 60 (230-400 mesh) or YMC gel 120 Å S-150 μm. The compounds were named using the software ACD Labs 10.0 Name module.

Hydroxylamine potassium solution in MeOH was prepared according to the procedure reported by C. Blackburn et. al. (U.S. Pat. Appl. Publ. 20120015943). Hydroxylamine hydrochloride (2.0 g, 29 mmol) in methanol (10 ml) was heated at 90° C. for 15 min. Everything dissolved. KOH (2.85 g, 50.8 mmol) was dissolved in MeOH (6 ml) and added to the solution of hydroxylamine hydrochloride (white precipitate upon addition). The mixture was heated at 90° C. for 30 min. Cooled to room temperature and centrifuged. The clear solution was taken out by a syringe.

Intermediate 1

Methyl 2-(4-bromophenyl)-1,3-benzoxazole-5-carboxylate

4-Bromobenzoyl chloride (438 mg, 2.00 mmol) and methyl 3-amino-4-hydroxybenzoate (334 mg, 2.00 mmol) in dioxane (1 ml) and MeCN (1 ml) were heated at 180° C. for 6 h. White material precipitated. The material was dissolved in chloroform and sat. NaHCO$_3$ was added. The mixture was filtered through a phase separator cartridge and solvents evaporated. Yield: 587 mg (88%); white solid. MS (ESI+) m/z 332/334 [M+H]$^+$. HPLC purity: 95%. $^1$H NMR (600 MHz, DMSO-d$_6$) δ ppm 8.32 (d, J=1.5 Hz, 1H) 8.10-8.15 (m, 2H) 8.05 (dd, J=8.5, 1.8 Hz, 1H) 7.91 (d, J=8.5 Hz, 1H) 7.83 (d, J=8.5 Hz, 2H) 3.89 (s, 3H).

Intermediate 2

Methyl 2-(4-aminophenyl)-1,3-benzoxazole-5-carboxylate

Methyl 3-amino-4-hydroxybenzoate (250 mg, 1.50 mmol) and 4-nitrobenzoyl chloride (277 mg, 1.50 mmol) in MeCN (2.5 ml) and dioxane (2.5 ml) were heated at 180° C. for 6 h in a microwave reactor. The solvents were evaporated and the residue suspended in MeOH (80 ml) and EtOAc (50 ml). Palladium on charcoal (10%, 50 mg) was added and the mixture was stirred under an atmosphere of H$_2$ at 45° C. for 2 h. The mixture was filtered through Celite and solvents evaporated. Yield: 508 mg. The material was used without further purification.

Intermediate 3

Methyl 2-(6-chloropyridin-3-yl)-1,3-benzoxazole-5-carboxylate

6-Chloronicotinc acid (266 mg, 1.69 mmol) in thionyl chloride (3 ml) was heated at reflux for 1 h before the solvent was evaporated.

The acid chloride from above (99.5 mg, 0.565 mmol) and methyl 3-amino-4-hydroxybenzoate (94.5 mg, 0.565 mmol) in dioxane (1.5 ml) and MeCN (1.5 ml) were heated at 180° C. for 6 h.

The mixture was dissolved in EtOAc and filtered through silica (1 mg) and solvents evaporated. Yield: 183 mg. MS (ESI+) m/z 299 [M+H]$^+$. HPLC purity: 70%.

Intermediate 4

Methyl 2-(methylsulfanyl)-1,3-benzoxazole-5-carboxylate

Methyl 3-amino-4-hydroxybenzoate (0.47 g, 2.8 mmol), carbon disulfide (0.43 mg, 5.6 mmol) and 1 M NaOH (aq, 4.2 ml) in methanol (20 ml) were heated at 50° C. in a sealed tube overnight. Water (5 ml) and sodium bicarbonate (1 g, excess) was added followed by iodomethane (0.27 g, 4.2 mmol). The reaction mixture was stirred at 50° C. overnight. The product was collected by filtration and washed with methanol/water and dried. Yield: 0.55 g (89%), light brown solid. MS (ESI+) m/z 224 [M+H]$^+$. HPLC purity: 97%. $^1$H NMR (600 MHz, DMSO-d$_6$) δ ppm 8.13-8.17 (m, 1H) 7.95 (dd, J=8.5, 1.8 Hz, 1H) 7.77 (dd, 1H) 3.88 (s, 3H) 2.79 (s, 3H).

Intermediate 5

Ethyl 2-iodo-1,3-benzothiazole-6-carboxylate

Ethyl 2-amino-1,3-benzothiazole-6-carboxylate (50 mg, 0.24 mmol) and isoamyl nitrite (78 μl, 0.96 mmol) were dissolved in MeCN (2 ml) and cooled to 0° C. Diiodomethane (39 μl, 0.48 mmol) was added and the cooling bath was removed. The mixture was stirred at room temperature for 3 d. Water and EtOAc were added and the phases were separated. The organic layer was washed with 5% sodium thiosulfate solution and brine and dried over sodium sulfate. The organic solvents were removed in vacuo. The residue was purified by flash column chromatography using 20% EtOAc in n-heptane. Yield: 37 mg (49%); off-white solid. MS (ESI+) m/z 334 [M+H]+. $^1$H NMR (600 MHz, CDCl$_3$) δ ppm: 8.55-8.58 (m, 1H) 8.10-8.14 (m, 1H) 8.05 (dd, 1H) 4.42 (q, J=7.22 Hz, 2H) 1.42 (t, J=7.02 Hz, 3H).

Intermediate 6

Methyl 5-amino-6-hydroxypyridine-3-carboxylate

Methyl 6-hydroxy-5-nitronicotinate (200 mg, 1.01 mmol) was dissolved in abs. EtOH (10 ml) and Pd/C (107 mg, 0.101 mmol, 10% w/w) was added. The mixture was stirred at room temperature under an atmosphere of hydrogen for 16 h. The crude mixture was filtered through a pad of Celite with MeOH. The solvents were removed in vacuo to obtain a crude product that was used in the next step without further purification. Yield: 63 mg (37%); off-white solid. MS (ESI+) m/z 169 [M+H]+.

Intermediate 7

Methyl benzothiophene-5-carboxylate

Conc. H$_2$SO$_4$ (2 ml) was added to a solution of 1-benzothiophene-5-carboxylic acid (425 mg, 2.38 mmol) in MeOH (15 ml). The mixture was refluxed for 3 h. After cooling EtOAc and water were added. The organic layer was washed with water and sat. NaHCO$_3$, dried (MgSO$_4$) and evaporated. Yield: 437 mg (96%); white solid.

Intermediate 8

Methyl 2-iodobenzothiophene-5-carboxylate

A solution of methyl benzothiophene-5-carboxylate (380 mg, 1.98 mmol) in THF (16 ml) was cooled to −78° C. Freshly prepared LDA solution (4.35 ml, ca. 0.5 M in THF/hexane, 2.17 mmol) was dropwise added and the mixture was stirred for 15 min. Iodine (602 mg, 2.37 mmol) was added and the reaction was allowed to reach room temperature over a period of 4 h. 1 M HCl and DCM were added. The organic phase was washed with Na$_2$S$_2$O$_3$ solution and evaporated. The crude product was purified by flash column chromatography using 10-20% EtOAc in n-heptane as eluent. Yield: 477 mg (76%); yellow solid. MS (ESI+) m/z 319 [M+H]+.

Intermediate 9

Methyl 3-chloro-1H-indole-6-carboxylate

Methyl indole-6-carboxylate (1.75 g, 10 mmol) and N-chlorosuccinimide (1.33 g, 10 mmol) were mixed in ethyl acetate (200 ml). The reaction mixture was stirred at room temperature overnight. Water was added. The organic phase was washed with 1 M Na$_2$CO$_3$ (aq) and brine, dried over MgSO$_4$, filtered and concentrated. The remaining solid was washed with water/acetonitrile and collected by filtration. Yield: 1.45 g (70%). White solid. MS (ESI+) m/z 210 [M+H]+. HPLC purity: 100%. $^1$H NMR (600 MHz, DMSO-d$_6$) δ ppm 11.78 (br. s., 1H) 8.02-8.12 (m, 1H) 7.79 (d, J=2.75 Hz, 1H) 7.72 (dd, J=8.39, 1.37 Hz, 1H) 7.58 (d, J=8.24 Hz, 1H) 3.86 (s, 3H).

Intermediate 10

Methyl 2-bromo-3-chloro-1H-indole-6-carboxylate

Methyl 3-chloro-1H-indole-6-carboxylate, INTERMEDIATE 9 (0.55 g, 2.6 mmol) and N-bromosuccinimide (0.52 g, 2.9 mmol) were mixed in ethyl acetate (10 ml). The reaction mixture was stirred at room temperature for 3 h. Water was added. The organic phase was washed with 1 M Na$_2$CO$_3$ (aq) and brine, dried over MgSO$_4$, filtered and concentrated. The residue was purified with flash chromatography (silica, 10-30% ethyl acetate in hexane). The pure fractions were pooled and concentrated. The residue was recrystallized from water/methanol. Yield: 0.22 g (29%); brown solid. MS (ESI+) m/z 288 [M+H]+. HPLC purity: 90%. $^1$H NMR (600 MHz, DMSO-d$_6$) δ ppm 12.72 (br. s., 1H) 7.97 (s, 1H) 7.74 (dd, J=8.4, 1.4 Hz, 1H) 7.56 (d, J=8.2 Hz, 1H) 3.87 (s, 3H).

Intermediate 11

Methyl 2-chloro-1H-benzimidazole-6-carboxylate

Methyl 2-oxo-2,3-dihydro-1H-benzimidazole-5-carboxylate (4.0 g, 21 mmol) was mixed with 20 ml of phosphorus oxychloride. The reaction mixture was stirred at 90° C. for 1 h and poured into an ice/water slurry. The aqueous mixture was extracted with ethyl acetate. The organic phase was dried over MgSO$_4$, filtered and concentrated. The residue was recrystallized first from acetonitrile/water and a second time from toluene/ethyl acetate. A first crop of precipitate was discarded from the toluene/ethyl acetate solution. The title product precipitated after concentrating the mother liquid slightly. Yield: 1.6 g (36%). White solid. MS (ESI+) m/z 211 [M+H]+. HPLC purity: 97%. $^1$H NMR (600 MHz, DMSO-d$_6$) δ ppm 13.66 (br. s., 1H) 8.10 (br. s., 1H) 7.86 (d, J=7.9 Hz, 1H) 7.61 (br. s., 1H) 3.87 (s, 3H).

Intermediate 12

Methyl 2-chloro-1-methyl-1H-benzimidazole-5-carboxylate

Step 1. Methyl 3-amino-4-(methylamino)benzoate (0.91 g, 5.0 mmol) and carbonyldiimidazole (0.89 g, 5.5 mmol) were mixed in 30 ml of acetonitrile. The reaction mixture was stirred at 70° C. for 3 h. A precipitate was formed. The reaction was quenched by the addition of 20 ml of water. After cooling the intermediate methyl 1-methyl-2-oxo-2,3-dihydro-1H-benzimidazole-5-carboxylate was collected by filtration and washed with acetonitrile and water. Yield: 0.97 g (94%). Light brown solid. MS (ESI+) m/z 207 [M+H]+. HPLC purity: 100%. $^1$H NMR (600 MHz, DMSO-d$_6$) δ ppm 11.12 (br. s., 1H) 7.71 (dd, J=8.2, 1.5 Hz, 1H) 7.51 (d, J=1.8 Hz, 1H) 7.20 (d, J=8.2 Hz, 1H) 3.83 (s, 3H) 3.32 (s, 3H).

Step 2. The product from above (0.65 g, 3.2 mmol) was mixed with 5 ml of phosphorus oxychloride. The reaction mixture was stirred at 90° C. for 1 h and poured into an ice/water slurry. The aqueous mixture was extracted with ethyl acetate. The organic phase was dried over MgSO$_4$, filtered and concentrated. The residue was recrystallized from acetonitrile/water. The title product was isolated by filtration. Yield: 0.50 g (69%). Light brown solid. MS (ESI+) m/z 225 [M+H]+. HPLC purity: 100%. $^1$H NMR (600 MHz, DMSO-d$_6$) δ ppm 8.18 (d, 1H) 7.94 (dd, J=8.5, 1.8 Hz, 1H) 7.72 (d, J=8.9 Hz, 1H) 3.87 (s, 3H) 3.84 (s, 3H).

Intermediate 13

1-Benzothiophene-6-carbonitrile

To a solution of 6-bromobenzothiophene (500 mg, 2.35 mmol) in DMF (6 ml) was added Zn(CN)$_2$ (413 mg, 3.52 mmol) and Pd(PPh$_3$)$_4$ (136 mg, 0.117 mmol). The reaction was heated in the microwave to 100° C. for 30 min. The mixture was filtered through a pad of Celite with EtOAc, the solvents were removed in vacuo and the crude product was purified by flash chromatography using 10-20% EtOAc in n-heptane as eluent. Yield: 325 mg (87%); yellow solid. HPLC purity: 100%.

Intermediate 14

2-Iodo-1-benzothiophene-6-carbonitrile

A solution of 1-benzothiophene-6-carbonitrile, INTERMEDIATE 13 (230 mg, 1.45 mmol) in THF (10 mL) was cooled to −78° C. Freshly prepared LDA solution (3.47 mL, ca. 0.5 M in THF/hexane, 1.73 mmol) was dropwise added and the mixture was stirred for 15 min. Iodine (440 mg, 1.73 mmol) were added and the reaction was allowed to reach −50° C. over a period of 1.5 h. 1 M HCl and DCM were added. the organic phase was washed with Na$_2$S$_2$O$_3$ solution. The organic phase was collected and the solvents removed in vacuo and the crude product was used without further purification. Yield: 394 mg (96%). yellow solid. MS(ESI+) m/z 286 [M+H]+.

Intermediate 15

Methyl 2-(6-chloropyridin-3-yl)-1,3-benzoxazole-5-carboxylate

6-Chloronicotinic acid (1.00 g, 6.35 mmol) in thionyl chloride (5 ml) was refluxed for 1 h before solvent was evaporated. The acid chloride was used without further purifications. Methyl 3-amino-4-hydroxybenzoate, (298 mg, 1.78 mmol) and 6-chloropyridine-3-carbonyl chloride, from above (313 mg, 1.78 mmol) in dioxane (2.5 ml) and MeCN (2.5 ml) were heated at 180° C. for 6 h. Solid material precipitated. The mixture was heated in MeCN/EtOAc, filtered and the filtrate concentrated. Yield: 500 mg (97%); white solid. The material was used without further purifications.

Intermediate 16

Methyl 2-(4-bromo-2-fluorophenyl)-1,3-benzoxazole-5-carboxylate

4-Bromo-2-fluorobenzoic acid (677 mg, 3.09 mmol) in thionyl chloride (3 ml) and toluene (3 ml) was refluxed for 4 h before solvents were evaporated. Yield: 710 mg (97%); colourless oil which solidified.

The acid chloride from above (171 mg, 0.720 mmol) and methyl 3-amino-4-hydroxybenzoate (120 mg, 0.720 mmol) in dioxane (1 ml) and MeCN (1 ml) were heated at 180° C. for 6 h. Solvents were evaporated and the residue purified by flash chromatography using hexanes/EtOAc 4:1 and 2:1 as eluents. Yield: 194 mg (77%); white solid. MS(ESI+) m/z 350/352 [M+H]$^+$. HPLC purity: 100%

Intermediate 17

Methyl 2-(4-bromo-2-methoxyphenyl)-1,3-benzoxazole-5-carboxylate

4-Bromo-2-methoxybenzoic acid (535 mg, 2.32 mmol) in toluene (4 ml) and thionyl chloride (4 ml) was heated at 60° C. for 3 h before solvents were evaporated. The acid chloride was dissolved in MeCN (10 ml) and dioxane (10 ml) and methyl 3-amino-4-hydroxybenzoate (388 mg, 2.32 mmol) was added. The mixture was heated at 180° C. for 6 h. Methanesulphonic acid (300 µl) was added and the mixture heated at 180° C. for 4 h. Water and 20% THF in DCM were added. The aqueous layer was extracted with 20% THF in DCM and the combined organic layers washed with sat. NaHCO$_3$. The mixture was filtered through a phase separating cartridge and evaporated. Yield: 1.2 g. MS(ESI+) m/z 362/364 [M+H]$^+$. HPLC purity: 90%. The material was used without further purification.

Intermediate 18

Methyl 2-(4-bromo-3-fluorophenyl)-1,3-benzoxazole-5-carboxylate

Oxalyl chloride (575 µl, 6.68 mmol) was added dropwise to a solution of 4-bromo-3-fluorobenzoic acid (731 mg, 3.34 mmol) and DMF (10 µl) in THF (10 ml) and the mixture stirred at rt for 2 h before solvents were evaporated.

The acid chloride from above and methyl 3-amino-4-hydroxybenzoate (558 mg, 3.34 mmol) in dioxane (10 ml) and MeCN (10 ml) were heated at 180° C. for 6 h. The solvents were evaporated and the residue purified by flash chromatography using 5% EtOAc in toluene as eluent. Yield: 914 mg (78%); white solid. $^1$H NMR (600 MHz, DMSO-d$_6$) δ ppm 8.35 (d, J=1.22 Hz, 1H) 8.05-8.14 (m, 2H) 7.96-8.03 (m, 2H) 7.94 (d, J=8.55 Hz, 1H) 3.91 (s, 3H).

Intermediate 19

Methyl 2-chloro-1,3-benzoxazole-5-carboxylate

Methyl 3-amino-4-hydroxybenzoate (3.18 g, 19.0 mmol), carbondisulfide (1.88 ml, 38.0 mmol) and 1 M NaOH (30 ml) in MeOH (150 ml) were heated at 50° C. for 3 d. 2 M HCl (20 ml) and EtOAc were added. The aqueous layer was extracted with EtOAc, combined organic layers dried (MgSO$_4$) and evaporated. Yield: 4.74 g; white solid. Thionyl chloride (30 ml) and DMF (2 ml) were added to the residue and the mixture was stirred at ambient overnight. Solvents were evaporated, and chloroform and water were added. The aqueous layer was extracted with chloroform and the combined organic layers were evaporated and the residue purified by flash chromatography using 10-20% EtOAc in heptane as eluent. Yield: 1.53 g (38%, two steps); white solid. $^1$H NMR (600 MHz, DMSO-d$_6$) δ ppm 8.28 (d, J=1.22 Hz, 1H) 8.08 (dd, J=8.70, 1.68 Hz, 1H) 7.91 (d, J=9.16 Hz, 1H) 3.90 (s, 3H).

Intermediate 20

Methyl 2-[(benzyloxy)methyl]-1,3-benzothiazole-5-carboxylate

Benzyloxyacetyl chloride (454 mg, 2.46 mmol) and methyl 3-amino-4-fluorobenzoate (416 mg, 2.46 mmol) in toluene (25 ml) were heated at reflux for 1 h. Lawessons reagent (1.99 g, 4.92 mmol) was added and the mixture was heated at 110° C. for 8 d. Water and EtOAc were added. The aqueous layer was extracted with EtOAc and combined organic layers evaporated. The residue was purified by flash chromatography using 20% EtOAc in hexanes as eluent. Yield: 393 mg (51%); beige solid. $^1$H NMR (600 MHz, DMSO-d$_6$) δ ppm 8.48 (d, J=1.22 Hz, 1H) 8.28 (d, J=8.55 Hz, 1H) 8.01 (dd, J=8.39, 1.68 Hz, 1H) 7.26-7.47 (m, 5H) 5.02 (s, 2H) 4.73 (s, 2H) 3.91 (s, 3H).

Intermediate 21

Methyl 2-(hydroxymethyl)-1,3-benzothiazole-5-carboxylate

Methyl 2-[(benzyloxy)methyl]-1,3-benzothiazole-5-carboxylate, INTERMEDIATE 20 (360 mg, 1.15 mmol) was dissolved in DCM (10 ml) and methanesulfonic acid (3 ml) was added. The mixture was stirred at rt for 3 h. Water and DCM were added. The aqueous phase was extracted with DCM and the combined organic layers were washed with sat. NaHCO$_3$, run through a phase separator and evaporated. Yield: 286.6 mg. The material was used without further purifications.

Intermediate 22

Methyl 2-bromomethyl-1,3-benzothiazole-5-carboxylate

Phosphorous tribromide (160 µl, 1.70 mmol) was added to methyl 2-(hydroxymethyl)-1,3-benzothiazole-5-carboxylate, INTERMEDIATE 21 in toluene (15 ml) and the mixture was refluxed for 15 min. Water and EtOAc were added. The organic layer was washed with sat. NaHCO$_3$, dried (MgSO$_4$) and evaporated. The residue was purified by flash chromatography using 15% EtOAc in hexanes as eluent. Yield: 68.2 mg (20%); white solid. MS(ESI+) m/z 286/288 [M+H]$^+$. HPLC purity: 100%

Intermediate 23

Methyl 2-bromo-1-benzofuran-5-carboxylate tert-Butyldimethylsilyl trifluoromethanesulfonate (0.95 g, 3.60 mmol) was added dropwise to a solution of methyl 3-formyl-4-hydroxybenzoate (0.50 g, 2.80 mmol) and lutidine (0.60 g, 5.60 mmol) in DCM (10 ml) at 0° C. The reaction mixture was allowed to reach rt overnight. Water was added and most of DCM evaporated. Isopropyl acetate was added. The organic phase was washed with water, sat. NaHCO$_3$ and brine, dried over MgSO$_4$, filtered and concentrated. The colorless oil was purified with flash chromatography (silica, 10% ethyl acetate in hexane). Yield: 0.66 g (79%), colorless oil. $^1$H NMR (600 MHz, CDCl$_3$) δ ppm 10.45 (s, 1H) 8.49 (d, J=2.1 Hz, 1H) 8.14 (dd, J=8.9, 2.4 Hz, 1H) 6.93 (d, J=8.5 Hz, 1H) 3.91 (s, 3H) 1.03 (s, 9H) 0.32 (s, 6H).

The material from above (0.66 g, 2.20 mmol), carbon tetrabromide (1.5 g, 4.4 mmol) and triphenylphosphine (1.7 g, 6.60 mmol) were dissolved in DCM (30 ml) at 0° C. The reaction mixture was allowed to reach rt overnight. The solvent was removed under reduced pressure. Water and isopropyl acetate were added. The organic phase was washed with sodium thiosulfate (aq), sat. NaHCO$_3$, water and brine, dried over MgSO$_4$, filtered and concentrated. The residue was purified with flash chromatography (silica, 0-20% ethyl acetate in hexane). Yield: 0.96 g (95%); colourless oil. $^1$H NMR (600 MHz, CDCl$_3$) δ ppm 8.34 (d, J=2.1 Hz, 1H) 7.92 (dd, J=8.5, 2.4 Hz, 1H) 7.52 (s, 1H) 6.83 (d, J=8.5 Hz, 1H) 3.89 (s, 3H) 1.02 (s, 9H) 0.24 (s, 6H).

The material from above (0.66 g, 2.20 mmol) and TBAF hydrate (0.86 g, 3.3 mmol) in THF (30 ml) were stirred at rt for 10 min. The solvent was evaporated and the residue was partitioned between water and isopropyl acetate. The organic phase was washed with water, sat. NaHCO$_3$ and brine, dried over MgSO$_4$, filtered and concentrated. The residue was recrystallized from water/methanol. Yield: 0.57 g (77%); white solid. $^1$H NMR (600 MHz, CDCl$_3$) δ ppm 8.24 (d, J=1.8 Hz, 1H) 7.94 (dd, J=8.4, 2.0 Hz, 1H) 7.52 (s, 1H) 6.87 (d, J=8.5 Hz, 1H) 5.54 (s, 1H) 3.90 (s, 3H).

The material from above (0.25 g, 0.74 mmol), CuI (42 mg, 0.20 mmol) and trisodium phosphate (0.25 g, 1.50 mmol) in THF (10 ml) was stirred in a closed vial at 60° C. for 3 d. The mixture was filtered and concentrated and residue purified with flash chromatography (silica, 5-20% ethyl acetate in hexane). Yield: 0.18 g (96%); white solid. $^1$H NMR (600 MHz, DMSO-d$_6$) δ ppm 8.26 (d, J=1.2 Hz, 1H) 7.93 (dd, J=8.9, 1.8 Hz, 1H) 7.69-7.77 (m, 1H) 7.26 (d, J=0.9 Hz, 1H) 3.87 (s, 3H).

Intermediate 24

Methyl 2-bromo-1-benzofuran-6-carboxylate

4-Formyl-3-hydroxybenzoic acid (0.75 g, 4.5 mmol) and methanesulphonic acid (300 µl) in MeOH (20 ml) were refluxed overnight. Water was added. The mixture was allowed to cool and solid material isolated by filtration. The solid material was washed with water/MeOH and dried. Yield: 0.64 g (80%); light brown solid. $^1$H NMR (600 MHz, CDCl$_3$) δ ppm 10.95 (s, 1H) 9.99 (s, 1H) 7.59-7.71 (m, 3H) 3.95 (s, 3H).

tert-Butyldimethylsilyl trifluoromethanesulfonate (1.2 g, 4.7 mmol) was added dropwise a solution of the material from above (0.64 g, 3.6 mmol) and lutidine (0.77 g, 7.2 mmol) in DCM (20 ml) at 0° C. The reaction mixture was allowed to reach rt overnight and more tert-butyldimethylsilyl trifluoromethanesulfonate was added dropwise until complete consumption of starting material. The reaction was quenched by addition of water, most of the DCM was removed under reduced pressure. Isopropyl acetate was added and the organic phase was washed with water, sat. NaHCO$_3$ and brine, dried over MgSO$_4$, filtered and concentrated. The light brown oil was used as such in the next step.

The crude material from above (3.6 mmol), carbon tetrabromide (2.4 g, 7.2 mmol) and triphenylphosphine (2.9 g, 11.0 mmol) were mixed in DCM (50 ml) at 0° C. The reaction mixture was stirred at rt for 1 h. The reaction was quenched by the addition of sodium thiosulfate (aq) and stirred for 10 min before organic solvent was removed under reduced pressure. Isopropyl acetate was added and the organic phase was washed with water, sat. NaHCO$_3$ (aq) and brine, dried over MgSO$_4$, filtered and concentrated. The residue was purified with flash chromatography (silica, 0-10% ethyl acetate in hexane). Yield: 1.4 g (86%); colourless oil. $^1$H NMR (600 MHz, CDCl$_3$) δ ppm 7.71 (d, J=7.9 Hz, 1H) 7.64 (dd, J=7.8, 1.4 Hz, 1H) 7.58 (s, 1H) 7.46 (d, J=1.8 Hz, 1H) 3.91 (s, 3H) 1.03 (s, 9H) 0.23 (s, 6H).

The material from above (1.4 g, 3.1 mmol) and TBAF hydrate (0.17 g, 6.2 mmol) in THF (50 ml) were stirred at rt for 20 min. CuI (0.17 mg, 0.9 mmol) was added and the mixture stirred at rt for 3 d. The solvent was removed under reduced pressure and the residue partitioned between water and isopropyl acetate. The organic phase was washed with water, 1 M HCl, sat. NaHCO$_3$, brine, dried over MgSO$_4$, filtered and concentrated. The residue was purified with flash chromatography (silica, 5-20% ethyl acetate in hexane). Yield: 0.41 g (52%); white solid. $^1$H NMR (600 MHz, DMSO-d$_6$) δ ppm 8.14 (s, 1H) 7.89 (dd, J=8.2, 1.5 Hz, 1H) 7.73 (d, J=8.2 Hz, 1H) 7.27 (d, 1H) 3.88 (s, 3H).

Example 1

N-Hydroxy-2-[4-(1-methylethyl)phenyl]-1,3-benzoxazole-5-carboxamide

General Procedure A

Methyl 3-amino-4-hydroxybenzoate (35.0 mg, 0.209 mmol) and 4-isopropylbenzoyl chloride (38.2 mg, 0.209 mmol) in dioxane (1 ml) and MeCN (1 ml) was heated at 180° C. for 6 h in a microwave reactor. Solvents were evaporated and hydroxylamine potassium salt in MeOH (ca. 1.7 M, 3 ml) was added. The mixture was heated at 60° C. for 1 h before quenched with AcOH (1.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 31.5 mg (51%, two steps); white solid.

Example 17

2-[4-(Difluoromethoxy)phenyl]-N-hydroxy-1,3-benzoxazole-5-carboxamide

General Procedure B

Methyl 3-amino-4-hydroxybenzoate (22 mg, 0.131 mmol) and 4-difluoromethoxy)benzaldehyde (0.131 mmol) in EtOH (2 ml) were heated at 70° C. overnight. Solvent was evaporated and the residue dissolved in DCM (2 ml). DDQ (30 mg, 0.131 mmol) was added and the mixture was stirred at ambient temperature for 1 h. Sat. NaHCO$_3$ (2 ml) and DCM (5 ml) were added. The organic layer was filtered through a short plug of silica (1 g) which was eluted with EtOA and the solvents evaporated.

Hydroxylamine potassium salt solution (ca 1.7 M in MeOH, 2 ml) was added to the crude material from above. The mixture was stirred at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 2.5 mg (6%); white solid.

Example 21

2-(2'-Fluorobiphenyl-4-yl)-N-hydroxy-1,3-benzoxazole-5-carboxamide

General Procedure C

PEPPSI-iPr™ (ca 2 mg) was added to a nitrogen flushed mixture of methyl 2-(4-bromophenyl)-1,3-benzoxazole-5-carboxylate, INTERMEDIATE 1 (26.0 mg, 0.0783 mmol), 2-fluorobenzeneboronic acid (16.4 mg, 0.117 mmol) and K$_2$CO$_3$ (21.6 mg, 0.157 mmol) in toluene (1 ml) and MeOH (1 ml). The mixture was heated at 100° C. for 30 min in microwave reactor, diluted with EtOAc and filtered through a short plug of silica (1 g). Solvents were evaporated and freshly prepared hydroxylamine potassium salt in MeOH (ca 1.7 M, 1.5 ml) was added to the residue. The mixture was heated at 60° C. for 1 h before quenched with AcOH (0.5 ml). The product was isolated by reversed phase chromatography (Kinetex C18, 5 µm, 21.2×100 mm, flow 25 ml/min, gradient 0.1% TFA in water/acetonitrile over 15 minutes). Yield: 8.1 mg (30%); white solid.

Example 29

2-(4-Cyclopropylphenyl)-N-hydroxy-1,3-benzoxazole-5-carboxamide

Palladium acetate (2 mg, 0.009 mmol) was added to a nitrogen flushed mixture of methyl 2-(4-bromophenyl)-1,3-benzoxazole-5-carboxylate, INTERMEDIATE 1 (36 mg, 0.100 mmol), cyclopropylboronic acid (13 mg, 0.150 mmol), K$_3$PO$_4$.H$_2$O (69 mg, 0.300 mmol) and tricyclohexylphosphine (5.2 mg, 0.018 mmol) in toluene (2 ml) and water (100 µl). The mixture was heated at 130° C. for 2 h in a microwave reactor. The mixture was diluted with EtOAc and filtered through a short plug of silica (1 g). The solvents were evaporated and hydroxylamine potassium salt in MeOH (ca 1.7 M, 2 ml) was added to the residue. The mixture was heated at 60° C. for 1 h before quenched with AcOH (1 ml) and the title compound isolated by reversed phase chromatography (Kinetex C18, 5 µm, 21.2×100 mm, flow 25 ml/min, gradient 0.1% TFA in water/acetonitrile over 15 minutes). Yield: 20.1 mg (68%, two steps); white solid.

Example 30

N-Hydroxy-2-[4'-(piperidin-1-ylmethyl)biphenyl-4-yl]-1,3-benzoxazole-5-carboxamide trifluoroacetate PEPPSI-iPr™ (2 mg) was added to a nitrogen flushed mixture of methyl 2-(4-bromophenyl)-1,3-benzoxazole-5-carboxylate, INTERMEDIATE 1 (110 mg, 0.331 mmol), 4-formylphenylboronic acid (60 mg, 0.397 mmol) and K$_2$CO$_3$ (69 mg 0.497 mmol) in MeOH (2 ml) and toluene (2 ml). The mixture was heated at 100° C. for 30 min in a microwave reactor. White solid precipitated. The solid was washed with water and MeOH and dried. Yield: 87 mg (74%); grey solid. MS (ESI+) m/z 358 [M+H]$^+$. HPLC purity: 100%. $^1$H NMR (600 MHz, DMSO-d$_6$) δ ppm 10.07 (s, 1H) 8.29-8.41 (m, 3H) 7.99-8.14 (m, 7H) 7.94 (d, J=8.5 Hz, 1H) 3.90 (s, 3H).

Sodium triacetoxyborohydride (18.2 mg, 0.086 mmol) was added to a suspension of the material from above (20.5 mg, 0.0573 mmol) and piperidine (8.5 µl, 0.086 mmol) in THF (2 ml). The mixture was stirred at ambient temperature for one week. The solvent was evaporated and hydroxylamine potassium salt in MeOH (ca 1.7 M, 1.5 ml) was added. The mixture was stirred at 60° C. for 1 h before quenched with AcOH (0.5 ml) and product isolated by reversed phase chromatography (Kinetex C18, 5 µm, 21.2×100 mm, flow 25 ml/min, gradient 0.1% TFA in water/acetonitrile over 15 minutes). Yield: 8.0 mg (26%, two steps); white solid.

Example 31

2-(4-Aminophenyl)-N-hydroxy-1,3-benzoxazole-5-carboxamide trifluoroacetate

Freshly prepared hydroxylamine potassium salt solution (ca 1.7 M in MeOH, 1.5 ml) was added to methyl 2-(4-aminophenyl)-1,3-benzoxazole-5-carboxylate, INTERMEDIATE 2 (21.5 mg, 0.080 mmol) and the mixture was heated at 60° C. for 1 h before quenching with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 7.0 mg (23%); white solid.

Example 32

2-(2-Chloro-6-fluorophenyl)-N-hydroxy-1,3-benzoxazole-5-carboxamide

Methyl 3-amino-4-hydroxybenzoate (28.8 mg, 0.172 mmol) and 2-chloro-3-fluorobenzoyl chloride (33.3 mg, 0.172 mmol) in dioxane (1 ml) and MeCN (1 ml) were heated at 210° C. for 30 min in a microwave reactor. Methansulphonic acid (20 µl) was added and mixture heated at 210° C. for 3 h. Solvents were evaporated and residue purified by flash chromatography using hexanes/EtOAc 4:1 as eluent. Yield: 23 mg (44%); white solid. Hydroxylamine potassium salt in MeOH (ca 1.7 M, 1.5 ml) was added to the material from above and the mixture heated at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 4.1 mg (18%); white solid.

Example 33

2-[4-(Diethylamino)phenyl]-N-hydroxy-1,3-benzoxazole-5-carboxamide trifluoroacetate Methyl 3-amino-4-hydroxybenzoate (24.2 mg, 0.145 mmol) and 4-diethylaminobenzaldehyde (25.6 mg, 0.145 mmol) in water (700 µl) and toluene (700 µl) were heated at 120° C. for 36 h in a sealed tube. Solvents were evaporated and residue purified by flash chromatography using hexanes/EtOAc 2:1 as eluent. Yield: 21 mg (44%).

Hydroxylamine potassium salt (ca 1.7 M in MeOH, 1 ml) was added to the product from above and the mixture heated at 60° C. for 20 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: Yield: 11.9 mg (42%); yellow oil.

Example 34

2-(2,6-Dichlorophenyl)-N-hydroxy-1,3-benzoxazole-5-carboxamide

Methyl 3-amino-4-hydroxybenzoate (28.5 mg, 0.170 mmol) and 2,6-dichlorobenzoyl chloride (35.7 mg, 0.170 mmol) in dioxane (1 ml) and MeCN (1 ml) were heated at 180° C. for 20 min in a microwave reactor. Methanesulphonic acid (20 µl) was added and heating continued for 6 h at 180° C. The mixture was diluted with $CHCl_3$ (10 ml) and filtered though silica (0.5 g). To the material from above was added hydroxylamine potassium salt (ca 1.7 M in MeOH, 1.5 ml) and the mixture was heated at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 25.9 mg (47%, two steps); white solid.

Example 35

N-Hydroxy-2-pyridin-2-yl-1,3-benzoxazole-5-carboxamide trifluoroacetate

HATU (116 mg, 0.305 mmol) was added to picolinic acid (37.5 mg, 0.305 mmol) and DIPEA (66 µl, 0.381 mmol) in DMF (2 ml). After 15 min, methyl 3-amino-4-fluorobenzoate (43 mg, 0.254 mmol) in DMF (1 ml) was added. The mixture was stirred at ambient temperature for 10 d before solvent was evaporated and residue dissolved in EtOAc. The solution was washed with sat. $NaHCO_3$, dried ($MgSO_4$) and evaporated.

Half of the crude material from above (0.127 mmol) was dissolved in dioxane (1.5 ml) and MeCN (1.5 ml). Potassium carbonate (35 mg, 0.254 mmol) was added and the mixture was heated at 180° C. for 2 h in a microwave reactor. Silica gel was added and solvents evaporated. The dry silica was applied on a flash column which was eluted with 35-50% EtOAc in hexanes. Yield: 6 mg (18%); colourless oil.

Hydroxylamine potassium salt in MeOH (ca 1.7 M, 1.5 ml) was added to the material from above and the mixture was heated at 60° C. for 45 min before quenched with AcOH (0.5 ml) and purified by reversed phase chromatography (Kinetex C18, 5 µm, 21.2×100 mm, flow 25 ml/min, gradient 0.1% TFA in water/acetonitrile over 15 minutes). Yield: 1.9 mg; colourless oil.

Example 36

2-(4-Cyanophenyl)-N-hydroxy-1,3-benzoxazole-5-carboxamide

Methyl 3-amino-4-hydroxybenzoate (321 mg, 1.92 mmol) and 4-cyanobenzoyl chloride (318 mg, 1.92 mmol) in dioxane (2 ml) and acetonitrile (2 ml) were heated at 180° C. for 8 h in a microwave reactor. The precipitate was filtered and recrystallized from MeCN. Yield: 338 mg (64%); white solid. MS (ESI+) m/z 279 $[M+H]^+$. HPLC purity: 95%.

The material from above (70.7 mg, 0.254 ml) in dioxane (500 µl) and 1 M NaOH (254 µl) was heated at 60° C. for overnight. Water and EtOAc were added. Organic layer was removed and aqueous layer acidified using 1 M HCl. The aqueous layer was extracted with EtOAc and the organic layer evaporated and dried under high vacuum. Yield: 48.4 mg (72%); white solid.

HATU (30.4 mg, 0.080 mmol) was added to a solution of the material from above (16.2 mg, 0.061 mmol), O-(tetrahydropyran-2-yl)-hydroxylamine (9.3 mg, 0.080 mmol) and DIPEA (16.7 µl, 0.096 mmol) in DMF (0.8 ml). The mixture was stirred at rt for 2 h before TFA (300 µl) and water (150 µl) were added and the mixture stirred at 50° C. for 1 h before the title compound was isolated by reversed phase chromatography (Kinetex C18, 5 µm, 21.2×100 mm, flow 25 ml/min, gradient 0.1% TFA in water/acetonitrile over 15 minutes). Yield: 8.7 mg (51%); white solid.

Example 37

N-Hydroxy-2-{4-[(methylsulfonyl)amino]phenyl}-1,3-benzoxazole-5-carboxamide Methanesulfonyl chloride (0.100 mmol) was added to a solution of methyl 2-(4-aminophenyl)-1,3-benzoxazole-5-carboxylate, INTERMEDIATE 2 (22 mg, 0.085 mmol) and triethylamine (25 µl, 0.200 mmol) in THF (1.5 ml) and pyridine (0.5 ml). The mixture was stirred at ambient temperature overnight and solvents evaporated. Hydroxylamine potassium salt in MeOH (ca 1.7 M, 1.5 ml) was added and the mixture heated at 60° C. for 30 min before quenched with AcOH (0.5 ml). The product was purified by reversed phase chromatography (Kinetex C18, 5 µm, 21.2×100 mm, flow 25 ml/min, gradient 0.1% TFA in water/acetonitrile over 15 minutes). Yield: 6.4 mg (22%, two steps); white solid.

Example 38

N-Hydroxy-2-{4-[(phenylsulfonyl)amino]phenyl}-1,3-benzoxazole-5-carboxamide Benzenesulfonyl chloride (0.100 mmol) was added to a solution of methyl 2-(4-aminophenyl)-1,3-benzoxazole-5-carboxylate, INTERMEDIATE 2 (22 mg, 0.085 mmol) and triethylamine (25 µl, 0.200 mmol) in THF (1.5 ml) and pyridine (0.5 ml). The mixture was stirred at ambient temperature overnight and solvents evaporated. Hydroxylamine potassium salt in MeOH (ca 1.7 M, 1.5 ml) was added and the mixture heated at 60° C. for 30 min before quenched with AcOH (0.5 ml). The product was purified by reversed phase chromatography (Kinetex C18, 5 μm, 21.2× 100 mm, flow 25 ml/min, gradient 0.1% TFA in water/acetonitrile over 15 minutes). Yield: 12.3 mg (35%, two steps); white solid.

Example 39

2-(1H-Benzotriazol-5-yl)-N-hydroxy-1,3-benzoxazole-5-carboxamide

Benzotriazole-5-carboxylic acid (99 mg, 0.540 mmol) in thionyl chloride (3 ml) was refluxed for 1 h before solvent was evaporated.

Methyl 3-amino-4-hydroxybenzoate (31.2 mg, 0.187 mmol) and the acid chloride from above (33.8 mg, 0.187 mmol) in dioxane (1.5 ml) and acetonitrile (1.5 ml) were heated at 180° C. for 6 h in a microwave reactor. The mixture was diluted with EtOAc and filtered through a short plug of silica (1 g) and solvents evaporated.

Hydroxylamine potassium salt in MeOH (ca 1.7 M, 2 ml) was added to the residue from above and the mixture heated at 60° C. for 45 min before quenched with AcOH (1 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 5.5 mg (10%); white solid.

Example 40

N-Hydroxy-2-(2-methylpyridin-3-yl)-1,3-benzoxazole-5-carboxamide trifluoroacetate 2-Methylnicotinic acid (100 mg, 0.730 mmol) in thionyl chloride (3 ml) was heated at reflux for 1 h before solvent was evaporated.

Methyl 3-amino-4-hydroxybenzoate (32.4 mg, 0.194 mmol) and the acid chloride from above (30.2 mg, 0.194 mmol) in dixoane (1.5 ml) and acetonitrile (1.5 ml) were heated at 180° C. for 6 h. Methanesulfonic acid (50 μl) was added and the mixture heated at 180° C. for 2 h. The solvents were evaporated and hydroxylamine potassium salt in MeOH (ca 1.7 M, 2 ml) was added. The mixture heated at 60° C. for 45 min before quenched with AcOH (1 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 14.0 mg (19%, two steps); white solid.

Example 41

N-Hydroxy-2-(6-pyrrolidin-1-ylpyridin-3-yl)-1,3-benzoxazole-5-carboxamide trifluoroacetate Methyl 2-(6-chloropyridin-3-yl)-1,3-benzoxazole-5-carboxylate, INTERMEDIATE 3 (50 mg, 0.173 mmol) and pyrrolidine (43 μl, 0.520 mmol) in dioxane (1.5 ml) and MeCN (1.5 ml) were heated at 150° C. for 20 min in a microwave reactor. Solvents were evaporated and product isolated by flash chromatography using 35-50% EtOAc in hexanes. Yield: 14.2 mg Hydroxylamine potassium salt in MeOH (ca 1.7 M, 1.5 ml) was added to the material from above and the mixture was stirred at 60° C. for 45 min before quenched with AcOH (0.5 ml). The title compound was isolated by reversed phase chromatography (Kinetex C18, 5 m, 21.2×100 mm, flow 25 ml/min, gradient 0.1% TFA in water/acetonitrile over 15 minutes). Yield: 10.8 mg (14%, two steps); white solid.

Example 42

N-Hydroxy-2-(phenylamino)-1,3-benzoxazole-5-carboxamide

General Procedure D

Methyl 2-(methylsulfanyl)-1,3-benzoxazole-5-carboxylate, INTERMEDIATE 4 (11 mg, 0.050 mmol) and aniline (0.075 mmol) in 1,3-dimethyl-2-imidazolidinone (400 μl) were heated at 120° C. for 4 days. The reaction mixture was diluted with methanol/water and purified with reversed phase chromatography (Gemini-NX, C18, 5 μm, 21×100 mm, flow 25 ml/min, gradient: water (50 mM ammonium bicarbonate, pH 10)/acetonitrile over 15 minutes). The pure fractions were combined, concentrated and dried in vacuum.

The residue was dissolved in methanol (500 μl). Hydroxylamine solution (50% w/w in water, 500 μl) and potassium hydroxide (10 mg/ml in methanol, 500 μl) were added. The reaction mixture was stirred at 60° C. for 1 h before being quenched with AcOH (500 μl). The title compound was isolated by reversed phase chromatography (Kinetex C18, 5 μm, 21.2×100 mm, flow 25 ml/min, gradient 0.1% TFA in water/acetonitrile over 15 minutes). Yield: 4 mg (30%, two steps); white solid.

Example 49

N-Hydroxy-2-[4-(1-methylethyl)phenyl]-1,3-benzoxazole-6-carboxamide

Methyl 4-amino-3-hydroxybenzoate (50 mg, 0.30 mmol) and 4-(1-methylethyl)benzoyl chloride (55 mg, 0.30 mmol) were placed in a microwave vial and dissolved in 1,4-dioxane (1 ml). The mixture was heated in the microwave reactor to 120° C. for 20 min. Phosphoroxy chloride (84 μl, 0.90 mmol) was added and the mixture was heated in the microwave for an additional 30 min at 130° C. The mixture was filtered through a pad of silica (1 g) with EtOAc. The organic solvents were removed in vacuo. The compound was purified by flash column chromatography using 20% EtOAc in n-heptane as eluent. Yield: 44 mg (50%); white solid. MS (ESI+) m/z 296 [M+H]+.

Methyl 2-[4-(1-methylethyl)phenyl]-1,3-benzoxazole-6-carboxylate from above (33 mg, 0.112 mmol) was dissolved in MeOH/water (3 ml/1 ml) and lithium hydroxide monohydrate (27 mg, 1.12 mmol) was added. The mixture was heated to 50° C. for 18 h. The mixture was acidified by 1M HCl and DCM was added. The phases were separated, the organic phase collected and evaporated. The crude compound was used in the next step without further purification. Yield: 31 mg (99%); white solid. MS (ESI+) m/z 282 [M+H]+.

2-[4-(1-Methylethyl)phenyl]-1,3-benzoxazole-6-carboxylic acid from above (30 mg, 0.107 mmol) and triethylamine (30 μl, 0.213 mmol) were dissolved in acetonitrile (3 ml). HATU (61 mg, 0.16 mmol) was added and the mixture was stirred for 30 min before O-(tetrahydropyran-2-yl)-hydroxylamine (25 mg, 0.213 mmol) was added and the mixture was stirred for 1 h at 50° C. TFA (150 μl) was added and stirring was continued for 3 h at 50° C. The title compound was isolated by reversed phase chromatography (Kinetex C18, 5 μm, 21.2×100 mm, flow 25 ml/min, gradient 0.1% TFA in water/acetonitrile over 15 minutes). Yield: 14 mg (44%); white solid.

Example 50

2-(4-Fluorophenyl)-N-hydroxy-1,3-benzoxazole-6-carboxamide

General Procedure E

Methyl 4-amino-3-hydroxybenzoate (18.0 mg, 0.108 mmol) and 4-fluorobenzoyl chloride (17.1 mg, 0.108 mmol) in dioxane (1 ml) and MeCN (1 ml) were heated at 180° C. for 6 h in microwave reactor. Methanesulfonic acid (20 µl) was added and heating at 180° C. continued for 4 h. Solvents were evaporated and the residue in toluene was filtered though a short plug of silica using 20% EtOAc in hexanes as eluent. Solvents were evaporated and hydroxylamine potassium salt in MeOH (ca. 1.7 M, 1.5 ml) was added. The mixture was heated at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 3.8 mg (13%, two steps); white solid.

Example 53

2-(6-Chloropyridin-3-yl)-N-hydroxy-1,3-benzoxazole-6-carboxamide

6-Chloronicotinic acid (266 mg, 1.69 mmol) in thionyl chloride (3 ml) was heated at reflux for 1 h before solvent was evaporated.

Methyl 4-amino-3-hydroxybenzoate (46 mg, 0.275 mmol) and the acid chloride from above (48.4 mg, 0.275 mmol) in dioxane (1.5 ml) and MeCN (1.5 ml) were heated at 180° C. for 2 h. EtOAc was added to the mixture and the solution was filtered through silica (1 g). Yield: 76 mg. MS (ESI+) m/z 289 [M+H]$^+$.

Hydroxylamine in water (50%, 0.5 ml) and potassium hydroxide (5 mg/ml, 1 ml) was added to the crude material from above (21.4 mg). The mixture was heated at 60° C. overnight before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 2.0 mg.

Example 54

2-(1H-Benzotriazol-5-yl)-N-hydroxy-1,3-benzoxazole-6-carboxamide

Benzotriazole-5-carboxylic acid (99 mg, 0.540 mmol) in thionyl chloride (3 ml) was refluxed for 1 h before solvent was evaporated.

Methyl 4-amino-3-hydroxybenzoate (24.9 mg, 0.149 mmol) and the acid chloride from above (27.0 mg, 0.149 mmol) in dioxane (1.5 ml) and acetonitrile (1.5 ml) was heated at 180° C. for 6 h in a microwave reactor. The mixture was diluted with EtOAc and filtered through silica (1 g) and solvents evaporated.

Hydroxylamine potassium salt in MeOH (ca 1.7 M, 2 ml) was added to the residue from above and the mixture heated at 60° C. for 45 min before quenched with AcOH (1 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 6.7 mg (15%); white solid.

Example 55

2-(2,3'-Bipyridin-5-yl)-N-hydroxy-1,3-benzoxazole-6-carboxamide trifluoroacetate

6-Chloronicotinic acid (266 mg, 1.69 mmol) in thionyl chloride (3 ml) was heated at reflux for 1 h before solvent was evaporated.

Methyl 4-amino-3-hydroxybenzoate (46 mg, 0.275 mmol) and the acid chloride from above (48.4 mg, 0.275 mmol) in dioxane (1.5 ml) and MeCN (1.5 ml) were heated at 180° C. for 2 h.

EtOAc was added to the mixture and the solution was filtered through silica (Ig). Yield: 76 mg. MS (ESI+) m/z 289 [M+H]$^+$. HPLC purity: 70%

PEPPSI-iPr™ (ca 5 mg) was added to a nitrogen flushed mixture of the material from above (50 mg, 0.175 mmol), 3-pyridine boronic acid (26 mg, 0.208 mmol) and K$_2$CO$_3$ (0.350 mmol) in toluene (1 ml) and MeOH (1 ml). The mixture was heated at 100° C. for 30 min in a microwave reactor before water and EtOAc were added. The organic phase was separated and intermediate isolated by flash chromatography using 35-100% EtOAc in hexanes as eluent. Yield: 6.9 mg (12%); white solid.

Hydroxylamine potassium salt in MeOH (ca 1.7 M, 1.5 ml) was added to the material from above and the mixture was heated at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes. Yield: Yield: 3.8 mg (5%, two steps); white solid.

Example 56

N-Hydroxy-2-[4-(1-methylethyl)phenyl]-1H-imidazo[4,5-c]pyridine-6-carboxamide

4-Isopropylbenzaldehyde (33 mg, 0.224 mmol) in DMF (1 ml) was added dropwise to a solution of methyl 4,5-diaminopyridine-2-carboxylate (25 mg, 0.15 mmol) and methanesulfonic acid (5 µl, 0.075 mmol) in DMF (1 ml) at 90° C. in an open flask. After 24 h the solvent was removed in vacuo. Water and DCM were added and the phases were separated. The organic phase was collected and the solvents were removed in vacuo. The crude product was used in the next step without further purification.

The material from above (20 mg, 0.068 mmol) in MeOH (0.5 ml) was added KOH in MeOH (10 mg/ml, 0.5 ml) and 50% hydroxylamine in water (1 ml). The mixture was stirred at 60° C. for 3 h before the product was isolated by reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 12.5 mg (62%); white solid.

Example 57

N-Hydroxy-2-[4-(1-methylethyl)phenyl]-1H-imidzo[4,5-b]pyridine-6-carboxamide

To methyl 6-chloro-5-nitropyridine-3-carboxylate (200 mg, 0.92 mmol) was added a 2 M solution of ammonia in EtOH (1.85 ml, 3.69 mmol) at 0° C. The cooling bath was removed and the mixture was stirred for 3 h. The solvents were removed in vacuo and the crude product taken to the next step. Yellow solid. MS (ESI+) m/z 198 [M+H]+.

Methyl 6-amino-5-nitropyridine-3-carboxylate from above (182 mg, 0.92 mmol) was dissolved in abs. EtOH (5 ml) and EtOAc (1 ml) and Pd/C (98 mg, 0.092 mmol, 10% w/w) was added. The mixture was stirred at room temperature under an atmosphere of hydrogen for 1 h. The crude mixture was filtered through a pad of Celite with EtOAc. The solvents were removed in vacuo to obtain a crude product that was used in the next step without further purification. Yield: 180 mg (quant.); yellow solid. MS (ESI+) m/z 168 [M+H]+. $^1$H NMR (600 MHz, CD$_3$OD) δ ppm 8.03 (d, J=1.83 Hz, 1H) 7.38 (d, J=2.14 Hz, 1H) 3.83 (s, 3H). 4-Isopropylbenzaldehyde (67 mg, 0.45 mmol) in DMF (1.5 ml) was added dropwise to a solution of methyl 5,6-diaminopyridine-3-carboxylate from above (50 mg, 0.30 mmol) and methanesulfonic acid (10 µl, 0.15 mmol) in DMF (1.5 ml) at 80° C. in an open flask. The mixture was stirred for 24 h. The solvent was removed in vacuo. Water and DCM were added and the phases were separated. The organic phase was collected and the solvents were removed in vacuo. The crude product was used in the next step without further purification. Yield: 51 mg (58%); yellow solid. MS (ESI+) m/z 296 [M+H]+.

The material above (15 mg, 0.051 mmol) in MeOH (0.4 ml) was added a KOH-solution (10 mg/ml in MeOH, 0.4 ml) and hydroxyl amine (50% w/w in water, 0.8 ml). The mixture was stirred for 4 h at 60° C. and at rt overnight. The title compound was isolated by reversed phase chromatography (Kinetex C18, 5 µm, 21.2×100 mm, flow 25 ml/min, gradient 0.1% TFA in water/acetonitrile over 15 minutes). Yield: 6.5 mg (43%); white solid.

Example 58

N-Hydroxy-2-[4-(1-methylethyl)phenyl]-1H-imidazo[4,5-c]pyridine-6-carboxamide

Methyl 6-amino-5-nitropyridine-2-carboxylate (60 mg, 0.304 mmol) was dissolved in abs. EtOH (5 ml) and Pd/C (31 mg, 0.030 mmol, 10% w/w) was added. The mixture was stirred at room temperature under an atmosphere of hydrogen for 16 h. The crude mixture was filtered through a pad of Celite with EtOAc. The solvents were removed in vacuo to obtain a crude product that was used in the next step without further purification. Yield: 61 mg (quant.).

4-Isopropylbenzaldehyde (40 mg, 0.27 mmol) in DMF (0.75 ml) was added dropwise to a solution of methyl 2,3-diaminopyridine-6-carboxylate from above (30 mg, 0.179 mmol) and methanesulfonic acid (6 µl, 0.09 mmol) in DMF (0.75 ml) at 80° C. in an open flask. The mixture was stirred for 2 h (monitored by LCMS). The solvent was removed in vacuo. Water and DCM were added and the phases were separated. The organic phase was collected and the solvents were removed in vacuo. The crude product was used in the next step without further purification. Yellow solid. MS (ESI+) m/z 296 [M+H]+.

To methyl 2-[4-(1-methylethyl)phenyl]-3H-imidazo[4,5-b]pyridine-5-carboxylate from above (20 mg, 0.068 mmol) in MeOH (0.5 ml) was added a KOH-solution (10 mg/ml in MeOH, 0.5 ml) and hydroxyl amine (50% w/w in water, 1.0 ml). The mixture was stirred for 90 min at 60° C. and at rt overnight. The title compound was isolated by reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 2 mg (10%); white solid.

Example 59

N-Hydroxy-2-[4-(1-methylethyl)phenyl]-1H-indole-6-carboxamide

A solution of methyl 3-amino-4-iodobenzoate (115 mg, 0.415 mmol) and triethylamine (116 µl, 0.83 mmol) in DCM (3 ml) was added dropwise to a cooled (0° C.) solution of trifluoroacetic acid anhydride (147 µl, 1.04 mmol) in DCM (1 ml). The cooling bath was removed and the mixture was stirred for 2 h. The crude product was poured into cold water and DCM was added. The phases were separated. The solvents were removed in vacuo and the crude product taken to the next step without further purification. Yield: 150 mg (96%); beige solid. MS (ESI+) m/z 374 [M+H]+. HPLC purity: 100%. $^1$H NMR (600 MHz, CDCl$_3$) δ ppm 8.76 (d, J=1.83 Hz, 1H) 8.30 (br. s., 1H) 7.95 (d, J=8.24 Hz, 1H) 7.64 (dd, J=8.24, 2.14 Hz, 1H) 3.93 (s, 3H).

A mixture of methyl 4-iodo-3-[(trifluoroacetyl)amino]benzoate from above (25 mg, 0.067 mmol), 1-ethynyl-4-(1-methylethyl)benzene (14.5 mg, 0.080 mmol), copper(I)-iodide (1.3 mg, 0.007 mmol), L-proline (2.3 mg, 0.020 mmol) and potassium carbonate (18.5 mg, 0.134 mmol) in DMF (0.5 ml) was heated in a sealed tube at 80° C. for 20 h. The crude product was poured into water and DCM was added. The water phase was extracted twice with DCM. The combined organic layers were evaporated and the crude product was purified by flash column chromatography using 20% EtOAc in n-heptane as eluent. Yield: 11 mg; white solid. MS (ESI+) m/z 294 [M+H]+. HPLC purity: 50%.

The material from above (5 mg, 0.017 mmol) in MeOH (1 ml) was added KOH in MeOH (10 mg/ml, 0.5 ml) and 50% hydroxylamine in water (0.75 ml) and the mixture was heated at 60° C. for 19 h. The title compound was isolated by reversed phase chromatography (Kinetex C18, 5 µm, 21.2×100 mm, flow 25 ml/min, gradient 0.1% TFA in water/acetonitrile over 15 minutes). Yield: 2 mg (40%); white solid.

Example 60

N-Hydroxy-2-[4-(1-methylethyl)phenyl]-1H-indole-5-carboxamide

A solution of methyl 4-amino-3-iodobenzoate (100 mg, 0.36 mmol) and triethylamine (101 µl, 0.72 mmol) in DCM (3 ml) was added dropwise to a cooled (0° C.) solution of trifluoroacetic acid anhydride (127 µl, 0.90 mmol) in DCM (1 ml). The cooling bath was removed and the mixture was stirred for 1.5 h. The crude product was poured into cold water and DCM was added. The phases were separated; solvents were removed in vacuo and the crude product taken to the next step without further purification. Yield: 129 mg (96%); white solid. MS (ESI+) m/z 374 [M+H]+. HPLC purity: 96%. $^1$H NMR (600 MHz, CDCl$_3$) δ ppm 8.51 (d, J=1.83 Hz, 1H) 8.47 (br. s., 1H) 8.36 (d, J=8.54 Hz, 1H) 8.08 (dd, J=8.85, 1.83 Hz, 1H) 3.93 (s, 3H).

A mixture of methyl 3-iodo-4-[(trifluoroacetyl)amino]benzoate from above (25 mg, 0.067 mmol), 1-ethynyl-4-(1-methylethyl)benzene (14.5 mg, 0.101 mmol), copper(I)-iodide (2.6 mg, 0.013 mmol), Pd(PPh$_3$)$_2$Cl$_2$ (4.7 mg, 0.007 mmol) and diethylamine (20 µl, 0.101 mmol) in DMF (0.5 ml) was heated in a sealed tube at 80° C. for 20 h. The mixture was poured into water and DCM was added. The water phase was extracted with DCM. The combined organic layers were evaporated and the crude product was purified by flash column chromatography using 20% EtOAc in n-heptane as eluent Yield: 13 mg (66%); white solid. MS (ESI+) m/z 294 [M+H]+. HPLC purity: 89%.

The material from above (13 mg, 0.044 mmol) in MeOH (0.5 ml) was added KOH in MeOH (10 mg/ml, 0.5 ml) and 50% hydroxylamine in water (1 ml). The mixture was stirred at 60° C. before the title compound was isolated by reversed phase chromatography (Kinetex C18, 5 µm, 21.2×100 mm, flow 25 ml/min, gradient 0.1% TFA in water/acetonitrile over 15 minutes). Yield: 4.5 mg (34%); off-white solid.

Example 61

N-Hydroxy-2-[4-(1-methylethyl)phenyl]-1,3-benzoxazole-6-carboxamide

Ethyl 2-iodo-1,3-benzothiazole-6-carboxylate, INTERMEDIATE 5 (15 mg, 0.045 mmol), Pd(PPh$_3$)$_4$ (5.2 mg, 0.005 mmol), 4-isopropylphenylboronic acid (11.1 mg, 0.068 mmol) and potassium carbonate (12.4 mg, 0.090 mmol) were place in a microwave vial. 1,4-dioxane/water (0.6 ml/0.15 ml) were added and the mixture was heated in a microwave reactor for 30 min at 140° C. The mixture was filtered through a pad of silica (1 g) with EtOAc. The organic solvents were removed in vacuo. The crude compound was used in the next step without further purification. MS (ESI+) m/z 298.

HATU (27 mg, 0.071 mmol) was added to a mixture of the material from above (14 mg, 0.047 mmol) and triethylamine (13 µl, 0.094 mmol) in MeCN (0.5 ml). O-(Tetrahydropyran-2-yl)-hydroxylamine (11 mg, 0.094 mmol) in MeCN (0.5 ml) was added and the mixture stirred for 2 h at 50° C. before TFA in water (0.1 M, 250 µl) and TFA (20 µl) were added. The mixture was stirred at 50° C. for 2 h before the title compound was isolated by reversed phase chromatography (Kinetex C18, 5 µm, 21.2×100 mm, flow 25 ml/min, gradient 0.1% TFA in water/acetonitrile over 15 minutes). Yield: 2.0 mg (14%, 2 steps); white solid.

Example 62

2-(1,3-Benzodioxol-5-yl)-N-hydroxy-1,3-benzothiazole-6-carboxamide

General Procedure F

Ethyl 2-iodo-1,3-benzothiazole-6-carboxylate INTERMEDIATE 5 (20 mg, 0.060 mmol) and 1,3-benzodioxole-5-boronic acid (14.9 mg, 0.090 mmol) in DME (0.6 ml) and water (0.15 ml) was added Pd(PPh$_3$)$_4$ (3.5 mg, 0.003 mmol) and K$_2$CO$_3$ (17 mg, 0.120 mmol) and the mixture was heated at 100° C. for 30 min in a microwave reactor. The mixture was filtered through a short plug of silica (1 g) and solvents evaporated. KOH in MeOH (5 mg/ml, 0.8 ml) and 50% hydroxylamine in water (0.6 ml) were added to the residue and the mixture heated at 60° C. overnight. The title compound was isolated by reversed phase chromatography (Kinetex C18, 5 µm, 21.2×100 mm, flow 25 ml/min, gradient 0.1% TFA in water/acetonitrile over 15 minutes). Yield: 0.7 mg (4%, two steps); white solid.

Example 75

N-Hydroxy-2-[4-(1-methylethyl)phenyl]-1,3-benzothiazole-5-carboxamide

To a solution of methyl 3-amino-4-fluorobenzoate (100 mg, 0.591 mmol) in DCM (3 ml) was added 4-(1-methylethyl)benzoyl chloride (162 mg, 0.887 mmol) and pyridine (96 µl, 1.18 mmol) at room temperature. The mixture was stirred for 1 h. 1 M HCl and DCM were added and the phases were separated, the organic phase collected and the volatiles were removed in vacuo. The compound was purified by flash column chromatography. Yield: 135 mg (72%); white solid. MS (ESI+) m/z 316 [M+H]+. HPLC purity: 99%.

To a solution of methyl 4-fluoro-3-({[4-(1-methylethyl)phenyl]carbonyl}amino)benzoate from above (50 mg, 0.159 mmol) in toluene (1 ml) was added Lawesson's reagent (32 mg, 0.079 mmol) and the reaction mixture was heated to 110° C. for 22 h. The solvent was evaporated and the residue was purified by flash column chromatography. Yield: 15 mg (29%); white solid. MS (ESI+) m/z 312 [M+H]+. HPLC purity: 99%.

To methyl 2-[4-(1-methylethyl)phenyl]-1,3-benzothiazole-5-carboxylate form above (15 mg, 0.048 mmol) in MeOH (0.6 ml) was added a KOH-solution (10 mg/ml in MeOH, 0.6 ml) and hydroxyl amine (50% w/w in water, 1.2 ml). The mixture was stirred for 2 h at 60° C. 1 M HCl and DCM were added and the phases were separated. The organic phase was collected and the solvents were removed in vacuo. The title compound was isolated by reversed phase chromatography (Kinetex C18, 5 µm, 21.2×100 mm, flow 25 ml/min, gradient 0.1% TFA in water/acetonitrile over 15 minutes). Yield: 9.0 mg (60%); white solid.

Example 76

2-(4-Fluorophenyl)-N-hydroxy-1,3-benzothiazole-5-carboxamide

General Procedure G

Methyl 3-amino-4-fluorobenzoate (21.0 mg, 0.124 mmol) and 4-fluorobenzoyl chloride (0.124 mmol) in toluene (2 ml) were heated at 110° C. for 1.5 h. Lawesson's reagent (40 mg, 0.100 mmol) was added and the mixture stirred at 110° C. overnight. Solvent was evaporated and residue purified by flash chromatography using 5-10% EtOAc in hexanes as eluent. Yield: 9.1 mg Hydroxylamine potassium salt in MeOH (ca 1.7 M, 1.5 ml) was added to the ester from above and the mixture was heated at 60° C. for 45 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: Yield: 3.3 mg (36%); white solid.

Example 80

2-(5-Bromopyridin-3-yl)-N-hydroxy-1,3-benzothiazole-5-carboxamide

HATU (116 mg, 0.305 mmol) was added to 5-bromonicotinic acid (61.6 mg, 0.305 mmol) and DIPEA (66 µl, 0.381 mmol) in DMF (2 ml). The mixture was stirred at rt for 15 min before methyl 3-amino-4-fluorobenzoate (43 mg, 0.254 mmol) in DMF (1 ml) was added. The mixture was stirred at ambient temperature for 10 d before solvent was evaporated and residue purified by flash chromatography using 10-20% EtOAc in hexanes as eluent. Yield: 28.7 mg (32%).

The amide from above (28.7 mg, 0.081 mmol) and Lawesson's reagent (32.8 mg, 0.081 mmol) in toluene (2 ml) was heated at 110° C. for 2 d. Solvent was evaporated and residue purified by flash chromatography using 20-35% EtOAc in hexanes as eluent. Yield: 4.7 mg (17%).

Hydroxylamine potassium salt in MeOH (ca 1.7 M, 1.5 ml) was added to the ester from above and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 0.8 mg (17%); white solid.

Example 81

N-Hydroxy-2-(7-methoxy-1-benzofuran-2-yl)-1,3-benzothiazole-5-carboxamide

HATU (116 mg, 0.305 mmol) was added to 7-methoxybenzofuran-2-carboxylic acid (58.6 mg, 0.305 mmol) and DIPEA (66 μl, 0.381 mmol) in DMF (2 ml). The mixture was stirred at rt for 15 min before methyl 3-amino-4-fluorobenzoate (43 mg, 0.254 mmol) in DMF (1 ml) was added. The mixture was stirred at ambient temperature for 10 d before solvent was evaporated and residue purified by flash chromatography using 10-20% EtOAc in hexanes as eluent. Yield: 40.1 mg (38%); white solid.

The amide from above (40.1 mg, 0.114 mmol) and Lawesson's reagent (51 mg, 0.114 mmol) in toluene (2 ml) was heated at 110° C. for 2 d. Solvent was evaporated and residue purified by flash chromatography using 20-35% EtOAc in hexanes as eluent. Yield: 3.3 mg (9%). Hydroxylamine potassium salt in MeOH (ca 1.7 M, 1.5 ml) was added to the ester from above and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 1.0 mg (30%); white solid.

Example 82

2-(4-Ethylphenyl)-N-hydroxy-1,3-benzothiazole-5-carboxamide

POCl$_3$ (44 μl, 0.470 mmol) was added to methyl 3-amino-4-fluorobenzoate (53.0 mg, 0.313 mmol) and 4-ethylbenzoic acid (47.0 mg, 0.313 mmol) in MeCN (2 ml) and the mixture was heated at 100° C. for 30 min. Solvents were evaporated and residue purified by flash chromatography using 10-20% EtOAc in hexanes. Yield: 18.5 mg (20%); white solid. The amide from above (18.5 mg, 0.061 mmol) and Lawesson's reagent (32 mg, 0.078 mmol) in toluene (2 ml) was heated at 110° C. for 2 d. Solvent was evaporated and residue purified by flash chromatography using 20-35% EtOAc in hexanes as eluent. Yield: 7.1 mg (39%). Hydroxylamine potassium salt in MeOH (ca 1.7 M, 1.5 ml) was added to the ester from above and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield; 5.1 mg (72%); white solid.

Example 83

N-Hydroxy-2-[4-(1-methylethyl)phenyl][1,3]oxazolo[5,4-b]pyridine-6-carboxamide

Methyl 5-amino-6-hydroxypyridine-3-carboxylate, INTERMEDIATE 6 (25 mg, 0.15 mmol) and 4-(1-methylethyl)benzoyl chloride (33 mg, 0.178 mmol) were placed in a microwave vial and dissolved in 1,4-dioxane (0.5 ml). The mixture was heated in the microwave reactor to 130° C. for 30 min. Phosphoroxy chloride (42 μl, 0.449 mmol) was added and the mixture was heated in the microwave for an additional 60 min at 125° C. The mixture was filtered through a pad of silica (1 g) with EtOAc. The organic solvents were removed in vacuo and the ester purified by flash column chromatography using 2-30% EtOAc in n-heptane as eluent. Yield: 15 mg (34%); colorless oil. MS (ESI+) m/z 297 [M+H]+.

KOH in MeOH (5 mg/ml, 0.4 ml) and 50% hydroxylamine in water (0.4 ml) were added to the ester from above (5 mg, 0.017 mmol) and the mixture stirred at room temperature for 75 min. The title compound was isolated by reversed phase chromatography (Kinetex C18, 5 μm, 21.2×100 mm, flow 25 ml/min, gradient 0.1% TFA in water/acetonitrile over 15 minutes). Yield: 1.5 mg (30%); white solid.

Example 84

N-Hydroxy-2-[4-(1-methylethyl)phenyl]-1H-pyrrolo[2,3-b]pyridine-5-carboxamide

A mixture of methyl-3-bromo-2-aminopyridine-5-carboxylate (20 mg, 0.087 mmol), 1-ethynyl-4-(1-methylethyl)benzene (18.7 mg, 0.130 mmol), copper(I)-iodide (3.3 mg, 0.017 mmol), Pd(PPh$_3$)$_2$Cl$_2$ (6.1 mg, 0.009 mmol) and triethylamine (24 μl, 0.173 mmol) in THF (0.8 ml) was heated in the microwave reactor at 100° C. for 60 min. The crude product was poured into water and DCM was added. The water phase was extracted with DCM. The phases were separated and the organic phase collected. The solvents were removed in vacuo and the crude product was purified by flash column chromatography using 50% EtOAc in n-heptane as eluent. Yield: 28 mg (quant.); yellow solid. MS (ESI+) m/z 295 [M+H]+.

To methyl 6-amino-5-{[4-(1-methylethyl)phenyl]ethynyl}pyridine-3-carboxylate from above (28 mg, 0.095 mmol) in NMP (1 ml) was added KOtBu (32 mg, 0.285 mmol). The mixture was heated to 60° C. for 1 h. The mixture was poured into 1 M HCl and DCM was added. The aqueous phase was extracted with DCM. The combined organic phases were evaporated. The carboxylic acid was isolated by reversed phase chromatography (Kinetex C18, 5 μm, 21.2×100 mm, flow 25 ml/min, gradient 0.1% TFA in water/acetonitrile over 15 minutes). Yield: 7 mg (26%); white solid. MS (ESI+) m/z 281 [M+H]+. HPLC purity: 96%.

HATU (14 mg, 0.037 mmol) was added to a mixture of 2-[4-(1-methylethyl)phenyl]-1H-pyrrolo[2,3-b]pyridine-5-carboxylic acid from above (7 mg, 0.025 mmol) and Et$_3$N (7 μl, 0.050 mmol) in MeCN (1 ml). After 30 min O-(tetrahydropyran-2-yl)-hydroxylamine (6 mg, 0.050 mmol) was added and the mixture stirred at 50° C. for 1 h before TFA (75 μl) was added and stirring continued at 50° C. for 3 h. The title compound was isolated by reversed phase chromatography (Kinetex C18, 5 μm, 21.2×100 mm, flow 25 ml/min, gradient 0.1% TFA in water/acetonitrile over 15 minutes). Yield: 4.2 mg (57%); light yellow solid.

Example 85

N-Hydroxy-2-[4-(1-methylethyl)phenyl]-1H-pyrrolo[3,2-b]pyridine-5-carboxamide

A mixture of methyl 5-amino-6-iodopyridine-2-carboxylate (Yonekubo, S. et. al. PCT Int. Appl., 2008129994, 30

Oct. 2008) (25 mg, 0.090 mmol), 1-ethynyl-4-(1-methylethyl)benzene (19.5 mg, 0.135 mmol), copper(I)-iodide (3.4 mg, 0.018 mmol), Pd(PPh$_3$)$_2$Cl$_2$ (6.3 mg, 0.009 mmol) and triethylamine (25 µl, 0.180 mmol) in THF (0.8 ml) was heated in a microwave reactor at 100° C. for 30 min. The mixture was poured into water and DCM was added. The aqueous phase was extracted with DCM. The combined organic layers were evaporated and the crude product purified by flash chromatography using 50% EtOAc in n-heptanes as eluent. Yield: 26 mg (98%); light-yellow solid. MS (ESI+) m/z 295 [M+H]+.

To methyl 5-amino-6-{[4-(1-methylethyl)phenyl]ethynyl}pyridine-2-carboxylate from above (26 mg, 0.088 mmol) in NMP (1 ml) was added KOtBu (30 mg, 0.265 mmol). The mixture was heated to 60° C. for 1.5 h. The mixture was poured into 1 M HCl and DCM was added. The aqueous phase was extracted with DCM. The combined organic layers were evaporated and residue purified by reversed phase chromatography (Kinetex C18, 5 µm, 21.2×100 mm, flow 25 ml/min, gradient 0.1% TFA in water/acetonitrile over 15 minutes). Yield: 15 mg (61%); yellow solid. MS (ESI+) m/z 281 [M+H]+. HPLC purity: 100%.

HATU (31 mg, 0.080 mmol) was added to a mixture of 2-[4-(1-methylethyl)phenyl]-1H-pyrrolo[2,3-b]pyridine-5-carboxylic acid from above (15 mg, 0.054 mmol) and Et$_3$N (15 µl, 0.107 mmol) in MeCN (1.5 ml). The mixture was stirred at room temperature for 30 min before O-(tetrahydropyran-2-yl)-hydroxylamine (11 mg, 0.107 mmol) was added and the mixture stirred at 50° C. for 1 h before TFA (150 µl) was added and stirring continued for 3 h at 50° C. The title compound was isolated by reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 5 mg (32%); light yellow solid.

Example 86

N-Hydroxy-6-[4-(1-methylethyl)phenyl]-7H-pyrrolo[2,3-d]pyrimidine-2-carboxamide

To a solution of sodium cyanide (28 mg, 0.576 mmol) in water (0.25 ml) at room temperature was added DMSO (0.75 ml), DABCO (54 mg, 0.480 mmol) and 4-amino-5-bromo-2-chloropyrimidine (100 mg, 0.48 mmol) in DMSO (0.5 ml). The mixture was stirred at 60° C. for 18 h. Water and DCM were added and the phases were separated. The organic phase was collected and solvents were removed in vacuo. The crude product was purified by flash column chromatography using 50% EtOAc in n-heptane as eluent. Yield: 67 mg (70%); yellow solid. MS (ESI+) m/z 199/201 [M+H]+. HPLC purity: 100%.

A mixture of 4-amino-5-bromopyrimidine-2-carbonitrile from above (30 mg, 0.151 mmol), 1-ethynyl-4-(1-methylethyl)benzene (33 mg, 0.226 mmol), copper(I)-iodide (5.7 mg, 0.030 mmol), Pd(PPh$_3$)$_2$Cl$_2$ (10.6 mg, 0.015 mmol) and Et$_3$N (42 µl, 0.301 mmol) in THF (0.8 ml) was heated in the microwave reactor at 100° C. for 30 min. The mixture was poured into water and DCM was added. The aqueous phase was extracted with DCM. The combined organic phases were evaporated and the crude product purified by flash column chromatography using 50% EOAc in n-heptane as eluent. Yield: 40 mg (quant.); yellow solid. MS (ESI+) m/z 263 [M+H]+. HPLC purity: 98%.

To a solution 4-amino-5-{[4-(1-methylethyl)phenyl]ethynyl}pyrimidine-2-carbonitrile from above (15 mg, 0.057 mmol) in anhydrous EtOH (0.8 ml) and water (0.2 ml) was added NaOH (11 mg, 0.286 mmol). The mixture was stirred at 80° C. for 48 h. 1 M HCl and DCM were added and the phases were separated. The organic phase was collected and solvents removed in vacuo. Yield: 18 mg; white solid. MS (ESI+) m/z 282 [M+H]+.

HATU (18 mg, 0.064 mmol) was added to 6-[4-(1-methylethyl)phenyl]-7H-pyrrolo[2,3-d]pyrimidine-2-carboxylic acid from above (18 mg, 0.064 mmol) and Et$_3$N (18 µl, 0.128 mmol) in MeCN (1.5 ml). The mixture was stirred at room temperature for 30 min before O-(tetrahydropyran-2-yl)-hydroxylamine (13 mg, 0.128 mmol) was added. The mixture was stirred at 50° C. for 3 h before TFA (180 til) was added and stirring continued at 50° C. for 3 h. The title compound was isolated by reversed phase chromatography (Gemini-NX C18, 5 µm, 21×50 mm, flow 25 ml/min, gradient: water (50 mM NH$_4$HCO$_3$ pH 10)/acetonitrile over 12 minutes). Yield: 5 mg (26%); light yellow solid.

Example 87

N-Hydroxy-2-[4-(1-methylethyl)phenyl]thieno[2,3-b]pyridine-5-carboxamide

Methyl 5-bromo-6-hydroxypyridine-3-carboxylate (200 mg, 0.862 mmol) was suspended in phosphorous oxychloride (0.80 ml, 8.62 mmol). The reaction mixture was heated at reflux for 2 h. The solvent was removed in vacuo. The resulting residue was concentrated from toluene to remove any excess phosphorous oxychloride and dried under high vacuum. Water and DCM were added to the crude product and the phases were separated. The organic phase was collected and the solvents removed in vacuo. Yield: 199 mg (92%); off-white solid. MS (ESI+) m/z 250/252/254 [M+H]+. HPLC purity: 100%.

To a solution of methyl 5-bromo-6-chloropyridine-3-carboxylate from above (100 mg, 0.399 mmol) in DMF (1 ml) was added potassium carbonate (83 mg, 0.599 mmol) and ethanethiol (43 µl, 0.599 mmol). The reaction mixture was stirred at room temperature for 20 h before water and DCM were added and the organic layer evaporated. The crude product was used in the next step without further purification. Yield: 106 mg (96%); off-white solid. MS (ESI+) m/z 276/278 [M+H]+. HPLC purity: 100%.

A mixture of methyl 5-bromo-6-(ethylsulfanyl)pyridine-3-carboxylate from above (50 mg, 0.181 mmol), 1-ethynyl-4-(1-methylethyl)benzene (31 mg, 0.217 mmol), copper(I)-iodide (6.9 mg, 0.036 mmol), Pd(PPh$_3$)$_2$Cl$_2$ (12.7 mg, 0.018 mmol) and triethylamine (50 µl, 0.240 mmol) in THF (1 ml) was heated in the microwave reactor at 110° C. for 60 min. The mixture was poured into water and DCM was added. The aqueous phase was extracted with DCM. The combined organic layers were evaporated and the crude product purified by flash column chromatography using 10% EtOAc in n-heptanes. Yield: 48 mg (78%); yellow solid. MS (ESI+) m/z 340 [M+H]+. HPLC purity: 85%.

To methyl 6-(ethylsulfanyl)-5-{[4-(1-methylethyl)phenyl]ethynyl}pyridine-3-carboxylate from above (48 mg, 0.141 mmol) EtOH (1 ml) was added p-toluenesulfonic acid monohydrate (27 mg, 0.141 mmol) and the mixture was heated in a microwave reactor at 140° C. for 7.5 h. The solvent was removed in vacuo and the crude product was purified by flash chromatography using 20% EtOAc in n-heptane. Yield: 17 mg (37%); yellow solid. MS (ESI+) m/z 326 [M+H]+.

Ethyl 2-[4-(1-methylethyl)phenyl]thieno[2,3-b]pyridine-5-carboxylate from above (15 mg, 0.048 mmol) was added KOH in MeOH (5 mg/ml, 1.2 ml) and 50% hydroxylamine in water (1.2 ml) and the mixture was stirred at 60° C. for

Example 88

N-Hydroxy-2-[4-(1-methylethyl)phenyl]-1-benzothiophene-6-carboxamide $K_2CO_3$ (40 mg, 0.292 mmol), Pd(OAc)$_2$ (2.2 mg, 0.010 mmol), tricyclohexylphosphine (5.5 mg, 0.019 mmol), and pivalic acid (6 mg, 0.058 mmol) were placed in a microwave vial equipped with a magnetic stir bar. 6-Cyanobenzothiophene, INTERMEDIATE 13 (31 mg, 0.195 mmol) and 1-bromo-4-(1-methylethyl)benzene (47 mg, 0.234 mmol) were added as well as DMF (0.6 ml). The sealed reaction vial was heated in a microwave reactor at 180° C. for 30 min. Water and DCM were added and the organic layer evaporated. The crude product was purified by flash column chromatography using 5% EtOAc in n-heptane as eluent. Yield: 18 mg (33%); white solid. MS (ESI+) m/z 278 [M+H]+. HPLC purity: 97%.

To a solution of 2-[4-(1-methylethyl)phenyl]-1-benzothiophene-6-carbonitrile from above (18 mg, 0.065 mmol) in anhydrous EtOH (1.2 ml) and water (0.3 ml) was added sodium hydroxide (38 mg, 0.973 mmol). The reaction was stirred at 90° C. for 26 h. 1 M HCl and DCM were added and the organic layer evaporated. The compound was used in the next step without further purification. Yield: 19 mg; white solid. MS (ESI+) m/z 297 [M+H]+.

HATU (37 mg, 0.097 mmol) was added to 2-[4-(1-methylethyl)phenyl]-1-benzothiophene-6-carboxylic acid from above (19 mg, 0.065 mmol) and Et$_3$N (18 µl, 0.130 mmol) in MeCN (1.5 ml). The mixture was stirred at room temperature for 30 min before O-(tetrahydropyran-2-yl)-hydroxylamine (13 mg, 0.130 mmol) was added. The mixture was stirred at 50° C. for 3 h before TFA (180 µl) was added and stirring continued at 50° C. for 3 h. Water and DCM were added and the organic layer separated. The title compound was isolated by reversed phase chromatography (Kinetex C18, 5 µm, 21.2×100 mm, flow 25 ml/min, gradient 0.1% TFA in water/acetonitrile over 15 minutes). Yield: 8 mg (40%); off-white solid.

Example 89

N-Hydroxy-2-[4-(1-methylethyl)phenyl]-1-benzothiophene-5-carboxamide

General Procedure H

Palladium acetate (4.7 mg, 0.021 mmol) was added to a nitrogen flushed mixture of methyl benzothiophene-5-carboxylate, INTERMEDIATE 7 (80.7 mg, 0.420 mmol), 4-bromocumene (83.6 mg, 0.420 mmol), potassium carbonate (87.1 mg, 0.630 mmol), pivalic acid (12.8 mg, 0.126 mmol) and tricyclohexylphosphine (11.8 mg, 0.042 mmol) in DMF (1 ml). The sealed tube was heated at 180° C. for 10 min in a microwave reactor. Water and EtOAc were added, and organic phase evaporated. The residue was purified by flash chromatography using 10% EtOAc in heptane as eluent. Yield: 26 mg (material contained some starting material). Freshly prepared hydroxylamine potassium salt solution (ca 1.7 M in MeOH, 1.5 ml) was added to the product from above and the mixture was heated at 60° C. for 1 h before quenching with AcOH (0.5 ml). The title compound was isolated by reversed phase chromatography (Kinetex C18, 5 m, 21.2×100 mm, flow 25 ml/min, gradient 0.1% TFA in water/acetonitrile over 15 minutes). Yield: 2.7 mg (2%, two steps); white solid.

Example 94

N-Hydroxy-2-(1H-pyrazol-4-yl)-1-benzothiophene-5-carboxamide

General Procedure I

To a solution of methyl 2-iodobenzothiophene-5-carboxylate, INTERMEDIATE 8 (20 mg, 0.063 mmol) and 4,4,5,5-tetramethyl-2-(1H-pyrazol-4-yl)-1,3,2-dioxaborolane (18.3 mg, 0.094 mmol) in DME (0.6 ml) and water (0.2 ml) were added $K_2CO_3$ (17 mg, 0.126 mmol) and Pd(PPh$_3$)$_4$ (4 mg, 0.003 mmol). The mixture was heated under microwave irradiation for 30 min at 120° C. The crude mixture was poured into water and extracted with DCM. The organic phase was collected and the solvents removed in vacuo.

To the intermediate from above was added KOH in MeOH (5 mg/ml, 1 ml) and 50% hydroxylamine in water (1 ml) and the mixture was heated at 60° C. for 90 min. AcOH and DCM/THF were added and the phases were separated. The organic phase was collected and the solvents were removed in vacuo. The title compound was isolated by reversed phase chromatography (Kinetex C18, 5 µm, 21.2×100 mm, flow 25 ml/min, gradient 0.1% TFA in water/acetonitrile over 15 minutes). Yield: 1.8 mg; white solid.

Example 110

N-Hydroxy-2-[4-(1-methylethyl)phenyl]thieno[3,2-b]pyridine-6-carboxamide

To a solution of 6-bromothieno[3,2-b]pyridine (Holladay, M et. al. WO 2015031613 A1) (565 mg, 3:7 mixture with 6-chlorothieno[3,2-b]pyridine) in DMF (10 ml) was added Zn(CN)$_2$ (620 mg, 5.28 mmol) and Pd(PPh$_3$)$_4$ (153 mg, 0.132 mmol). The reaction was heated in a microwave reactor at 125° C. for 180 min. The mixture was filtered through a pad of Celite with EtOAc, the solvents were removed in vacuo and the crude product was purified by flash column chromatography using 20-50% EtOAc in n-heptane as eluent. Yield: 40 mg (ca. 20%); yellow solid. MS (ESI+) m/z 161 [M+H]+. HPLC purity: 100%.

A solution of thieno[3,2-b]pyridine-6-carbonitrile from above (40 mg, 0.25 mmol) in THF (3 ml) was cooled to −78° C. Freshly prepared LDA solution (0.60 ml, ca. 0.5 M in THF/hexane, 0.30 mmol) was added dropwise and the mixture was stirred for 15 min. Iodine (76 mg, 0.30 mmol) was added and the reaction was allowed to reach −50° C. over a period of 1 h. 1 M HCl and DCM were added and the organic phase was washed with Na$_2$S$_2$O$_3$ solution and evaporated. Yield: 61 mg (85%); yellow solid. MS (ESI+) m/z 287 [M+H]+.

Pd(PPh$_3$)$_4$ (4 mg, 0.004 mmol) was added to a mixture of 2-iodothieno[3,2-b]pyridine-6-carbonitrile from above (20 mg, 0.070 mmol), 4-isopropylphenylboronic acid (17 mg, 0.105 mmol) and $K_2CO_3$ (19 mg, 0.140 mmol) in 1,4-dioxane (0.6 ml) and water (1.5 ml). The mixture was heated at 100° C. for 30 min in a microwave reactor. The crude mixture was filtered through a pad of silica (1 g) with EtOAc and the solvents removed in vacuo. The residue was purified by flash chromatography using 20% EtOAc in n-heptane as eluent. Yield 12 mg (62%). MS (ESI+) m/z 279 [M+H]+.

To a solution of 2-[4-(1-methylethyl)phenyl]thieno[3,2-b]pyridine-6-carbonitrile from above (12 mg, 0.043 mmol) in anhydrous EtOH (1.2 ml) and water (0.3 ml) was added sodium hydroxide (43 mg, 1.08 mmol). The reaction was stirred at 90° C. for 90 min. 1 M HCl and DCM/THF were added and the phases were separated. The organic phase was collected and solvents were removed in vacuo. Off-white solid. MS (ESI+) m/z 298 [M+H]+. HPLC purity: 98%. The residue was dissolved in MeCN (1 ml). Et$_3$N (12 μl, 0.086 mmol) and HATU (25 mg, 0.065 mmol) were added and the mixture was stirred at room temperature for 30 min before O-(tetrahydropyran-2-yl)-hydroxylamine (13 mg, 0.130 mmol) was added and the mixture stirred at 50° C. for 3 h. TFA (120 μl) was added and stirring continued at 50° C. for 3 h. The title compound was isolated by reversed phase chromatography (Kinetex C18, 5 μm, 21.2×100 mm, flow 25 ml/min, gradient 0.1% TFA in water/acetonitrile over 15 minutes). Yield: 6.9 mg (51%); yellow solid.

Example 111

N-Hydroxy-2-[4-(1-methylethyl)phenyl]-1-benzofuran-5-carboxamide

Pd(PPh$_3$)$_2$Cl$_2$ (8.6 mg, 0.012 mmol) was added to a nitrogen flushed mixture of methyl 4-hydroxy-3-iodobenzoate (34 mg, 0.122 mmol), 4-isopropylphenylacetylene (26.4 mg, 0.183 mmol), CuI (4.6 mg, 0.024 mmol) and Et$_3$N (24.7 mg, 0.245 mmol) in THF (2 ml). The mixture was heated at 100° C. for 30 min in a microwave reactor. Solvent was evaporated and residue purified by flash chromatography using 5%-10% EtOAc in heptanes. Yield: 14.4 mg (40%); yellow solid. MS (ESI+) m/z 295 [M+H]+. HPLC purity: 80%.

Freshly prepared hydroxylamine potassium salt solution (ca 1.7 M in MeOH, 1.5 ml) was added to the product from above (14.4 mg, 0.049 mmol) and the mixture was heated at 60° C. for 1 h before quenching with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 4.6 mg (32%); white solid.

Example 112

N-Hydroxy-2-[4-(1-methylethyl)phenyl]-1-benzofuran-6-carboxamide

Pd(PPh$_3$)$_2$Cl$_2$ (11.0 mg, 0.016 mmol) was added to a nitrogen flushed mixture of methyl 3-hydroxy-4-iodobenzoate (43.4 mg, 0.156 mmol), 4-isopropylphenylacetylene (33.8 mg, 0.234 mmol), CuI (5.9 mg, 0.031 mmol) and Et$_3$N (32 mg, 0.312 mmol) in THF (2 ml). The mixture was heated at 100° C. for 30 min in a microwave reactor. Solvent was evaporated and residue purified by flash chromatography using 5%-10% EtOAc in heptanes. Yield: 9.7 mg (21%); yellow solid.

Freshly prepared hydroxylamine potassium salt solution (ca 1.7 M in MeOH, 1.5 ml) was added to the product from above and the mixture was heated at 60° C. for 1 h before quenching with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 3.1 mg (32%); white solid.

Example 113

N-Hydroxy-2-[4-(1-methylethyl)phenyl]furo[2,3-b]pyridine-5-carboxamide

Pd(PPh$_3$)$_2$Cl$_2$ (12.5 mg, 0.0177 mmol) was added to a nitrogen flushed mixture of methyl 5-bromo-6-hydroxynicotinate (82.1 mg, 0.354 mmol), 4-isopropylphenylacetylene (77 mg, 0.531 mmol), and CuI (6.7 mg, 0.0354 mmol) in Et$_3$N (1 ml). The mixture was heated in at 80° C. overnight in a sealed vial. Solvent was evaporated and the crude material purified by flash chromatography using 10-20% EtOAc in hexanes as eluent. Yield: 6.0 mg (6%); white solid. Freshly prepared hydroxylamine potassium salt solution (ca 1.7 M in MeOH, 1.5 ml) was added the product from above and the mixture was heated at 60° C. for 1 h before quenching with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 2.0 mg (33%); white solid.

Example 114

N-Hydroxy-2-[4-(1-methylethyl)phenyl]furo[3,2-b]pyridine-5-carboxamide

5-Hydroxypicolinic acid (229 mg, 1.65 mmol) was dissolved in 25% ammonia in water (10 ml). A solution iodine (418 mg, 1.65 mmol) and KI (1.37 g, 8.25 mmol) in water (20 ml) was added dropwise. The mixture was stirred at ambient temperature overnight. The pH was adjusted to 4 using 10% citric acid. Aqueous layer was extracted several times with EtOAc. Combined organic layers were dried (MgSO$_4$) and concentrated. Yield: 473 mg (108%); brown oil. The crude material from above was dissolved in MeOH (5 ml) and thionyl chloride (340 μl, 4.95 mmol) was added dropwise. The mixture was heated at refluxed for 2 h. EtOAc and sat. NaHCO$_3$ were added. Aqueous layer was extracted with EtOAc. The combined organic layers were dried (MgSO$_4$) and evaporated. The residue was purified by flash chromatography using 3% MeOH in DCM. Yield: 140.1 mg (30%); white solid. MS (ESI+) m/z 280 [M+H]+. HPLC purity: 90%

Pd(PPh$_3$)$_2$Cl$_2$ (19.2 mg, 0.0271 mmol) was added to a nitrogen flushed mixture of the material from above (75.5 mg, 0.271 mmol), 4-isopropylphenylacetylene (58.5 mg, 0.406 mmol), triethylamine (75 μl, 0.542 mmol) and CuI (10.3 mg, 0.054 mmol) in THF (1 ml). The mixture was heated at 100° C. for 30 min in a microwave reactor. Solvent was evaporated and the crude material purified by flash chromatography using 0-5% MeOH in DCM as eluent. Yield: 70.1 mg (88%); yellow solid.

Freshly prepared hydroxylamine potassium salt solution (ca 1.7 M in MeOH, 1.5 ml) was added to the product from above (16.3 mg, 0.055 mmol), and the mixture was heated at 60° C. for 45 min. before quenched with AcOH (0.5 ml) and purified by reversed phase chromatography (Kinetex C18, 5 μm, 21.2×100 mm, flow 25 ml/min, gradient 0.1% TFA in water/acetonitrile over 15 minutes). Yield: 5.4 mg (33%); white solid.

Example 115

N-Hydroxy-2-[4-(1-methylethyl)phenyl]furo[3,2-b]pyridine-6-carboxamide

Thionyl chloride (780 μl, 10.7 mmol) was added dropwise to a suspension of 5-hydroxynicotinic acid (497 mg, 3.57 mmol) in MeOH (5 ml) at ambient temperature. The mixture was heated at 60° C. overnight. 0.1 M Potassium phosphate buffer (pH 7) (50 ml) was added and the mixture extracted with EtOAc. The combined organic layers were dried (MgSO$_4$). Yield: 354 mg (65%); white solid.

The material from above (354 mg, 2.31 mmol) was suspended in water (35 ml). Sodium carbonate (490 mg, 4.62 mmol) and iodine (586 mg, 2.31 mmol) were added. The mixture was stirred at ambient temperature for 1.5 h. The mixture was neutralized using 1 M HCl. The aqueous mixture was extracted with EtOAc and the combined organic layers were dried (MgSO$_4$) and evaporated. The residue was purified by flash chromatography using 2% MeOH in DCM as eluent. Yield: 226.3 mg; (35%) white solid.

Pd(PPh$_3$)$_2$Cl$_2$ (5.2 mg, 0.00735 mmol) was added to a nitrogen flushed mixture of methyl 6-iodo-5-hydroxynicotinate from above (41 mg, 0.147 mmol), 4-isopropylphenylacetylene (31.8 mg, 0.220 mmol), triethylamine (41 µl 0.294 mmol) and CuI (2.8 mg, 0.0147 mmol) in THF (1 ml). The mixture was heated at 100° C. for 30 min in a microwave reactor. Solvent was evaporated and the residue purified by flash chromatography using hexanes/EtOAc 2:1 as eluent. Yield: 27 mg (62%); pale yellow solid.

Freshly prepared hydroxylamine potassium salt solution (ca 1.7 M in MeOH, 1.5 ml) was added to the product from above (27 mg, 0.091 mmol) and the mixture was heated at 60° C. for 1 h before quenching with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 22.0 mg (82%); yellow solid.

Example 116

N-Hydroxy-2-[4-(1-methylethyl)phenyl]furo[2,3-b]pyridine-6-carboxamide

Pd(PPh$_3$)$_2$Cl$_2$ (30 mg, 0.0424 mmol) was added to a nitrogen flushed mixture of methyl 5-bromo-6-oxo-1,6-dihydropyridine-2-carboxylate (98.4 mg, 0.424 mmol), 4-isopropylphenylacetylene (92 mg, 0.636 mmol), CuI (16.1 mg, 0.0848 mmol) and Et$_3$N (600 µl) in THF (1.5 ml) and the mixture was heated at 100° C. in microwave reactor for 15 min. Solvent evaporated and residue purified by flash chromatography using 20-33% EtOAc as eluent. Yield: 55.5 mg (44%); beige solid.

Hydroxylamine potassium salt solution (ca 1.7 M in MeOH, 1.5 ml was added to the material from above (21.0 mg, 0.071 mmol) and the mixture was stirred at 60° C. for 1 h before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 15.7 mg (75%); white solid.

Example 117

2-[(Diethylamino)methyl]-N-hydroxy-1-benzofuran-6-carboxamide trifluoroacetate

General Procedure J

Pd(PPh$_3$)$_2$Cl$_2$ (6.2 mg, 0.0087 mmol) was added to a nitrogen flushed mixture of methyl 3-hydroxy-4-iodobenzoate (49 mg, 0.176 mmol), 3-diethylamino-1-propyne (29.4 mg, 0.264 mmol), CuI (3.4 mg, 0.0176 mmol) and triethylamine (61 µl, 0.440 mmol) in THF (2 ml). The mixture was heated at 100° C. for 30 min in a microwave reactor. Sat. NaHCO$_3$ and EtOAc was added and the aqueous phase was extracted with EtOAc. Combined organic layers were evaporated and residue purified by flash chromatography. Yield: 7.9 mg (17%)

Hydroxylamine potassium salt in MeOH (ca 1.7 M, 1.5 ml) was added to the ester from above and the mixture heated at 60° C. before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 7.2 mg (63%); colourless oil.

Example 120

3-Chloro-N-hydroxy-2-phenyl-1H-indole-6-carboxamide

General Procedure K

Methyl 2-bromo-3-chloro-1H-indole-6-carboxylate, INTERMEDIATE 10 (44 mg, 0.14 mmol), phenylboronic acid (26 mg, 0.21 mmol), triethylamine (42 mg, 0.42 mmol), Pd(dppf)Cl$_2$ (5 mg, 7 µmol) and water (100 µl) were mixed in acetonitrile (2 ml). The reaction mixture was stirred at 80° C. overnight. Water and toluene were added. The organic phase was washed with sat NaHCO$_3$ and brine, dried over MgSO$_4$, filtered and concentrated. The residue was purified with reversed phase chromatography (Kinetex, C18, 5 µm, 21×100 mm, flow 25 ml/min, gradient: water (0.1% TFA)/acetonitrile over 15 minutes). The pure fractions were combined, concentrated and dried in vacuum.

Freshly prepared hydroxylamine potassium salt solution (ca 1.7 M in MeOH, 1.5 ml) was added to the product from above and the mixture was heated at 60° C. for 1 h before quenching with AcOH (0.1 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 3.8 mg (9%, two steps); white solid.

Example 122

2-Bromo-3-chloro-N-hydroxy-1H-indole-6-carboxamide

Freshly prepared hydroxylamine potassium salt solution (ca 1.7 M in MeOH, 1.5 ml) was added to methyl methyl 2-bromo-3-chloro-1H-indole-6-carboxylate, INTERMEDIATE 10, (24 mg, 75 µmol) and the mixture was heated at 60° C. for 1 h before quenching with AcOH (0.2 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 4 mg (18%).

Example 123

N-Hydroxy-2-(phenylamino)-1,3-benzoxazole-5-carboxamide

General Procedure L

Methyl 2-chloro-1H-benzimidazole-6-carboxylate, INTERMEDIATE 11 (11 mg, 0.050 mmol) and aniline (0.075 mmol) in 1,3-dimethyl-2-imidazolidinone (400 µl) were heated at 120° C. for 2 days. The reaction mixture was diluted with methanol/water and purified with reversed phase chromatography (Gemini-NX, C18, 5 µm, 21×100 mm, flow 25 ml/min, gradient: water (50 mM ammonium bicarbonate, pH 10)/acetonitrile over 15 minutes). The pure fractions were combined, concentrated and dried in vacuum.

Freshly prepared hydroxylamine potassium salt solution (ca 1.7 M in MeOH, 0.7 ml) was added to the product from above and the mixture was stirred at room temperature overnight before quenching with AcOH (0.2 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 3.8 mg (9%, two steps); white solid.

Example 137

N-Hydroxy-1-methyl-2-(phenylamino)-1H-benzimidazole-5-carboxamide

General Procedure M

Methyl 2-chloro-1H-benzimidazole-6-carboxylate, INTERMEDIATE 12 (11.3 mg, 0.050 mmol) and aniline (0.075 mmol) in 1,3-dimethyl-2-imidazolidinone (400 µl) were heated at 120° C. for 2 days. The reaction mixture was diluted with methanol/water and purified with reversed phase chromatography (Gemini-NX, C18, 5 µm, 21×100 mm, flow 25 ml/min, gradient: water (50 mM ammonium bicarbonate, pH 10)/acetonitrile over 15 minutes). The pure fractions were combined, concentrated and dried in vacuum.

Freshly prepared hydroxylamine potassium salt solution (ca 1.7 M in MeOH, 0.7 ml) was added to the product from above and the mixture was stirred at room temperature overnight before quenching with AcOH (0.2 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 9 mg (67%, two steps); white solid.

Example 147

2-(3,4-Dimethoxyphenyl)-N-hydroxy-1-benzothiophene-6-carboxamide

General Procedure N

Pd(PPh$_3$)$_4$ (4 mg, 0.004 mmol) was added to a mixture of 2-iodo-1-benzothiophene-6-carbonitrile, INTERMEDIATE 14 (20 mg, 0.070 mmol), 3,4-dimethoxyphenylboronic acid (17.2 mg, 0.094 mmol) and K$_2$CO$_3$ (19 mg, 0.140 mmol) in 1,4-dioxane (0.6 ml) and water (150 µl). The mixture was heated at 100° C. for 30 min in a microwave reactor. The crude mixture was filtered through a short plug of silica with EtOAc and the solvents removed in vacuo. The residue was purified by reversed phase chromatography (Kinetex C18, 5 µm, 21.2×100 mm, flow 25 ml/min, gradient 0.1% TFA in water/acetonitrile over 15 minutes). Yield: 11.4 mg (52%); white solid.

EtOH (1 ml) and 1 M NaOH (1 ml) were added to the nitrile from above and the mixture heated at 75° C. for 3 d. EtOAc and 1 M HCl were added. The organic layer was separated and evaporated. The residue was dissolved in DMF (1 ml) and DIPEA (12.6 µl, 0.072 mmol), HATU (16.5 mg, 0.043 mmol) and O-(tetrahydropyran-2-yl)-hydroxylamine (5.5 mg, 0.043 mmol) were added. The mixture were stirred at rt overnight and TFA (200 µl) and water (50 µl) were added. The mixture was stirred for 2 h and the title compound isolated by reversed phase chromatography (Kinetex C18, 5 µm, 21.2×100 mm, flow 25 ml/min, gradient 0.1% TFA in water/acetonitrile over 15 minutes). Yield: 7.1 mg (63%, two steps); white solid.

Example 151

N-Hydroxy-2-(hydroxymethyl)-1-benzofuran-5-carboxamide

Pd(PPh$_3$)$_2$Cl$_2$ (42.8 mg, 0.0605 mmol) was added to a nitrogen flushed mixture of methyl 4-hydroxy-3-iodobenzoate (337 mg, 1.21 mmol), propargyl alcohol (105 µl, 1.81 mmol), CuI (23 mg, 0.121 mmol) and triethylamine (420 µl, 3.03 mmol) in THF (3 ml). The mixture was heated at 100° C. for 30 min in a microwave reactor. Solvent was evaporated and residue purified by flash chromatography using hexanes/EtOAc 2:1 as eluent. Yield: 84.5 mg (34%); beige solid. MS(ESI+) m/z 207 [M+H]$^+$. HPLC purity: 95%. $^1$H NMR (600 MHz, CD$_3$OD) δ ppm 8.27 (d, J=1.2 Hz, 1H) 7.97 (dd, J=8.9, 1.8 Hz, 1H) 7.52 (d, J=8.9 Hz, 1H) 6.81 (s, 1H) 4.69 (s, 2H) 3.91 (s, 3H).

Hydroxylamine potassium salt in MeOH (ca 1.7 M, 1.5 ml) was added to the ester from above (5.6 mg, 0.027 mmol) and the mixture was heated at 60° C. for 1 h before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 2.0 mg (36%); white solid.

Example 152

N-Hydroxy-2-[6-(4-methylpiperidin-1-yl)pyridin-3-yl]-1,3-benzoxazole-5-carboxamide trifluoroacetate General Procedure O Methyl 2-(6-chloropyridin-3-yl)-1,3-benzoxazole-5-carboxylate, INTERMEDIATE 15 (50 mg, 0.173 mmol) and 4-methylpiperidine (51.6 mg, 0.519 mmol) in dioxane (2 ml) and MeCN (1 ml) were heated at 150° C. for 20 min in a microwave reactor. Solvents were evaporated and hydroxylamine potassium salt (ca 1.7 M in MeOH, 1.5 ml) was added. The mixture was heated at 60° C. for 30 min before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 18.6 mg (46%, two steps); white solid.

Example 161

N-Hydroxy-2-(6-phenylpyridin-3-yl)-1,3-benzoxazole-5-carboxamide trifluoroacetate PEPPSI-iPr™ (ca 2 mg) was added to a mixture of ethyl 2-(6-chloropyridin-3-yl)-1,3-benzoxazole-5-carboxylate, INTERMEDIATE 15 (23 mg, 0.080 mmol), phenylboronic acid (14.6 mg, 0.120 mmol) and potassium carbonate (22 mg, 0.160 mmol) in toluene (1 ml) and MeOH (1 ml). The mixture was heated at 100° C. for 30 min in a microwave reactor. Water and EtOAc were added and the organic layer was separated and evaporated.

Hydroxylamine potassium salt (ca 1.7 M in MeOH, 1.5 ml) was added to the ester from above and the mixture was stirred at 60° C. for 1 h. before trifluoroacetic acid (300 µl) was added and the title compound was isolated by reversed phase chromatography (Kinetex C18, 5 µm, 21.2×100 mm, flow 25 ml/min, gradient 0.1% TFA in water/acetonitrile over 15 minutes). Yield: 3.1 mg (9%, two steps); white solid.

Example 162

2-[(3-Fluorophenoxy)methyl]-N-hydroxy-1-benzo-furan-5-carboxamide

Pd(PPh$_3$)$_2$Cl$_2$ (42.8 mg, 0.0605 mmol) was added to a nitrogen flushed mixture of methyl 4-hydroxy-3-iodobenzoate (337 mg, 1.21 mmol), propargyl alcohol (105 µl, 1.81 mmol), CuI (23 mg, 0.121 mmol) and triethylamine (420 µl, 3.03 mmol) in THF (3 ml). The mixture was heated at 100° C. for 30 min in a microwave reactor. Solvent was evaporated and residue purified by flash chromatography using hexanes/EtOAc 2:1 as eluent. Yield: 84.5 mg (34%); beige solid. MS(ESI+) m/z 207 [M+H]$^+$. HPLC purity: 95%. $^1$H NMR (600 MHz, CD$_3$OD) δ ppm 8.27 (d, J=1.2 Hz, 1H) 7.97 (dd, J=8.9, 1.8 Hz, 1H) 7.52 (d, J=8.9 Hz, 1H) 6.81 (s, 1H) 4.69 (s, 2H) 3.91 (s, 3H).

3-Fluorophenol (10.3 mg, 0.092 mmol) was added to a mixture of the material from above (19 mg, 0.092 mmol), triphenylphosphine (36 mg, 0.138 mmol) and DEAD (22 µl, 0.138 mmol) in THF (2 ml). The mixture was stirred at rt for 2 h. The solvent was evaporated and product was isolated by flash chromatography using 10%-20% EtOAc in hexanes as eluent. Yield: 12.2 mg (44%); colourless oil.

Hydroxylamine potassium salt (ca 1.7 M in MeOH, 1.5 ml) was added to the material from above and the mixture heated at 60° C. for 1 h before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 6.6 mg (53%); white solid.

Example 163

2-[(4-tert-Butylphenoxy)methyl]-N-hydroxy-1-benzofuran-5-carboxamide

Pd(PPh$_3$)$_2$Cl$_2$ (42.8 mg, 0.0605 mmol) was added to a nitrogen flushed mixture of methyl 4-hydroxy-3-iodobenzoate (337 mg, 1.21 mmol), propargyl alcohol (105 µl, 1.81 mmol), CuI (23 mg, 0.121 mmol) and triethylamine (420 µl, 3.03 mmol) in THF (3 ml). The mixture was heated at 100° C. for 30 min in a microwave reactor. Solvent was evaporated and residue purified by flash chromatography using hexanes/EtOAc 2:1 as eluent. Yield: 84.5 mg (34%); beige solid. MS(ESI+) m/z 207 [M+H]$^+$. HPLC purity: 95%. $^1$H NMR (600 MHz, CD$_3$OD) δ ppm 8.27 (d, J=1.2 Hz, 1H) 7.97 (dd, J=8.9, 1.8 Hz, 1H) 7.52 (d, J=8.9 Hz, 1H) 6.81 (s, 1H) 4.69 (s, 2H) 3.91 (s, 3H).

4-tert-Butylphenol (13.8 mg, 0.092 mmol) was added to a mixture of the material from above (19 mg, 0.092 mmol), triphenylphosphine (36 mg, 0.138 mmol) and DEAD (22 µl, 0.138 mmol) in THF (2 ml). The mixture was stirred at rt for 2 h. The solvent was evaporated and product was isolated by flash chromatography using 10%-20% EtOAc in hexanes as eluent. Yield: 7.3 mg (23%); white solid Hydroxylamine potassium salt (ca 1.7 M in MeOH, 1.5 ml) was added to the material from above and the mixture heated at 60° C. for 1 h before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 5.7 mg (76%); white solid.

Example 164

N-Hydroxy-2-{6-[(1-methylethyl)sulfanyl]pyridin-3-yl}-1,3-benzoxazole-5-carboxamide Methyl 2-(6-chloropyridin-3-yl)-1,3-benzoxazole-5-carboxylate, INTERMEDIATE 15 (23 mg, 0.080 mmol), potassium carbonate (16.6 mg, 0.120 mmol) and 2-propanthiol (9.1 mg, 0.120 mmol) in MeCN (2 ml) was heated at 150° C. for 30 min. Solvent was evaporated. Hydroxylamine potassium salt (ca 1.7 M in MeOH, 1.5 ml) was added to the residue and the mixture was heated at 60° C. for 1 h. The title compound was isolated by reversed phase chromatography (Kinetex C18, 5 µm, 21.2×100 mm, flow 25 ml/min, gradient 0.1% TFA in water/acetonitrile over 15 minutes). Yield: 6.2 mg (23%, two steps); white solid.

Example 165

2-(4-Bromo-2-fluorophenyl)-N-hydroxy-1,3-benzoxazole-5-carboxamide

Methyl 2-(4-bromo-2-fluorophenyl)-1,3-benzoxazole-5-carboxylate, INTERMEDIATE 16 (19.1 mg, 0.054 mmol) in KOH in MeOH (5 mg/ml, 1 ml) and 50% hydroxylamine in water (0.5 ml) was heated at 60° C. for 1 h. 2 M HCl (pH ca 6) and EtOAc were added. The organic layer was separated, solvents were evaporated and the residue purified by reversed phase chromatography (Kinetex C18, 5 µm, 21.2×100 mm, flow 25 ml/min, gradient 0.1% TFA in water/acetonitrile over 15 minutes): Yield: 12.9 mg (68%); white solid.

Example 166

2-[2-Fluoro-4-(1-methylethyl)phenyl]-N-hydroxy-1,3-benzoxazole-5-carboxamide PEPPSI-iPr™ (ca 5 mg) was added to a mixture of methyl 2-(4-bromo-2-fluorophenyl)-1,3-benzoxazole-5-carboxylate, INTERMEDIATE 16 (80.0 mg, 0.228 mmol), isopropenylboronic acid pinacol ester (58 mg, 0.343 mmol) and potassium carbonate (49 mg, 0.353 mmol) in toluene (1 ml) and MeOH (1 ml). The mixture was heated at 100° C. for 30 min. Solvents were evaporated and residue purified by flash chromatography using 20% EtOAc in hexanes as eluent. Yield: 61.1 mg (86%); white solid. MS(ESI+) m/z 312 [M+H]$^+$. HPLC purity: 95%.

10% palladium on charcoal (11 mg) was added to the material from above (60 mg, 0.193 mmol) in MeOH (2.5 ml) and EtOAc (5 ml) and the mixture was stirred under an atmosphere of H$_2$ (balloon) at rt for 2 h. The mixture was filtered through Celite and solvents evaporated. Yield: 61 mg (100%); white solid To the ester from above (16.2 mg, 0.052 mmol) was added KOH in MeOH (5 mg/ml, 1 ml) and hydroxylamine (50% in water, 0.5 ml). The mixture was heated at 60° C. for 1 h before quenched with AcOH (0.5 ml). The title compound was isolated by reversed phase chromatography (Kinetex C18, 5 µm, 21.2×100 mm, flow 25 ml/min, gradient 0.1% TFA in water/acetonitrile over 15 minutes). Yield: 5.3 mg (32%); white solid.

Example 167

N-Hydroxy-2-[3-(1-methylethyl)phenyl]-1,3-benzoxazole-5-carboxamide

Methyl 3-amino-4-hydroxybenzoate (168 mg, 1.00 mmol) and 3-bromobenzoyl chloride (132 μl, 1.00 mmol) in dioxane (2 ml) and MeCN (2 ml) was heated at 180° C. for 4 h in a microwave reactor. Chloroform and sat. NaHCO$_3$ were added. Aqueous layer was extracted with chloroform and combined organic layers were dried (MgSO$_4$) and evaporated. Yield: 332 mg (100%); white solid. MS(ESI+) m/z 332/334 [M+H]$^+$. HPLC purity: 98%.

PEPPSI-iPr™ (ca 2 mg) was added to a mixture of the bromide from above (33 mg, 0.100 mmol), 2-isopropylboronic acid pinacol ester (25 mg, 0.150 mmol) and potassium carbonate (20.7 mg, 0.150 mmol) in toluene (1 ml) and MeOH (1 ml). The mixture was heated at 100° C. for 30 min in a microwave reactor. The mixture was diluted with EtOAc and filtered through a short plug of silica and solvents evaporated. The residue was dissolved in MeOH (2.5 ml) and EtOAc (5 ml). Palladium (10% on C, 30 mg) was added and the mixture stirred under H$_2$ for 4 h before filtered through Celite and the solvents evaporated.

Hydroxylamine (50% in water, 0.5 ml) and KOH in MeOH (5 mg/ml, 1 ml) was added to the material from above and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 11.0 mg (27%, three steps); white solid.

Example 168

2-(4-Bromo-2-morpholin-4-ylphenyl)-N-hydroxy-1,3-benzoxazole-5-carboxamide

Methyl 2-(4-bromo-2-fluorophenyl)-1,3-benzoxazole-5-carboxylate, INTERMEDIATE 16 (28 mg, 0.080 mmol) and morpholine (50 μl) in MeCN (2 ml) were heated at 200° C. for 1 h. The solvent was evaporated. Hydroxylamine potassium salt (ca 1.7 M in MeOH, 1.5 ml) was added to the residue and the mixture was stirred at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 17.5 mg (52%, two steps); yellow solid.

Example 170

N-Hydroxy-2-[4-(1-methylethyl)-2-pyrrolidin-1-ylphenyl]-1,3-benzoxazole-5-carboxamide PEPPSI-iPr™ (ca 5 mg) was added to a mixture of methyl 2-(4-bromo-2-fluorophenyl)-1,3-benzoxazole-5-carboxylate, INTERMEDIATE 16 (80.0 mg, 0.228 mmol), isopropenylboronic acid pinacol ester (58 mg, 0.343 mmol) and potassium carbonate (49 mg, 0.353 mmol) in toluene (1 ml) and MeOH (1 ml). The mixture was heated at 100° C. for 30 min. Solvents were evaporated and residue purified by flash chromatography using 20% EtOAc in hexanes as eluent. Yield: 61.1 mg (86%); white solid. MS(ESI+) m/z 312 [M+H]$^+$. HPLC purity: 95%.

The material from above (60 mg, 0.193 mmol) in MeOH (2.5 ml) and EtOAc (5 ml) was added 10% palladium on charcoal (11 mg) and the mixture was stirred under an atmosphere of H$_2$ (balloon) at rt for 2 h. The mixture was filtered through Celite and solvents evaporated. Yield: 61 mg (100%); white solid The fluoride from above (20 mg, 0.064 mmol) and pyrrolidine (100 μl) in MeCN (2 ml) and THF (1 ml) were heated at 200° C. for 30 min in a microwave reactor. Solvents were evaporated and hydroxylamine potassium salt in MeOH (ca 1.7 M, 1.5 ml) was added to the residue. The mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 15.7 mg (67%, two steps); yellow solid.

Example 171

N-Hydroxy-2-[6-(1-methylethyl)pyridin-3-yl]-1,3-benzoxazole-5-carboxamide

PEPPSI-iPr™ (ca 5 mg) was added to a mixture of methyl 2-(6-chloropyridin-3-yl)-1,3-benzoxazole-5-carboxylate, INTERMEDIATE 15 (104 mg, 0.360 mmol), 2-propenylboronic acid pinacol ester (91 mg, 0.54 mmol) and potassium carbonate (75 mg, 0.54 mmol) in MeOH (1.5 ml) and toluene (1.5 ml). The mixture was heated at 100° C. for 30 min in a microwave reactor. Solvents were evaporated and residue purified by flash chromatography using 20% EtOAc in hexanes as eluent. Yield: 62.2 mg (59%); white solid.

Palladium (10% on C, 10 mg) was added to the material from above (24.4 mg, 0.082 mmol) in EtOAc (5 ml), THF (5 ml) and MeOH (2.5 ml). The mixture was stirred under an atmosphere of H$_2$ overnight, filtered through Celite and solvents evaporated.

Hydroxylamine potassium salt (ca 1.7 M in MeOH, 1.5 ml) was added to the material from above and the mixture stirred at 60° C. before quenched with AcOH (0.5 ml). The product was isolated by reversed phase chromatography (Kinetex C18, 5 μm, 21.2×100 mm, flow 25 ml/min, gradient 0.1% TFA in water/acetonitrile over 15 minutes). Yield: 10.3 mg (42%, two steps); white solid.

Example 172

2-(4-Bromo-2-ethoxyphenyl)-N-hydroxy-1,3-benzoxazole-5-carboxamide

Methyl 2-(4-bromo-2-fluorophenyl)-1,3-benzoxazole-5-carboxylate, INTERMEDIATE 16 (38 mg, 0.108 mmol) and K$_2$CO$_3$ (22 mg, 0.163 mmol) in EtOH (1 ml) and THF (1 ml) was heated at 150° C. for 2.5 h. The mixture was filtered and filtrate evaporated. Hydroxylamine potassium salt (ca 1.7 M in MeOH, 1.5 ml) was added to the residue and the mixture stirred at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 4.7 mg (15%, two steps); white solid.

Example 173

2-(3-Fluorobiphenyl-4-yl)-N-hydroxy-1,3-benzoxazole-5-carboxamide

General Procedure P

PEPPSI-iPr™ (ca 2 mg) was added to a mixture of methyl 2-(4-bromo-2-fluorophenyl)-1,3-benzoxazole-5-carboxylate, INTERMEDIATE 16 (28 mg, 0.080 mmol), phenylboronic acid (14.6 mg, 0.120 mmol) and potassium carbonate (22 mg, 0.160 mmol) in toluene (1 ml) and MeOH (1 ml). The mixture was heated at 100° C. for 30 min in a microwave reactor. Water and EtOAc/THF were added and organic layer was filtered and evaporated. Hydroxylamine potassium salt (ca 1.7 M in MeOH, 1.5 ml) was added to the residue and the mixture was stirred at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 8.8 mg (32%, two steps); white solid.

Example 194

N-Hydroxy-2-[3-(piperidin-1-ylmethyl)phenyl]-1-benzothiophene-5-carboxamide trifluoroacetate PEPPSI-iPr™ (ca 2 mg) was added to a mixture of methyl 2-iodobenzothiophene-5-carboxylate, INTERMEDIATE 8 (40.8 mg, 0.128 mmol), 3-formylbenzeneboronic acid (23.0 mg, 0.153 mmol) and potassium carbonate (26.5 mg, 0.192 mmol) in toluene (1 ml) and MeOH (1 ml). The mixture was heated at 100° C. for 30 min in a microwave reactor. Solvent was evaporated and residue dissolved in EtOAc and filtered through silica (0.5 g). Yield: 40.5 mg.

The material from above was dissolved in 1,2-dichloroethane (3 ml) and piperidine (25.2 μl, 0.256 mmol) and sodium triacetoxyborohydride (43 mg, 0.205 mmol) were added. The mixture was stirred at rt for 1 h. Water was added and organic layer separated and evaporated.

Hydroxylamine potassium salt (ca 1.7 M in MeOH, 1.5 ml) was added to the material from above and the mixture heated at 60° C. for 45 min before quenched with AcOH (0.5 ml). The material was isolated by reversed phase chromatography (Kinetex C18, 5 μm, 21.2×100 mm, flow 25 ml/min, gradient 0.1% TFA in water/acetonitrile over 15 minutes). Yield: 21.6 mg (35%, three steps); white solid.

Example 195

N-Hydroxy-2-(3-methoxybiphenyl-4-yl)-1,3-benzoxazole-5-carboxamide

General Procedure Q

PEPPSI-iPr™ (ca 2 mg) was added to a mixture of methyl 2-(4-bromo-2-methoxyphenyl)-1,3-benzoxazole-5-carboxylate, INTERMEDIATE 17 (29 mg, 0.080 mmol), phenylboronic acid (12.2 mg, 0.100 mmol) and potassium carbonate (16.6 mg, 0.120 mmol) in toluene (1 ml) and MeOH (1 ml). The mixture was heated at 100° C. for 30 min in a microwave reactor. Water and EtOAc were added. Organic layer was filtered and evaporated. Hydroxylamine potassium salt (ca 1.7 M in MeOH, 1.5 ml) was added to the residue and the mixture was stirred at 60° C. for 45 min before quenched with AcOH (0.5 ml). The title compound was isolated by reversed phase chromatography (Kinetex C18, 5 μm, 21.2× 100 mm, flow 25 ml/min, gradient 0.1% TFA in water/acetonitrile over 15 minutes). Yield: 7.9 mg (27%, two steps); white solid.

Example 201

N-Hydroxy-2-[3-(piperidin-1-ylmethyl)phenyl]-1,3-benzoxazole-5-carboxamide trifluoroacetate General Procedure R 3-Carboxybenzaldehyde (609 mg, 4.05 mmol) in thionyl chloride (4 ml) and toluene (4 ml) was heated at 60° C. for 4 h before solvents were evaporated.

The acid chloride from above and methyl 3-amino-4-hydroxybenzoate (675 mg, 4.04 mmol) in dioxane (2.5 ml) and MeCN (2.5 ml) were heated at 180° C. for 6 h. Water and dioxane were added and solid material isolated by centrifugation, The solid material was washed with MeOH and dried. Yield: 877 mg (77%); yellow solid. MS(ESI+) m/z 282 [M+H]$^+$. HPLC purity: 75%. $^1$H NMR (600 MHz, DMSO-d$_6$) δ ppm 10.17 (s, 1H) 8.71 (s, 1H) 8.47-8.57 (m, 1H) 8.37 (d, J=1.83 Hz, 1H) 8.18 (d, J=7.63 Hz, 1H) 8.09 (dd, J=8.55, 1.53 Hz, 1H) 7.97 (d, J=8.55 Hz, 1H) 7.87 (t, J=7.78 Hz, 1H) 3.91 (s, 3H).

The aldehyde from above (28.1 mg, 0.100 mmol), AcOH (5 μl) and piperidine (25 μl, 0.250 mmol) in THF (2 ml) was stirred at rt for 1 h before sodium triacetoxyborohydride (42 mg, 0.20 mmol) was added. The mixture was stirred at rt overnight. Water and EtOAc were added. The organic layer separated, filtered and evaporated. KOH in MeOH (5 mg/ml, 1 ml) and 50% hydroxylamine in water (0.5 ml) were added to the residue and the mixture was heated at 60° C. for 3 h before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 4.0 mg (9%, two steps); colourless oil.

Example 206

N-Hydroxy-2-[4-(piperidin-1-ylmethyl)phenyl]-1,3-benzoxazole-5-carboxamide trifluoroacetate General Procedure S 4-Carboxybenzaldehyde (582 mg, 3.87 mmol) and thionyl chloride (4 ml) and toluene (4 ml) was heated at 60° C. for 4 h before solvents were evaporated.

The acid chloride from above and methyl 3-amino-4-hydroxybenzoate (647 mg, 3.87 mmol) in doxane (2.5 ml) and MeCN (2.5 ml) were heated at 180° C. for 6 h. Water and dioxane were added and solid material isolated by centrifugation and washed with MeOH. Yield: 1.11 g; yellow solid. $^1$H NMR (600 MHz, DMSO-d$_6$) δ ppm 10.14 (s, 1H) 8.45 (d, J=7.93 Hz, 2H) 8.41 (d, J=1.22 Hz, 1H) 8.16 (d, J=8.54 Hz, 2H) 8.12 (dd, J=8.55, 1.83 Hz, 1H) 7.99 (d, J=8.55 Hz, 1H) 3.91 (s, 3H).

The aldehyde from above (28.1 mg, 0.100 mmol), AcOH (5 μl) and piperidine (25 μl, 0.250 mmol) in THF (2 ml) was stirred at rt for 1 h before sodium triacetoxyborohydride (42 mg, 0.20 mmol) was added the mixture was stirred at rt for 3 d. Water and EtOAc were added. The organic layer was separated, filtered and evaporated. Hydroxylamine potassium salt in MeOH (ca 1.7 M, 1.5 ml) was added to the residue and the mixture was heated at 60° C. for 3 h before quenched with AcOH (0.5 ml). The title compound was isolated by reversed phase chromatography (Kinetex C18, 5

μm, 21.2×100 mm, flow 25 ml/min, gradient 0.1% TFA in water/acetonitrile over 15 minutes). Yield: 9.5 mg (20%, two steps); colourless oil.

Example 211

2-[3-Fluoro-4-(1-methylethyl)phenyl]-N-hydroxy-1,3-benzoxazole-5-carboxamide

PEPPSI-iPr™ (ca 2 mg) was added to a mixture of methyl 2-(4-bromo-3-fluorophenyl)-1,3-benzoxazole-5-carboxylate, INTERMEDIATE 18 (88 mg, 0.251 mmol), isopropenylboronic acid pinacol ester (50 mg, 0.302 mmol) and potassium carbonate (52 mg, 0.377 mmol) in toluene (2 ml) and MeOH (2 ml) was heated at 100° C. for 30 min in a microwave reactor. Solvents were evaporated and the residue was purified by flash chromatography. Yield: 24.3 mg (31%); white solid.

The material from above was dissolved in MeOH (10 ml) and EtOAc (5 ml) and 10% Pd on charcoal (19 mg) was added. The mixture was stirred under $H_2$ for 3 h, filtered through Celite and solvents evaporated. Hydroxylamine potassium salt (ca 1.7 M in MeOH, 1.5 ml) was added to the residue and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 10.5 mg (43%); white solid.

Example 214

2-(4-Bromo-2-chlorophenyl)-N-hydroxy-1,3-benzoxazole-5-carboxamide

Oxalyl chloride (730 μl, 8.49 mmol) was added dropwise to a solution of 4-bromo-2-chlorobenzoic acid (1.00 g, 4.24 mmol) in THF (10 ml) and the mixture was stirred at rt for 1 h before solvents were evaporated and the residue was dissolved in dioxane (10 ml) and MeCN (10 ml). Methyl 3-amino-4-hydroxybenzoate (708 mg, 4.24 mmol) was added and the mixture was heated at 180° C. for 6 h. Solvents evaporated and residue purified by flash chromatography using 5% EtOAc in toluene. Yield: 969 mg (62%); white solid. $^1$H NMR (600 MHz, DMSO-d$_6$) δ ppm 8.39 (d, J=1.22 Hz, 1H) 8.09-8.13 (m, 2H) 8.05 (d, J=1.83 Hz, 1H) 7.96 (d, J=9.16 Hz, 1H) 7.83 (dd, J=8.39, 1.98 Hz, 1H) 3.91 (s, 3H).

To the material from above (28 mg, 0.076 mmol) was added hydroxylamine potassium salt (ca 1.7 M in MeOH, 1 ml) and the mixture was heated at 60° C. for 45 min before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 13.2 mg (47%); white solid.

Example 215

N-Hydroxy-2-(6-methoxypyridin-3-yl)-1,3-benzoxazole-5-carboxamide trifluoroacetate PEPPSI-iPr™ (ca 5 mg) was added to a mixture of methyl 2-chloro-1,3-benzoxazole-5-carboxylate, INTERMEDIATE 19 (33 mg, 0.156 mmol), 6-methoxypyridine-3-boronic acid (29 mg, 0.187 mmol) and potassium carbonate (32 mg, 0.233 mmol) in toluene (1 ml) and MeOH (1 ml) and the mixture was heated at 100° C. for 1 h. Water and toluene were added. The organic layer was separated and evaporated. Hydroxylamine potassium salt in MeOH (ca 1.7 M, 1.5 ml) was added, and the mixture was heated at 60° C. for 1 h before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 11.5 mg (18%, two steps); white solid.

Example 216

N-Hydroxy-2-(2-methoxypyridin-3-yl)-1,3-benzoxazole-5-carboxamide trifluoroacetate PEPPSI-iPr™ (ca 5 mg) was added to a mixture of methyl 2-chloro-1,3-benzoxazole-5-carboxylate, INTERMEDIATE 19 (33 mg, 0.156 mmol), 2-methoxypyridine-3-boronic acid (29 mg, 0.187 mmol) and potassium carbonate (32 mg, 0.233 mmol) in toluene (1 ml) and MeOH (1 ml) and the mixture was heated at 100° C. for 1 h. Water and toluene were added. The organic layer was separated and evaporated. Hydroxylamine potassium salt in MeOH (ca 1.7 M, 1.5 ml) was added and the mixture was heated at 60° C. for 1 h before quenched with AcOH (0.5 ml). The title compound was isolated reversed phase chromatography (Kinetex C18, 5 μm, 21.2×100 mm, flow 25 ml/min, gradient 0.1% TFA in water/acetonitrile over 15 minutes). Yield: 7.1 mg (11%, two steps); white solid.

Example 217

2-(4-Bromo-3-fluorophenyl)-N-hydroxy-1,3-benzoxazole-5-carboxamide

Hydroxylamine potassium salt (1.7 M in MeOH, 1 ml) was added to methyl 2-(4-bromo-3-fluorophenyl)-1,3-benzoxazole-5-carboxylate, INTERMEDIATE 18 (25.9 mg, 0.074 mmol) and the mixture was stirred at rt for 2 h before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 12.8 mg (49%); white solid.

Example 218

2-(4-Bromo-2-methoxyphenyl)-N-hydroxy-1,3-benzoxazole-5-carboxamide

Hydroxylamine potassium salt (ca 1.7 M in MeOH, 1 ml) was added to methyl 2-(4-bromo-2-methoxyphenyl)-1,3-benzoxazole-5-carboxylate, INTERMEDIATE 17 (22.9 mg, 0.063 mmol) and the mixture was stirred at rt for 2 h before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 5.3 mg (23%); white solid.

Example 219

2-(2,3-Dihydro-1,4-benzodioxin-6-yl)-N-hydroxy-1,3-benzoxazole-5-carboxamide General Procedure T 1,4-Benzodioxan-6-carboxaldehyde (16.4 mg, 0.100 mmol), potassium cyanide (6 mg, 0.100 mmol) and methyl 3-amino-4-hydroxybenzoate (13 mg, 0.075 mmol) in DMF (500 μl) was stirred at 70° C. overnight. Solvent was evaporated and water and isopropyl acetate were added. The organic phase was concentrated and MeOH (0.4 ml), KOH in MeOH (10 mg/ml, 0.5 ml) and 50% hydroxylamine in water (0.4 ml) was added to the residue. The mixture was stirred at 50° C. for 1 h before quenched with AcOH (0.4 ml): The title compound was isolated by reversed phase chromatography (Kinetex C18, 5 μm, 21.2×100 mm, flow 25 ml/min, gradient 0.1% TFA in water/acetonitrile over 15 minutes). Yield: 7.0 mg (41%); white solid.

Example 229

N-Hydroxy-2-[(4-propylphenyl)amino]-1,3-benzoxazole-5-carboxamide

General Procedure U

Methyl 2-chloro-1,3-benzoxazole-5-carboxylate, INTERMEDIATE 19 (16 mg, 0.075 mmol), 4-propylaniline (10.1 mg, 0.075 mmol) and DIPEA (10 μl, 0.075 mmol) in DMI (400 μl) was stirred at 80° C. overnight. The intermediate was purified with reversed phase chromatography (Kinetex, C18, 5 μm, 21×100 mm, flow 25 ml/min, gradient: water (0.1% TFA)/acetonitrile over 15 minutes).

MeOH (400 μl), KOH in MeOH (10 mg/ml, 400 μl) and 50% hydroxylamine in water (400 μl) was added to the ester from above. The mixture was stirred at 60° C. for 2 h before quenched with AcOH (400 μl). The title compound was isolated by reversed phase chromatography (Kinetex C18, 5 μm, 21.2×100 mm, flow 25 ml/min, gradient 0.1% TFA in water/acetonitrile over 15 minutes). Yield: 5.0 mg (20%); white solid.

Example 256

N-Hydroxy-2-[4-({[(1-methyl-1H-indol-3-yl)methyl]amino}methyl)piperidin-1-yl]-1,3-benzoxazole-5-carboxamide trifluoroacetate General Procedure V Methyl 2-chloro-1,3-benzoxazole-5-carboxylate, INTERMEDIATE 19 (211 mg, 1.00 mmol), 4-(N—BOC-aminomethyl)piperidine (240 mg, 0.10 mmol) and potassium carbonate (280 mg, 2.00 mmol) in MeCN (30 ml) was stirred at 50° C. for 1 h. The solvent was removed under vacuum and the residue partitioned between water and ethyl acetate. The organic phase was washed with water, 0.5 M $H_2SO_4$, sat. $NaHCO_3$ and brine, dried over MgSO4, filtered and concentrated. Yield: 380 mg (98%). $^1$H NMR (600 MHz, DMSO-d6) δ ppm 7.77 (d, J=1.2 Hz, 1H) 7.68 (dd, J=8.4, 1.7 Hz, 1H) 7.49 (d, J=7.9 Hz, 1H) 6.92 (t, J=5.8 Hz, 1H) 4.10-4.18 (m, 2H) 3.84 (s, 3H) 3.11 (td, J=12.7, 2.6 Hz, 2H) 2.85 (t, J=6.4 Hz, 2H) 1.61-1.77 (m, 3H) 1.38 (s, 9H) 1.11-1.22 (m, 2H)

The material from above was dissolved in MeOH (10 ml) and 2 M HCl (10 ml) was added. The reaction mixture was stirred at 60° for 2 hour. Water and solid sodium carbonate was added until pH~10. The product was extracted repeatedly with ethyl acetate. The combined organic phase was washed with brine, dried over MgSO4, filtered and concentrated. Yield: 200 mg (70%). MS (ESI+) m/z 290 [M+H]+, LCMS purity: 100%. $^1$H NMR (600 MHz, DMSO-d$_6$) δ ppm 7.77 (d, 1H) 7.64-7.70 (m, 1H) 7.50 (d, J=8.2 Hz, 1H) 4.11-4.21 (m, 2H) 3.84 (s, 3H) 3.11 (td, J=12.8, 2.7 Hz, 2H) 2.47 (d, J=6.7 Hz, 2H) 1.76-1.85 (m, 2H) 1.48-1.57 (m, 1H) 1.12-1.23 (m, 2H).

The amine from above (22 mg, 0.075 mmol), sodium triacetoxyborohydride (32 mg, 0.150 mmol) and 1-methyl-indole-3-carboxaldehyde (12 mg, 0.075 mmol) in DCE (2 ml) was stirred at rt overnight. The reaction mixture was quenched by adding conc. ammonia in water and the intermediate was isolated by with reversed phase chromatography (Gemini-NX, C18, 5 μm, 21×100 mm, flow 25 ml/min, gradient: water (50 mM ammonium bicarbonate, pH 10)/acetonitrile over 15 minutes).

MeOH (400 μl), KOH in MeOH (10 mg/ml, 400 μl) and 50% hydroxylamine in water (400 μl) was added to the ester from above. The mixture was stirred at 60° C. for 2 h before quenched with AcOH (400 μl). The title compound was isolated by reversed phase chromatography (Kinetex C18, 5 μm, 21.2×100 mm, flow 25 ml/min, gradient 0.1% TFA in water/acetonitrile over 15 minutes). Yield: 10.0 mg (20%); white solid.

Example 270

2-[(Benzyloxy)methyl]-N-hydroxy-1,3-benzothiazole-5-carboxamide

KOH in MeOH (10 mg/ml, 1 ml) and 50% hydroxylamine in water (0.5 ml) was added to methyl 2-[(benzyloxy)methyl]-1,3-benzothiazole-5-carboxylate, INTERMEDIATE 20 (32.5 mg. 0.104 mmol) and the mixture was heated at 60° C. for 2 h before quenched with AcOH (0.5 ml). The title compound was isolated by reversed phase chromatography (Kinetex C18, 5 am, 21.2×100 mm, flow 25 ml/min, gradient 0.1% TFA in water/acetonitrile over 15 minutes). Yield: 19.2 mg (59%); white solid.

Example 271

N-Hydroxy-2-(hydroxymethyl)-1,3-benzothiazole-5-carboxamide

KOH (10 mg/ml, 1 ml) and 50% hydroxylamine in water was added to methyl 2-(hydroxymethyl)-1,3-benzothiazole-5-carboxylate, INTERMEDIATE 21 (21.1 mg, 0.094 mmol) and the mixture was stirred at 60° C. for 1 h before quenched with AcOH (0.5 ml) and the title compound isolated by reversed phase chromatography (Kinetex C18, 5 μm, 21.2×100 mm, flow 25 ml/min, gradient 0.1% TFA in water/acetonitrile over 15 minutes). Yield: 3.6 mg (17%); white solid.

Example 272

N-Hydroxy-2-(4-pyridin-4-ylbenzyl)-1,3-benzothiazole-5-carboxamide trifluoroacetate Methyl 3-amino-4-fluorobenzoate (88 mg, 0.530 mmol) and 4-chlorophenylacetyl chloride (77 μl, 0.520 mmol) in toluene (6 ml) were heated at 100° C. for 1 h. Lawesson reagent (210 mg, 0.520 mmol) was added and the mixture was heated at 110° C. overnight. Solvent was evaporated and residue purified by flash chromatography using 20% EtOAc in hexanes as eluent. Yield: 72.4 mg (44%); white solid. MS(ESI+) m/z 318 [M+H]⁺. HPLC purity: 100% PEPPSI-iPr™ (ca 5 mg) was added to a mixture of the chloride from above (54.4 mg, 0.171 mmol), 4-pyridineboronic acid (25.2 mg, 0.205 mmol) and potassium carbonate (35.5 mg, 0.256 mmol) in toluene (2 ml) and MeOH (2 ml). The mixture was heated at 100° C. for 45 min in a microwave reactor. Water and EtOAc were added. The aqueous layer was extracted with EtOAc and combined organic layer evaporated.

KOH (10 mg/ml, 1 ml) and 50% hydroxylamine in water (0.5 ml) was added to the residue from above and the mixture was stirred at ambient temperature overnight before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 14.6 mg (18%, two steps).

Example 273

N-Hydroxy-2-(piperidin-1-ylmethyl)-1,3-benzothiazole-5-carboxamide

Piperidine (25 μl, 0.238 mmol) was added to a solution of methyl 2-bromomethyl-1,3-benzothiazole-5-carboxylate, INTERMEDIATE 22 (22.5 mg, 0.079 mmol) in MeCN (2 ml) and the mixture was stirred at rt for 15 min. Solvent was evaporated and KOH in MeOH (10 mg/ml, 1 ml) and 50% hydroxylamine in water (0.5 ml) were added. The mixture was stirred at rt overnight. The title compound was isolated by reversed phase chromatography (Gemini-NX C18, 5 μm, 21×50 mm, flow 25 ml/min, gradient: water (50 mM $NH_4HCO_3$ pH 10)/acetonitrile over 12 minutes). Yield: 15.3 mg (66%, two steps); white solid.

Example 274

2-{[Bis(2-methylpropyl)amino]methyl}-N-hydroxy-1,3-benzothiazole-5-carboxamide trifluoroacetate Diisobutylamine (41 μl, 0.238 mmol) was added to a solution of methyl 2-bromomethyl-1,3-benzothiazole-5-carboxylate, INTERMEDIATE 22 (22.5 mg, 0.079 mmol) in MeCN (2 ml) and the mixture was stirred at rt for 20 min and at 60° C. for 2 h. Solvent was evaporated and KOH in MeOH (10 mg/ml, 1 ml) and 50% hydroxylamine in water (0.5 ml) were added. The mixture was stirred at rt overnight before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 19.2 mg (54%, two steps); white solid.

Example 275

N-Hydroxy-2-({[4-(1-methylethyl)phenyl]amino}methyl)-1,3-benzothiazole-5-carboxamide Methyl 2-bromomethyl-1,3-benzothiazole-5-carboxylate, INTERMEDIATE 22 (22.5 mg, 0.079 mmol), 4-isopropylaniline (22 mg, 0.158 mmol) and potassium carbonate (22 mg, 0.158 mmol) in MeCN (2 ml) was stirred at rt for 20 min and at 60° C. for 2 h. Solvent was evaporated and KOH in MeOH (10 mg/ml, 1 ml) and 50% hydroxylamine in water (0.5 ml) were added. The mixture was stirred at rt overnight before quenched with AcOH (0.5 ml). The title compound was isolated by reversed phase chromatography (Kinetex C18, 5 μm, 21.2×100 mm, flow 25 ml/min, gradient 0.1% TFA in water/acetonitrile over 15 minutes). Yield: 18.0 mg (67%, two steps); white solid.

Example 276

N-Hydroxy-2-phenyl-1-benzofuran-5-carboxamide

General Procedure W

PEPPSI-iPr™ (ca 2 mg) was added to a mixture of methyl 2-bromo-1-benzofuran-5-carboxylate, INTERMEDIATE 23 (13 mg, 0.050 mmol), benzeneboronic acid (7 mg, 0.060 mmol) and potassium carbonate (14 mg, 0.100 mmol) in toluene/MeOH (2:1, 2 ml). The mixture was heated at 100° C. in a microwave reactor for 30 min. Water and isopropyl acetate were added. The organic phase was washed with water and concentrated. The residue was purified with reversed phase chromatography (Gemini-NX, C18, 5 μm, 21×100 mm, flow 25 ml/min, gradient: water (50 mM ammonium bicarbonate, pH 10)/acetonitrile over 15 minutes).

To the ester from above was added MeOH (400 μl), 50% hydroxylamine in water (400 μl) and KOH in MeOH (10 mg/ml, 500 μl). The mixture was stirred at 50° C. for 1 h, quenched with AcOH (200 μl) and the title compound isolated with reversed phase chromatography (Kinetex, C18, 5 μm, 21×100 mm, flow 25 ml/min, gradient: water (0.1% TFA)/acetonitrile over 15 minutes). Yield: 7.0 mg (54%); white solid.

Example 282

N-Hydroxy-2-phenyl-1-benzofuran-6-carboxamide

General Procedure X

PEPPSI-iPr™ (ca 2 mg) was added to a mixture of methyl 2-bromo-1-benzofuran-6-carboxylate, INTERMEDIATE 24 (13 mg, 0.050 mmol), benzeneboronic acid (7 mg, 0.060 mmol) and potassium carbonate (14 mg, 0.100 mmol) in toluene/MeOH (2:1, 2 ml). The mixture was heated at 100° C. in a microwave reactor for 30 min. Water and isopropyl acetate were added. The organic phase was washed with water and concentrated. The residue was purified with reversed phase chromatography (Gemini-NX, C18, 5 μm, 21×100 mm, flow 25 ml/min, gradient: water (50 mM ammonium bicarbonate, pH 10)/acetonitrile over 15 minutes).

To the ester from above was added MeOH (400 μl), 50% hydroxylamine in water (400 μl) and KOH in MeOH (10 mg/ml, 500 μl). The mixture was stirred at 50° C. for 1 h, quenched with AcOH (200 μl) and the title compound isolated with reversed phase chromatography (Kinetex, C18, 5 μm, 21×100 mm, flow 25 ml/min, gradient: water (0.1% TFA)/acetonitrile over 15 minutes). Yield: 5.0 mg (36%); white solid.

Examples of the present invention are listed in Table 1, with analytical data and synthetic details listed in Table 2.

TABLE 1

| Ex. | Chemical name | Structural formula |
|---|---|---|
| 1 | N-hydroxy-2-[4-(1-methylethyl)phenyl]-1,3-benzoxazole-5-carboxamide | |
| 2 | 2-(4-bromophenyl)-N-hydroxy-1,3-benzoxazole-5-carboxamide | |
| 3 | 2-[3,5-bis(trifluoromethyl)phenyl]-N-hydroxy-1,3-benzoxazole-5-carboxamide | |
| 4 | 2-(4-tert-butylphenyl)-N-hydroxy-1,3-benzoxazole-5-carboxamide | |
| 5 | 2-(3,4-difluorophenyl)-N-hydroxy-1,3-benzoxazole-5-carboxamide | |
| 6 | N-hydroxy-2-[3-(trifluoromethyl)phenyl]-1,3-benzoxazole-5-carboxamide | |
| 7 | N-hydroxy-2-phenyl-1,3-benzoxazole-5-carboxamide | |
| 8 | 2-(1,3-benzodioxol-5-yl)-N-hydroxy-1,3-benzoxazole-5-carboxamide | |

TABLE 1-continued

| Ex. | Chemical name | Structural formula |
|---|---|---|
| 9 | N-hydroxy-2-[4-(trifluoromethoxy)phenyl]-1,3-benzoxazole-5-carboxamide | |
| 10 | 2-(2,6-difluorophenyl)-N-hydroxy-1,3-benzoxazole-5-carboxamide | |
| 11 | N-hydroxy-2-(4-methoxyphenyl)-1,3-benzoxazole-5-carboxamide | |
| 12 | 2-(2-chlorophenyl)-N-hydroxy-1,3-benzoxazole-5-carboxamide | |
| 13 | N-hydroxy-2-pyridin-3-yl-1,3-benzoxazole-5-carboxamide | |
| 14 | 2-(2,5-dichlorophenyl)-N-hydroxy-1,3-benzoxazole-5-carboxamide | |
| 15 | N-hydroxy-2-(6-morpholin-4-ylpyridin-3-yl)-1,3-benzoxazole-5-carboxamide | |
| 16 | 2-(3-bromophenyl)-N-hydroxy-1,3-benzoxazole-5-carboxamide | |

TABLE 1-continued

| Ex. | Chemical name |
|---|---|
| 17 | 2-[4-(difluoromethoxy)phenyl]-N-hydroxy-1,3-benzoxazole-5-carboxamide |
| 18 | N-hydroxy-2-[4-(trifluoromethyl)phenyl]-1,3-benzoxazole-5-carboxamide |
| 19 | 2-(3,4-dimethoxyphenyl)-N-hydroxy-1,3-benzoxazole-5-carboxamide |
| 20 | 2-(2,5-dimethoxyphenyl)-N-hydroxy-1,3-benzoxazole-5-carboxamide |
| 21 | 2-(2'-fluorobiphenyl-4-yl)-N-hydroxy-1,3-benzoxazole-5-carboxamide |
| 22 | N-hydroxy-2-(4-pyridin-4-ylphenyl)-1,3-benzoxazole-5-carboxamide |
| 23 | N-hydroxy-2-(4-pyridin-3-ylphenyl)-1,3-benzoxazole-5-carboxamide |
| 24 | 2-biphenyl-4-yl-N-hydroxy-1,3-benzoxazole-5-carboxamide |
| 25 | 2-(2'-fluoro-3'-methoxybiphenyl-4-yl)-N-hydroxy-1,3-benzoxazole-5-carboxamide |

TABLE 1-continued

| Ex. | Chemical name |
|---|---|
| 26 | N-hydroxy-2-[4-(4-methoxypyridin-3-yl)phenyl]-1,3-benzoxazole-5-carboxamide |
| 27 | N-hydroxy-2-[4-(6-methoxypyridin-3-yl)phenyl]-1,3-benzoxazole-5-carboxamide |
| 28 | N-hydroxy-2-[4-(2-methoxypyridin-3-yl)phenyl]-1,3-benzoxazole-5-carboxamide |
| 29 | 2-(4-cyclopropylphenyl)-N-hydroxy-1,3-benzoxazole-5-carboxamide |
| 30 | N-hydroxy-2-[4'-(piperidin-1-ylmethyl)biphenyl-4-yl]-1,3-benzoxazole-5-carboxamide |
| 31 | 2-(4-aminophenyl)-N-hydroxy-1,3-benzoxazole-5-carboxamide |
| 32 | 2-(2-chloro-6-fluorophenyl)-N-hydroxy-1,3-benzoxazole-5-carboxamide |
| 33 | 2-[4-(diethylamino)phenyl]-N-hydroxy-1,3-benzoxazole-5-carboxamide |
| 34 | 2-(2,6-dichlorophenyl)-N-hydroxy-1,3-benzoxazole-5-carboxamide |

TABLE 1-continued

| Ex. | Chemical name | Structural formula |
| --- | --- | --- |
| 35 | N-hydroxy-2-pyridin-2-yl-1,3-benzoxazole-5-carboxamide | |
| 36 | 2-(4-cyanophenyl)-N-hydroxy-1,3-benzoxazole-5-carboxamide | |
| 37 | N-hydroxy-2-{4-[(methylsulfonyl)amino]phenyl}-1,3-benzoxazole-5-carboxamide | |
| 38 | N-hydroxy-2-{4-[(phenylsulfonyl)amino]phenyl}-1,3-benzoxazole-5-carboxamide | |
| 39 | 2-(1H-benzotriazol-5-yl)-N-hydroxy-1,3-benzoxazole-5-carboxamide | |
| 40 | N-hydroxy-2-(2-methylpyridin-3-yl)-1,3-benzoxazole-5-carboxamide | |
| 41 | N-hydroxy-2-(6-pyrrolidin-1-ylpyridin-3-yl)-1,3-benzoxazole-5-carboxamide | |
| 42 | N-hydroxy-2-(phenylamino)-1,3-benzoxazole-5-carboxamide | |

TABLE 1-continued

| Ex. | Chemical name | Structural formula |
|---|---|---|
| 43 | N-hydroxy-2-{[4-(1-methylethyl)phenyl]amino}-1,3-benzoxazole-5-carboxamide | 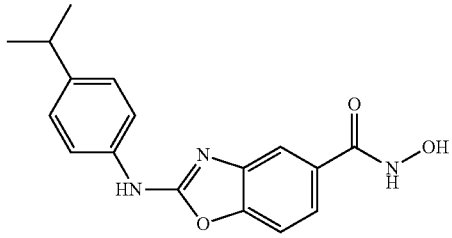 [SMILES: CC(C)c1ccc(Nc2nc3cc(C(=O)NO)ccc3o2)cc1] |
| 44 | 2-[benzyl(methyl)amino]-N-hydroxy-1,3-benzoxazole-5-carboxamide | 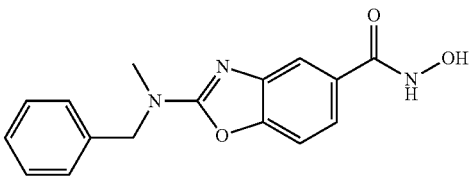 [SMILES: CN(Cc1ccccc1)c1nc2cc(C(=O)NO)ccc2o1] |
| 45 | N-hydroxy-2-[(2-phenylethyl)amino]-1,3-benzoxazole-5-carboxamide | 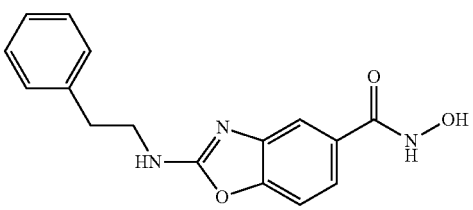 [SMILES: O=C(NO)c1ccc2oc(NCCc3ccccc3)nc2c1] |
| 46 | 2-(3,4-dihydroisoquinolin-2(1H)-yl)-N-hydroxy-1,3-benzoxazole-5-carboxamide | 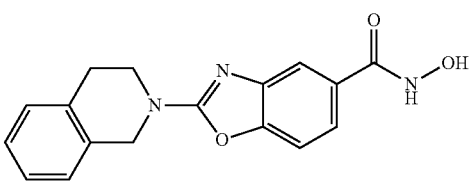 [SMILES: O=C(NO)c1ccc2oc(N3CCc4ccccc4C3)nc2c1] |
| 47 | 2-{[3-(benzyloxy)phenyl]amino}-N-hydroxy-1,3-benzoxazole-5-carboxamide | 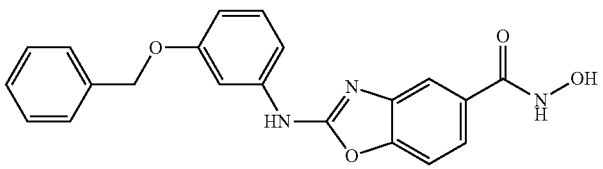 [SMILES: O=C(NO)c1ccc2oc(Nc3cccc(OCc4ccccc4)c3)nc2c1] |
| 48 | 2-(4-benzylpiperidin-1-yl)-N-hydroxy-1,3-benzoxazole-5-carboxamide | 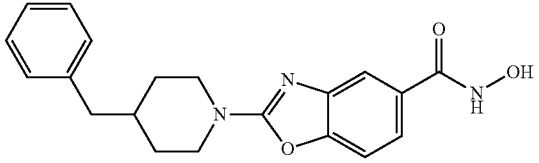 [SMILES: O=C(NO)c1ccc2oc(N3CCC(Cc4ccccc4)CC3)nc2c1] |
| 49 | N-hydroxy-2-[4-(1-methylethyl)phenyl]-1,3-benzoxazole-6-carboxamide | 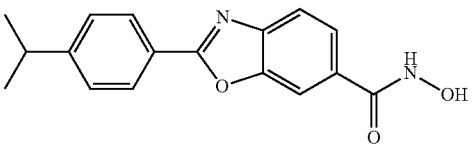 [SMILES: CC(C)c1ccc(-c2nc3ccc(C(=O)NO)cc3o2)cc1] |
| 50 | 2-(4-fluorophenyl)-N-hydroxy-1,3-benzoxazole-6-carboxamide | 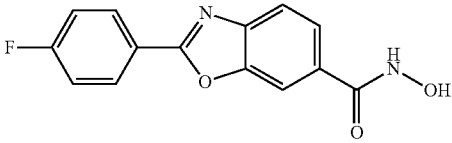 [SMILES: O=C(NO)c1ccc2nc(-c3ccc(F)cc3)oc2c1] |

TABLE 1-continued

| Ex. | Chemical name |
|---|---|
| 51 | 2-(4-tert-butylphenyl)-N-hydroxy-1,3-benzoxazole-6-carboxamide |
| 52 | N-hydroxy-2-(4-methoxyphenyl)-1,3-benzoxazole-6-carboxamide |
| 53 | 2-(6-chloropyridin-3-yl)-N-hydroxy-1,3-benzoxazole-6-carboxamide |
| 54 | 2-(1H-benzotriazol-5-yl)-N-hydroxy-1,3-benzoxazole-6-carboxamide |
| 55 | 2-(2,3'-bipyridin-5-yl)-N-hydroxy-1,3-benzoxazole-6-carboxamide |
| 56 | N-hydroxy-2-[4-(1-methylethyl)phenyl]-1H-imidazo[4,5-c]pyridine-6-carboxamide |
| 57 | N-hydroxy-2-[4-(1-methylethyl)phenyl]-1H-imidazo[4,5-b]pyridine-6-carboxamide |
| 58 | N-hydroxy-2-[4-(1-methylethyl)phenyl]-1H-imidazo[4,5-c]pyridine-6-carboxamide |
| 59 | N-hydroxy-2-[4-(1-methylethyl)phenyl]-1H-indole-6-carboxamide |

TABLE 1-continued

| Ex. | Chemical name |
|---|---|
| 60 | N-hydroxy-2-[4-(1-methylethyl)phenyl]-1H-indole-5-carboxamide |
| 61 | N-hydroxy-2-[4-(1-methylethyl)phenyl]-1,3-benzothiazole-6-carboxamide |
| 62 | 2-(1,3-benzodioxol-5-yl)-N-hydroxy-1,3-benzothiazole-6-carboxamide |
| 63 | N-hydroxy-2-pyridin-4-yl-1,3-benzothiazole-6-carboxamide |
| 64 | N-hydroxy-2-[4-(methylsulfonyl)phenyl]-1,3-benzothiazole-6-carboxamide |
| 65 | 2-(2,3-dihydro-1-benzofuran-5-yl)-N-hydroxy-1,3-benzothiazole-6-carboxamide |
| 66 | 2-(2,3-dihydro-1,4-benzodioxin-6-yl)-N-hydroxy-1,3-benzothiazole-6-carboxamide |
| 67 | 2-(4-butylphenyl)-N-hydroxy-1,3-benzothiazole-6-carboxamide |
| 68 | N-hydroxy-2-thiophen-3-yl-1,3-benzothiazole-6-carboxamide |

TABLE 1-continued

| Ex. | Chemical name | Structural formula |
|---|---|---|
| 69 | 2-(1-benzofuran-2-yl)-N-hydroxy-1,3-benzothiazole-6-carboxamide | |
| 70 | N-hydroxy-2-quinolin-8-yl-1,3-benzothiazole-6-carboxamide | |
| 71 | N-hydroxy-2-naphthalen-2-yl-1,3-benzothiazole-6-carboxamide | |
| 72 | 2-[3-(benzyloxy)phenyl]-N-hydroxy-1,3-benzothiazole-6-carboxamide | |
| 73 | 2-(2-fluoro-3-methoxyphenyl)-N-hydroxy-1,3-benzothiazole-6-carboxamide | |
| 74 | 2-(5-chloro-2-methoxyphenyl)-N-hydroxy-1,3-benzothiazole-6-carboxamide | |
| 75 | N-hydroxy-2-[4-(1-methylethyl)phenyl]-1,3-benzothiazole-5-carboxamide | |
| 76 | 2-(4-fluorophenyl)-N-hydroxy-1,3-benzothiazole-5-carboxamide | |

TABLE 1-continued

| Ex. | Chemical name |
|---|---|
| 77 | 2-(4-tert-butylphenyl)-N-hydroxy-1,3-benzothiazole-5-carboxamide |
| 78 | N-hydroxy-2-(4-methoxyphenyl)-1,3-benzothiazole-5-carboxamide |
| 79 | 2-(4-fluorobenzyl)-N-hydroxy-1,3-benzothiazole-5-carboxamide |
| 80 | 2-(5-bromopyridin-3-yl)-N-hydroxy-1,3-benzothiazole-5-carboxamide |
| 81 | N-hydroxy-2-(7-methoxy-1-benzofuran-2-yl)-1,3-benzothiazole-5-carboxamide |
| 82 | 2-(4-ethylphenyl)-N-hydroxy-1,3-benzothiazole-5-carboxamide |
| 83 | N-hydroxy-2-[4-(1-methylethyl)phenyl][1,3]oxazolo[5,4-b]pyridine-6-carboxamide |
| 84 | N-hydroxy-2-[4-(1-methylethyl)phenyl]-1H-pyrrolo[2,3-b]pyridine-5-carboxamide |
| 85 | N-hydroxy-2-[4-(1-methylethyl)phenyl]-1H-pyrrolo[3,2-b]pyridine-5-carboxamide |

TABLE 1-continued

| Ex. | Chemical name |
|---|---|
| 86 | N-hydroxy-6-[4-(1-methylethyl)phenyl]-7H-pyrrolo[2,3-d]pyrimidine-2-carboxamide |
| 87 | N-hydroxy-2-[4-(1-methylethyl)phenyl[thieno[2,3-b]pyridine-5-carboxamide |
| 88 | N-hydroxy-2-[4-(1-methylethyl)phenyl]-1-benzothiophene-6-carboxamide |
| 89 | N-hydroxy-2-[4-(1-methylethyl)phenyl]-1-benzothiophene-5-carboxamide |
| 90 | N-hydroxy-2-[3-(trifluoromethyl)phenyl]-1-benzothiophene-5-carboxamide |
| 91 | 2-[4-fluoro-3-(trifluoromethyl)phenyl]-N-hydroxy-1-benzothiophene-5-carboxamide |
| 92 | N-hydroxy-2-(3-methoxyphenyl)-1-benzothiophene-5-carboxamide |
| 93 | N-hydroxy-2-(4-methoxyphenyl)-1-benzothiophene-5-carboxamide |
| 94 | N-hydroxy-2-(1H-pyrazol-4-yl)-1-benzothiophene-5-carboxamide |

TABLE 1-continued

| Ex. | Chemical name | Structural formula |
|---|---|---|
| 95 | N-hydroxy-2-(1H-indol-5-yl)-1-benzothiophene-5-carboxamide | |
| 96 | N-hydroxy-2-pyridin-3-yl-1-benzothiophene-5-carboxamide | |
| 97 | N-hydroxy-2-(2-methoxypyridin-3-yl)-1-benzothiophene-5-carboxamide | |
| 98 | N-hydroxy-2-(6-methoxypyridin-3-yl)-1-benzothiophene-5-carboxamide | |
| 99 | N-hydroxy-2-(1-methyl-1H-pyrazol-4-yl)-1-benzothiophene-5-carboxamide | |
| 100 | 2-(3,5-dimethylisoxazol-4-yl)-N-hydroxy-1-benzothiophene-5-carboxamide | |
| 101 | N-hydroxy-2-[4-(trifluoromethyl)phenyl]-1-benzothiophene-5-carboxamide | |
| 102 | N-hydroxy-2-[4-(trifluoromethoxy)phenyl]-1-benzothiophene-5-carboxamide | |
| 103 | 2-(4-tert-butylphenyl)-N-hydroxy-1-benzothiophene-5-carboxamide | |

TABLE 1-continued

| Ex. | Chemical name | Structural formula |
|---|---|---|
| 104 | 2-[(E)-2-(4-fluorophenyl)ethenyl]-N-hydroxy-1-benzothiophene-5-carboxamide | |
| 105 | 2-(5-fluoro-2-hydroxyphenyl)-N-hydroxy-1-benzothiophene-5-carboxamide | |
| 106 | 2-(5-fluoro-2-methoxyphenyl)-N-hydroxy-1-benzothiophene-5-carboxyamide | |
| 107 | 2-[3-chloro-4-(1-methylethoxy)phenyl]-N-hydroxy-1-benzothiophene-5-carboxamide | |
| 108 | 2-[4-(dimethylcarbamoyl)phenyl]-N-hydroxy-1-benzothiophene-5-carboxamide | |
| 109 | N-hydroxy-2-{4-[(methylsulfonyl)amino]phenyl}-1-benzothiophene-5-carboxamide | |
| 110 | N-hydroxy-2-[4-(1-methylethyl)phenyl]thieno[3,2-b]pyridine-6-carboxamide | |
| 111 | N-hydroxy-2-[4-(1-methylethyl)phenyl]-1-benzofuran-5-carboxamide | |

TABLE 1-continued

| Ex. | Chemical name | Structural formula |
|---|---|---|
| 112 | N-hydroxy-2-[4-(1-methylethyl)phenyl]-1-benzofuran-6-carboxamide | |
| 113 | N-hydroxy-2-[4-(1-methylethyl)phenyl]furo[2,3-b]pyridine-5-carboxamide | |
| 114 | N-hydroxy-2-[4-(1-methylethyl)phenyl]furo[3,2-b]pyridine-5-carboxamide | |
| 115 | N-hydroxy-2-[4-(1-methylethyl)phenyl]furo[3,2-b]pyridine-6-carboxamide | |
| 116 | N-hydroxy-2-[4-(1-methylethyl)phenyl]furo[2,3-b]pyridine-6-carboxamide | |
| 117 | 2-[(diethylamino)methyl]-N-hydroxy-1-benzofuran-6-carboxamide | |
| 118 | N-hydroxy-2-(1-hydroxy-1-methylethyl)-1-benzofuran-6-carboxamide | |
| 119 | N-hydroxy-2-(hydroxymethyl)-1-benzofuran-6-carboxamide | |
| 120 | 3-chloro-N-hydroxy-2-phenyl-1H-indole-6-carboxamide | |

TABLE 1-continued

| Ex. | Chemical name | Structural formula |
|---|---|---|
| 121 | 3-chloro-N-hydroxy-2-[4-(1-methylethyl)phenyl]-1H-indole-6-carboxamide | |
| 122 | 2-bromo-3-chloro-N-hydroxy-1H-indole-6-carboxamide | |
| 123 | N-hydroxy-2-(phenylamino)-1H-benzo[d]imidazole-6-carboxamide | |
| 124 | N-hydroxy-2-((4-isopropylphenyl)amino)-1H-benzo[d]imidazole-6-carboxamide | |
| 125 | 2-((([1,1'-biphenyl]-4-ylmethyl)amino)-N-hydroxy-1H-benzo[d]imidazole-6-carboxamide | |
| 126 | 2-(4-(4-fluorophenyl)piperazin-1-yl)-N-hydroxy-1H-benzo[d]imidazole-6-carboxamide | |
| 127 | 2-(benzylamino)-N-hydroxy-1H-benzo[d]imidazole-6-carboxamide | |
| 128 | 2-((4-bromophenyl)amino)-N-hydroxy-1H-benzo[d]imidazole-6-carboxamide | |

TABLE 1-continued

| Ex. | Chemical name | Structural formula |
|---|---|---|
| 129 | 2-((3-bromophenyl)amino)-N-hydroxy-1H-benzo[d]imidazole-6-carboxamide | |
| 130 | 2-(benzyl(methyl)amino)-N-hydroxy-1H-benzo[d]imidazole-6-carboxamide | |
| 131 | 2-(benzyl(phenyl)amino)-N-hydroxy-1H-benzo[d]imidazole-6-carboxamide | |
| 132 | 2-((3-(benzyloxy)phenyl)amino)-N-hydroxy-1H-benzo[d]imidazole-6-carboxamide | |
| 133 | 2-(4-benzylpiperidin-1-yl)-N-hydroxy-1H-benzo[d]imidazole-6-carboxamide | |
| 134 | 2-((4-chlorophenyl)(methyl)amino)-N-hydroxy-1H-benzo[d]imidazole-6-carboxamide | |
| 135 | tert-butyl (1-(6-(hydroxycarbamoyl)-1H-benzo[d]imidazol-2-yl)piperidin-4-yl)carbamate | |
| 136 | 2-([1,1'-biphenyl]-3-ylamino)-N-hydroxy-1H-benzo[d]imidazole-6-carboxamide | |

TABLE 1-continued

| Ex. | Chemical name | Structural formula |
|---|---|---|
| 137 | N-hydroxy-1-methyl-2-(phenylamino)-1H-benzo[d]imidazole-5-carboxamide | 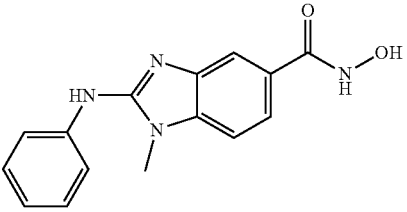 [SMILES: Cn1c(Nc2ccccc2)nc2cc(C(=O)NO)ccc21] |
| 138 | N-hydroxy-2-((4-isopropylphenyl)amino)-1-methyl-1H-benzo[d]imidazole-5-carboxamide | 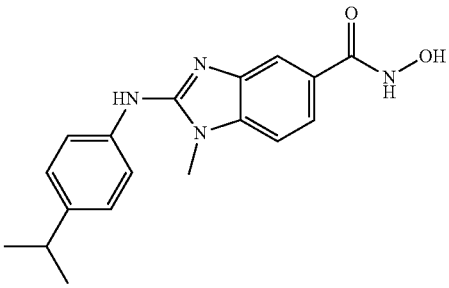 [SMILES: CC(C)c1ccc(Nc2nc3cc(C(=O)NO)ccc3n2C)cc1] |
| 139 | 2-(benzyl(methyl)amino)-N-hydroxy-1-methyl-1H-benzo[d]imidazole-5-carboxamide | 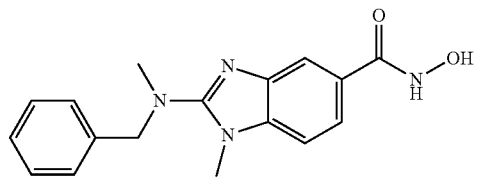 [SMILES: CN(Cc1ccccc1)c1nc2cc(C(=O)NO)ccc2n1C] |
| 140 | N-hydroxy-1-methyl-2-(phenethylamino)-1H-benzo[d]imidazole-5-carboxamide | 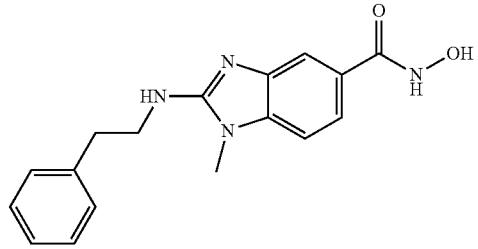 [SMILES: Cn1c(NCCc2ccccc2)nc2cc(C(=O)NO)ccc21] |
| 141 | 2-(benzyl(phenyl)amino)-N-hydroxy-1-methyl-1H-benzo[d]imidazole-5-carboxamide | 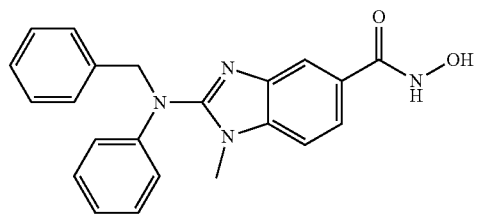 [SMILES: Cn1c(N(Cc2ccccc2)c2ccccc2)nc2cc(C(=O)NO)ccc21] |
| 142 | 2-((3-(benzyloxy)phenyl)amino)-N-hydroxy-1-methyl-1H-benzo[d]imidazole-5-carboxamide | 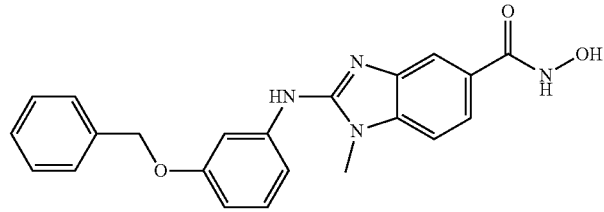 [SMILES: Cn1c(Nc2cccc(OCc3ccccc3)c2)nc2cc(C(=O)NO)ccc21] |

TABLE 1-continued

| Ex. | Chemical name |
|---|---|
| 143 | 2-(4-benzylpiperidin-1-yl)-N-hydroxy-1-methyl-1H-benzo[d]imidazole-5-carboxamide |
| 144 | 2-([1,1'-biphenyl]-3-ylamino)-N-hydroxy-1-methyl-1H-benzo[d]imidazole-5-carboxamide |
| 145 | 2-(3,4-dihydroisoquinolin-2(1H)-yl)-N-hydroxy-1-methyl-1H-benzo[d]imidazole-5-carboxamide |
| 146 | 2-((4-chlorophenyl)(methyl)amino)-N-hydroxy-1-methyl-1H-benzo[d]imidazole-5-carboxamide |
| 147 | 2-(3,4-dimethoxyphenyl)-N-hydroxy-1-benzothiophene-6-carboxamide |
| 148 | 2-dibenzo[b,d]furan-4-yl-N-hydroxy-1-benzothiophene-6-carboxamide |
| 149 | 2-furan-3-yl-N-hydroxy-1-benzothiophene-6-carboxamide |

TABLE 1-continued

| Ex. | Chemical name |
|---|---|
| 150 | N-hydroxy-2-(4-hydroxy-3-methoxyphenyl)-1-benzothiophene-6-carboxamide |
| 151 | N-hydroxy-2-(hydroxymethyl)-1-benzofuran-5-carboxamide |
| 152 | N-hydroxy-2-[6-(4-methylpiperidin-1-yl)pyridin-3-yl]-1,3-benzoxazole-5-carboxamide trifluoroacetate |
| 153 | N-hydroxy-2-{6-[(1-phenylethyl)amino]pyridin-3-yl}-1,3-benzoxazole-5-carboxamide trifluoroacetate |
| 154 | 2-{6-[(cis)-2,6-dimethylmorpholin-4-yl]pyridin-3-yl}-N-hydroxy-1,3-benzoxazole-5-carboxamide trifluoroacetate |
| 155 | N-hydroxy-2-{6-[(2-methylpropyl)amino]pyridin-3-yl}-1,3-benzoxazole-5-carboxamide trifluoroacetate |
| 156 | 2-{6-[bis(2-methoxyethyl)amino]pyridin-3-yl}-N-hydroxy-1,3-benzoxazole-5-carboxamide trifluoroacetate |
| 157 | N-hydroxy-2-{6-[(pyridin-2-ylmethyl)amino]pyridin-3-yl}-1,3-benzoxazole-5-carboxamide trifluoroacetate |
| 158 | 2-[6-(cycloheptylamino)pyridin-3-yl]-N-hydroxy-1,3-benzoxazole-5-carboxamide trifluoroacetate |

TABLE 1-continued

| Ex. | Chemical name | Structural formula |
|---|---|---|
| 159 | N-hydroxy-2-{6-[(2R)-2-(methoxymethyl)pyrrolidin-1-yl]pyridin-3-yl}-1,3-benzoxazole-5-carboxamide trifluoroacetate | |
| 160 | N-hydroxy-2-{6-[4-(2-methoxyphenyl)piperazin-1-yl]pyridin-3-yl}-1,3-benzoxazole-5-carboxamide trifluoroacetate | |
| 161 | N-hydroxy-2-(6-phenylpyridin-3-yl)-1,3-benzoxazole-5-carboxamide trifluoroacetate | |
| 162 | 2-[3-fluorophenoxy)methyl]-N-hydroxy-1-benzofuran-5-carboxamide | |
| 163 | 2-[(4-tert-butylphenoxy)methyl]-N-hydroxy-1-benzofuran-5-carboxamide | |
| 164 | N-hydroxy-2-{6-[(1-methylethyl)sulfanyl]pyridin-3-yl}-1,3-benzoxazole-5-carboxamide | |
| 165 | 2-(4-bromo-2-fluorophenyl)-N-hydroxy-1,3-benzoxazole-5-carboxamide | |
| 166 | 2-[2-fluoro-4-(1-methylethyl)phenyl]-N-hydroxy-1,3-benzoxazole-5-carboxamide | |

TABLE 1-continued

| Ex. | Chemical name |
|---|---|
| 167 | N-hydroxy-2-[3-(1-methylethyl)phenyl]-1,3-benzoxazole-5-carboxamide |
| 168 | 2-(4-bromo-2-morpholin-4-ylphenyl)-N-hydroxy-1,3-benzoxazole-5-carboxamide |
| 169 | 2-(4-fluorophenyl)-N-hydroxy-1,3-benzoxazole-5-carboxamide |
| 170 | N-hydroxy-2-[4-(1-methylethyl)-2-pyrrolidin-1-ylphenyl]-1,3-benzoxazole-5-carboxamide |
| 171 | N-hydroxy-2-[6-(1-methylethyl)pyridin-3-yl]-1,3-benzoxazole-5-carboxamide |
| 172 | 2-(4-bromo-2-ethoxyphenyl)-N-hydroxy-1,3-benzoxazole-5-carboxamide |
| 173 | 2-(3-fluorobiphenyl-4-yl)-N-hydroxy-1,3-benzoxazole-5-carboxamide |

TABLE 1-continued

| Ex. | Chemical name |
|---|---|
| 174 | 2-(2',3-difluorobiphenyl-4-yl)-N-hydroxy-1,3-benzoxazole-5-carboxamide |
| 175 | 2-(2-fluoro-4-pyridin-3-ylphenyl)-N-hydroxy-1,3-benzoxazole-5-carboxamide |
| 176 | 2-[2-fluoro-4-(6-methoxypyridin-3-yl)phenyl]-N-hydroxy-1,3-benzoxazole-5-carboxamide |
| 177 | N-hydroxy-2-(2'-methoxybiphenyl-4-yl)-1,3-benzoxazole-5-carboxamide |
| 178 | 2-(2',5'-difluorobiphenyl-4-yl)-N-hydroxy-1,3-benzoxazole-5-carboxamide |
| 179 | 2-(5'-chloro-2'-methoxybiphenyl-4-yl)-N-hydroxy-1,3-benzoxazole-5-carboxamide |
| 180 | N-hydroxy-2-[4'-(methylsulfonyl)biphenyl-4-yl]-1,3-benzoxazole-5-carboxamide |
| 181 | 2-[4-(3,5-dimethylisoxazol-4-yl)phenyl]-N-hydroxy-1,3-benzoxazole-5-carboxamide |

TABLE 1-continued

| Ex. | Chemical name | Structural formula |
|---|---|---|
| 182 | N-hydroxy-2-(2'-hydroxybiphenyl-4-yl)-1,3-benzoxazole-5-carboxamide | |
| 183 | 2-(3'-fluoro-4'-hydroxybiphenyl-4-yl)-N-hydroxy-1,3-benzoxazole-5-carboxamide | |
| 184 | 2-(5'-fluoro-2'-hydroxybiphenyl-4-yl)-N-hydroxy-1,3-benzoxazole-5-carboxamide | |
| 185 | N-hydroxy-2-[3'-(methylsulfonyl)biphenyl-4-yl]-1,3-benzoxazole-5-carboxamide | |
| 186 | 2-(3-fluoro-3',4'-dimethoxybiphenyl-4-yl)-N-hydroxy-1,3-benzoxazole-5-carboxamide | |
| 187 | 2-[3-fluoro-4'-(hydroxymethyl)biphenyl-4-yl]-N-hydroxy-1,3-benzoxazole-5-carboxamide | |
| 188 | 2-[3-fluoro-2'-(hydroxymethyl)biphenyl-4-yl]-N-hydroxy-1,3-benzoxazole-5-carboxamide | |
| 189 | 2-(3-fluoro-4'-hydroxybiphenyl-4-yl)-N-hydroxy-1,3-benzoxazole-5-carboxamide | |

TABLE 1-continued

| Ex. | Chemical name | Structural formula |
|---|---|---|
| 190 | 2-[4-(2,3-dihydro-1-benzofuran-5-yl)-2-fluorophenyl]-N-hydroxy-1,3-benzoxazole-5-carboxamide | 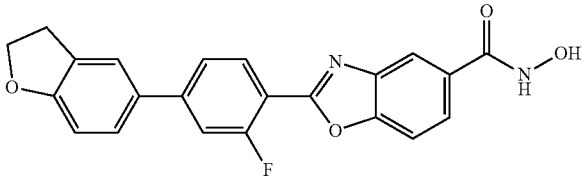 [SMILES: O=C(NO)c1ccc2oc(-c3ccc(-c4ccc5c(c4)CCO5)cc3F)nc2c1] |
| 191 | 2-(3,3'-difluoro-2'-hydroxybiphenyl-4-yl)-N-hydroxy-1,3-benzoxazole-5-carboxamide | 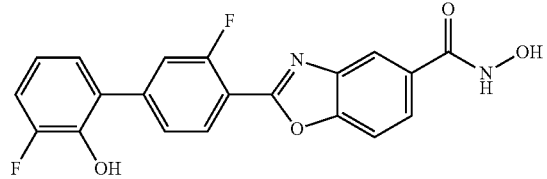 [SMILES: O=C(NO)c1ccc2oc(-c3ccc(-c4cccc(F)c4O)cc3F)nc2c1] |
| 192 | 2-[4-(2,3-dihydro-1,4-benzodioxin-6-yl)-2-fluorophenyl]-N-hydroxy-1,3-benzoxazole-5-carboxamide | 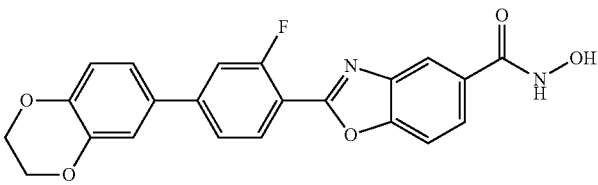 |
| 193 | 2-(3,5'-difluoro-2'-methoxybiphenyl-4-yl)-N-hydroxy-1,3-benzoxazole-5-carboxamide | 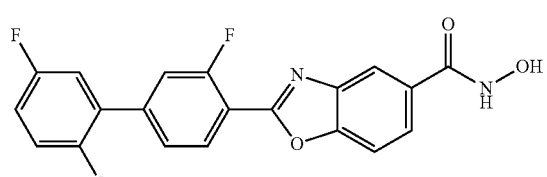 |
| 194 | N-hydroxy-2-[3-(piperidin-1-ylmethyl)phenyl]-1-benzothiophene-5-carboxamide trifluoroacetate | 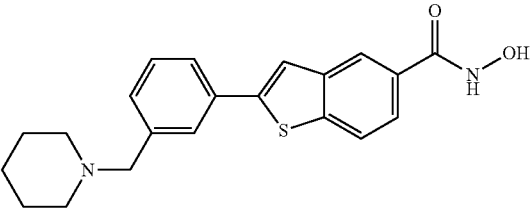 [SMILES: O=C(NO)c1ccc2sc(-c3cccc(CN4CCCCC4)c3)cc2c1] |
| 195 | N-hydroxy-2-(3-methoxybiphenyl-4-yl)-1,3-benzoxazole-5-carboxamide | 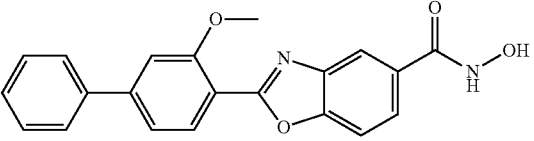 [SMILES: COc1cc(-c2ccccc2)ccc1-c1nc2cc(C(=O)NO)ccc2o1] |
| 196 | 2-(2'-fluoro-3-methoxybiphenyl-4-yl)-N-hydroxy-1,3-benzoxazole-5-carboxamide | 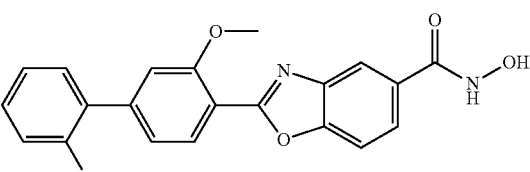 |
| 197 | 2-(2'-fluoro-3,3'-dimethoxybiphenyl-4-yl)-N-hydroxy-1,3-benzoxazole-5-carboxamide | 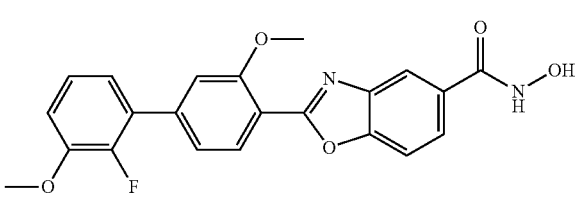 [SMILES: COc1cc(-c2cccc(OC)c2F)ccc1-c1nc2cc(C(=O)NO)ccc2o1] |

TABLE 1-continued

| Ex. | Chemical name |
|---|---|
| 198 | N-hydroxy-2-[3-methoxy-4'-(1-methylethyl)biphenyl-4-yl]-1,3-benzoxazole-5-carboxamide |
| 199 | 2-(4'-fluoro-3-methoxybiphenyl-4-yl)-N-hydroxy-1,3-benzoxazole-5-carboxamide |
| 200 | 2-(4'-amino-3,3'-dimethoxybiphenyl-4-yl)-N-hydroxy-1,3-benzoxazole-5-carboxamide |
| 201 | N-hydroxy-2-[3-(piperidin-1-ylmethyl)phenyl]-1,3-benzoxazole-5-carboxamide trifluoroacetate |
| 202 | 2-(3-{[(cis)-2,6-dimethylmorpholin-4-yl]methyl}phenyl)-N-hydroxy-1,3-benzoxazole-5-carboxamide trifluoroacetate |
| 203 | 2-(3-{[bis(2-methylpropyl)amino]methyl}phenyl)-N-hydroxy-1,3-benzoxazole-5-carboxamide trifluoroacetate |
| 204 | 2-(3-{[cyclohexyl(methyl)amino]methyl}phenyl)-N-hydroxy-1,3-benzoxazole-5-carboxamide trifluoroacetate |

TABLE 1-continued

| Ex. | Chemical name |
|---|---|
| 205 | N-hydroxy-2-(3-{[(2-methoxy-ethyl)(methyl)amino]methyl}phenyl)-1,3-benzoxazole-5-carboxamide trifluoroacetate |
| 206 | N-hydroxy-2-[4-(piperidin-1-ylmethyl)phenyl]-1,3-benzoxazole-5-carboxamide trifluoroacetate |
| 207 | 2-(4-{[(cis)-2,6-dimethylmorpholin-4-yl]methyl}phenyl)-N-hydroxy-1,3-benzoxazole-5-carboxamide trifluoroacetate |
| 208 | 2-(4-{[bis(2-methylpropyl)amino]methyl}phenyl)-N-hydroxy-1,3-benzoxazole-5-carboxamide trifluoroacetate |
| 209 | N-hydroxy-2-{4-[(4-pyridin-4-ylpiperazin-1-yl)methyl]phenyl}-1,3-benzoxazole-5-carboxamide trifluoroacetate |
| 210 | 2-{4-[(tert-butylamino)methyl]phenyl}-N-hydroxy-1,3-benzoxazole-5-carboxamide trifluoroacetate |
| 211 | 2-[3-fluoro-4-(1-methylethyl)phenyl]-N-hydroxy-1,3-benzoxazole-5-carboxamide |

TABLE 1-continued

| Ex. | Chemical name | Structural formula |
|---|---|---|
| 212 | 2-(3,4-dimethylphenyl)-N-hydroxy-1,3-benzoxazole-5-carboxamide | |
| 213 | N-hydroxy-2-(4-propylphenyl)-1,3-benzoxazole-5-carboxamide | |
| 214 | 2-(4-bromo-2-chlorophenyl)-N-hydroxy-1,3-benzoxazole-5-carboxamide | |
| 215 | N-hydroxy-2-(6-methoxypyridin-3-yl)-1,3-benzoxazole-5-carboxamide trifluoroacetate | |
| 216 | N-hydroxy-2-(2-methoxypyridin-3-yl)-1,3-benzoxazole-5-carboxamide trifluoroacetate | |
| 217 | 2-(4-bromo-3-fluorophenyl)-N-hydroxy-1,3-benzoxazole-5-carboxamide | |
| 218 | 2-(4-bromo-2-methoxyphenyl)-N-hydroxy-1,3-benzoxazole-5-carboxamide | |
| 219 | 2-(2,3-dihydro-1,4-benzodioxin-6-yl)-N-hydroxy-1,3-benzoxazole-5-carboxamide | |

TABLE 1-continued

| Ex. | Chemical name |
|---|---|
| 220 | N-hydroxy-2-(3-hydroxyphenyl)-1,3-benzoxazole-5-carboxamide |
| 221 | N-hydroxy-2-(2-hydroxyphenyl)-1,3-benzoxazole-5-carboxamide |
| 222 | N-hydroxy-2-(2-hydroxynaphthalen-1-yl)-1,3-benzoxazole-5-carboxamide |
| 223 | N-hydroxy-2-(4-hydroxyphenyl)-1,3-benzoxazole-5-carboxamide |
| 224 | N-hydroxy-2-(2-phenyl-1H-imidazol-5-yl)-1,3-benzoxazole-5-carboxamide |
| 225 | N-hydroxy-2-(2-methoxyphenyl)-1,3-benzoxazole-5-carboxamide |
| 226 | 2-(5-chloro-2-hydroxyphenyl)-N-hydroxy-1,3-benzoxazole-5-carboxamide |
| 227 | N-hydroxy-2-(4-hydroxy-2-methoxyphenyl)-1,3-benzoxazole-5-carboxamide |

TABLE 1-continued

| Ex. | Chemical name | Structural formula |
|---|---|---|
| 228 | N-hydroxy-2-(2-methyl-1H-indol-3-yl)-1,3-benzoxazole-5-carboxamide | |
| 229 | N-hydroxy-2-[(4-propylphenyl)amino]-1,3-benzoxazole-5-carboxamide | |
| 230 | 2-(biphenyl-3-ylamino)-N-hydroxy-1,3-benzoxazole-5-carboxamide | |
| 231 | 2-[(3-fluorophenyl)amino]-N-hydroxy-1,3-benzoxazole-5-carboxamide | |
| 232 | 2-(cyclooctylamino)-N-hydroxy-1,3-benzoxazole-5-carboxamide | |
| 233 | N-hydroxy-2-[(3-methoxyphenyl)amino]-1,3-benzoxazole-5-carboxamide | |
| 234 | 2-[(biphenyl-4-ylmethyl)amino]-N-hydroxy-1,3-benzoxazole-5-carboxamide | |
| 235 | N-hydroxy-2-[(4-methoxybenzyl)amino]-1,3-benzoxazole-5-carboxamide | |

TABLE 1-continued

| Ex. | Chemical name | Structural formula |
|---|---|---|
| 236 | N-hydroxy-2-[(4-methoxyphenyl)amino]-1,3-benzoxazole-5-carboxamide | |
| 237 | N-hydroxy-2-[(naphthalen-1-ylmethyl)amino]-1,3-benzoxazole-5-carboxamide | |
| 238 | N-hydroxy-2-[(2-methoxyphenyl)amino]-1,3-benzoxazole-5-carboxamide | |
| 239 | 2-(benzylamino)-N-hydroxy-1,3-benzoxazole-5-carboxamide | |
| 240 | 2-(cyclohexylamino)-N-hydroxy-1,3-benzoxazole-5-carboxamide | |
| 241 | 2-[benzyl(phenyl)amino]-N-hydroxy-1,3-benzoxazole-5-carboxamide | |
| 242 | N-hydroxy-2-[(4-methoxybenzyl)(methyl)amino]-1,3-benzoxazole-5-carboxamide | |

TABLE 1-continued

| Ex. | Chemical name | Structural formula |
|---|---|---|
| 243 | N-hydroxy-2-{[2-(4-methoxyphenyl)ethyl]amino}-1,3-benzoxazole-5-carboxamide | |
| 244 | 2-{(3,4-dimethoxybenzyl)[2-(dimethylamino)ethyl]amino}-N-hydroxy-1,3-benzoxazole-5-carboxamide trifluoroacetate | |
| 245 | N-hydroxy-2-{[4-(2-morpholin-4-ylethoxy)phenyl]amino}-1,3-benzoxazole-5-carboxamide trifluoroacetate | |
| 246 | 2-{[4-(2-ethoxyethoxy)phenyl]amino}-N-hydroxy-1,3-benzoxazole-5-carboxamide | |
| 247 | N-hydroxy-2-{[3-(2-morpholin-4-ylethoxy)phenyl]amino}-1,3-benzoxazole-5-carboxamide trifluoroacetate | |

TABLE 1-continued

| Ex. | Chemical name | Structural formula |
|---|---|---|
| 248 | 2-{[3-(2-ethoxyethoxy)phenyl]amino}-N-hydroxy-1,3-benzoxazole-5-carboxamide | 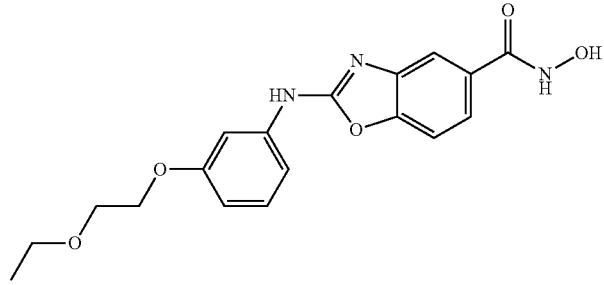 [SMILES: CCOCCOc1cccc(Nc2nc3cc(C(=O)NO)ccc3o2)c1] |
| 249 | 2-(4-chlorobenzyl)-N-hydroxy-1,3-benzothiazole-5-carboxamide | 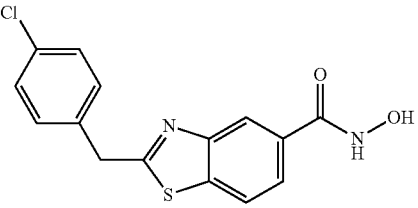 [SMILES: O=C(NO)c1ccc2sc(Cc3ccc(Cl)cc3)nc2c1] |
| 250 | N-hydroxy-2-[2-(methylsulfonyl)phenyl]-1,3-benzothiazole-6-carboxamide | 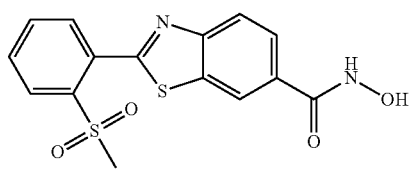 [SMILES: CS(=O)(=O)c1ccccc1-c1nc2ccc(C(=O)NO)cc2s1] |
| 251 | N-hydroxy-2-[3-(hydroxymethyl)phenyl]-1,3-benzothiazole-6-carboxamide | 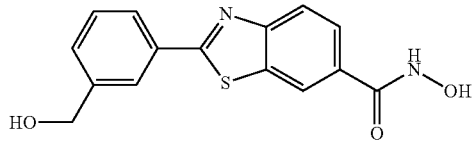 [SMILES: O=C(NO)c1ccc2nc(-c3cccc(CO)c3)sc2c1] |
| 252 | N-hydroxy-2-[4-(hydroxymethyl)phenyl]-1,3-benzothiazole-6-carboxamide | 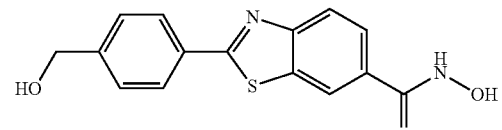 |
| 253 | N-hydroxy-2-(6-methoxypyridin-3-yl)-1,3-benzothiazole-6-carboxamide trifluoroacetate | 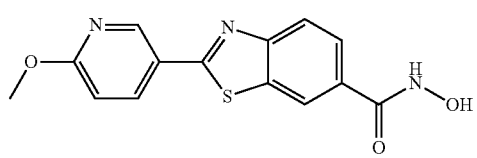 [SMILES: COc1ccc(-c2nc3ccc(C(=O)NO)cc3s2)cn1] |
| 254 | N-hydroxy-2-(3-hydroxyphenyl)-1,3-benzothiazole-6-carboxamide | 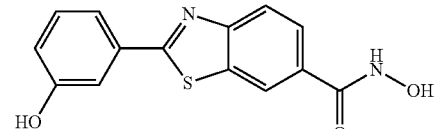 |
| 255 | N-hydroxy-2-(4-hydroxyphenyl)-1,3-benzothiazole-6-carboxamide | 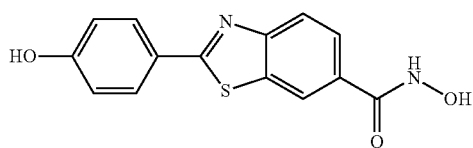 [SMILES: O=C(NO)c1ccc2nc(-c3ccc(O)cc3)sc2c1] |

TABLE 1-continued

| Ex. | Chemical name | Structural formula |
|---|---|---|
| 256 | N-hydroxy-2-[4-({[(1-methyl-1H-indol-3-yl)methyl]amino}methyl)piperidin-1-yl]-1,3-benzoxazole-5-carboxamide trifluoroacetate | |
| 257 | 2-{4-[(benzylamino)methyl]piperidin-1-yl}-N-hydroxy-1,3-benzoxazole-5-carboxamide trifluoroacetate | |
| 258 | N-hydroxy-2-{[2-(1-methylethyl)phenyl]amino}-1,3-benzoxazole-5-carboxamide | |
| 259 | N-hydroxy-2-[(2-methylphenyl)amino]-1,3-benzoxazole-5-carboxamide | |
| 260 | N-hydroxy-2-[methyl(4-methylphenyl)amino]-1,3-benzoxazole-5-carboxamide | |
| 261 | N-hydroxy-2-[(4-methoxyphenyl)(methyl)amino]-1,3-benzoxazole-5-carboxamide | |
| 262 | 2-{[1-(3-fluorophenyl)cyclohexyl]amino}-N-hydroxy-1,3-benzoxazole-5-carboxamide | |

TABLE 1-continued

| Ex. | Chemical name | Structural formula |
|---|---|---|
| 263 | N-hydroxy-2-[(4-methylphenyl)amino]-1,3-benzoxazole-5-carboxamide | |
| 264 | 2-(diethylamino)-N-hydroxy-1,3-benzoxazole-5-carboxamide | |
| 265 | 2-(2,6-dimethoxypyridin-3-yl)-N-hydroxy-1,3-benzothiazole-6-carboxamide trifluoroacetate | |
| 266 | N-hydroxy-2-[6-(1-methylethoxy)pyridin-3-yl]-1,3-benzothiazole-6-carboxamide trifluoroacetate | |
| 267 | N-hydroxy-2-(2-methoxypyridin-4-yl)-1,3-benzothiazole-6-carboxamide trifluoroacetate | |
| 268 | N-hydroxy-2-(5-methoxypyridin-3-yl)-1,3-benzothiazole-6-carboxamide trifluoroacetate | |
| 269 | 2-{4-[(dimethylamino)methyl]phenyl}-N-hydroxy-1,3-benzothiazole-6-carboxamide trifluoroacetate | |
| 270 | 2-[(benzyloxy)methyl]-N-hydroxy-1,3-benzothiazole-5-carboxamide | |
| 271 | N-hydroxy-2-(hydroxymethyl)-1,3-benzothiazole-5-carboxamide | |

TABLE 1-continued

| Ex. | Chemical name |
|---|---|
| 272 | N-hydroxy-2-(4-pyridin-4-ylbenzyl)-1,3-benzothiazole-5-carboxamide trifluoroacetate |
| 273 | N-hydroxy-2-(piperidin-1-ylmethyl)-1,3-benzothiazole-5-carboxamide |
| 274 | 2-{[bis(2-methylpropyl)amino]methyl}-N-hydroxy-1,3-benzothiazole-5-carboxamide trifluoroacetate |
| 275 | N-hydroxy-2-({[4-(1-methylethyl)phenyl]amino}methyl)-1,3-benzothiazole-5-carboxamide |
| 276 | N-hydroxy-2-phenyl-1-benzofuran-5-carboxamide |
| 277 | 2-(3-fluorophenyl)-N-hydroxy-1-benzofuran-5-carboxamide |
| 278 | N-hydroxy-2-(6-methoxypyridin-3-yl)-1-benzofuran-5-carboxamide |
| 279 | N-hydroxy-2-(4-methoxyphenyl)-1-benzofuran-5-carboxamide |

TABLE 1-continued

| Ex. | Chemical name | Structural formula |
|---|---|---|
| 280 | N-hydroxy-2-pyrimidin-5-yl-1-benzofuran-5-carboxamide | |
| 281 | N-hydroxy-2-[2-(hydroxymethyl)phenyl]-1-benzofuran-5-carboxamide | |
| 282 | N-hydroxy-2-phenyl-1-benzofuran-6-carboxamide | |
| 283 | 2-{4-[(dimethylamino)methyl]phenyl}-N-hydroxy-1-benzofuran-6-carboxamide trifluoroacetate | |
| 284 | N-hydroxy-2-(3-hydroxypheny)-1-benzofuran-6-carboxamide | |
| 285 | N-hydroxy-2-(3-methoxyphenyl)-1-benzofuran-6-carboxamide | |

TABLE 2

| Ex. | MS (ESI)+ m/z [M + H]+ | 1H NMR (600 MHz, DMSO-d$_6$ δ ppm (unless otherwise stated) | General procedure |
|---|---|---|---|
| 1 | 297 | $^1$H NMR (600 MHz, CD$_3$OD) δ ppm 8.17-8.21 (m, 2 H) 8.12 (d, J = 1.22 Hz, 1 H) 7.85 (dd, J = 8.55, 1.83 Hz, 1 H) 7.76 (d, J = 8.24 Hz, 1 H) 7.45-7.51 (m, 2 H) 3.03 (spt, 1 H) 1.32 (d, J = 7.02 Hz, 6 H) | A |
| 2 | 333/335 | 11.33 (br. s., 1 H) 9.10 (s, 1 H) 8.13 (d, J = 8.5 Hz, 2 H) 7.63-7.95 (m, 4 H) | A |
| 3 | 391 | 11.38 (s, 1 H) 9.13 (s, 1 H) 8.72 (s, 2 H) 8.45 (s, 1 H) 8.22 (s, 1 H) 7.79-8.02 (m, 2 H) | A |
| 4 | 311 | 11.31 (s, 1 H) 8.05-8.27 (m, 3 H) 7.75-7.90 (m, 2 H) 7.64 (d, J = 8.5 Hz, 2 H) 1.32 (s, 9 H) | A |
| 5 | 291 | 11.34 (s, 1 H) 9.10 (s, 1 H) 8.18-8.25 (m, 1 H) 8.16 (s, 1 H) 8.08 (ddd, J = 6.5, 4.2, 2.1 Hz, 1 H) 7.86 (s, 2 H) 7.71 (dt, J = 10.4, 8.5 Hz, 1 H) | A |
| 6 | 323 | 11.35 (s, 1 H) 9.11 (s, 1 H) 8.50 (d, J = 7.9 Hz, 1 H) 8.44 (s, 1 H) 8.19 (s, 1 H) 8.03 (d, J = 7.9 Hz, 2 H) 7.75-7.96 (m, 2 H) | A |
| 7 | 255 | 11.32 (s, 1 H) 8.19-8.23 (m, 2 H) 8.15 (s, 1 H) 7.82-7.88 (m, 2 H) 7.59-7.68 (m, 3 H) | A |
| 8 | 299 | 11.30 (s, 1 H) 9.08 (br. s., 1 H) 8.09 (s, 1 H) 7.72-7.89 (m, 3 H) 7.65 (d, J = 1.8 Hz, 1 H) 7.14 (d, J = 7.9 Hz, 1 H) 6.17 (s, 2 H) | A |
| 9 | 339 | 11.34 (s, 1 H) 9.10 (s, 1 H) 8.33 (q, J = 4.9 Hz, 2 H) 8.17 (s, 1 H) 7.74-7.96 (m, 2 H) 7.62 (d, J = 8.2 Hz, 2 H) | A |

TABLE 2-continued

| Ex. | MS (ESI)+ m/z [M + H]+ | 1H NMR (600 MHz, DMSO-d6 δ ppm (unless otherwise stated) | General procedure |
|---|---|---|---|
| 10 | 291 | 11.37 (br. s., 1 H) 8.25 (s, 1 H) 7.88-7.99 (m, 2 H) 7.72-7.83 (m, 1 H) 7.42 (t, J = 8.7 Hz, 2 H) | A |
| 11 | 285 | 11.32 (s, 1 H) 8.16 (d, J = 9.2 Hz, 2 H) 8.11 (s, 1 H) 7.82 (s, 2 H) 7.18 (d, J = 8.9 Hz, 2 H) 3.88 (s, 3 H) | A |
| 12 | 289 | $^1$H NMR (600 MHz, CD$_3$OD) δ ppm 8.20 (d, J = 1.2 Hz, 1 H) 8.16 (dd, J = 7.9, 1.5 Hz, 1 H) 7.91 (dd, J = 8.5, 1.5 Hz, 1 H) 7.80 (d, J = 8.5 Hz, 1 H) 7.66 (d, J = 7.9 Hz, 1 H) 7.60 (td, J = 7.8, 1.8 Hz, 1 H) 7.54 (td, J = 7.5, 1.2 Hz, 1 H) | A |
| 13 | 256 | $^1$H NMR (600 MHz, CD$_3$OD) δ ppm 9.44 (br. s., 1 H) 8.81 (d, J = 4.3 Hz, 1 H) 8.72 (ddd, J = 8.1, 1.8, 1.7 Hz, 1 H) 8.20 (d, J = 1.2 Hz, 1 H) 7.91 (dd, J = 8.5, 1.8 Hz, 1 H) 7.82 (d, J = 8.5 Hz, 1 H) 7.74 (dd, J = 7.8, 4.7 Hz, 1 H) | A |
| 14 | 323 | 11.35 (br. s., 1 H) 9.13 (br. s., 1 H) 8.14-8.29 (m, 2 H) 7.86-7.98 (m, 3 H) 7.70 (dd, J = 8.5, 2.1 Hz, 1 H) | A |
| 15 | 341 | $^1$H NMR (600 MHz, CD$_3$OD) δ ppm 8.91 (d, J = 1.8 Hz, 1 H) 8.36 (dd, J = 9.2, 2.4 Hz, 1 H) 8.08 (d, J = 1.2 Hz, 1 H) 7.82 (dd, J = 8.5, 1.8 Hz, 1 H) 7.72 (d, J = 7.9 Hz, 1 H) 7.09 (d, J = 9.2 Hz, 1 H) 3.78-3.89 (m, 4 H) 3.65-3.78 (m, 4 H) | A |
| 16 | 333/335 | 11.34 (br. s., 1 H) 9.12 (br. s., 1 H) 8.34 (t, J = 1.8 Hz, 1 H) 8.20-8.24 (m, 1 H) 8.18-8.20 (m, 1 H) 7.89 (s, 3 H) 7.61 (t, J = 7.9 Hz, 1 H) | A |
| 17 | 321 | $^1$H NMR (600 MHz, CD$_3$OD) δ ppm 8.28-8.34 (m, 2 H) 8.13 (d, J = 1.2 Hz, 1 H) 7.86 (dd, J = 8.5, 1.8 Hz, 1 H) 7.76 (d, J = 8.5 Hz, 1 H) 7.36 (d, J = 8.9 Hz, 2 H) 7.02 (t, 1 H) | B |
| 18 | 323 | 11.37 (s, 1 H) 9.13 (s, 1 H) 8.43 (d, J = 8.2 Hz, 2 H) 8.22 (s, 1 H) 8.01 (d, J = 8.2 Hz, 2 H) 7.85-7.96 (m, 2 H) | B |
| 19 | 315 | 11.33 (s, 1 H) 9.10 (br. s., 1 H) 8.11 (s, 1 H) 7.77-7.92 (m, 3 H) 7.70 (d, J = 2.1 Hz, 1 H) 7.20 (d, J = 8.5 Hz, 1 H) 3.91 (s, 3 H) 3.88 (s, 3 H) | B |
| 20 | 315 | $^1$H NMR (600 MHz, CD$_3$OD) δ ppm 8.04-8.13 (m, 2 H) 7.82 (dd, J = 8.4, 1.7 Hz, 1 H) 7.71 (d, J = 7.9 Hz, 1 H) 6.71-6.80 (m, 2 H) 4.01 (s, 3 H) 3.92 (s, 3 H) | B |
| 21 | 349 | 11.34 (s, 1 H) 9.10 (br. s., 1 H) 8.31 (d, J = 8.2 Hz, 2 H) 8.17 (s, 1 H) 7.84-7.93 (m, 2 H) 7.82 (d, J = 7.0 Hz, 2 H) 7.64 (td, J = 8.0, 1.4 Hz, 1 H) 7.43-7.51 (m, 1 H) 7.26-7.42 (m, 2 H) | C |
| 22 | 332 | $^1$H NMR (600 MHz, CD$_3$OD) d ppm 8.85 (d, J = 6.7 Hz, 2 H) 8.49 (d, J = 8.5 Hz, 2 H) 8.30 (d, J = 6.7 Hz, 2 H) 8.19 (d, J = 1.2 Hz, 1 H) 8.16 (d, J = 8.5 Hz, 2 H) 7.90 (dd, J = 8.5, 1.8 Hz, 1 H) 7.81 (d, J = 8.5 Hz, 1 H) | C |
| 23 | 332 | 11.34 (br. s., 1 H) 9.07 (d, J = 1.8 Hz, 1 H) 8.68 (dd, J = 4.9, 1.5 Hz, 1 H) 8.27-8.39 (m, 3 H) 8.18 (s, 1 H) 8.04 (d, J = 8.5 Hz, 2 H) 7.80-7.93 (m, 2 H) 7.65 (dd, J = 7.9, 4.9 Hz, 1 H) | C |
| 24 | 331 | 11.33 (s, 1 H) 9.10 (br. s., 1 H) 8.29 (d, J = 8.5 Hz, 2 H) 8.17 (s, 1 H) 7.94 (d, J = 8.5 Hz, 2 H) 7.83-7.90 (m, 2 H) 7.78 (d, J = 7.3 Hz, 2 H) 7.51 (t, J = 7.6 Hz, 2 H) 7.43 (t, J = 7.3 Hz, 1 H) | C |
| 25 | 379 | 11.34 (s, 1 H) 9.09 (br. s., 1 H) 8.30 (d, J = 8.5 Hz, 2 H) 8.17 (s, 1 H) 7.83-7.91 (m, 2 H) 7.79 (d, J = 7.0 Hz, 2 H) 7.20-7.30 (m, 2 H) 7.14 (td, J = 7.0, 2.1 Hz, 1 H) 3.88 (s, 3 H) | C |
| 26 | 362 | 11.33 (br. s., 1 H) 8.62 (d, J = 2.4 Hz, 1 H) 8.28 (d, J = 8.5 Hz, 2 H) 8.14 (dd, J = 8.5, 2.7 Hz, 2 H) 7.94 (d, J = 8.5 Hz, 2 H) 7.83-7.90 (m, 2 H) 6.95 (d, J = 8.5 Hz, 1 H) 3.91 (s, 3 H) | C |
| 27 | 362 | 11.33 (s, 1 H) 8.62 (d, J = 2.7 Hz, 1 H) 8.28 (d, J = 8.5 Hz, 2 H) 8.09-8.19 (m, 2 H) 7.94 (d, J = 8.5 Hz, 2 H) 7.79-7.89 (m, 2 H) 6.96 (d, J = 8.5 Hz, 1 H) 3.91 (s, 3 H) | C |
| 28 | 362 | 11.33 (s, 1 H) 9.10 (br. s., 1 H) 8.26 (d, J = 8.5 Hz, 2 H) 8.23 (dd, J = 5.0, 2.0 Hz, 1 H) 8.17 (s, 1 H) 7.84-7.89 (m, 3 H) 7.82 (d, J = 8.5 Hz, 2 H) 7.14 (dd, J = 7.3, 4.9 Hz, 1 H) 3.91 (s, 3 H) | C |
| 29 | 295 | 11.31 (s, 1 H) 9.08 (d, J = 1.5 Hz, 1 H) 8.11 (s, 1 H) 8.07 (d, J = 8.5 Hz, 2 H) 7.82 (s, 2 H) 7.30 (d, J = 8.5 Hz, 2 H) 1.97-2.07 (m, 1 H) 1.02-1.09 (m, 2 H) 0.79 (dd, J = 4.9, 2.1 Hz, 2 H) | Separate procedure |
| 30 | 428 | 11.34 (s, 1 H) 9.35 (br. s., 1 H) 8.31 (d, J = 8.5 Hz, 2 H) 8.17 (s, 1 H) 7.98 (d, J = 8.5 Hz, 2 H) 7.91 (d, J = 8.2 Hz, 4 H) 7.63 (d, J = 8.2 Hz, 2 H) 4.34 (d, J = 5.2 Hz, 2 H) 3.36 (d, J = 11.6 Hz, 2 H) 2.90 (d, J = 11.9 Hz, 2 H) 1.32-1.87 (m, 6 H) | Separate procedure |
| 31 | 270 | 11.25 (br. s., 1 H) 7.99 (s, 1 H) 7.85 (q, J = 4.6 Hz, 2 H) 7.71 (d, J = 2.4 Hz, 2 H) 6.68 (d, J = 8.5 Hz, 2 H) | Separate procedure |
| 32 | 307 | $^1$H NMR (600 MHz, CD$_3$OD) d ppm 8.24 (d, J = 1.2 Hz, 1 H) 7.95 (dd, J = 8.5, 1.5 Hz, 1 H) 7.82 (d, J = 8.5 Hz, 1 H) 7.67 (td, J = 8.4, 6.1 Hz, 1 H) 7.52 (d, J = 8.2 Hz, 1 H) 7.37 (t, J = 8.5 Hz, 1 H) | Separate procedure |
| 33 | 326 | 11.27 (br. s., 1 H) 8.01-8.03 (m, 1 H) 7.98 (d, J = 9.2 Hz, 2 H) 7.72-7.75 (m, 2 H) 6.83 (d, J = 8.8 Hz, 2 H) 3.45 (q, J = 7.2 Hz, 4 H) 1.14 (t, J = 7.0 Hz, 6 H) | Separate procedure |
| 34 | 323 | 11.35 (br. s., 1 H) 9.14 (br. s., 1 H) 8.24 (s, 1 H) 8.20 (d, J = 7.6 Hz, 1 H) 8.05 (d, J = 7.3 Hz, 1 H) 7.88-7.96 (m, 3 H) | Separate procedure |

TABLE 2-continued

| Ex. | MS (ESI)+ m/z [M + H]+ | 1H NMR (600 MHz, DMSO-$d_6$ δ ppm (unless otherwise stated) | General procedure |
|---|---|---|---|
| 35 | 256 | $^1$H NMR (600 MHz, CD$_3$OD) d ppm 8.78 (d, J = 4.9 Hz, 1 H) 8.42 (d, J = 7.9 Hz, 1 H) 8.22 (d, J = 1.2 Hz, 1 H) 8.08 (td, J = 7.7, 1.7 Hz, 1 H) 7.92 (dd, J = 8.5, 1.8 Hz, 1 H) 7.83 (d, J = 8.5 Hz, 1 H) 7.65 (dd, J = 6.1, 1.5 Hz, 1 H) | Separate procedure |
| 36 | 280 | 11.36 (br. s., 1 H) 9.14 (br. s., 1 H) 8.38 (d, J = 8.5 Hz, 2 H) 8.22 (s, 1 H) 8.11 (d, J = 8.5 Hz, 2 H) 7.92 (s, 2 H) | Separate procedure |
| 37 | 348 | 11.33 (s, 1 H) 10.38 (s, 1 H) 8.18 (d, J = 8.8 Hz, 2 H) 8.13 (s, 1 H) 7.78-7.89 (m, 2 H) 7.41 (d, J = 8.9 Hz, 2 H) 3.14 (s, 3 H) | Separate procedure |
| 38 | 410 | 11.31 (br. s., 1 H) 10.91 (s, 1 H) 8.06-8.12 (m, 3 H) 7.84-7.88 (m, 2 H) 7.81 (s, 2 H) 7.54-7.67 (m, 3 H) 7.34 (d, J = 8.9 Hz, 2 H) | Separate procedure |
| 39 | 296 | n.d. | Separate procedure |
| 40 | 270 | 11.35 (br. s., 1 H) 8.71 (dd, J = 4.9, 1.5 Hz, 1 H) 8.55 (dd, J = 7.9, 1.5 Hz, 1 H) 8.23 (s, 1 H) 7.91 (s, 2 H) 7.56 (dd, J = 7.9, 4.9 Hz, 1 H) 2.98 (s, 3 H) | Separate procedure |
| 41 | 325 | 11.30 (br. s., 1 H) 8.86 (d, J = 1.8 Hz, 1 H) 8.21 (dd, J = 9.2, 2.4 Hz, 1 H) 8.06 (s, 1 H) 7.78 (s, 2 H) 6.71 (d, J = 9.2 Hz, 1 H) 3.52 (br. s., 4 H) 1.86-2.15 (m, 4 H) | Separate procedure |
| 42 | 270 | 11.19 (s, 1 H) 10.74 (s, 1 H) 9.01 (s, 1 H) 7.79 (d, J = 1.5 Hz, 1 H) 7.75 (d, J = 7.6 Hz, 2 H) 7.57-7.61 (m, 1 H) 7.53-7.57 (m, 1 H) 7.33-7.43 (m, 2 H) 7.03-7.09 (m, 1 H) | D |
| 43 | 312 | 11.18 (s, 1 H) 10.62 (s, 1 H) 9.00 (s, 1 H) 7.77 (d, J = 1.2 Hz, 1 H) 7.62-7.66 (m, 2 H) 7.55-7.59 (m, 1 H) 7.51-7.55 (m, 1 H) 7.23-7.28 (m, 2 H) 2.87 (qd, J = 6.9, 6.7 Hz, 1 H) 1.20 (d, J = 7.0 Hz, 6 H) | D |
| 44 | 298 | 11.14 (s, 1 H) 7.63 (s, 1 H) 7.46 (s, 2 H) 7.25-7.40 (m, 5 H) 4.76 (s, 2 H) 3.12 (s, 3 H) | D |
| 45 | 298 | 11.11 (br. s., 1 H) 8.21 (t, 1 H) 7.60 (d, J = 1.5 Hz, 1 H) 7.41-7.47 (m, 1 H) 7.36-7.40 (m, 1 H) 7.15-7.34 (m, 5 H) 3.51-3.57 (m, 2 H) 2.91 (t, J = 7.3 Hz, 2 H) | D |
| 46 | 310 | 11.16 (br. s., 1 H) 7.66 (s, 1 H) 7.48 (s, 2 H) 7.19-7.33 (m, 4 H) 4.82 (s, 2 H) 3.89 (t, J = 6.0 Hz, 2 H) 2.97 (t, J = 6.0 Hz, 2 H) | D |
| 47 | 376 | 11.18 (s, 1 H) 10.75 (s, 1 H) 9.00 (s, 1 H) 7.81 (d, J = 1.2 Hz, 1 H) 7.57-7.60 (m, 1 H) 7.52-7.56 (m, 2 H) 7.47-7.51 (m, 2 H) 7.39-7.44 (m, 2 H) 7.32-7.37 (m, 1 H) 7.23-7.32 (m, 2 H) 6.68-6.76 (m, 1 H) 5.12 (s, 2 H) | D |
| 48 | 352 | 11.13 (br. s., 1 H) 7.61 (d, J = 1.5 Hz, 1 H) 7.40-7.48 (m, 2 H) 7.26-7.32 (m, 2 H) 7.16-7.22 (m, 3 H) 4.10-4.16 (m, 2 H) 3.07 (td, J = 12.8, 2.7 Hz, 2 H) 2.55 (d, J = 7.3 Hz, 2 H) 1.81 (ddd, J = 11.1, 7.4, 3.5 Hz, 1 H) 1.64-1.72 (m, 2 H) 1.17-1.31 (m, J = 12.5, 12.3, 12.3, 4.1 Hz, 2 H) | D |
| 49 | 297 | $^1$H NMR (600 MHz, CD$_3$OD) δ ppm 8.18-8.21 (m, 2 H) 8.08 (d, J = 1.22 Hz, 1 H) 7.81-7.83 (m, 1 H) 7.77-7.80 (m, 1 H) 7.47-7.50 (m, 2 H) 3.03 (spt, J = 7.17, 6.93 Hz, 1 H) 1.32 (d, J = 7.02 Hz, 6 H) | Separate procedure |
| 50 | 273 | 11.36 (br. s., 1 H) 9.15 (br. s., 1 H) 8.25-8.38 (m, 2 H) 8.14 (s, 1 H) 7.77-7.92 (m, 2 H) 7.36-7.54 (m, 2 H) | E |
| 51 | 311 | 11.35 (s, 1 H) 9.14 (s, 1 H) 8.16 (d, J = 8.5 Hz, 2 H) 8.13 (s, 1 H) 7.80-7.88 (m, 2 H) 7.64-7.69 (m, 2 H) 1.34 (s, 9 H) | E |
| 52 | 285 | 11.33 (s, 1 H) 9.13 (br. s., 1 H) 8.13-8.22 (m, 2 H) 8.10 (s, 1 H) 7.81 (s, 2 H) 7.18 (d, J = 8.9 Hz, 2 H) 3.88 (s, 3 H) | E |
| 53 | 290 | $^1$H NMR (600 MHz, CD$_3$OD) δ ppm 9.23 (d, J = 2.4 Hz, 1 H) 8.61 (dd, J = 8.2, 2.4 Hz, 1 H) 8.12 (s, 1 H) 7.85 (s, 2 H) 7.70 (d, J = 7.6 Hz, 1 H) | Separate procedure |
| 54 | 296 | 11.39 (br. s., 1 H) 9.16 (br. s., 1 H) 8.79 (br. s., 1 H) 8.31 (d, J = 8.5 Hz, 1 H) 8.18 (s, 1 H) 8.10-8.16 (m, 1 H) 7.89-7.94 (m, 1 H) 7.85-7.88 (m, 1 H) | Separate procedure |
| 55 | 333 | 11.41 (br. s., 1 H) 9.50 (d, J = 1.5 Hz, 1 H) 9.41 (d, J = 2.1 Hz, 1 H) 8.73 (dd, J = 4.9, 1.5 Hz, 1 H) 8.69 (dd, J = 8.4, 2.3 Hz, 1 H) 8.62 (d, J = 7.9 Hz, 1 H) 8.37 (d, J = 8.5 Hz, 1 H) 8.19 (s, 1 H) 7.92-7.99 (m, 1 H) 7.89 (dd, J = 8.2, 1.5 Hz, 1 H) 7.64 (dd, J = 8.1, 4.7 Hz, 1 H) | Separate procedure |
| 56 | 297 | 8.88 (s, 1 H) 8.16 (d, J = 8.24 Hz, 2 H) 8.12 (s, 1 H) 7.48 (d, J = 8.24 Hz, 2 H) 2.99 (spt, 1 H) 1.26 (d, J = 6.71 Hz, 6 H) | Separate procedure |
| 57 | 297 | 8.74 (d, J = 1.83 Hz, 1 H) 8.29 (d, J = 1.83 Hz, 1 H) 8.17 (d, J = 8.24 Hz, 2 H) 7.47 (d, J = 8.24 Hz, 2 H) 2.99 (spt, 1 H) 1.26 (d, J = 7.02 Hz, 6 H) | Separate procedure |
| 58 | 297 | $^1$H NMR (600 MHz, CD$_3$OD) δ ppm 8.10 (d, J = 8.24 Hz, 2 H) 8.05-8.07 (m, 1 H) 8.02-8.05 (m, 1 H) 7.49 (d, J = 8.24 Hz, 2 H) 3.03 (spt, J = 7.00 Hz, 1 H) 1.32 (d, J = 7.00 Hz, 6 H) | Separate procedure |
| 59 | 295 | $^1$H NMR (600 MHz, CD$_3$OD) δ ppm 7.87 (s, 1 H) 7.75 (d, 2 H) 7.56 (d, J = 8.54 Hz, 1 H) 7.39 (dd, J = 8.39, 1.37 Hz, 1 H) 7.33 (d, J = 8.24 Hz, 2 H) 6.82 (s, 1 H) 2.95 (spt, J = 6.90 Hz, 1 H) 1.29 (d, J = 7.02 Hz, 6 H) | Separate procedure |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 60 | 295 | 7.99 (d, J = 1.22 Hz, 1 H) 7.73 (d, J = 8.54 Hz, 2 H) 7.52 (dd, J = 8.39, 1.68 Hz, 1 H) 7.43 (d, J = 8.54 Hz, 1 H) 7.32 (d, J = 8.24 Hz, 2 H) 6.86 (s, 1 H) 2.94 (spt, J = 7.00 Hz, 1 H) 1.29 (d, J = 7.02 Hz, 6 H) | Separate procedure |
| 61 | 313 | $^1$H NMR (600 MHz, CD$_3$OD) δ ppm 8.42 (s, 1 H) 8.03-8.08 (m, 3 H) 7.89 (dd, J = 8.55, 1.53 Hz, 1 H) 7.44 (d, J = 8.24 Hz, 2 H) 3.01 (spt, J = 6.92 Hz, 1 H) 1.31 (d, J = 6.71 Hz, 6 H) | Separate procedure |
| 62 | 315 | $^1$H NMR (600 MHz, CD$_3$OD) δ ppm 8.38 (d, J = 1.53 Hz, 1 H) 8.01 (d, J = 8.54 Hz, 1 H) 7.87 (dd, J = 8.55, 1.83 Hz, 1 H) 7.66 (dd, J = 8.24, 1.83 Hz, 1 H) 7.62 (d, J = 1.53 Hz, 1 H) 6.99 (d, J = 8.24 Hz, 1 H) 6.09 (s, 2 H). | F |
| 63 | 272 | $^1$H NMR (600 MHz, CD$_3$OD) δ ppm 8.81-8.85 (m, 2 H) 8.53 (d, J = 1.22 Hz, 1 H) 8.30-8.33 (m, 2 H) 8.21 (d, J = 8.55 Hz, 1 H) 7.97 (dd, J = 8.55, 1.53 Hz, 1 H) | F |
| 64 | 349 | $^1$H NMR (600 MHz, CD$_3$OD) δ ppm 8.48 (d, J = 1.22 Hz, 1 H) 8.40 (d, J = 8.55 Hz, 2 H) 8.12-8.16 (m, 3 H) 7.93 (dd, J = 8.55, 1.53 Hz, 1 H) 3.20 (s, 3 H) | F |
| 65 | 313 | $^1$H NMR (600 MHz, CD$_3$OD) δ ppm 8.37 (d, J = 1.22 Hz, 1 H) 7.95-8.00 (m, 2 H) 7.89 (dd, J = 8.24, 2.14 Hz, 1 H) 7.86 (dd, J = 8.55, 1.83 Hz, 1 H) 6.88 (d, J = 8.24 Hz, 1 H) 4.66 (t, J = 8.70 Hz, 2 H) 3.32 (t, J = 8.70 Hz, 2 H) | F |
| 66 | 329 | $^1$H NMR (600 MHz, CD$_3$OD) δ ppm 8.38 (d, J = 1.53 Hz, 1 H) 8.00 (d, J = 8.54 Hz, 1 H) 7.86 (dd, J = 8.39, 1.68 Hz, 1 H) 7.62 (d, J = 2.14 Hz, 1 H) 7.59 (dd, J = 8.39, 2.29 Hz, 1 H) 6.99 (d, J = 8.54 Hz, 1 H) 4.33-4.35 (m, 2 H) 4.30-4.33 (m, 2 H) | F |
| 67 | 327 | $^1$H NMR (600 MHz, CD$_3$OD) δ ppm 8.41 (d, J = 1.53 Hz, 1 H) 8.01-8.06 (m, 3 H) 7.88 (dd, J = 8.55, 1.53 Hz, 1 H) 7.38 (d, J = 8.55 Hz, 2 H) 2.71 (t, J = 7.93 Hz, 2 H) 1.62-1.69 (m, 2 H) 1.36-1.44 (m, 2 H) 0.96 (t, J = 7.32 Hz, 3 H) | F |
| 68 | 277 | $^1$H NMR (600 MHz, CD$_3$OD) δ ppm 8.40 (d, J = 1.22 Hz, 1 H) 8.27 (dd, J = 2.90, 1.37 Hz, 1 H) 8.02 (d, J = 8.54 Hz, 1 H) 7.88 (dd, J = 8.55, 1.53 Hz, 1 H) 7.74 (dd, J = 5.19, 1.22 Hz, 1 H) 7.63 (dd, J = 5.04, 2.90 Hz, 1 H) | F |
| 69 | 311 | $^1$H NMR (600 MHz, CD$_3$OD) δ ppm 8.48 (d, J = 1.22 Hz, 1 H) 8.10 (d, J = 8.55 Hz, 1 H) 7.94 (dd, J = 8.55, 1.83 Hz, 1 H) 7.78 (d, J = 7.63 Hz, 1 H) 7.75 (s, 1 H) 7.65 (d, J = 9.16 Hz, 1 H) 7.48 (dd, J = 15.56, 1.22 Hz, 1 H) 7.36 (t, J = 7.48 Hz, 1 H). | F |
| 70 | 322 | 11.36 (br. s., 1 H) 10.07 (br. s., 1 H) 9.20 (d, J = 4.27, 1.83 Hz, 1 H) 9.06 (dd, J = 7.48, 1.37 Hz, 1 H) 8.61 (dd, J = 8.39, 1.68 Hz, 1 H) 8.56 (d, J = 1.22 Hz, 1 H) 8.28 (dd, J = 8.09, 1.37 Hz, 1 H) 8.16 (d, J = 8.85 Hz, 1 H) 7.91 (dd, J = 8.55, 1.83 Hz, 1 H) 7.88 (t, J = 7.63 Hz, 1 H) 7.77 (dd, J = 8.24, 4.27 Hz, 1 H). | F |
| 71 | 321 | 11.38 (s, 1 H) 9.15 (br. s., 1 H) 8.75 (d, J = 1.22 Hz, 1 H) 8.59 (d, J = 1.22 Hz, 1 H) 8.25 (dd, J = 8.55, 1.83 Hz, 1 H) 8.19 (d, J = 6.71 Hz, 1 H) 8.15 (d, J = 8.55 Hz, 1 H) 8.13 (d, J = 8.85 Hz, 1 H) 8.02-8.05 (m, 1 H) 7.93 (dd, J = 8.55, 1.53 Hz, 1 H) 7.62-7.68 (m, J = 7.02, 6.79, 6.68, 6.68 Hz, 2 H) | F |
| 72 | 377 | $^1$H NMR (600 MHz, CD$_3$OD) δ ppm 8.42 (d, J = 1.22 Hz, 1 H) 8.07 (d, J = 8.55 Hz, 1 H) 7.90 (dd, J = 8.54, 1.83 Hz, 1 H) 7.77 (d, J = 2.44 Hz, 1 H) 7.69 (d, J = 7.63 Hz, 1 H) 7.43-7.51 (m, 3 H) 7.39 (t, J = 7.63 Hz, 2 H) 7.33 (d, J = 7.32 Hz, 1 H) 7.22 (dd, J = 7.48, 2.59 Hz, 1 H) 5.21 (s, 2 H) | F |
| 73 | 319 | $^1$H NMR (600 MHz, CD$_3$OD) d ppm 8.46 (d, J = 1.22 Hz, 1 H) 8.12 (d, J = 8.55 Hz, 1 H) 7.88-7.93 (m, 2 H) 7.27-7.34 (m, 2 H) 3.96 (s, 3 H). | F |
| 74 | 335/337 | 11.35 (s, 1 H) 9.13 (d, J = 1.53 Hz, 1 H) 8.53 (d, J = 1.53 Hz, 1 H) 8.41 (d, J = 2.75 Hz, 1 H) 8.13 (d, J = 8.54 Hz, 1 H) 7.91 (dd, J = 8.55, 1.83 Hz, 1 H) 7.65 (dd, J = 8.85, 2.75 Hz, 1 H) 7.39 (d, J = 8.85 Hz, 1 H) 4.10 (s, 3 H) | F |
| 75 | 313 | $^1$H NMR (600 MHz, CD$_3$OD) δ ppm 8.37 (d, J = 1.22 Hz, 1 H) 8.09 (d, J = 8.24 Hz, 1 H) 8.04 (d, J = 8.54 Hz, 2 H) 7.81 (dd, J = 8.39, 1.68 Hz, 1 H) 7.44 (d, J = 8.24 Hz, 2 H) 3.01 (spt, J = 6.97 Hz, 1 H) 1.31 (d, J = 6.71 Hz, 6 H) | Separate procedure |
| 76 | 289 | 11.39 (br. s., 1 H) 9.14 (br. s., 1 H) 8.41 (d, J = 1.2 Hz, 1 H) 8.24 (d, J = 8.2 Hz, 1 H) 8.15-8.21 (m, 2 H) 7.85 (dd, J = 8.5, 1.5 Hz, 1 H) 7.44 (t, J = 8.9 Hz, 2 H) | G |
| 77 | 327 | 11.38 (s, 1 H) 9.14 (d, J = 1.5 Hz, 1 H) 8.39 (d, J = 1.2 Hz, 1 H) 8.22 (d, J = 8.2 Hz, 1 H) 8.04 (d, J = 8.5 Hz, 2 H) 7.84 (dd, J = 8.4, 1.7 Hz, 1 H) 7.56-7.68 (m, 2 H) 1.34 (s, 9 H) | G |
| 78 | 301 | 11.37 (s, 1 H) 9.13 (d, J = 1.2 Hz, 1 H) 8.35 (d, J = 1.2 Hz, 1 H) 8.19 (d, J = 8.2 Hz, 1 H) 8.01-8.11 (m, 2 H) 7.81 (dd, J = 8.2, 1.5 Hz, 1 H) 7.00-7.22 (m, 2 H) 3.87 (s, 3 H) | G |
| 79 | 303 | 11.34 (s, 1 H) 9.10 (br. s., 1 H) 8.30 (d, J = 1.2 Hz, 1 H) 8.10 (d, J = 8.2 Hz, 1 H) 7.78 (dd, J = 8.4, 1.7 Hz, 1 H) 7.46 (dd, J = 8.9, 5.5 Hz, 2 H) 7.20 (dd, J = 9.2, 4.3 Hz, 2 H) 4.50 (s, 2 H) | G |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 80 | 350/352 | n.d. | Separate procedure |
| 81 | 341 | n.d. | Separate procedure |
| 82 | 299 | 11.39 (d, J = 1.2 Hz, 1 H) 9.14 (d, J = 1.8 Hz, 1 H) 8.39 (d, J = 1.2 Hz, 1 H) 8.22 (d, J = 8.8 Hz, 1 H) 8.03 (d, J = 8.2 Hz, 2 H) 7.83 (dd, J = 8.4, 1.7 Hz, 1 H) 7.44 (d, J = 8.5 Hz, 2 H) 2.71 (q, J = 7.6 Hz, 2 H) 1.23 (t, J = 7.6 Hz, 3 H) | Separate procedure |
| 83 | 298 | $^1$H NMR (600 MHz, CD$_3$OD) δ ppm 8.73 (d, J = 2.14 Hz, 1 H) 8.45 (d, J = 2.14 Hz, 1 H) 8.22 (d, J = 8.55 Hz, 2 H) 7.51 (d, J = 8.24 Hz, 2 H) 3.04 (spt, J = 6.87 Hz, 1 H) 1.32 (d, J = 7.02 Hz, 6 H) | Separate procedure |
| 84 | 296 | $^1$H NMR (600 MHz, CD$_3$OD) δ ppm 8.59 (d, J = 1.53 Hz, 1 H) 8.38 (d, J = 1.83 Hz, 1 H) 7.80 (d, J = 8.24 Hz, 2 H) 7.37 (d, J = 8.24 Hz, 2 H) 6.94 (s, 1 H) 2.97 (spt, J = 6.90 Hz, 1 H) 1.30 (d, J = 7.02 Hz, 6 H) | Separate procedure |
| 85 | 296 | 7.85 (d, J = 8.55 Hz, 2 H) 7.83 (d, J = 9.16 Hz, 1 H) 7.75 (d, J = 8.24 Hz, 1 H) 7.37 (d, J = 8.24 Hz, 2 H) 7.00 (s, 1 H) 2.90-2.96 (m, 1 H) 1.23 (d, J = 7.02 Hz, 6 H) | Separate procedure |
| 86 | 297 | 8.98 (s, 1 H) 7.89 (d, J = 8.55 Hz, 2 H) 7.37 (d, J = 8.24 Hz, 2 H) 7.06 (s, 1 H) 2.93 (spt, J = 6.85 Hz, 1 H) 1.22 (d, J = 7.02 Hz, 6 H) | Separate procedure |
| 87 | 313 | $^1$H NMR (600 MHz, CD$_3$OD) δ ppm 8.80 (d, J = 1.83 Hz, 0 H) 8.50 (d, J = 1.83 Hz, 1 H) 7.73 (d, J = 8.24 Hz, 2 H) 7.71 (s, 1 H) 7.37 (d, J = 7.93 Hz, 2 H) 2.93-3.02 (m, 1 H) 1.29 (d, J = 7.02 Hz, 6 H) | Separate procedure |
| 88 | 312 | $^1$H NMR (600 MHz, CD$_3$OD) δ ppm 8.27 (s, 1 H) 7.86 (d, J = 8.24 Hz, 1 H) 7.69-7.74 (m, 4 H) 7.34 (d, J = 8.24 Hz, 2 H) 2.92-3.00 (m, 1 H) 1.29 (d, J = 6.71 Hz, 6 H) | Separate procedure |
| 89 | 312 | $^1$H NMR (600 MHz, CD$_3$OD) δ ppm 8.19 (d, J = 1.5 Hz, 1 H) 7.93 (d, J = 8.2 Hz, 1 H) 7.61-7.76 (m, 4 H) 7.33 (d, J = 8.2 Hz, 2 H) 2.87-3.03 (m, 1 H) 1.29 (d, J = 7.0 Hz, 6 H) | H |
| 90 | 338 | $^1$H NMR (600 MHz, CD$_3$OD) δ ppm 8.26 (d, J = 1.22 Hz, 1 H) 8.02-8.06 (m, 2 H) 7.99 (d, J = 8.24 Hz, 1 H) 7.91 (s, 1 H) 7.73 (dd, J = 8.39, 1.68 Hz, 1 H) 7.64-7.70 (m, 2 H) 4.58 (s, 2 H) | H |
| 91 | 356 | $^1$H NMR (600 MHz, CD$_3$OD) δ ppm 8.25 (d, J = 1.53 Hz, 1 H) 8.08 (ddd, J = 10.91, 2.44, 2.21 Hz, 1 H) 8.05 (dd, J = 6.56, 2.29 Hz, 1 H) 7.98 (d, J = 8.24 Hz, 1 H) 7.86 (s, 1 H) 7.73 (dd, J = 8.39, 1.68 Hz, 1 H) 7.47 (d, J = 9.77 Hz, 1 H) | H |
| 92 | 300 | $^1$H NMR (600 MHz, CD$_3$OD) δ ppm 8.21 (d, J = 1.53 Hz, 1 H) 7.94 (d, J = 8.24 Hz, 1 H) 7.76 (s, 1 H) 7.69 (dd, J = 8.39, 1.68 Hz, 1 H) 7.33-7.39 (m, 2 H) 7.30 (d, J = 2.14 Hz, 1 H) 6.96 (dt, J = 7.63, 1.98 Hz, 1 H) 3.87 (s, 3 H) | H |
| 93 | 300 | $^1$H NMR (600 MHz, CD$_3$OD) δ ppm 8.17 (d, J = 1.22 Hz, 1 H) 7.92 (d, J = 8.24 Hz, 1 H) 7.71 (d, J = 8.85 Hz, 2 H) 7.65 (dd, J = 8.24, 1.53 Hz, 1 H) 7.62 (s, 1 H) 7.02 (d, J = 8.85 Hz, 2 H) 3.85 (s, 3 H) | H |
| 94 | 260 | $^1$H NMR (600 MHz, CD$_3$OD) δ ppm 8.13 (d, J = 1.22 Hz, 1 H) 8.07 (br. s., 1 H) 7.87-7.94 (m, 2 H) 7.63 (dd, J = 8.24, 1.53 Hz, 1 H) 7.51 (s, 1 H) | I |
| 95 | 309 | $^1$H NMR (600 MHz, CD$_3$OD) δ ppm 8.16 (d, J = 1.53 Hz, 1 H) 7.95 (d, J = 1.22 Hz, 1 H) 7.90 (d, J = 8.24 Hz, 1 H) 7.60-7.65 (m, 2 H) 7.55 (dd, J = 8.55, 1.83 Hz, 1 H) 7.45 (d, J = 8.55 Hz, 1 H) 7.28 d, J = 3.05 Hz, 1 H) 6.52 (d, J = 2.44 Hz, 1 H) | I |
| 96 | 271 | $^1$H NMR (600 MHz, CD$_3$OD) δ ppm 9.09 (d, J = 1.83 Hz, 1 H) 8.63 (dd, J = 5.19, 1.22 Hz, 1 H) 8.47 (ddd, J = 8.55, 1.83, 1.53 Hz, 1 H) 8.29 (d, J = 1.53 Hz, 1 H) 8.00-8.04 (m, 2 H) 7.72-7.77 (m, 2 H) | I |
| 97 | 301 | $^1$H NMR (600 MHz, CD$_3$OD) δ ppm 8.21 (d, J = 1.22 Hz, 1 H) 8.15 (dd, J = 4.88, 1.83 Hz, 1 H) 8.13 (d, J = 7.32, 1.83 Hz, 1 H) 7.99 (s, 1 H) 7.94 (d, J = 8.24 Hz, 1 H) 7.69 (dd, J = 8.39, 1.68 Hz, 1 H) 7.08 (dd, J = 7.32, 4.88 Hz, 1 H) 4.10 (s, 3 H) | I |
| 98 | 301 | $^1$H NMR (600 MHz, CD$_3$OD) δ ppm 8.53 (d, J = 1.83 Hz, 1 H) 8.20 (d, J = 1.53 Hz, 1 H) 8.07 (dd, J = 8.55, 2.44 Hz, 1 H) 7.95 (d, J = 8.54 Hz, 1 H) 7.72 (s, 1 H) 7.69 (dd, J = 8.39, 1.68 Hz, 1 H) 6.90 (d, J = 8.85 Hz, 1 H) 3.96 (s, 3 H) | I |
| 99 | 274 | $^1$H NMR (600 MHz, CD$_3$OD) δ ppm 8.12 (d, J = 1.53 Hz, 1 H) 8.01 (s, 1 H) 7.88 (d, J = 8.24 Hz, 1 H) 7.83 (s, 1 H) 7.63 (dd, J = 8.39, 1.68 Hz, 1 H) 7.47 (s, 1 H) 3.94 (s, 3 H) | I |
| 100 | 289 | $^1$H NMR (600 MHz, CD$_3$OD) δ ppm 8.24 (d, J = 1.53 Hz, 1 H) 7.97 (d, J = 8.54 Hz, 1 H) 7.72 (dd, J = 8.39, 1.68 Hz, 1 H) 7.48 (s, 1 H) 2.57 (s, 3 H) 2.40 (s, 3 H) | I |
| 101 | 338 | $^1$H NMR (600 MHz, CD$_3$OD) δ ppm 9.08 (s, 1 H) 8.30 (d, J = 1.22 Hz, 1 H) 8.15 (s, 1 H) 8.11 (d, J = 8.54 Hz, 1 H) 8.04 (d, J = 7.93 Hz, 2 H) 7.86 (d, J = 8.24 Hz, 2 H) 7.76 (dd, J = 8.39, 1.68 Hz, 1 H) 6.52 (s, 1 H) | I |

TABLE 2-continued

| Ex. | MS (ESI)+ m/z [M + H]+ | 1H NMR (600 MHz, DMSO-$d_6$ δ ppm (unless otherwise stated) | General procedure |
|---|---|---|---|
| 102 | 354 | 11.33 (s, 1 H) 9.07 (d, J = 1.53 Hz, 1 H) 8.27 (d, J = 1.53 Hz, 1 H) 8.08 (d, J = 8.54 Hz, 1 H) 8.01 (s, 1 H) 7.92-7.96 (m, 2 H) 7.74 (dd, J = 8.54, 1.53 Hz, 1 H) 7.50 (d, J = 7.93 Hz, 2 H) | I |
| 103 | 326 | $^1$H NMR (600 MHz, CD$_3$OD) δ ppm 8.19 (d, J = 1.22 Hz, 1 H) 7.93 (d, J = 8.55 Hz, 1 H) 7.71 (s, 1 H) 7.70 (d, J = 8.85 Hz, 2 H) 7.67 (dd, J = 8.39, 1.68 Hz, 1 H) 7.50 (d, J = 8.54 Hz, 2 H) 1.36 (s, 9 H) | I |
| 104 | 314 | $^1$H NMR (600 MHz, CD$_3$OD) δ ppm 8.12 (d, J = 1.53 Hz, 1 H) 7.88 (d, J = 8.24 Hz, 1 H) 7.67 (dd, J = 8.39, 1.68 Hz, 1 H) 7.60 (dd, J = 8.70, 5.34 Hz, 2 H) 7.40-7.44 (m, 2 H) 7.08-7.13 (m, 2 H) 7.05 (d, J = 16.17 Hz, 1 H) | I |
| 105 | 304 | $^1$H NMR (600 MHz, CD$_3$OD) δ ppm 8.19 (d, J = 1.53 Hz, 1 H) 7.98 (s, 1 H) 7.93 (d, J = 8.54 Hz, 1 H) 7.67 (dd, J = 8.39, 1.68 Hz, 1 H) 7.43 (dd, J = 9.77, 2.75 Hz, 1 H) 6.87-6.97 (m, 2 H) | I |
| 106 | 318 | 11.30 (br. s., 1 H) 8.25 (d, J = 1.22 Hz, 1 H) 8.09 (s, 1 H) 8.04 (d, J = 8.24 Hz, 1 H) 7.74 (dd, J = 9.61, 2.90 Hz, 1 H) 7.72 (dd, J = 8.39, 1.68 Hz, 1 H) 7.22-7.26 (m, 2 H) 3.95 (s, 3 H) | I |
| 107 | 362/364 | 11.31 (s, 1 H) 9.06 (d, J = 1.53 Hz, 1 H) 8.20 (d, J = 1.53 Hz, 1 H) 8.04 (d, J = 8.24 Hz, 1 H) 7.92 (s, 1 H) 7.89 (d, J = 2.44 Hz, 1 H) 7.70 (dd, J = 8.39, 1.68 Hz, 1 H) 7.68 (dd, J = 8.54, 2.44 Hz, 1 H) 7.29 (d, J = 9.16 Hz, 1 H) 4.73-4.79 (m, 1 H) 1.33 (d, J = 6.10 Hz, 6 H) | I |
| 108 | 341 | $^1$H NMR (600 MHz, CD$_3$OD) δ ppm 8.24 (d, J = 1.53 Hz, 1 H) 7.97 (d, J = 8.24 Hz, 1 H) 7.88 (s, 1 H) 7.87 (d, J = 4.88 Hz, 2 H) 7.71 (dd, J = 8.39, 1.68 Hz, 1 H) 7.53 (d, J = 8.54 Hz, 2 H) 3.12 (s, 3 H) 3.05 (s, 3 H) | I |
| 109 | 363 | $^1$H NMR (600 MHz, CD$_3$OD) δ ppm 8.19 (d, J = 1.53 Hz, 1 H) 7.93 (d, J = 8.24 Hz, 1 H) 7.74-7.77 (m, 2 H) 7.71 (s, 1 H) 7.67 (dd, J = 8.39, 1.68 Hz, 1 H) 7.33-7.35 (m, 2 H) 3.01 (s, 3 H) | I |
| 110 | 313 | 11.42 (br. s., 1 H) 8.95 (d, J = 1.83 Hz, 1 H) 8.76 (d, J = 1.83 Hz, 1 H) 8.03 (s, 1 H) 7.83 (d, J = 8.55 Hz, 2 H) 7.41 (d, J = 8.24 Hz, 2 H) 2.89-3.00 (m, 1 H) 1.24 (d, J = 7.02 Hz, 6 H). | Separate procedure |
| 111 | 296 | 11.18 (br. s., 1 H) 8.99 (br. s., 1 H) 8.03 (d, J = 1.2 Hz, 1 H) 7.84 (d, J = 8.2 Hz, 2 H) 7.68-7.72 (m, 1 H) 7.63-7.67 (m, 1 H) 7.44 (s, 1 H) 7.38 (d, J = 8.2 Hz, 2 H) 2.93 (quin, J = 6.9 Hz, 1 H) 1.22 (d, J = 7.0 Hz, 6 H) | Separate procedure |
| 112 | 296 | $^1$H NMR (600 MHz, CD$_3$OD) δ ppm 7.94 (s, 1 H) 7.86 (d, J = 8.5 Hz, 2 H) 7.66 (s, 2 H) 7.37 (d, J = 8.2 Hz, 2 H) 7.20 (s, 1 H) 2.91-3.01 (m, 1 H) 1.29 (d, J = 7.0 Hz, 6 H) | Separate procedure |
| 113 | 297 | $^1$H NMR (600 MHz, CD$_3$OD) δ ppm 8.61 (d, J = 2.1 Hz, 1 H) 8.39 (d, J = 1.8 Hz, 1 H) 7.88 (d, J = 8.5 Hz, 2 H) 7.40 (d, J = 8.2 Hz, 2 H) 7.29 (s, 1 H) 2.88-3.09 (m, 1 H) 1.30 (d, J = 7.0 Hz, 6 H) | Separate procedure |
| 114 | 297 | $^1$H NMR (600 MHz, CD$_3$OD) δ ppm 8.01 (s, 2 H) 7.91 (d, J = 8.5 Hz, 2 H) 7.41 (d, J = 8.2 Hz, 2 H) 7.34 (s, 1 H) 2.91-3.07 (m, 1 H) 1.30 (d, J = 7.0 Hz, 6 H) | Separate procedure |
| 115 | 297 | $^1$H NMR (600 MHz, CD$_3$OD) δ ppm 8.87 (s, 1 H) 8.37 (s, 1 H) 7.97 (d, J = 8.5 Hz, 2 H) 7.26-7.50 (m, 3 H) 2.78-3.06 (m, 1 H) 1.31 (d, J = 6.7 Hz, 6 H) | Separate procedure |
| 116 | 297 | 11.48 (br. s., 1 H) 9.05 (br. s., 1 H) 8.21 (d, J = 7.9 Hz, 1 H) 7.95 (d, J = 7.9 Hz, 1 H) 7.88 (d, J = 8.2 Hz, 2 H) 7.51 (s, 1 H) 7.42 (d, J = 8.2 Hz, 2 H) 2.89-3.03 (m, 1 H) 1.23 (d, J = 7.0 Hz, 6 H) | Separate procedure |
| 117 | 263 | $^1$H NMR (600 MHz, CD$_3$OD) δ ppm 7.99 (s, 1 H) 7.74-7.77 (m, 1 H) 7.69-7.72 (m, 1 H) 7.24 (s, 1 H) 4.65 (s, 2 H) 1.40 (t, J = 7.3 Hz, 6 H) (methylene signals together with solvent peak) | J |
| 118 | 236 | 11.20 (s, 1 H) 7.88 (s, 1 H) 7.48-7.73 (m, 2 H) 6.73 (s, 1 H) 1.52 (s, 6 H) | J |
| 119 | 208 | $^1$H NMR (600 MHz, CD$_3$OD) δ ppm 7.87 (s, 1 H) 7.62 (d, J = 1.2 Hz, 2 H) 6.77 (s, 1 H) 4.69 (s, 2 H) | J |
| 120 | 287 | 12.05 (s, 1 H) 11.23 (br. s., 1 H) 8.95 (s, 1 H) 7.90-7.94 (m, 2 H) 7.88 (s, 1 H) 7.53-7.61 (m, 4 H) 7.43-7.49 (m, 1 H) | K |
| 121 | 329 | 11.97 (s, 1 H) 11.22 (s, 1 H) 8.94 (br. s., 1 H) 7.87 (s, 1 H) 7.81-7.86 (m, 2 H) 7.50-7.58 (m, 2 H) 7.41-7.47 (m, 2 H) 2.97 (quin, J = 6.9 Hz, 1 H) 1.26 (d, J = 6.7 Hz, 6 H) | K |
| 122 | 289 | 12.56 (br. s., 1 H) 11.23 (br. s., 1 H) 8.97 (s, 1 H) 7.79 (s, 1 H) 7.53-7.57 (m, 1 H) 7.45-7.51 (m, 1 H) | Separate procedure |
| 123 | 269 | 11.21 (br. s., 1 H) 7.76 (d, J = 0.9 Hz, 1 H) 7.62 (d, J = 8.2 Hz, 1 H) 7.57 (d, J = 7.3 Hz, 2 H) 7.47 (t, J = 7.6 Hz, 2 H) 7.40 (d, J = 8.2 Hz, 1 H) 7.24 (br. s., 1 H) | L |
| 124 | 311 | 11.22 (br. s., 1 H) 7.74 (d, J = 1.2 Hz, 1 H) 7.63 (d, J = 8.2 Hz, 1 H) 7.42-7.49 (m, 2 H) 7.39 (d, J = 8.2 Hz, 1 H) 7.34-7.37 (m, 2 H) 2.94 (dt, J = 13.8, 7.0 Hz, 1 H) 1.24 (d, J = 6.7 Hz, 6 H) | L |
| 125 | 359 | n.d. | L |

TABLE 2-continued

| Ex. | MS (ESI)+ m/z [M + H]+ | 1H NMR (600 MHz, DMSO-d6 δ ppm (unless otherwise stated) | General procedure |
|---|---|---|---|
| 126 | 356 | 11.31 (br. s., 1 H) 7.73 (d, J = 1.2 Hz, 1 H) 7.69 (dd, J = 8.5, 1.5 Hz, 1 H) 7.45 (d, J = 8.5 Hz, 1 H) 6.98-7.19 (m, 4 H) 3.78 (d, J = 5.2 Hz, 4 H) 3.32 (d, J = 5.2 Hz, 4 H) | L |
| 127 | 283 | 11.26 (br. s., 1 H) 7.71 (s, 1 H) 7.64 (dd, J = 8.5, 1.5 Hz, 1 H) 7.30-7.43 (m, 6 H) 4.63 (d, J = 6.1 Hz, 2 H) | L |
| 128 | 347 | 11.17 (br. s., 1 H) 7.75 (d, J = 1.2 Hz, 1 H) 7.61 (br. s., 5 H) 7.39 (d, J = 8.5 Hz, 1 H) | L |
| 129 | 347 | 11.18 (br. s., 1 H) 7.98 (br. s., 1 H) 7.78 (d, J = 1.2 Hz, 1 H) 7.61 (d, J = 8.5 Hz, 1 H) 7.54 (d, J = 7.6 Hz, 1 H) 7.42 (d, J = 8.2 Hz, 1 H) 7.39 (t, J = 7.8 Hz, 1 H) 7.35 (br. s., 1 H) | L |
| 130 | 297 | 11.30 (br. s., 1 H) 9.04 (br. s., 1 H) 7.72 (s, 1 H) 7.68 (d, J = 8.2 Hz, 1 H) 7.23-7.48 (m, 6 H) 4.82 (s, 2 H) 3.18 (s, 3 H) | L |
| 131 | 359 | 11.26 (br. s., 1 H) 7.71 (s, 1 H) 7.66 (d, J = 8.2 Hz, 1 H) 7.23-7.54 (m, 11 H) 5.24 (s, 2 H) | L |
| 132 | 375 | 11.21 (br. s., 1 H) 7.77 (d, J = 0.9 Hz, 1 H) 7.62 (d, J = 8.2 Hz, 1 H) 7.45-7.51 (m, 2 H) 7.26-7.44 (m, 6 H) 7.10 (d, J = 7.3 Hz, 1 H) 6.88 (br. s., 1 H) 5.14 (s, 2 H) | L |
| 133 | 351 | 1.29 (br. s., 1 H) 9.03 (br. s., 1 H) 7.70 (s, 1 H) 7.67 (d, J = 8.5 Hz, 1 H) 7.40 (d, J = 8.2 Hz, 1 H) 7.31 (t, J = 7.6 Hz, 2 H) 7.17-7.24 (m, 3 H) 4.00 (d, J = 12.8 Hz, 1 H) 3.20-3.28 (m, 2 H) 2.57 (d, J = 7.0 Hz, 2 H) 1.83-1.92 (m, 1 H) 1.74 (d, J = 10.7 Hz, 2 H) 1.29-1.39 (m, 2 H) | L |
| 134 | 317 | 11.25 (br. s., 1 H) 7.69 (s, 1 H) 7.55-7.68 (m, 5 H) 7.37 (d, J = 8.2 Hz, 1 H) 3.54 (s, 3 H) | L |
| 135 | 376 | 11.28 (br. s., 1 H) 7.70 (s, 1 H) 7.66 (d, J = 7.9 Hz, 1 H) 7.40 (d, J = 8.2 Hz, 1 H) 6.99 (d, J = 7.3 Hz, 1 H) 3.89-3.99 (m, 2 H) 3.60 (br. s., 2 H) 1.86-1.97 (m, 2 H) 1.46-1.59 (m, 2 H) 1.40 (s, 9 H) | L |
| 136 | 345 | 11.22 (br. s., 1 H) 7.87 (br. s., 1 H) 7.77 (s, 1 H) 7.72 (d, J = 7.3 Hz, 2 H) 7.36-7.66 (m, 8 H) | L |
| 137 | 283 | 11.23 (br. s., 1 H) 7.17-7.79 (m, 8 H) 3.78 (s, 3 H) | M |
| 138 | 325 | 11.25 (br. s., 1 H) 7.31-7.81 (m, 7 H) 3.77 (s, 3 H) 2.95 (dt, J = 13.8, 7.0 Hz, 1 H) 1.24 (d, J = 7.0 Hz, 6 H) | M |
| 139 | 311 | 11.29 (br. s., 1 H) 7.79 (s, 1 H) 7.73 (d, J = 8.2 Hz, 1 H) 7.62 (d, J = 8.2 Hz, 1 H) 7.32-7.45 (m, 5 H) 4.77 (br. s., 2 H) 3.78 (s, 3 H) 3.12 (br. s., 3 H) | M |
| 140 | 311 | 11.30 (br. s., 1 H) 7.65-7.76 (m, 2 H) 7.56 (d, J = 8.2 Hz, 1 H) 7.30-7.38 (m, 4 H) 7.19-7.27 (m, 1 H) 3.64-3.71 (m, 2 H) 3.62 (s, 3 H) 2.94-3.03 (m, 2 H) | M |
| 141 | 373 | 11.18 (br. s., 1 H) 7.89 (d, J = 1.2 Hz, 1 H) 7.68 (dd, J = 8.4, 1.4 Hz, 1 H) 7.50 (d, J = 8.2 Hz, 1 H) 7.44-7.48 (m, 2 H) 7.28-7.36 (m, 4 H) 7.19-7.26 (m, 1 H) 7.03-7.14 (m, 3 H) 5.23 (s, 2 H) 3.27 (s, 3 H) | M |
| 142 | 389 | 11.22 (br. s., 1 H) 7.77 (s, 1 H) 7.68 (br. s., 1 H) 7.56 (br. s., 1 H) 7.45-7.51 (m, 2 H) 7.31-7.44 (m, 5 H) 7.19 (br. s., 1 H) 6.90 (br. s., 1 H) 5.14 (s, 2 H) 3.76 (s, 3 H) | M |
| 143 | 365 | 11.29 (br. s., 1 H) 7.79 (d, J = 1.2 Hz, 1 H) 7.73 (d, J = 8.2 Hz, 1 H) 7.61 (d, J = 7.9 Hz, 1 H) 7.27-7.35 (m, 2 H) 7.12-7.25 (m, 3 H) 3.82 (d, J = 12.8 Hz, 2 H) 3.70 (s, 3 H) 3.16 (br. s., 2 H) 2.60 (d, J = 7.0 Hz, 2 H) 1.80-1.92 (m, 1 H) 1.73 (d, J = 11.0 Hz, 2 H) 1.33-1.50 (m, J = 12.5, 12.3, 12.3, 3.8 Hz, 2 H) | M |
| 144 | 359 | 11.23 (br. s., 1 H) 7.95 (br. s., 1 H) 7.77 (s, 1 H) 7.54-7.73 (m, 7 H) 7.51 (t, J = 7.6 Hz, 2 H) 7.41 (t, J = 7.3 Hz, 1 H) 3.80 (s, 3 H) | M |
| 145 | 323 | 11.27 (br. s., 1 H) 7.82 (d, J = 1.2 Hz, 1 H) 7.72 (d, J = 8.2 Hz, 1 H) 7.61 (d, J = 7.3 Hz, 1 H) 7.20-7.29 (m, 4 H) 4.74 (br. s., 2 H) 3.81 (br. s., 5 H) 3.08 (t, J = 5.8 Hz, 2 H) | M |
| 146 | 331 | 7.92 (d, J = 1.2 Hz, 1 H) 7.71 (dd, J = 8.4, 1.4 Hz, 1 H) 7.54 (d, J = 8.2 Hz, 1 H) 7.39-7.45 (m, 2 H) 7.07-7.15 (m, 2 H) 3.49 (s, 3 H) 3.32 (s, 3 H) | M |
| 147 | 330 | 11.26 (br. s., 1 H) 9.06 (br. s., 1 H) 8.33 (s, 1 H) 7.81-7.92 (m, 2 H) 7.74 (dd, J = 8.2, 1.5 Hz, 1 H) 7.38 (d, J = 2.1 Hz, 1 H) 7.31 (dd, J = 8.2, 2.1 Hz, 1 H) 7.06 (d, J = 8.2 Hz, 1 H) 3.88 (s, 3 H) 3.81 (s, 3 H) | N |
| 148 | 360 | 11.33 (s, 1 H) 9.11 (s, 1 H) 8.45 (s, 1 H) 8.38 (s, 1 H) 8.24 (t, J = 7.5 Hz, 2 H) 8.05 (d, J = 8.2 Hz, 1 H) 7.96 (d, J = 6.7 Hz, 1 H) 7.88 (d, J = 8.2 Hz, 1 H) 7.82 (dd, J = 8.5, 1.5 Hz, 1 H) 7.62 (dd, J = 15.6, 1.2 Hz, 1 H) 7.56 (t, J = 7.6 Hz, 1 H) 7.49 (t, J = 7.5 Hz, 1 H) | N |
| 149 | 260 | 11.26 (s, 1 H) 9.06 (s, 1 H) 8.33 (s, 1 H) 8.26 (s, 1 H) 7.80-7.88 (m, 2 H) 7.74 (dd, J = 8.2, 1.5 Hz, 1 H) 7.68 (s, 1 H) 7.01 (d, J = 1.2 Hz, 1 H) | N |
| 150 | 316 | 11.25 (s, 1 H) 9.46 (s, 1 H) 9.05 (s, 1 H) 8.31 (s, 1 H) 7.69-7.87 (m, 3 H) 7.35 (d, J = 2.1 Hz, 1 H) 7.20 (dd, J = 8.2, 2.1 Hz, 1 H) 6.87 (d, J = 8.2 Hz, 1 H) 3.88 (s, 3 H) | N |

TABLE 2-continued

| Ex. | MS (ESI)+ m/z [M + H]+ | 1H NMR (600 MHz, DMSO-d6 δ ppm (unless otherwise stated) | General procedure |
|---|---|---|---|
| 151 | 208 | 1H NMR (600 MHz, METHANOL-d4) d ppm 7.98 (d, J = 1.5 Hz, 1 H) 7.68 (dd, J = 8.5, 1.8 Hz, 1 H) 7.52 (d, J = 8.9 Hz, 1 H) 6.78 (s, 1 H) 4.68 (s, 2 H) | Separate procedure |
| 152 | 353 | 11.30 (br. s., 1 H) 8.87 (d, J = 2.4 Hz, 1 H) 8.17 (dd, J = 9.2, 2.4 Hz, 1 H) 8.06 (s, 1 H) 7.78 (d, J = 1.2 Hz, 2 H) 7.02 (d, J = 9.2 Hz, 1 H) 4.46 (d, J = 13.1 Hz, 2 H) 2.95 (s, 2 H) 1.60-1.85 (m, 3 H) 1.10 (dd, J = 12.4, 2.3 Hz, 2 H) 0.93 (d, J = 6.4 Hz, 3 H) | O |
| 153 | 375 | 11.29 (br. s., 1 H) 8.75 (d, J = 1.8 Hz, 1 H) 7.92-8.17 (m, 3 H) 7.76 (s, 2 H) 7.40 (d, J = 7.3 Hz, 2 H) 7.33 (t, J = 7.6 Hz, 2 H) 7.17-7.26 (m, 1 H) 6.71 (br. s., 1 H) 5.20 (br. s., 1 H) 1.48 (d, J = 6.7 Hz, 3 H) | O |
| 154 | 369 | 11.31 (br. s., 1 H) 8.90 (d, J = 2.4 Hz, 1 H) 8.23 (dd, J = 9.2, 2.4 Hz, 1 H) 8.07 (s, 1 H) 7.79 (s, 2 H) 7.06 (d, J = 8.9 Hz, 1 H) 4.36 (d, J = 12.5 Hz, 2 H) 3.54-3.68 (m, J = 8.7, 8.4, 8.4, 6.3 Hz, 2 H) 2.57 (d, J = 2.4 Hz, 2 H) 1.18 (d, J = 6.4 Hz, 6 H) | O |
| 155 | 327 | 11.30 (br. s., 1 H) 8.77 (d, J = 2.1 Hz, 1 H) 7.93-8.29 (m, 2 H) 7.78 (s, 3 H) 6.75 (d, J = 8.9 Hz, 1 H) 3.19 (br. s., 2 H) 1.88 (dt, J = 13.5, 6.8 Hz, 1 H) 0.94 (d, J = 6.7 Hz, 6 H) | O |
| 156 | 387 | 11.30 (br. s., 1 H) 8.86 (d, J = 2.4 Hz, 1 H) 8.17 (dd, J = 9.2, 2.4 Hz, 1 H) 8.06 (s, 1 H) 7.78 (s, 2 H) 6.91 (d, J = 9.2 Hz, 1 H) 3.78 (t, J = 5.3 Hz, 4 H) 3.55 (t, J = 5.8 Hz, 4 H) 3.27 (s, 6 H) | O |
| 157 | 362 | 11.30 (br. s., 1 H) 8.78 (d, J = 2.1 Hz, 1 H) 8.62 (d, J = 4.6 Hz, 1 H) 8.12-8.23 (m, 2 H) 8.05 (s, 1 H) 7.92-8.01 (m, 1 H) 7.78 (s, 2 H) 7.39-7.60 (m, 2 H) 6.83 (d, J = 8.5 Hz, 1 H) 4.77 (br. s., 2 H) | O |
| 158 | 367 | 11.30 (br. s., 1 H) 8.77 (d, J = 2.4 Hz, 1 H) 7.99-8.18 (m, 2 H) 7.77 (s, 2 H) 7.66 (br. s., 1 H) 6.69 (d, J = 9.2 Hz, 1 H) 1.92 (dd, J = 9.8, 3.4 Hz, 2 H) 1.34-1.72 (m, 10 H) | O |
| 159 | 369 | 11.30 (br. s., 1 H) 8.88 (d, J = 2.1 Hz, 1 H) 8.20 (dd, J = 8.9, 2.4 Hz, 1 H) 8.06 (s, 1 H) 7.78 (s, 2 H) 6.75 (br. s., 1 H) 3.31-3.62 (m, 4 H) 3.28 (s, 3 H) 1.87-2.13 (m, 4 H) | O |
| 160 | 446 | 11.31 (br. s., 1 H) 8.93 (d, J = 2.4 Hz, 1 H) 8.24 (dd, J = 8.9, 2.4 Hz, 1 H) 8.08 (s, 1 H) 7.80 (s, 2 H) 6.78-7.17 (m, 5 H) 3.77-3.90 (m, 7 H) 3.10 (t, J = 4.6 Hz, 4 H) | O |
| 161 | 332 | 11.37 (s, 1 H) 9.45 (d, J = 2.4 Hz, 1 H) 9.13 (s, 1 H) 8.63 (dd, J = 8.2, 2.4 Hz, 1 H) 8.17-8.32 (m, 3 H) 7.85-7.96 (m, 2 H) 7.48-7.64 (m, 3 H) | Separate procedure |
| 162 | 302 | 11.21 (s, 1 H) 9.01 (d, J = 1.5 Hz, 1 H) 8.08 (d, J = 1.8 Hz, 1 H) 7.74 (dd, J = 8.7, 1.7 Hz, 1 H) 7.66 (d, J = 8.5 Hz, 1 H) 7.24-7.42 (m, 1 H) 7.17 (s, 1 H) 7.00 (dt, J = 11.3, 2.4 Hz, 1 H) 6.93 (dd, J = 8.2, 1.8 Hz, 1 H) 6.81 (td, J = 8.2, 2.1 Hz, 1 H) 5.31 (s, 2 H) | Separate procedure |
| 163 | 340 | 11.21 (s, 1 H) 9.00 (br. s., 1 H) 8.06 (d, J = 1.5 Hz, 1 H) 7.73 (dd, J = 8.5, 1.8 Hz, 1 H) 7.65 (d, J = 8.5 Hz, 1 H) 7.31 (d, J = 8.9 Hz, 2 H) 7.12 (s, 1 H) 6.99 (d, J = 8.9 Hz, 2 H) 5.25 (s, 2 H) 1.25 (s, 9 H) | Separate procedure |
| 164 | 330 | 11.35 (s, 1 H) 9.20 (d, J = 1.5 Hz, 1 H) 8.34 (dd, J = 8.5, 2.4 Hz, 1 H) 8.16 (s, 1 H) 7.87 (s, 2 H) 7.51 (d, J = 8.5 Hz, 1 H) 3.95-4.17 (m, 1 H) 1.40 (d, J = 6.7 Hz, 6 H) | Separate procedure |
| 165 | 351/353 | 11.36 (br. s., 1 H) 9.13 (s, 1 H) 8.11-8.26 (m, 2 H) 7.83-7.98 (m, 3 H) 7.70 (dd, J = 8.5, 1.8 Hz, 1 H) | Separate procedure |
| 166 | 315 | 11.34 (s, 1 H) 8.11-8.22 (m, 2 H) 7.79-7.92 (m, 2 H) 7.40 (dd, J = 12.5, 1.5 Hz, 1 H) 7.36 (dd, J = 8.4, 1.4 Hz, 1 H) 3.00-3.06 (m, 1 H) 1.26 (d, J = 7.0 Hz, 6 H) | Separate procedure |
| 167 | 297 | 11.34 (s, 1 H) 8.16 (s, 1 H) 8.09 (s, 1 H) 8.02-8.06 (m, 1 H) 7.83-7.90 (m, 2 H) 7.54-7.58 (m, 2 H) 3.02-3.09 (m, 1 H) 1.28 (d, J = 7.0 Hz, 6 H) | Separate procedure |
| 168 | 418/420 | 11.32 (s, 1 H) 9.10 (br. s., 1 H) 8.18 (s, 1 H) 7.95 (d, J = 8.9 Hz, 1 H) 7.85-7.89 (m, 2 H) 7.34-7.39 (m, 2 H) 3.72-3.76 (m, 4 H) 2.96-3.00 (m, 4 H) | Separate procedure |
| 169 | 273 | 11.34 (s, 1 H) 9.11 (s, 1 H) 8.23-8.35 (m, 2 H) 8.16 (s, 1 H) 7.87 (s, 2 H) 7.40-7.56 (m, 2 H) | A |
| 170 | 366 | 11.29 (br. s., 1 H) 8.10-8.13 (m, 1 H) 7.80 (s, 2 H) 7.56 (d, J = 7.9 Hz, 1 H) 6.80 (s, 1 H) 6.75 (dd, J = 7.9, 1.2 Hz, 1 H) 3.04-3.17 (m, 4 H) 2.85-3.00 (m, 1 H) 1.68-1.92 (m, 4 H) 1.24 (d, J = 6.7 Hz, 6 H) | Separate procedure |
| 171 | 298 | 11.35 (br. s., 1 H) 9.29 (d, J = 1.5 Hz, 1 H) 8.48 (dd, J = 8.1, 2.3 Hz, 1 H) 8.18 (s, 1 H) 7.82-7.99 (m, 2 H) 7.57 (d, J = 8.2 Hz, 1 H) 3.16 (quin, J = 6.9 Hz, 1 H) 1.29 (d, J = 6.7 Hz, 6 H) | Separate procedure |
| 172 | 377/379 | 11.33 (s, 1 H) 9.09 (d, J = 1.5 Hz, 1 H) 8.16 (d, J = 1.2 Hz, 1 H) 7.97 (d, J = 8.2 Hz, 1 H) 7.77-7.91 (m, 2 H) 7.50 (d, J = 1.8 Hz, 1 H) 7.35 (dd, J = 8.2, 1.8 Hz, 1 H) 4.26 (q, J = 7.0 Hz, 2 H) 1.39 (t, J = 7.0 Hz, 3 H) | Separate procedure |
| 173 | 349 | 11.36 (s, 1 H) 9.13 (d, J = 1.2 Hz, 1 H) 8.32 (t, J = 7.9 Hz, 1 H) 8.22 (s, 1 H) 7.77-7.98 (m, 6 H) 7.54 (t, J = 7.5 Hz, 3 H) | P |

TABLE 2-continued

| Ex. | MS (ESI)+ m/z [M + H]+ | 1H NMR (600 MHz, DMSO-d6 δ ppm (unless otherwise stated) | General procedure |
|---|---|---|---|
| 174 | 367 | 11.37 (s, 1 H) 9.13 (br. s., 1 H) 8.35 (t, J = 8.1 Hz, 1 H) 8.23 (s, 1 H) 7.86-7.96 (m, 2 H) 7.64-7.78 (m, 3 H) 7.49-7.58 (m, 1 H) 7.31-7.43 (m, 2 H) | P |
| 175 | 350 | 11.37 (br. s., 1 H) 9.10 (s, 1 H) 8.69 (d, J = 4.3 Hz, 1 H) 8.28-8.44 (m, 2 H) 8.23 (s, 1 H) 8.01 (dd, J = 12.4, 1.7 Hz, 1 H) 7.87-7.95 (m, 3 H) 7.61 (dd, J = 7.9, 4.9 Hz, 1 H) | P |
| 176 | 380 | 11.36 (s, 1 H) 9.13 (br. s., 1 H) 8.70 (d, J = 2.7 Hz, 1 H) 8.30 (t, J = 8.1 Hz, 1 H) 8.17-8.24 (m, 2 H) 7.88-7.94 (m, 3 H) 7.82 (dd, J = 8.2, 1.8 Hz, 1 H) 6.98 (d, J = 8.9 Hz, 1 H) 3.93 (s, 3 H) | P |
| 177 | 361 | 11.35 (s, 1 H) 9.11 (s, 1 H) 8.25 (d, J = 8.5 Hz, 2 H) 8.18 (s, 1 H) 7.82-7.91 (m, 2 H) 7.68-7.78 (m, 2 H) 7.36-7.47 (m, 2 H) 7.17 (d, J = 7.6 Hz, 1 H) 7.08 (t, J = 7.5 Hz, 1 H) 3.81 (s, 3 H) | C |
| 178 | 367 | 11.36 (br. s., 1 H) 9.12 (s, 1 H) 8.29-8.39 (m, 2 H) 8.20 (s, 1 H) 7.78-7.96 (m, 4 H) 7.52-7.64 (m, 1 H) 7.40-7.50 (m, 1 H) 7.28-7.38 (m, 1 H) | C |
| 179 | 395 | 11.35 (s, 1 H) 9.12 (d, J = 1.5 Hz, 1 H) 8.26 (d, J = 8.5 Hz, 2 H) 8.18 (s, 1 H) 7.83-7.95 (m, 2 H) 7.77 (d, J = 8.5 Hz, 2 H) 7.40-7.49 (m, 2 H) 7.20 (d, J = 8.9 Hz, 1 H) 3.82 (s, 3 H) | C |
| 180 | 409 | 11.36 (s, 1 H) 9.12 (d, J = 1.5 Hz, 1 H) 8.36 (d, J = 8.9 Hz, 2 H) 8.20 (s, 1 H) 7.99-8.10 (m, 6 H) 7.84-7.95 (m, 2 H) 3.29 (s, 3 H) | C |
| 181 | 350 | 11.35 (br. s., 1 H) 8.26-8.35 (m, 2 H) 8.18 (s, 1 H) 7.83-7.94 (m, 2 H) 7.67 (d, J = 8.5 Hz, 2 H) 2.48 (s, 3 H) 2.30 (s, 3 H) | C |
| 182 | 347 | 11.34 (br. s., 1 H) 9.77 (s, 1 H) 9.11 (s, 1 H) 8.24 (d, J = 8.5 Hz, 2 H) 8.18 (s, 1 H) 7.79-7.91 (m, 4 H) 7.37 (dd, J = 7.6, 1.8 Hz, 1 H) 7.23 (dd, J = 15.4, 1.7 Hz, 1 H) 6.99 (d, J = 8.2 Hz, 1 H) 6.91-6.95 (m, 1 H) | C |
| 183 | 365 | 8.28 (d, J = 8.5 Hz, 2 H) 8.13 (d, J = 1.2 Hz, 1 H) 7.85 (dd, J = 8.4, 1.7 Hz, 1 H) 7.80 (d, J = 8.5 Hz, 2 H) 7.76 (d, J = 8.5 Hz, 1 H) 7.47 (dd, J = 12.2, 2.1 Hz, 1 H) 7.39 (dd, J = 8.4, 1.4 Hz, 1 H) 7.03 (d, J = 8.9 Hz, 1 H) | C |
| 184 | 365 | 11.35 (s, 1 H) 9.80 (s, 1 H) 9.11 (s, 1 H) 8.25 (d, J = 8.5 Hz, 2 H) 8.18 (s, 1 H) 7.80-7.91 (m, 4 H) 7.18-7.31 (m, 1 H) 7.04-7.13 (m, 1 H) 6.92-7.02 (m, 1 H) | C |
| 185 | 409 | 11.36 (s, 1 H) 9.12 (s, 1 H) 8.36 (d, J = 8.5 Hz, 2 H) 8.29 (t, J = 1.7 Hz, 1 H) 8.20 (s, 1 H) 8.17 (d, J = 8.5 Hz, 1 H) 8.07 (d, J = 8.9 Hz, 2 H) 7.99 (d, J = 8.5 Hz, 1 H) 7.87-7.92 (m, 2 H) 7.81 (t, J = 7.8 Hz, 1 H) 3.33 (s, 3 H) | C |
| 186 | 409 | 11.36 (s, 1 H) 9.11 (br. s., 1 H) 8.27 (t, J = 8.1 Hz, 1 H) 8.20 (s, 1 H) 7.85-7.94 (m, 3 H) 7.81 (dd, J = 8.2, 1.8 Hz, 1 H) 7.39-7.45 (m, 2 H) 7.09 (d, J = 8.2 Hz, 1 H) 3.89 (s, 3 H) 3.83 (s, 3 H) | P |
| 187 | 379 | 11.36 (s, 1 H) 9.13 (d, J = 1.2 Hz, 1 H) 8.31 (t, J = 7.9 Hz, 1 H) 8.21 (s, 1 H) 7.74-7.99 (m, 6 H) 7.47 (d, J = 8.5 Hz, 2 H) 5.28 (t, J = 5.8 Hz, 1 H) 4.57 (d, J = 5.8 Hz, 2 H) | P |
| 188 | 379 | 11.36 (d, J = 1.2 Hz, 1 H) 9.13 (d, J = 1.5 Hz, 1 H) 8.29 (t, J = 7.8 Hz, 1 H) 8.22 (s, 1 H) 7.84-7.94 (m, 2 H) 7.27-7.66 (m, 6 H) 5.28 (t, J = 5.3 Hz, 1 H) 4.46 (d, J = 5.2 Hz, 2 H) | P |
| 189 | 365 | 11.35 (s, 1 H) 9.84 (s, 1 H) 9.12 (s, 1 H) 8.25 (t, J = 7.9 Hz, 1 H) 8.20 (s, 1 H) 7.86-7.93 (m, 2 H) 7.67-7.78 (m, 4 H) 6.87-6.93 (m, 2 H) | P |
| 190 | 391 | 1H NMR (600 MHz, METHANOL-d4) d ppm 8.26 (t, J = 7.9 Hz, 1 H) 8.17 (d, J = 1.5 Hz, 1 H) 7.88 (dd, J = 8.5, 1.8 Hz, 1 H) 7.78 (d, J = 8.5 Hz, 1 H) 7.61-7.66 (m, 2 H) 7.59 (dd, J = 12.5, 1.5 Hz, 1 H) 7.51 (dd, J = 8.4, 2.0 Hz, 1 H) 6.85 (d, J = 8.2 Hz, 1 H) 4.62 (t, J = 8.7 Hz, 2 H) | P |
| 191 | 383 | 11.36 (s, 1 H) 10.04 (s, 1 H) 9.13 (d, J = 1.5 Hz, 1 H) 8.29 (t, J = 8.1 Hz, 1 H) 8.22 (s, 1 H) 7.88-7.97 (m, 2 H) 7.65-7.74 (m, 2 H) 7.24-7.31 (m, 2 H) 6.93-7.00 (m, 1 H) | P |
| 192 | 407 | 11.35 (s, 1 H) 9.12 (d, J = 1.5 Hz, 1 H) 8.25 (t, J = 8.1 Hz, 1 H) 8.20 (s, 1 H) 7.86-7.92 (m, 2 H) 7.80 (dd, J = 12.7, 1.7 Hz, 1 H) 7.74 (dd, J = 8.2, 1.8 Hz, 1 H) 7.39 (d, J = 2.4 Hz, 1 H) 7.35 (dd, J = 8.4, 2.3 Hz, 1 H) 6.99 (d, J = 8.2 Hz, 1 H) 4.31 (s, 4 H) | P |
| 193 | 397 | 11.36 (s, 1 H) 9.13 (br. s., 1 H) 8.27 (t, J = 8.1 Hz, 1 H) 8.22 (s, 1 H) 7.85-7.98 (m, 2 H) 7.68 (dd, J = 12.2, 1.5 Hz, 1 H) 7.64 (dd, J = 8.2, 1.5 Hz, 1 H) 7.37 (dd, J = 9.2, 3.1 Hz, 1 H) 7.27 (dd, J = 8.2, 3.1 Hz, 1 H) 7.20 (dd, J = 9.2, 4.9 Hz, 1 H) 3.82 (s, 3 H) | P |
| 194 | 367 | 11.33 (s, 1 H) 9.38 (br. s., 1 H) 9.08 (br. s., 1 H) 8.27 (d, J = 1.22 Hz, 1 H) 8.09 (d, J = 8.55 Hz, 1 H) 7.98 (s, 1 H) 7.90-7.97 (m, 2 H) 7.75 (dd, J = 8.39, 1.68 Hz, 1 H) 7.61 (t, J = 7.63 Hz, 1 H) 7.53 (d, J = 7.32 Hz, 1 H) 4.37 (d, J = 5.19 Hz, 2 H) 2.86-2.99 (m, 2 H) 1.85 (d, J = 14.95 Hz, 2 H) 1.51-1.77 (m, 4 H) 1.39 (t, J = 3.81 Hz, 2 H) | Separate procedure |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 195 | 361 | 11.33 (s, 1 H) 9.10 (br. s., 1 H) 8.07-8.21 (m, 2 H) 7.75-7.94 (m, 4 H) 7.42-7.56 (m, 5 H) 4.06 (s, 3 H) | Q |
| 196 | 379 | 11.34 (br. s., 1 H) 8.07-8.27 (m, 2 H) 7.87 (s, 2 H) 7.70 (td, J = 7.86, 1.68 Hz, 1 H) 7.50 (m, 1 H) 7.43 (s, 1 H) 7.32-7.41 (m, 3 H) 4.02 (s, 3 H) | Q |
| 197 | 409 | 11.33 (s, 1 H) 8.12-8.22 (m, 2 H) 7.87 (s, 2 H) 7.40 (s, 1 H) 7.13-7.36 (m, 4 H) 4.01 (s, 3 H) 3.90 (s, 3 H) | Q |
| 198 | 403 | 11.33 (s, 1 H) 9.10 (s, 1 H) 8.07-8.22 (m, 2 H) 7.85 (s, 2 H) 7.75 (d, J = 8.24 Hz, 2 H) 7.32-7.54 (m, 4 H) 4.05 (s, 3 H) 2.86-3.07 (m, 1 H) 1.26 (d, J = 6.71 Hz, 6 H) | Q |
| 199 | 379 | 11.33 (s, 1 H) 9.10 (br. s., 1 H) 8.10-8.19 (m, 2 H) 7.87-7.94 (m, 2 H) 7.86 (s, 2 H) 7.51 (d, J = 1.53 Hz, 1 H) 7.45 (dd, J = 8.09, 1.68 Hz, 1 H) 7.32-7.41 (m, 2 H) 4.06 (s, 3 H) | Q |
| 200 | 406 | 11.32 (s, 1 H) 8.15 (s, 1 H) 8.08 (d, J = 8.54 Hz, 1 H) 7.84 (d, J = 1.22 Hz, 2 H) 7.38-7.45 (m, 3 H) 7.22-7.31 (m, 3 H) 6.84 (d, J = 7.93 Hz, 1 H) 4.05 (s, 3 H) 3.92 (s, 3 H) | Q |
| 201 | 352 | 1H NMR (600 MHz, METHANOL-d4) d ppm 8.43 (s, 1 H) 8.36-8.42 (m, 1 H) 8.16 (d, J = 1.22 Hz, 1 H) 7.87 (dd, J = 8.55, 1.83 Hz, 1 H) 7.71-7.79 (m, 3 H) 4.44 (s, 2 H) 3.52 (d, J = 12.21 Hz, 2 H) 3.00-3.07 (m, 2 H) 1.70-2.00 (m, 5 H) 1.54 (s, 1 H) | R |
| 202 | 382 | 1H NMR (600 MHz, METHANOL-d4) d ppm 8.43 (s, 1 H) 8.36-8.40 (m, 1 H) 8.14 (d, J = 1.53 Hz, 1 H) 7.85 (dd, J = 8.54, 1.53 Hz, 1 H) 7.72-7.79 (m, 3 H) 4.49 (s, 2 H) 3.83-3.90 (m, 2 H) 3.42 (d, J = 11.90 Hz, 2 H) 2.84 (t, J = 11.60 Hz, 2 H) 1.23 (d, J = 6.10 Hz, 6 H) | R |
| 203 | 396 | 1H NMR (600 MHz, METHANOL-d4) d ppm 8.47 (s, 1 H) 8.41 (d, J = 7.63 Hz, 1 H) 8.17 (d, J = 1.53 Hz, 1 H) 7.88 (dd, J = 8.54, 1.53 Hz, 1 H) 7.72-7.84 (m, J = 15.91, 7.90, 7.78, 7.78 Hz, 3 H) 4.58 (s, 2 H) 3.05 (d, J = 6.41 Hz, 4 H) 2.11-2.35 (m, 2 H) 0.99-1.17 (m, 12 H) | R |
| 204 | 380 | 1H NMR (600 MHz, METHANOL-d4) d ppm 8.44 (s, 1 H) 8.36-8.41 (m, 1 H) 8.16 (d, J = 1.53 Hz, 1 H) 7.87 (dd, J = 8.55, 1.53 Hz, 1 H) 7.69-7.81 (m, 3 H) 4.66 (d, J = 13.12 Hz, 1 H) 4.32 (d, J = 13.12 Hz, 1 H) 3.33-3.44 (m, 1 H) 2.78 (s, 3 H) 2.09-2.32 (m, 2 H) 1.93-2.05 (m, 2 H) 1.58-1.85 (m, 3 H) 1.19-1.50 (m, 3 H) | R |
| 205 | 356 | 1H NMR (600 MHz, METHANOL-d4) d ppm 8.44 (s, 1 H) 8.40 (dt, J = 7.32, 1.68 Hz, 1 H) 8.17 (d, J = 1.22 Hz, 1 H) 7.88 (dd, J = 8.55, 1.83 Hz, 1 H) 7.72-7.80 (m, 3 H) 4.40-4.64 (m, 2 H) 3.72-3.79 (m, 2 H) 3.43 (s, 3 H) 2.91 (s, 3 H) | R |
| 206 | 352 | 1H NMR (600 MHz, METHANOL-d4) d ppm 8.34 (d, J = 8.24 Hz, 2 H) 8.13 (d, J = 1.22 Hz, 1 H) 7.86 (dd, J = 8.55, 1.53 Hz, 1 H) 7.76 (d, J = 8.54 Hz, 2 H) 7.73 (d, J = 8.55 Hz, 2 H) 4.40 (s, 2 H) 3.51 (d, J = 12.51 Hz, 2 H) 2.97-3.07 (m, 2 H) 1.69-2.00 (m, 5 H) 1.48-1.59 (m, 1 H) | S |
| 207 | 382 | 1H NMR (600 MHz, METHANOL-d4) d ppm 8.32 (d, J = 8.55 Hz, 2 H) 8.10 (d, J = 1.22 Hz, 1 H) 7.84 (dd, J = 8.55, 1.53 Hz, 1 H) 7.71-7.76 (m, 3 H) 4.45 (s, 2 H) 3.88 (br. s., 2 H) 3.42 (d, J = 12.21 Hz, 2 H) 2.82 (t, J = 11.75 Hz, 2 H) 1.23 (d, J = 6.41 Hz, 6 H) | S |
| 208 | 396 | 1H NMR (600 MHz, METHANOL-d4) d ppm 8.39 (d, J = 8.24 Hz, 2 H) 8.17 (d, J = 1.22 Hz, 1 H) 7.88 (dd, J = 8.55, 1.53 Hz, 1 H) 7.76-7.80 (m, 3 H) 4.54 (s, 2 H) 3.04 (t, J = 5.95 Hz, 4 H) 2.18-2.28 (m, 2 H) 1.02-1.13 (m, 12 H) | S |
| 209 | 430 | 1H NMR (600 MHz, METHANOL-d4) d ppm 8.34 (d, J = 8.24 Hz, 2 H) 8.26 (d, J = 7.63 Hz, 2 H) 8.12 (d, J = 1.22 Hz, 1 H) 7.85 (dd, J = 8.55, 1.83 Hz, 1 H) 7.76 (d, J = 8.54 Hz, 3 H) 7.28 (d, J = 7.63 Hz, 2 H) 4.49 (s, 2 H) 4.05 (br. s., 4 H) 3.39-3.54 (m, 4 H) | S |
| 210 | 340 | 1H NMR (600 MHz, METHANOL-d4) d ppm 8.22-8.36 (m, 2 H) 7.81-7.92 (m, 1 H) 7.59-7.79 (m, 4 H) 4.30 (s, 2 H) 1.50 (s, 9 H) | S |
| 211 | 315 | 11.35 (br. s., 1 H) 9.12 (s, 1 H) 8.17 (s, 1 H) 8.02 (dd, J = 7.93, 1.83 Hz, 1 H) 7.90 (dd, J = 10.83, 1.68 Hz, 1 H) 7.86-7.88 (m, 2 H) 7.62 (t, J = 7.78 Hz, 1 H) 3.18-3.28 (m, 1 H) 1.27 (d, J = 7.02 Hz, 6 H) | Separate procedure |
| 212 | 283 | 11.33 (s, 1 H) 8.13 (s, 1 H) 8.01 (s, 1 H) 7.94 (dd, J = 7.78, 1.68 Hz, 1 H) 7.84 (d, J = 1.22 Hz, 2 H) 7.40 (d, J = 7.94 Hz, 1 H) 2.36 (s, 3 H) 2.33 (s, 3 H) | A |
| 213 | 297 | 11.33 (s, 1 H) 9.10 (s, 1 H) 8.07-8.21 (m, 3 H) 7.76-7.95 (m, 2 H) 7.46 (d, J = 8.24 Hz, 2 H) 2.67 (t, J = 7.63 Hz, 2 H) 1.61-1.71 (m, 2 H) 0.92 (t, J = 7.32 Hz, 3 H) | A |
| 214 | 369 | 11.36 (br. s., 1 H) 9.13 (s, 1 H) 8.23 (s, 1 H) 8.13 (d, J = 8.24 Hz, 1 H) 8.06 (d, J = 1.83 Hz, 1 H) 7.90-7.94 (m, 2 H) 7.83 (dd, J = 8.39, 1.98 Hz, 1 H) | Separate procedure |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 215 | 286 | 11.34 (s, 1 H) 9.01 (d, J = 1.83 Hz, 1 H) 8.45 (dd, J = 8.85, 2.44 Hz, 1 H) 8.14 (s, 1 H) 7.79-7.90 (m, 2 H) 7.07 (d, J = 7.93 Hz, 1 H) 3.98 (s, 3 H) | Separate procedure |
| 216 | 286 | 11.35 (s, 1 H) 9.12 (s, 1 H) 8.50 (dd, J = 7.48, 1.98 Hz, 1 H) 8.46 (dd, J = 4.88, 1.83 Hz, 1 H) 8.16-8.20 (m, 1 H) 7.83-7.91 (m, 2 H) 7.26 (dd, J = 7.63, 4.88 Hz, 1 H) 4.05 (s, 3 H) | Separate procedure |
| 217 | 351/353 | 11.37 (br. s., 1 H) 9.13 (s, 1 H) 8.19 (s, 1 H) 8.11-8.15 (m, 1 H) 7.96-8.02 (m, 2 H) 7.87-7.93 (m, 2 H) | Separate procedure |
| 218 | 363/365 | 11.33 (s, 1 H) 9.11 (s, 1 H) 8.16 (s, 1 H) 7.99 (d, J = 8.55 Hz, 1 H) 7.78-7.90 (m, 2 H) 7.52 (d, J = 1.83 Hz, 1 H) 7.37 (dd, J = 8.24, 1.83 Hz, 1 H) 3.98 (s, 3 H) | Separate procedure |
| 219 | 313 | 11.31 (br. s., 1 H) 9.09 (br. s., 1 H) 8.11 (t, J = 1.2 Hz, 1 H) 7.80-7.85 (m, 2 H) 7.71 (dd, J = 8.5, 2.1 Hz, 1 H) 7.64 (d, J = 2.1 Hz, 1 H) 7.10 (d, J = 8.5 Hz, 1 H) 4.31-4.43 (m, 4 H) | T |
| 220 | 271 | 11.33 (s, 1 H) 9.98 (s, 1 H) 9.10 (s, 1 H) 8.15 (s, 1 H) 7.82-7.89 (m, 2 H) 7.62-7.69 (m, 1 H) 7.58-7.62 (m, 1 H) 7.43 (t, J = 7.9 Hz, 1 H) 7.04 (ddd, J = 8.2, 2.4, 0.9 Hz, 1 H) | T |
| 221 | 271 | n.d. | T |
| 222 | 321 | n.d. | T |
| 223 | 271 | 11.30 (br. s., 1 H) 10.38 (s, 1 H) 9.08 (s, 1 H) 8.08 (t, J = 1.1 Hz, 1 H) 8.04-8.07 (m, 2 H) 7.76-7.81 (m, 2 H) 6.94-7.01 (m, 2 H) | T |
| 224 | 231 | 11.33 (s, 1 H) 8.27 (br. s., 1 H) 8.10 (s, 1 H) 8.08 (br. s., 1 H) 8.07 (br. s., 1 H) 7.78-7.84 (m, 2 H) 7.50-7.56 (m, 2 H) 7.42-7.47 (m, 1 H) | T |
| 225 | 285 | 11.32 (s, 1 H) 9.10 (s, 1 H) 8.16 (t, J = 1.2 Hz, 1 H) 8.04 (dd, J = 7.6, 1.8 Hz, 1 H) 7.83-7.87 (m, 2 H) 7.60-7.66 (m, 1 H) 7.30 (d, J = 7.9 Hz, 1 H) 7.16 (td, J = 7.5, 0.9 Hz, 1 H) 3.94 (s, 3 H) | T |
| 226 | 305 | n.d. | T |
| 227 | 301 | n.d. | T |
| 228 | 308 | 12.01 (s, 1 H) 11.27 (br. s., 1 H) 8.23-8.28 (m, 1 H) 8.06 (d, J = 1.2 Hz, 1 H) 7.78-7.83 (m, 1 H) 7.72-7.77 (m, 1 H) 7.41-7.47 (m, 1 H) 7.17-7.25 (m, 2 H) 2.87 (s, 3 H) | T |
| 229 | 321 | 11.18 (s, 1 H) 10.63 (s, 1 H) 9.00 (br. s., 1 H) 7.77 (d, J = 1.5 Hz, 1 H) 7.61-7.67 (m, 2 H) 7.55-7.60 (m, 1 H) 7.50-7.55 (m, 1 H) 7.14-7.24 (m, 2 H) 2.51-2.56 (m, 2 H) 1.47-1.65 (m, 2 H) 0.90 (t, J = 7.3 Hz, 3 H) | U |
| 230 | 346 | n.d. | U |
| 231 | 288 | 11.20 (s, 1 H) 11.01 (s, 1 H) 9.02 (d, J = 1.5 Hz, 1 H) 7.84 (d, J = 0.9 Hz, 1 H) 7.75 (ddd, J = 11.7, 2.3, 2.1 Hz, 1 H) 7.60-7.64 (m, 1 H) 7.56-7.60 (m, 1 H) 7.44-7.50 (m, 1 H) 7.37-7.44 (m, 1 H) 6.83-6.93 (m, 1 H) | U |
| 232 | 304 | 11.10 (br. s., 1 H) 8.11 (d, J = 7.6 Hz, 1 H) 7.58 (d, J = 1.2 Hz, 1 H) 7.40-7.45 (m, 1 H) 7.32-7.39 (m, 1 H) 3.69-3.88 (m, 1 H) 1.38-1.98 (m, 14 H) | U |
| 233 | 300 | 11.19 (s, 1 H) 10.73 (s, 1 H) 9.01 (d, J = 1.5 Hz, 1 H) 7.80 (d, J = 0.9 Hz, 1 H) 7.57-7.61 (m, 1 H) 7.53-7.57 (m, 1 H) 7.40-7.47 (m, 1 H) 7.43 (none, 1 H) 7.24-7.31 (m, 2 H) 6.61-6.67 (m, 1 H) 3.78 (s, 3 H) | U |
| 234 | 360 | 11.11 (br. s., 1 H) 8.69 (t, J = 6.3 Hz, 1 H) 7.62-7.69 (m, 4 H) 7.60 (d, J = 1.5 Hz, 1 H) 7.40-7.49 (m, 6 H) 7.30-7.38 (m, 1 H) 4.58 (d, J = 6.1 Hz, 2 H) | U |
| 235 | 314 | 11.11 (br. s., 1 H) 8.57 (t, J = 6.1 Hz, 1 H) 7.59 (d, J = 1.2 Hz, 1 H) 7.42-7.47 (m, 1 H) 7.36-7.42 (m, 1 H) 7.26-7.33 (m, 2 H) 6.86-6.94 (m, 2 H) 4.45 (d, J = 6.1 Hz, 2 H) 3.72 (s, 3 H) | U |
| 236 | 300 | 11.17 (br. s., 1 H) 10.52 (s, 1 H) 7.74 (d, J = 1.2 Hz, 1 H) 7.62-7.68 (m, 2 H) 7.54-7.58 (m, 1 H) 7.49-7.53 (m, 1 H) 6.95-7.01 (m, 2 H) 3.75 (s, 3 H) | U |
| 237 | 334 | 11.12 (s, 1 H) 8.72 (t, J = 6.0 Hz, 1 H) 8.16 (d, J = 8.2 Hz, 1 H) 7.94-8.01 (m, 1 H) 7.88 (d, J = 8.2 Hz, 1 H) 7.36-7.63 (m, 7 H) 5.01 (d, J = 5.8 Hz, 2 H) | U |
| 238 | 300 | 11.17 (br. s., 1 H) 9.77 (s, 1 H) 8.10 (dd, J = 7.9, 1.2 Hz, 1 H) 7.74 (d, J = 1.5 Hz, 1 H) 7.54-7.58 (m, 1 H) 7.48-7.53 (m, 1 H) 6.96-7.15 (m, 4 H) 3.85 (s, 3 H) | U |
| 239 | 284 | 11.11 (br. s., 1 H) 8.64 (t, J = 6.3 Hz, 1 H) 7.59 (d, J = 1.2 Hz, 1 H) 7.23-7.47 (m, 7 H) 4.53 (d, J = 6.1 Hz, 2 H) | U |
| 240 | 276 | 11.11 (br. s., 1 H) 8.08 (d, J = 7.9 Hz, 1 H) 7.57 (d, J = 1.8 Hz, 1 H) 7.40-7.45 (m, 1 H) 7.33-7.39 (m, 1 H) 3.50-3.59 (m, 1 H) 1.11-1.99 (m, 10 H) | U |
| 241 | 360 | 11.17 (br. s., 1 H) 7.72 (d, J = 1.5 Hz, 1 H) 7.15-7.54 (m, 12 H) 5.27 (s, 2 H) | U |
| 242 | 328 | 11.14 (br. s., 1 H) 7.63 (t, J = 1.1 Hz, 1 H) 7.43-7.47 (m, 2 H) 7.23-7.30 (m, 2 H) 6.88-6.96 (m, 2 H) 4.67 (s, 2 H) 3.73 (s, 3 H) 3.07 (s, 3 H) | U |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 243 | 328 | 11.11 (br. s., 1 H) 8.19 (t, J = 5.6 Hz, 1 H) 7.60 (d, J = 1.5 Hz, 1 H) 7.42-7.46 (m, 1 H) 7.35-7.40 (m, 1 H) 7.12-7.20 (m, 2 H) 6.82-6.88 (m, 2 H) 3.71 (s, 3 H) 3.41-3.55 (m, 2 H) 2.84 (t, J = 7.3 Hz, 2 H) | U |
| 244 | 415 | 11.18 (br. s., 1 H) 9.40 (br. s., 1 H) 7.69 (t, J = 1.1 Hz, 1 H) 7.50-7.53 (m, 2 H) 6.98 (d, J = 1.8 Hz, 1 H) 6.92-6.96 (m, 1 H) 6.88 (dd, J = 8.2, 2.1 Hz, 1 H) 4.71 (s, 2 H) 3.84 (t, J = 6.3 Hz, 2 H) 3.73 (d, J = 1.8 Hz, 6 H) 3.38-3.43 (m, 2 H) 2.88 (d, J = 4.6 Hz, 5 H) | U |
| 245 | 399 | 11.18 (br. s., 1 H) 10.61 (s, 1 H) 7.75 (d, J = 1.2 Hz, 1 H) 7.65-7.72 (m, 2 H) 7.55-7.61 (m, 1 H) 7.49-7.55 (m, 1 H) 7.01-7.10 (m, 2 H) 4.31-4.38 (m, 2 H) 3.97-4.03 (m, 2 H) 3.48-3.75 (m, 6 H) 3.18-3.26 (m, 2 H) | U |
| 246 | 358 | 11.17 (s, 1 H) 10.53 (s, 1 H) 8.99 (br. s., 1 H) 7.75 (d, J = 1.2 Hz, 1 H) 7.61-7.67 (m, 2 H) 7.54-7.57 (m, 1 H) 7.48-7.53 (m, 1 H) 6.95-7.03 (m, 2 H) 4.03-4.09 (m, 2 H) 3.64-3.72 (m, 2 H) 3.51 (q, J = 7.0 Hz, 2 H) 1.14 (t, J = 7.0 Hz, 3 H) | U |
| 247 | 399 | 11.20 (br. s., 1 H) 10.81 (s, 1 H) 9.94 (br. s., 1 H) 7.79 (d, J = 1.2 Hz, 1 H) 7.52-7.63 (m, 3 H) 7.34 (t, J = 8.1 Hz, 1 H) 7.24-7.31 (m, 1 H) 6.73 (dd, J = 8.1, 1.7 Hz, 1 H) 4.34-4.41 (m, 2 H) 3.98-4.04 (m, 2 H) 3.50-3.76 (m, 6 H) 3.23 (br. s., 2 H) | U |
| 248 | 358 | 11.18 (s, 1 H) 10.73 (s, 1 H) 9.01 (s, 1 H) 7.82 (d, J = 1.2 Hz, 1 H) 7.52-7.61 (m, 2 H) 7.46 (t, J = 2.1 Hz, 1 H) 7.22-7.31 (m, 2 H) 6.62-6.68 (m, 1 H) 4.07-4.11 (m, 2 H) 3.69-3.75 (m, 2 H) 3.52 (q, J = 7.0 Hz, 2 H) 1.15 (t, J = 7.0 Hz, 3 H) | U |
| 249 | 319 | 11.34 (s, 1 H) 9.10 (br. s., 1 H) 8.30 (d, J = 1.22 Hz, 1 H) 8.10 (d, J = 7.93 Hz, 1 H) 7.78 (dd, J = 8.39, 1.68 Hz, 1 H) 7.34-7.51 (m, 4 H) 4.52 (s, 2 H) | G |
| 250 | 349 | 11.39 (br. s., 1 H) 8.60 (d, J = 1.22 Hz, 1 H) 8.18-8.21 (m, 1 H) 8.16 (d, J = 7.93 Hz, 1 H) 7.87-7.97 (m, 4 H) 3.60 (s, 3 H) | F |
| 251 | 301 | 11.35 (br. s., 1 H) 9.14 (br. s., 1 H) 8.55 (d, J = 1.22 Hz, 1 H) 8.06-8.16 (m, 2 H) 7.96-8.03 (m, 1 H) 7.91 (dd, J = 8.39, 1.68 Hz, 1 H) 7.47-7.63 (m, 2 H) 4.63 (d, J = 5.80 Hz, 2 H) | F |
| 252 | 301 | 11.35 (d, J = 1.22 Hz, 1 H) 9.14 (d, J = 1.53 Hz, 1 H) 8.54 (d, J = 1.22 Hz, 1 H) 8.09 (dd, J = 8.55, 1.53 Hz, 2 H) 7.90 (dd, J = 8.55, 1.53 Hz, 1 H) 7.53 (d, J = 8.55 Hz, 2 H) 5.38 (t, J = 5.80 Hz, 1 H) 4.60 (d, J = 5.49 Hz, 2 H) | F |
| 253 | 302 | 11.35 (s, 1 H) 9.14 (br. s., 1 H) 8.93 (d, J = 3.36 Hz, 1 H) 8.54 (d, J = 1.22 Hz, 1 H) 8.39 (dd, J = 8.70, 2.59 Hz, 1 H) 8.09 (d, J = 8.55 Hz, 1 H) 7.90 (dd, J = 8.54, 1.83 Hz, 1 H) 7.04 (d, J = 9.46 Hz, 1 H) 3.97 (s, 3 H) | F |
| 254 | 287 | 11.35 (s, 1 H) 9.92 (s, 1 H) 9.14 (d, J = 1.22 Hz, 1 H) 8.53 (d, J = 1.22 Hz, 1 H) 8.09 (d, J = 8.54 Hz, 1 H) 7.90 (dd, J = 8.39, 1.68 Hz, 1 H) 7.49-7.57 (m, 1 H) 7.39 (t, J = 8.09 Hz, 1 H) 6.99 (dd, J = 9.16, 1.53 Hz, 1 H) | F |
| 255 | 287 | 11.31 (br. s., 1 H) 10.29 (br. s., 1 H) 8.47 (d, J = 1.83 Hz, 1 H) 8.01 (d, J = 8.55 Hz, 1 H) 7.94-7.98 (m, 2 H) 7.86 (dd, J = 8.39, 1.68 Hz, 1 H) 6.94 (q, J = 4.98 Hz, 2 H) | F |
| 256 | n.d. | 11.15 (br. s., 1 H) 8.60 (br. s., 2 H) 7.72-7.79 (m, 1 H) 7.62 (d, J = 1.2 Hz, 1 H) 7.40-7.53 (m, 4 H) 7.21-7.26 (m, 1 H) 7.12-7.17 (m, 1 H) 4.32 (t, J = 5.3 Hz, 2 H) 4.11-4.18 (m, 2 H) 3.82 (s, 3 H) 3.13 (td, J = 12.7, 2.4 Hz, 2 H) 2.88-2.96 (m, 2 H) 1.94-2.04 (m, 1 H) 1.79-1.90 (m, 2 H) 1.22-1.35 (m, J = 12.4, 12.3, 12.3, 4.1 Hz, 2 H) | V |
| 257 | 381 | 11.15 (br. s., 1 H) 8.78 (br. s., 2 H) 7.62 (d, J = 1.2 Hz, 1 H) 7.39-7.53 (m, 7 H) 4.12-4.21 (m, 4 H) 3.10-3.16 (m, 2 H) 2.87-2.93 (m, 2 H) 1.95-2.04 (m, 1 H) 1.81-1.89 (m, 2 H) 1.25-1.37 (m, J = 12.5, 12.4, 12.4, 4.3 Hz, 2 H) | V |
| 258 | 312 | 11.15 (br. s., 1 H) 9.86 (br. s., 1 H) 7.64 (s, 1 H) 7.54-7.58 (m, 1 H) 7.44-7.53 (m, 2 H) 7.33-7.41 (m, 1 H) 7.20-7.29 (m, 2 H) 3.25-3.33 (m, 1 H) 1.16 (d, J = 6.7 Hz, 6 H) | U |
| 259 | 284 | 11.16 (s, 1 H) 9.82 (s, 1 H) 8.98 (br. s., 1 H) 7.76 (d, J = 7.6 Hz, 1 H) 7.69 (d, J = 1.2 Hz, 1 H) 7.47-7.59 (m, 2 H) 7.22-7.30 (m, 2 H) 7.08-7.14 (m, 1 H) 2.30 (s, 3 H) | U |
| 260 | 298 | 11.16 (br. s., 1 H) 7.69 (d, J = 1.2 Hz, 1 H) 7.46-7.51 (m, 1 H) 7.42-7.45 (m, 1 H) 7.35-7.42 (m, 2 H) 7.24-7.29 (m, 2 H) 3.53 (s, 3 H) 2.34 (s, 3 H) | U |
| 261 | 314 | 11.16 (br. s., 1 H) 7.68 (d, J = 1.2 Hz, 1 H) 7.38-7.48 (m, 4 H) 6.99-7.04 (m, 2 H) 3.80 (s, 3 H) 3.50 (s, 3 H) | U |
| 262 | 370 | 11.02 (br. s., 1 H) 8.41 (s, 1 H) 7.48 (d, J = 1.2 Hz, 1 H) 7.41-7.44 (m, 1 H) 7.37-7.40 (m, 1 H) 7.31-7.36 (m, 1 H) 7.26-7.30 (m, 1 H) 7.22 (ddd, J = 11.0, 2.3, 2.0 Hz, 1 H) 7.01 (td, J = 8.3, 1.7 Hz, 1 H) 1.27-1.82 (m, 10 H) | U |

TABLE 2-continued

| Ex. | MS (ESI)+ m/z [M + H]+ | 1H NMR (600 MHz, DMSO-d$_6$ δ ppm (unless otherwise stated) | General procedure |
|---|---|---|---|
| 263 | 284 | 11.17 (s, 1 H) 10.62 (s, 1 H) 9.00 (s, 1 H) 7.77 (d, J = 1.2 Hz, 1 H) 7.60-7.66 (m, 2 H) 7.51-7.59 (m, 2 H) 7.16-7.21 (m, 2 H) 2.28 (s, 3 H) | U |
| 264 | 250 | 11.12 (br. s., 1 H) 7.58-7.61 (m, 1 H) 7.41-7.44 (m, 2 H) 3.55 (q, J = 7.0 Hz, 4 H) 1.21 (t, J = 7.2 Hz, 6 H) | U |
| 265 | 332 | 11.32 (br. s., 1 H) 8.68 (d, J = 8.55 Hz, 1 H) 8.49 (d, J = 1.22 Hz, 1 H) 8.03 (d, J = 8.54 Hz, 1 H) 7.87 (dd, J = 8.55, 1.83 Hz, 1 H) 6.67 (d, J = 8.54 Hz, 1 H) 4.18 (s, 3 H) 3.99 (s, 3 H) | F |
| 266 | 330 | 11.35 (s, 1 H) 9.13 (br. s., 1 H) 8.90 (d, J = 3.36 Hz, 1 H) 8.53 (d, J = 1.22 Hz, 1 H) 8.36 (dd, J = 8.70, 2.59 Hz, 1 H) 8.08 (d, J = 8.54 Hz, 1 H) 7.89 (dd, J = 8.54, 1.83 Hz, 1 H) 6.95 (d, J = 9.46 Hz, 1 H) 5.26-5.45 (m, 1 H) 1.35 (d, J = 6.10 Hz, 6 H) | F |
| 267 | 302 | 11.40 (br. s., 1 H) 9.17 (br. s., 1 H) 8.61 (d, J = 1.2 Hz, 1 H) 8.40 (d, J = 4.6 Hz, 1 H) 8.19 (d, J = 8.5 Hz, 1 H) 7.94 (dd, J = 8.5, 1.8 Hz, 1 H) 7.66 (dd, J = 5.5, 1.5 Hz, 1 H) 7.44 (d, J = 1.5 Hz, 1 H) 3.95 (s, 3 H) | F |
| 268 | 302 | 11.38 (br. s., 1 H) 8.88 (d, J = 1.5 Hz, 1 H) 8.60 (d, J = 1.2 Hz, 1 H) 8.51 (d, J = 2.7 Hz, 1 H) 8.17 (d, J = 8.5 Hz, 1 H) 7.98 (dd, J = 3.1, 1.8 Hz, 1 H) 7.93 (dd, J = 8.5, 1.8 Hz, 1 H) 3.98 (s, 3 H) | F |
| 269 | 328 | 11.38 (s, 1 H) 9.79 (br. s., 1 H) 9.16 (br. s., 1 H) 8.58 (d, J = 1.2 Hz, 1 H) 8.24 (d, J = 8.2 Hz, 2 H) 8.13 (d, J = 8.5 Hz, 1 H) 7.92 (dd, J = 8.5, 1.8 Hz, 1 H) 7.71 (d, J = 8.2 Hz, 2 H) 4.39 (br. s., 2 H) 2.78 (s, 6 H) | F |
| 270 | 315 | 11.38 (br. s., 1 H) 9.12 (s, 1 H) 8.33 (d, J = 1.2 Hz, 1 H) 8.20 (d, J = 8.2 Hz, 1 H) 7.83 (dd, J = 8.4, 1.7 Hz, 1 H) 7.26-7.47 (m, 5 H) 5.00 (s, 2 H) 4.72 (s, 2 H) | Separate procedure |
| 271 | 225 | 11.36 (s, 1 H) 9.10 (d, J = 1.5 Hz, 1 H) 8.28 (d, J = 1.2 Hz, 1 H) 8.17 (d, J = 8.9 Hz, 1 H) 7.79 (dd, J = 8.4, 1.7 Hz, 1 H) 6.23-6.41 (m, 1 H) 4.88 (d, J = 6.1 Hz, 2 H) | Separate procedure |
| 272 | 362 | 11.35 (br. s., 1 H) 8.78 (d, J = 6.4 Hz, 2 H) 8.31 (d, J = 1.2 Hz, 1 H) 8.11 (d, J = 8.2 Hz, 1 H) 8.03 (d, J = 5.5 Hz, 2 H) 7.93 (d, J = 8.2 Hz, 2 H) 7.79 (dd, J = 8.4, 1.7 Hz, 1 H) 7.62 (d, J = 8.2 Hz, 2 H) 4.62 (s, 2 H) | Separate procedure |
| 273 | 292 | 8.26 (d, J = 1.2 Hz, 1 H) 8.11 (d, J = 8.2 Hz, 1 H) 7.79 (dd, J = 8.4, 1.7 Hz, 1 H) 6.03 (br. s., 1 H) 3.91 (s, 2 H) 2.53 (br. s., 4 H) 1.37-1.63 (m, 6 H) | Separate procedure |
| 274 | 336 | n.d. | Separate procedure |
| 275 | 342 | 11.36 (s, 1 H) 8.30 (d, J = 1.5 Hz, 1 H) 8.08 (d, J = 8.2 Hz, 1 H) 7.77 (dd, J = 8.4, 1.7 Hz, 1 H) 6.95 (d, J = 8.5 Hz, 2 H) 6.55 (d, J = 8.5 Hz, 2 H) 4.68 (s, 2 H) 2.63-2.81 (m, 1 H) 1.10 (d, J = 6.7 Hz, 6 H) | Separate procedure |
| 276 | 254 | 11.24 (s, 1 H) 9.02 (br. s., 1 H) 8.07 (d, J = 1.2 Hz, 1 H) 7.92-7.97 (m, 2 H) 7.72-7.76 (m, 1 H) 7.67-7.71 (m, 1 H) 7.51-7.55 (m, 3 H) 7.42-7.46 (m, 1 H) | W |
| 277 | 272 | 11.25 (br. s., 1 H) 9.03 (s, 1 H) 8.09 (d, J = 1.5 Hz, 1 H) 7.74-7.81 (m, 3 H) 7.69-7.73 (m, 1 H) 7.66 (s, 1 H) 7.54-7.61 (m, 1 H) 7.28 (td, J = 8.5, 2.1 Hz, 1 H) | W |
| 278 | 285 | 11.24 (br. s., 1 H) 9.02 (s, 1 H) 8.76 (d, J = 2.4 Hz, 1 H) 8.24 (dd, J = 8.9, 2.4 Hz, 1 H) 8.06 (d, J = 1.5 Hz, 1 H) 7.66-7.74 (m, 2 H) 7.50 (s, 1 H) 6.99 (d, J = 8.5 Hz, 1 H) 3.93 (s, 3 H) | W |
| 279 | 284 | 11.22 (s, 1 H) 9.00 (s, 1 H) 8.02 (d, J = 1.2 Hz, 1 H) 7.83-7.91 (m, 2 H) 7.61-7.73 (m, 2 H) 7.37 (s, 1 H) 7.05-7.13 (m, 2 H) 3.83 (s, 3 H) | W |
| 280 | 256 | 11.28 (s, 1 H) 9.36 (s, 2 H) 9.23 (s, 1 H) 9.06 (s, 1 H) 8.14 (d, J = 1.2 Hz, 1 H) 7.84 (s, 1 H) 7.79-7.83 (m, 1 H) 7.73-7.78 (m, 1 H) | W |
| 281 | 284 | 11.24 (s, 1 H) 9.02 (br. s., 1 H) 8.10 (d, J = 1.2 Hz, 1 H) 7.85 (dd, J = 7.6, 1.2 Hz, 1 H) 7.73-7.76 (m, 1 H) 7.65-7.71 (m, 2 H) 7.41-7.51 (m, 2 H) 7.34 (s, 1 H) 4.75 (s, 2 H) | W |
| 282 | 254 | 11.27 (s, 1 H) 9.06 (s, 1 H) 7.89-8.05 (m, 3 H) 7.66-7.76 (m, 2 H) 7.50-7.60 (m, 3 H) 7.41-7.49 (m, 1 H) | X |
| 283 | 311 | 11.30 (s, 1 H) 9.09 (br. s., 1 H) 8.05-8.10 (m, 2 H) 8.01 (s, 1 H) 7.69-7.79 (m, 2 H) 7.62-7.67 (m, 2 H) 7.61 (s, 1 H) 4.34 (s, 2 H) 2.77 (s, 6 H) | X |
| 284 | 270 | 11.26 (s, 1 H) 9.74 (s, 1 H) 9.06 (s, 1 H) 7.98 (s, 1 H) 7.70 (s, 2 H) 7.42 (s, 1 H) 7.36-7.41 (m, 1 H) 7.29-7.34 (m, 2 H) 6.84 (dd, J = 8.2, 1.5 Hz, 1 | X |
| 285 | 284 | 11.27 (s, 1 H) 9.06 (br. s., 1 H) 8.00 (s, 1 H) 7.66-7.76 (m, 2 H) 7.52-7.58 (m, 2 H) 7.47-7.51 (m, 1 H) 7.45 (t, J = 7.9 Hz, 1 H) 7.03 (dd, J = 8.2, 1.8 Hz, 1 H) 3.86 (s, 3 H) | X |

Biological Tests
Method for Measurement of Enzymatic Activity of HDACs
Materials & Methods All Examples were tested in HDAC1,2,3,6 and 8 in vitro enzymatic assays. The assay principle is well known (Hauser et al. 2009, Bradner et al. 2010) and all necessary reagents like enzymes, substrates, developer and reference compounds are commercially available (see e.g. BPS Biosciences http://www.bpsbioscience.com/). Stock solutions (10 mM in DMSO) of compounds were serially diluted 1:3 in 11 concentrations with a top concentration of 200 µM for HDAC1,2,3 and 2 µM for HDAC6 and HDAC8. The enzymatic reactions were conducted in a mixture containing assay buffer, bovine serum albumin, HDAC substrate, and a test compound. After enzymatic reaction, developer was added and after an additional incubation time, fluorescence intensity was measured at an excitation wavelength of 360 nm and an emission wavelength of 460 nm. All experiments were performed in duplicate.

Results

IC50 values for HDAC6 inhibition of some compounds of the invention are shown in Table 3.

TABLE 3

IC$_{50}$ values for inhibition of HDAC6 for Examples of the invention.

| Example | IC50 (nM) |
| --- | --- |
| 1 | 26 |
| 2 | 4 |
| 4 | 5 |
| 5 | 36 |
| 7 | 15 |
| 8 | 14 |
| 11 | 8 |
| 12 | 5 |
| 15 | 28 |
| 16 | 7 |
| 21 | 28 |
| 22 | 13 |
| 23 | 11 |
| 26 | 5 |
| 29 | 10 |
| 30 | 14 |
| 33 | 22 |
| 36 | 56 |
| 39 | 26 |
| 40 | 54 |
| 41 | 22 |
| 42 | 14 |
| 44 | 63 |
| 45 | 21 |
| 46 | 48 |
| 47 | 31 |
| 48 | 73 |
| 49 | 9 |
| 50 | 34 |
| 51 | 22 |
| 52 | 17 |
| 54 | 60 |
| 55 | 81 |
| 57 | 11 |
| 60 | 62 |
| 75 | 13 |
| 76 | 18 |
| 78 | 12 |
| 79 | 7 |
| 80 | 30 |
| 81 | 33 |
| 82 | 11 |
| 83 | 25 |
| 84 | 19 |
| 87 | 42 |
| 88 | 37 |

TABLE 3-continued

IC$_{50}$ values for inhibition of HDAC6 for Examples of the invention.

| Example | IC50 (nM) |
| --- | --- |
| 89 | 55 |
| 90 | 28 |
| 93 | 9 |
| 95 | 22 |
| 96 | 64 |
| 97 | 47 |
| 99 | 16 |
| 100 | 36 |
| 102 | 70 |
| 105 | 37 |
| 106 | 86 |
| 108 | 35 |
| 109 | 86 |
| 110 | 50 |
| 112 | 7 |
| 113 | 22 |
| 115 | 23 |
| 117 | 64 |
| 119 | 74 |
| 125 | 7 |
| 126 | 85 |
| 127 | 60 |
| 132 | 17 |
| 136 | 72 |
| 137 | 39 |
| 138 | 22 |
| 139 | 30 |
| 140 | 10 |
| 141 | 22 |
| 142 | 1 |
| 143 | 7 |
| 144 | 7 |
| 145 | 42 |
| 149 | 49 |
| 150 | 53 |
| 152 | 30 |
| 158 | 34 |
| 160 | 21 |
| 161 | 22 |
| 162 | 7 |
| 163 | 58 |
| 173 | 20 |
| 175 | 34 |
| 180 | 8 |
| 181 | 31 |
| 196 | 20 |
| 202 | 53 |
| 205 | 64 |
| 207 | 73 |
| 209 | 35 |
| 211 | 38 |
| 219 | 44 |
| 220 | 32 |
| 228 | 27 |
| 230 | 7 |
| 232 | 51 |
| 234 | 4 |
| 241 | 27 |
| 244 | 63 |
| 256 | 41 |
| 262 | 9 |
| 263 | 9 |
| 270 | 4 |
| 271 | 37 |
| 272 | 6 |
| 273 | 16 |
| 274 | 16 |
| 275 | 8 |
| 278 | 96 |
| 281 | 92 |
| 282 | 9 |
| 283 | 7 |
| 284 | 4 |
| 285 | 4 |

The selectivity of compounds of the invention for HDAC6 over other isoenzymes in the HDAC family is illustrated in Table 4.

TABLE 4

Selectivity profiling against selected HDAC isoforms

| Example | IC50 (nM) HDAC1 | IC50 (nM) HDAC2 | IC50 (nM) HDAC3 | IC50 (nM) HDAC6 | IC50 (nM) HDAC8 |
|---|---|---|---|---|---|
| 1 | 4000 | 13000 | 1700 | 26 | 1200 |
| 4 | 1100 | 19000 | 410 | 5 | 1000 |
| 9 | 6000 | 76000 | 1700 | 38 | 800 |
| 12 | 1200 | 52000 | 560 | 5 | 880 |
| 18 | 2000 | 11000 | 1600 | 37 | 1300 |
| 21 | 5600 | >200000 | 1800 | 28 | 700 |
| 27 | >200000 | >200000 | 820 | 3 | >2000 |
| 28 | 5600 | 28000 | 1800 | 28 | 700 |
| 29 | 2100 | 10000 | 1000 | 10 | 1400 |
| 43 | 5100 | >200000 | 3500 | 51 | 200 |
| 70 | 6100 | 19000 | 2300 | 65 | 320 |
| 75 | 900 | 5500 | 500 | 3 | 28 |
| 76 | 1500 | 6600 | 450 | 18 | 340 |
| 77 | 1800 | 9400 | 930 | 22 | 410 |
| 88 | 26000 | 14000 | 10000 | 14 | 1100 |
| 89 | 100000 | 90000 | 90000 | 26 | >2000 |
| 96 | 9700 | 55000 | 7200 | 64 | 960 |
| 100 | 14000 | 74000 | 18000 | 36 | 760 |
| 113 | 500 | 2000 | 330 | 22 | 120 |
| 117 | 19000 | 69000 | 25000 | 26 | 1400 |
| 132 | 1200 | 24000 | 370 | 17 | 240 |
| 162 | 550 | 3500 | 320 | 7 | 1500 |
| 176 | >200000 | >200000 | 960 | 16 | 384 |
| 285 | 470 | 6900 | 640 | 4 | 210 |

Method for Measurement of Cell Viability

The CellTiter-Blue® Cell Viability Assay (Promega) provides a homogeneous, fluorometric method for estimating the number of viable cells present in multi-well plates. The assay uses the indicator dye resazurin to measure the metabolic capacity of cells. Viable cells retain the ability to reduce resazurin into resorufin, which is highly fluorescent. Non-viable cells rapidly lose metabolic capacity and do not reduce the indicator dye, and thus do not generate a fluorescent signal.

Materials & Methods

Stock solutions (10 mM in DMSO) of compounds were serially diluted 1:2 in 11 concentrations. 50 nL/well (10 mM compound stock in DMSO) was acoustically dispensed in 384-well assay plates with an acoustic dispenser (EDC Biosystems ATS-100AV). Final starting concentration in the assay was 20 µM (0.2% DMSO) for test compounds. The following cell-lines (and origin) have been primarily used: PaCa2 (pancreatic), U266 (multiple myeloma), AMO-1 (plasmacytoma), and MDA-MB-231 (breast adenocarcinoma). PBMCs (peripheral blood mononuclear cells) from healthy donors were used as control cells. Cells were seeded in assay plates (384-well black/clear, Greiner #781091) pre-dispensed with compounds, 25 µL/well, and cultured for 72 hours. After 72 hours, Celltiter Blue reagent (Promega # G8081) was diluted 1:10 with PBS and then added to wells (5 µL/well). The plates were incubated for 2 hours following addition of reagent. The plates were read in an EnVision fluorescence reader (PerkinElmer) with Ex544 nm/Em590 nm. Results were calculated as % cell viability compared to background (cells treated with 0.2% DMSO).

Results

Cell viability IC50 values of some compounds of the invention for a selection of tumor cell lines and healthy PBMCs are shown in Table 5.

TABLE 5

IC$_{50}$ values for Examples of the invention based on cell viability in different cells after 72 hours of treatment with compounds of the invention

| Example | IC50 (µM) U266 | IC50 (µM) AMO-1 | IC50 (µM) PaCa2 | IC50 (µM) MDA-MB-231 | IC50 (µM) healthy PBMC |
|---|---|---|---|---|---|
| 1 | 0.62 | 0.39 | 0.98 | 0.65 | >20 |
| 4 | 0.49 | 0.38 | 0.75 | 0.81 | >20 |
| 9 | 0.91 | 0.90 | 1.9 | 1.4 | >20 |
| 21 | 0.94 | 0.64 | 1.2 | 1.1 | >20 |
| 26 | 1.1 | 0.61 | 1.1 | 1.7 | >20 |
| 27 | 0.89 | 0.62 | 0.81 | 3.1 | >20 |
| 28 | 0.62 | 0.38 | 1.0 | 0.75 | >20 |
| 43 | 1.1 | 0.68 | 1.7 | 0.37 | >20 |
| 59 | 1.7 | 0.66 | 1.4 | 1.2 | >20 |
| 61 | 1.1 | 0.81 | 0.9 | 1.8 | >20 |
| 75 | 0.49 | 0.41 | 1.3 | 0.40 | >20 |
| 77 | 0.48 | 0.34 | 1.4 | 1.8 | >20 |
| 88 | 0.42 | 0.36 | 0.82 | 1.1 | >20 |
| 89 | 0.43 | 0.44 | 0.68 | 0.81 | >20 |
| 90 | 0.58 | 0.50 | 0.80 | 0.81 | >20 |
| 102 | 0.64 | 0.47 | 2.48 | 0.41 | >20 |
| 103 | 0.55 | 0.49 | 1.46 | 0.60 | >20 |
| 107 | 0.42 | 0.37 | 1.3 | 0.42 | >20 |
| 111 | 0.67 | 0.67 | 1.3 | 1.2 | >20 |
| 112 | 0.58 | 0.46 | 0.89 | 1.2 | >20 |
| 193 | 1.2 | 2.3 | 2.2 | 0.98 | >20 |

Method for Measurement of Apoptosis

The Annexin A5 (or Annexin V) affinity assay provides a method to quantify the number of cells undergoing apoptosis. The assay uses the protein annexin A5 conjugated to fluorescein (FITC Annexin V) and the fluorescent dye propidium iodide (PI) to label early apoptotic (annexin V positive, PI negative) and necrotic/dead cells (annexin V positive, PI positive) quantified by flow cytometry. The annexin A5 protein binds to membrane surfaces containing negatively charged phoshpolipids (phosphatidylserine) which are exposed by apoptotic and dead cells, but not by normal cells. PI binds to nucleic acids in cells which have completely lost the integrity of their plasma membrane, i.e. necrotic cells.

Materials & Methods

Standard Annexin V assay protocol was followed (see e.g. http://www.biolegend.com/pop_pdf.php?id=5161 and application references therein). 10,000 cells of each cell line were cultured in 400 µl of medium in 48 well plates. Compounds from 10 mM DMSO stock solutions were added to cells (DMSO content was 0.2%) and incubated for 48 or 72 hours followed by addition of FITC-Annexin V (BioLegend) and PI staining solution (BD Biosciences). The cells were analyzed by flow cytometry, at least 4,000 single cells were analyzed. Compounds were tested either individually at four different concentrations (1, 2.5, 5 and 10 µM) or in combination with 1 µM dexamethasone.

Results

Annexin V assay results for one compound of the invention (Example 1) with and without 1 µM dexamethasone for the multiple myeloma cell lines OPM-2 and U266 are given in Table 6. In Table 6, the % apoptosis values with compound(s) present are relative to the absence of compounds (only 0.2% DMSO present).

TABLE 6

% apoptosis following 72 hours treatment with different concentrations of Example 1 (Ex. 1) alone or in combination with 1 µM of dexamethasone (DEX).

| Compound concentrations (µM) | % apoptosis OPM-2 | % apoptosis U266 |
|---|---|---|
| 1 µM Ex. 1 | 3 | 30 |
| 1 µM DEX | 35 | 42 |
| 1 µM Ex. 1 + 1 µM DEX | 85 | 83 |
| 2.5 µM Ex. 1 | 37 | 59 |
| 2.5 µM Ex. 1 + 1 µM DEX | 82 | 79 |
| 5 µM Ex. 1 | 38 | 43 |
| 5 µM Ex. 1 + 1 µM DEX | 88 | 74 |
| 10 µM Ex. 1 | 59 | 88 |
| 10 µM Ex. 1 + 1 µM DEX | 87 | 79 |

REFERENCES

Aldana-Masangkay G I, Sakamoto K M. The role of HDAC6 in cancer. J Biomed Biotechnol 2011, doi: 10.1155/2011/875824

Balasubramanian S, Ramos J, Luo W, Sirisawad M, Verner E, Buggy J J. A novel histone deacetylase 8 (HDAC8)-specific inhibitor PCI-34051 induces apoptosis in T-cell lymphomas. Leukemia. 2008; 22:1026-1034.

Balasubramanian, S.; Verner, E. V.; Buggy, J. J. Isoform-specific histone deacetylase inhibitors: the next step? Cancer Lett. 2009, 280, 211

Bazzaro M, Lin Z, Santillan A et al., "Ubiquitin proteasome system stress underlies synergistic killing of ovarian cancer cells by bortezomib and a novel HDAC6 inhibitor," Clinical Cancer Research, 2008, vol. 14, no. 22, pp. 7340-7347.

Best, J. D.; Carey, N. Epigenetic therapies for non-oncology indications. Drug Discovery Today 2010, 15, 1008-1014.

Bradner J E, West N, Grachan M L, Greenberg E F, Haggarty S J, Warnow T et al. Chemical phylogenetics of histone deacetylases. Nat Chem Biol 2010, 6, 238-243.

Brana I, Taberno J. Cardiotoxicity, Annals of Oncology 2010, 21, Supplement 7: vii173-vii179.

Chen, Y.; He, R.; D'Annibale, M. A.; Langley, B.; Kozikowski, A. P. Studies of benzamide- and thiol-based histone deacetylase inhibitorsin models of oxidative-stress-induced neuronal death: identification of some HDAC3-selective inhibitors. ChemMedChem 2009, 4, 842-852.

Choudhary C, Kumar C, Gnad F, Nielsen M L, Rehman M, Walther T C et al. Lysine acetylation targets protein complexes and co-regulates major cellular functions. Science 2009, 325, 834-840.

Cook C, Gendron T F, Scheffel K, Carlomagno Y, Dunmore J, DeTure M, Petrucelli L. Loss of HDAC6, a novel CHIP substrate, alleviates abnormal tau accumulation. Hum Mol Genet 2012, 21, 2936-2945.

Cook C, Petrucelli L. 2013. Tau triage decisions mediated by the chaperone network. J Alzheimers Dis 33 Suppl 1:S145-S151.

de Zoeten, E. F.; Wang, L.; Butler, K.; Beier, U. H.; Akimova, T.; Sai, H.; Bradner, J. E.; Mazitschek, R.; Kozikowski, A. P.; Matthias, P.; Hancock, W. W. Histone deacetylase 6 and heat shock protein 90 control the functions of Foxp3(+) T-regulatory cells. Mol. Cell. Biol. 2011, 31, 2066-2078

D'Ydewalle C, Krishnan J, Chiheb D M, Van Damme P, Irobi J, Kozikowski A P, Vanden Berghe P, Timmerman V, Robberecht W, Van Den Bosch L: HDAC6 inhibitors reverse axonal loss in a mouse model of mutant HSPB 1-induced Charcot-Marie-Tooth disease. Nat Med 2011, 17:968-974.

Espallergues J, Teegarden S L, Veerakumar A, Boulden J, Challis C, Jochems J, Chan M, Petersen T, Deneris E, Matthias P, Hahn C G, Lucki I, Beck S G, Berton O. HDAC6 regulates glucocorticoid receptor signaling in serotonin pathways with critical impact on stress resilience. J Neurosci 2012, 32, 4400-4416.

Fukada M, Hanai A, Nakayama A, Suzuki T, Miyata N, Rodriguiz R M, Wetsel W C, Yao T P, Kawaguchi Y. Loss of deacetylation activity of HDAC6 affects emotional behavior in mice. PLoS ONE 2012, 7, e30924.

George, P., Bali, P., Annavarapu, S., Scuto, A., Fiskus, W., Guo, F., Sigua, C., Sondarva, G., Moscinski, L., Atadja, P. et al. Combination of the histone deacetylase inhibitor LBH589 and the hsp90 inhibitor 17-AAG is highly active against human CML-BC cells and AML cells with activating mutation of FLT-3. Blood, 2005, 105, 1768-1776.

Govindarajan N, Rao P, Burkhardt S, Sananbenesi F, Schliter O M, Bradke F, Lu J, Fischer A: Reducing HDAC6 µmeliorates cognitive deficits in a mouse model for Alzheimer's disease. EMBO Mol Med 2013, 5:52-63.

Greer J. M.; McCombe, P. A. The role of epigenetic mechanisms and processes in autoimmune disorders. Biologics 2012, 6, 307-327.

Gregoretti, I. V., Lee, Y. M. & Goodson, H. V. Molecular evolution of the histone deacetylase family: functional implications of phylogenetic analysis. J. Mol. Biol. 2004, 338, 17-31.

Hauser A T, Jung M, Jung M. Assays for histone deacetylases. Curr Top Med Chem 2009, 9, 227-234.

Hideshima, T.; Bradner, J. E.; Wong J. et al., Small-molecule inhibition of proteasome and aggresome function induces synergistic antitumor activity in multiple myeloma, Proc. Natl. Acad. Sci. U.S.A., 2005, 102, 8567-8572.

Jochems J, Boulden J, Lee B G, Blendy J A, Jarpe M, Mazitschek R, Van Duzer J H, Jones S and Berton O. Antidepressant-Like Properties of Novel HDAC6-Selective Inhibitors with Improved Brain Bioavailability. Neuropsychopharmacology 2014, 39, 389-400.

Kalin J H, Bergman J A. Development and therapeutic implications of selective histone deacetylase 6 inhibitors. J Med Chem 2013, 56, 6297-6313.

Karberg, S. Switching on epigenetic therapy. Cell 2009, 139, 1029-1031.

Kawaguchi Y. Loss of deacetylation activity of Hdac6 affects emotional behavior in mice. PloS One 2012, 7, e30924.

Kim, C.; Choi, H.; Jung, E. S.; Lee, W.; Oh, S.; Jeon, N. L.; Mook-Jung, I. HDAC6 inhibitor blocks amyloid beta-induced impairment of mitochondrial transport in hippocampal neurons. PLoS One 2012, 7, e42983.

Kim, D.; Frank, C. L.; Dobbin, M. M.; Tsunemoto, R. K.; Tu, W.; Peng, P. L.; Guan, J. S.; Lee, B. H.; Moy, L. Y.; Giusti, P.; Broodie, N.; Mazitschek, R.; Delalle, I.; Haggarty, S. J.; Neve, R. L.; Lu, Y.; Tsai, L. H. Deregulation of HDAC1 by p25/Cdk5 in neurotoxicity. Neuron 2008, 60, 803-817.

Kouzarides, T. Chromatin modifications and their function. Cell 2007, 128, 693-705.

Lee J. K.; Zheng B. Role of myelin-associated inhibitors in axonal repair after spinal cord injury. Exp Neurol 2012, 235:33-42.

Lee, Y. S.; Lim, K. H.; Guo, X.; Kawaguchi, Y.; Gao, Y.; Barrientos, T.; Ordentlich, P.; Wang, X. F.; Counter, C.

M.; Yao, T. P. The cytoplasmic deacetylase HDAC6 is required for efficient oncogenic tumorigenesis. Cancer Res. 2008, 68, 7561-7569.

Morris M J, Karra A S, Monteggia L M. Histone deacetylates govern cellular mechanisms underlying behavioral and synaptic plasticity in the developing and adult brain. Behav Pharmacol. 2010, 21, 409-419.

Parmigiani, R. B.; Xu, W. S.; Venta-Perez, G.; Erdjument-Bromage, H.; Yaneva, M.; Tempst, P.; Marks, P. A. HDAC6 is a specific deacetylase of peroxiredoxins and is involved in redox regulation. Proc. Natl. Acad. Sci. U.S.A. 2008, 105, 9633-9638.

Prince H M, Bishton M J, Harrison S J. Clinical studies of histone deacetylase inhibitors. Clin Cancer Res 2009; 15, 3958-3969.

Raje N, Vogl D T, Hari P N, Jagannath S, Jones S S, Supko J G, Leone G, Wheeler C, Orlowski R Z, Richardson P G, and Lonial S. ACY-1215, a Selective Histone Deacetylase (HDAC) 6 Inhibitor: Interim Results Of Combination Therapy With Bortezomib In Patients With Multiple Myeloma (MM). ASH 2013 Annual Meeting Abstract 759.

Rao, R., Fiskus, W., Yang, Y., Lee, P., Joshi, R., Fernandez, P., Mandawat, A., Atadja, P., Bradner, J. E. and Bhalla, K. HDAC6 inhibition enhances 17-AAG-mediated abrogation of hsp90 chaperone function in human leukemia cells. Blood, 2008, 112, 1886-1893.

Santo L, Hideshima T, Kung A L, Tseng J-C, Tamang D, Yang M, Jarpe M, van Duzer J H, Mazitschek R, Ogier W C, Cirstea D, Rodig S, Eda H, Scullen T, Canavese M, Bradner J, Anderson K C, Jones S S, Raje N. Preclinical activity, pharmacodynamic, and pharmacokinetic properties of a selective HDAC6 inhibitor, ACY-1215, in combination with bortezomib in multiple myeloma. Blood 2012, 119:11, 2579-2589.

Simões-Pires C, Zwick V, Nurisso A, Schenker E, Carrupt P-A and Cuendet M. HDAC6 as a target for neurodegenerative diseases: what makes it different from the other HDACs?Molecular Neurodegeneration 2013, 8:7, 1-16.

Smith, B. C., Hallows, W. C. & Denu, J. M. Mechanisms and molecular probes of sirtuins. Chem. Biol. 2008, 15, 1002-1013.

Southwood C M, Peppi M, Dryden S, Tainsky M A, Gow A. Microtubule deacetylases, SirT2 and HDAC6, in the nervous system. Neurochem Res 2007, 32, 187-195.

Ververis, K., Hiong, A., Karagiannis, T. C., and Licciardi, P. V. "Histone deacetylase inhibitors (HDACIs): multitargeted anticancer agents", Biologics: Targets and Therapy 2013, 7 47-60.

Witt, O.; Deubzer, H. E.; Milde, T.; Oehme, I. HDAC family: What are the cancer relevant targets? Cancer Lett. 2009, 277, 8-21.

Xu X, Kozikowski A P, Pozzo-Miller L. A selective histone deacetylase-6 inhibitor improves BDNF trafficking in hippocampal neurons from Mecp2 knockout mice: implications for Rett syndrome. Frontiers in Cellular Neuroscience 2014, 8:68, 1-9.

Zhang, Y.; Kwon, S.; Yamaguchi, T.; Cubizolles, F.; Rousseaux, S.; Kneissel, M.; Cao, C.; Li, N.; Cheng, H. L.; Chua, K.; Lombard, D.; Mizeracki, A.; Matthias, G.; Alt, F. W.; Khochbin, S.; Matthias, P. Mice lacking histone deacetylase 6 have hyperacetylated tubulin but are viable and develop normally. Mol. Cell. Biol. 2008, 28, 1688-1701.

Zhao, S. et al. Regulation of cellular metabolism by protein lysine acetylation. Science 2010, 327, 1000-1004.

The invention claimed is:

1. A compound of formula (Ia) or (Ib)

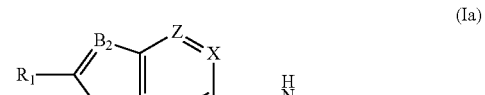

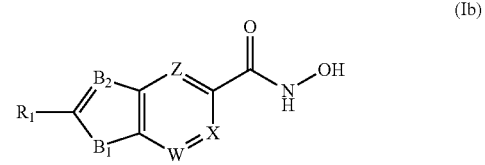

or a pharmaceutically acceptable salt thereof, wherein $R_1$ is

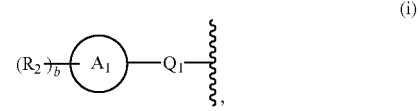

wherein
each $R_2$ is independently selected from C1-C6 alkyl, C3-C6 cycloalkyl, halogen, cyano, $R_3Y_1$-$Q_2$, $R_4R_5N$-$Q_3$, $R_6S(O)_2$-$Q_4$, and

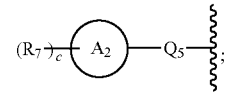

and two $R_2$ attached to adjacent atoms of ring $A_1$, together with the atoms to which they are attached, may form a 5- to 10-membered monocyclic or bicyclic ring, said ring optionally being substituted by one or more moieties selected from C1-C6 alkyl, C1-C6 alkoxy, halogen, and hydroxy;

$R_3$ is selected from H, C1-C6 alkyl, $R_8O$-$Q_6$, and $R_9R_{10}N$-$Q_7$;

$R_4$ and $R_5$ are independently selected from H, C1-C6 alkyl, C3-C8 cycloalkyl and $R_{11}O$-$Q_8$;

or $R_4$ and $R_5$, together with the nitrogen atom to which they are both attached, form a 5- or 6-membered ring, which ring is optionally substituted by one or more moieties selected from C1-C6 alkyl and $R_{12}O$-$Q_9$;

$R_6$ is selected from H and C1-C6 alkyl;

each $R_7$ is independently selected from C1-C6 alkyl, halogen, $R_{13}O$-$Q_{10}$, $R_{14}R_{15}N$-$Q_{11}$, and $R_{16}S(O)_2$-$Q_{12}$, and two $R_7$ attached to adjacent atoms of ring $A_2$, together with the atoms to which they are attached, may form a 5- or 6-membered ring;

$R_8$ is selected from H and C1-C6 alkyl;

$R_9$ and $R_{10}$ are independently selected from H and C1-C6 alkyl; or $R_9$ and $R_{10}$, together with the nitrogen atom to which they are both attached, form a 5- or 6-membered ring;

each one of $R_{11}$, $R_{12}$ and $R_{13}$ is selected from H and C1-C6 alkyl;

$R_{14}$ and $R_{15}$ are independently selected from H and C1-C6 alkyl; or $R_{14}$ and $R_{15}$, together with the nitrogen atom to which they are both attached, form a 5- or 6-membered ring;

$R_{16}$ is selected from H and C1-C6 alkyl;

ring $A_1$ and ring $A_2$ are independently selected from phenyl and 5- or 6-membered heteroaryl;

b and c are integers of from 0 to 3;

$Q_1$ is selected from a direct bond, C1-C3 alkylene, C2-C4 alkenylene, and $Q_{13}$-$Y_2$-$Q_{14}$;

$Q_2$ is selected from a direct bond and C1-C3 alkylene;

$Q_3$ is selected from a direct bond, C1-C3 alkylene, and C(O);

$Q_4$ is selected from a direct bond, C1-C3 alkylene, and $NR_{17}$;

$Q_5$ is selected from a direct bond, C1-C3 alkylene, $S(O)_2$ $NR_{18}$, $Q_{15}$-$Y_3$-$Q_{16}$, and

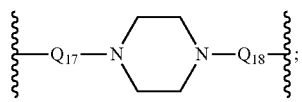

each one of $Q_6$, $Q_7$ and $Q_8$ is independently selected from C1-C3 alkylene;

each one of $Q_9$ and $Q_{10}$ is independently selected from a direct bond and C1-C3 alkylene;

$Q_{11}$ is selected from a direct bond, C1-C3 alkylene, and C(O);

$Q_{12}$ is selected from a direct bond, C1-C3 alkylene, and $NR_{19}$;

$Q_{13}$ is selected from a direct bond, C1-C3 alkylene, and C1-C3 alkylene substituted by $R_{20}$ and $R_{21}$;

each one of $Q_{14}$, $Q_{15}$, $Q_{16}$, $Q_{17}$ and $Q_{18}$ is independently selected from a direct bond and C1-C3 alkylene;

each one of $R_{17}$, $R_{18}$, and $R_{19}$ is independently selected from H and C1-C3 alkyl;

$R_{20}$ and $R_{21}$ are attached to the same carbon atom and form together with the carbon atom to which they are attached a C3-C6 cycloalkyl;

$Y_1$ is selected from O and S;

$Y_2$ is selected from O, and $NR_{22}$;

$Y_3$ is selected from O and $NR_{23}$;

$R_{22}$ is selected from H, phenyl, and C1-C3 alkyl, which alkyl is optionally substituted by a substituent selected from phenyl and $NR_{24}R_{25}$;

$R_{23}$ is H or C1-C3 alkyl; and $R_{24}$ and $R_{25}$ are independently selected from H and C1-C3 alkyl, or $R_{24}$ and $R_{25}$ form, together with the nitrogen atom to which they are both attached, a 5- or 6-membered ring;

(ii) $R_{26}R_{27}N$-$Q_{19}$, wherein $R_{26}$ and $R_{27}$ are independently selected from H, C1-C6 alkyl and C3-C8 cycloalkyl; or $R_{26}$ and $R_{27}$, together with the nitrogen atom to which they are both attached, form a 5- or 6-membered ring optionally substituted by one or more moieties $R_{28}$;

each $R_{28}$ is independently selected from $R_{29}OC(O)NR_{30}$, and and two $R_{28}$ attached to adjacent atoms of the ring, together with the atoms to which they are attached, may form a 5- or 6-membered ring;

$R_{29}$ and $R_{30}$ are independently selected from H and C1-C6 alkyl;

$R_{31}$ is selected from C1-C6 alkyl and halogen;

d is an integer of from 0 to 3;

ring $A_3$ is selected from 5- to 10-membered aryl or heteroaryl;

$Q_{19}$ is a direct bond or C1-C3 alkylene;

$Q_{20}$ is selected from a direct bond, C1-C3 alkylene and $Q_{21}$-$NR_{32}$-$Q_{22}$;

$Q_{21}$ and $Q_{22}$ are independently selected from a direct bond and C1-C3 alkylene; and $R_{32}$ is selected from H and C1-C6 alkyl; or (iv) hydroxy-C1-C6 alkyl;

$B_1$ is O or S;

$B_2$ is N or $CR_{34}$;

W is N or $CR_{35}$;

X is N or $CR_{36}$;

Z is N or $CR_{37}$;

$R_{34}$ is H, C1-C3 alkyl or halogen;

$R_{35}$, $R_{36}$ and $R_{37}$ are independently selected from H and F; and any alkyl, or cycloalkyl is optionally substituted with one or more F;

provided that when $Q_1$ is a direct bond or C1-C3 alkylene, and ring $A_1$ is phenyl, b is not 0; and provided that the compound is not 2-amino-N-hydroxy-benzo[d]thiazole-5-carboxamide.

2. The compound or pharmaceutically acceptable salt of claim 1, wherein $R_1$ is selected from

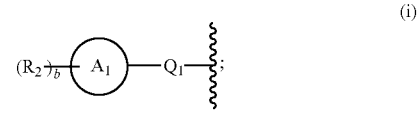

and (ii) $R_{26}R_{27}N$-$Q_{19}$, wherein $R_2$, b, ring $A_1$, $Q_1$, $R_{26}$, $R_{27}$ and $Q_{19}$ are as defined in claim 1.

3. The compound of claim 1, wherein b is an integer of from 1 to 3.

4. The compound or pharmaceutically acceptable salt of claim 1, wherein $R_2$ is selected from C1-C6 alkyl, halogen and

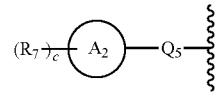

wherein $R_7$, c, ring $A_2$ and $Q_5$ are as defined in claim 1.

5. The compound or pharmaceutically acceptable salt of claim 1, wherein $R_{26}$ and $R_{27}$, together with the nitrogen atom to which they are both attached, form a 5- or 6-membered ring substituted by one moiety $R_{28}$; and $R_{28}$ is

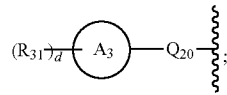

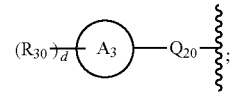

wherein $R_{30}$, d, ring $A_3$ and $Q_{20}$ are as defined in claim 1.

6. The compound or pharmaceutically acceptable salt of claim 1, wherein $B_2$ is N.

7. The compound or pharmaceutically acceptable salt of claim 1, wherein $B_1$ is O.

8. The compound or pharmaceutically acceptable salt of claim 1, wherein W is $CR_{35}$, X is $CR_{36}$ and Z is $CR_{37}$.

9. A compound according to claim 1, selected from
N-hydroxy-2-[4-(1-methylethyl)phenyl]-1,3-benzoxazole-5-carboxamide,
2-(4-bromophenyl)-N-hydroxy-1,3-benzoxazole-5-carboxamide,
2-[3,5-bis(trifluoromethyl)phenyl]-N-hydroxy-1,3-benzoxazole-5-carboxamide,
2-(4-tert-butylphenyl)-N-hydroxy-1,3-benzoxazole-5-carboxamide,
2-(3,4-difluorophenyl)-N-hydroxy-1,3-benzoxazole-5-carboxamide,
N-hydroxy-2-[3-(trifluoromethyl)phenyl]-1,3-benzoxazole-5-carboxamide,
2-(1,3-benzodioxol-5-yl)-N-hydroxy-1,3-benzoxazole-5-carboxamide,
N-hydroxy-2-[4-(trifluoromethoxy)phenyl]-1,3-benzoxazole-5-carboxamide,
2-(2,6-difluorophenyl)-N-hydroxy-1,3-benzoxazole-5-carboxamide,
N-hydroxy-2-(4-methoxyphenyl)-1,3-benzoxazole-5-carboxamide,
2-(2-chlorophenyl)-N-hydroxy-1,3-benzoxazole-5-carboxamide,
N-hydroxy-2-pyridin-3-yl-1,3-benzoxazole-5-carboxamide,
2-(2,5-dichlorophenyl)-N-hydroxy-1,3-benzoxazole-5-carboxamide,
N-hydroxy-2-(6-morpholin-4-ylpyridin-3-yl)-1,3-benzoxazole-5-carboxamide,
2-(3-bromophenyl)-N-hydroxy-1,3-benzoxazole-5-carboxamide,
2-[4-(difluoromethoxy)phenyl]-N-hydroxy-1,3-benzoxazole-5-carboxamide,
N-hydroxy-2-[4-(trifluoromethyl)phenyl]-1,3-benzoxazole-5-carboxamide,
2-(3,4-dimethoxyphenyl)-N-hydroxy-1,3-benzoxazole-5-carboxamide,
2-(2,5-dimethoxyphenyl)-N-hydroxy-1,3-benzoxazole-5-carboxamide,
2-(2'-fluorobiphenyl-4-yl)-N-hydroxy-1,3-benzoxazole-5-carboxamide,
N-hydroxy-2-(4-pyridin-4-ylphenyl)-1,3-benzoxazole-5-carboxamide,
N-hydroxy-2-(4-pyridin-3-ylphenyl)-1,3-benzoxazole-5-carboxamide,
2-biphenyl-4-yl-N-hydroxy-1,3-benzoxazole-5-carboxamide,
2-(2'-fluoro-3'-methoxybiphenyl-4-yl)-N-hydroxy-1,3-benzoxazole-5-carboxamide,
N-hydroxy-2-[4-(4-methoxypyridin-3-yl)phenyl]-1,3-benzoxazole-5-carboxamide,
N-hydroxy-2-[4-(6-methoxypyridin-3-yl)phenyl]-1,3-benzoxazole-5-carboxamide,
N-hydroxy-2-[4-(2-methoxypyridin-3-yl)phenyl]-1,3-benzoxazole-5-carboxamide,
2-(4-cyclopropylphenyl)-N-hydroxy-1,3-benzoxazole-5-carboxamide,
N-hydroxy-2-[4'-(piperidin-1-ylmethyl)biphenyl-4-yl]-1,3-benzoxazole-5-carboxamide,
2-(4-aminophenyl)-N-hydroxy-1,3-benzoxazole-5-carboxamide,
2-(2-chloro-6-fluorophenyl)-N-hydroxy-1,3-benzoxazole-5-carboxamide,
2-[4-(diethylamino)phenyl]-N-hydroxy-1,3-benzoxazole-5-carboxamide,
2-(2,6-dichlorophenyl)-N-hydroxy-1,3-benzoxazole-5-carboxamide,
N-hydroxy-2-pyridin-2-yl-1,3-benzoxazole-5-carboxamide,
2-(4-cyanophenyl)-N-hydroxy-1,3-benzoxazole-5-carboxamide,
N-hydroxy-2-{4-[(methylsulfonyl)amino]phenyl}-1,3-benzoxazole-5-carboxamide,
N-hydroxy-2-{4-[(phenylsulfonyl)amino]phenyl}-1,3-benzoxazole-5-carboxamide,
2-(1H-benzotriazol-5-yl)-N-hydroxy-1,3-benzoxazole-5-carboxamide,
N-hydroxy-2-(2-methylpyridin-3-yl)-1,3-benzoxazole-5-carboxamide,
N-hydroxy-2-(6-pyrrolidin-1-ylpyridin-3-yl)-1,3-benzoxazole-5-carboxamide,
N-hydroxy-2-(phenylamino)-1,3-benzoxazole-5-carboxamide,
N-hydroxy-2-{[4-(1-methylethyl)phenyl]amino}-1,3-benzoxazole-5-carboxamide,
2-[benzyl(methyl)amino]-N-hydroxy-1,3-benzoxazole-5-carboxamide,
N-hydroxy-2-[(2-phenylethyl)amino]-1,3-benzoxazole-5-carboxamide,
2-(3,4-dihydroisoquinolin-2(1H)-yl)-N-hydroxy-1,3-benzoxazole-5-carboxamide,
2-{[3-(benzyloxy)phenyl]amino}-N-hydroxy-1,3-benzoxazole-5-carboxamide,
2-(4-benzylpiperidin-1-yl)-N-hydroxy-1,3-benzoxazole-5-carboxamide,
N-hydroxy-2-[4-(1-methylethyl)phenyl]-1,3-benzoxazole-6-carboxamide,
2-(4-fluorophenyl)-N-hydroxy-1,3-benzoxazole-6-carboxamide,
2-(4-tert-butylphenyl)-N-hydroxy-1,3-benzoxazole-6-carboxamide,
N-hydroxy-2-(4-methoxyphenyl)-1,3-benzoxazole-6-carboxamide,
2-(6-chloropyridin-3-yl)-N-hydroxy-1,3-benzoxazole-6-carboxamide,
2-(1H-benzotriazol-5-yl)-N-hydroxy-1,3-benzoxazole-6-carboxamide,
2-(2,3'-bipyridin-5-yl)-N-hydroxy-1,3-benzoxazole-6-carboxamide,
N-hydroxy-2-[4-(1-methylethyl)phenyl]-1,3-benzothiazole-6-carboxamide,
2-(1,3-benzodioxol-5-yl)-N-hydroxy-1,3-benzothiazole-6-carboxamide,
N-hydroxy-2-pyridin-4-yl-1,3-benzothiazole-6-carboxamide,
N-hydroxy-2-[4-(methylsulfonyl)phenyl]-1,3-benzothiazole-6-carboxamide,
2-(2,3-dihydro-1-benzofuran-5-yl)-N-hydroxy-1,3-benzothiazole-6-carboxamide,
2-(2,3-dihydro-1,4-benzodioxin-6-yl)-N-hydroxy-1,3-benzothiazole-6-carboxamide,
2-(4-butylphenyl)-N-hydroxy-1,3-benzothiazole-6-carboxamide,
N-hydroxy-2-thiophen-3-yl-1,3-benzothiazole-6-carboxamide, 2-(1-benzofuran-2-yl)-N-hydroxy-1,3-benzothiazole-6-carboxamide,
N-hydroxy-2-quinolin-8-yl-1,3-benzothiazole-6-carboxamide,
N-hydroxy-2-naphthalen-2-yl-1,3-benzothiazole-6-carboxamide,
2-[3-(benzyloxy)phenyl]-N-hydroxy-1,3-benzothiazole-6-carboxamide,
2-(2-fluoro-3-methoxyphenyl)-N-hydroxy-1,3-benzothiazole-6-carboxamide,
2-(5-chloro-2-methoxyphenyl)-N-hydroxy-1,3-benzothiazole-6-carboxamide,
N-hydroxy-2-[4-(1-methylethyl)phenyl]-1,3-benzothiazole-5-carboxamide,
2-(4-fluorophenyl)-N-hydroxy-1,3-benzothiazole-5-carboxamide,
2-(4-tert-butylphenyl)-N-hydroxy-1,3-benzothiazole-5-carboxamide,
N-hydroxy-2-(4-methoxyphenyl)-1,3-benzothiazole-5-carboxamide,
2-(4-fluorobenzyl)-N-hydroxy-1,3-benzothiazole-5-carboxamide,
2-(5-bromopyridin-3-yl)-N-hydroxy-1,3-benzothiazole-5-carboxamide,
N-hydroxy-2-(7-methoxy-1-benzofuran-2-yl)-1,3-benzothiazole-5-carboxamide,
2-(4-ethylphenyl)-N-hydroxy-1,3-benzothiazole-5-carboxamide,
N-hydroxy-2-[4-(1-methylethyl)phenyl][1,3]oxazolo[5,4-b]pyridine-6-carboxamide,
N-hydroxy-2-[4-(1-methylethyl)phenyl]thieno[2,3-b]pyridine-5-carboxamide,
N-hydroxy-2-[4-(1-methylethyl)phenyl]-1-benzothiophene-6-carboxamide,
N-hydroxy-2-[4-(1-methylethyl)phenyl]-1-benzothiophene-5-carboxamide,
N-hydroxy-2-[3-(trifluoromethyl)phenyl]-1-benzothiophene-5-carboxamide,
2-[4-fluoro-3-(trifluoromethyl)phenyl]-N-hydroxy-1-benzothiophene-5-carboxamide,
N-hydroxy-2-(3-methoxyphenyl)-1-benzothiophene-5-carboxamide,
N-hydroxy-2-(4-methoxyphenyl)-1-benzothiophene-5-carboxamide,
N-hydroxy-2-(1H-pyrazol-4-yl)-1-benzothiophene-5-carboxamide,
N-hydroxy-2-(1H-indol-5-yl)-1-benzothiophene-5-carboxamide,
N-hydroxy-2-pyridin-3-yl-1-benzothiophene-5-carboxamide,
N-hydroxy-2-(2-methoxypyridin-3-yl)-1-benzothiophene-5-carboxamide,
N-hydroxy-2-(6-methoxypyridin-3-yl)-1-benzothiophene-5-carboxamide,
N-hydroxy-2-(1-methyl-1H-pyrazol-4-yl)-1-benzothiophene-5-carboxamide,
2-(3,5-dimethylisoxazol-4-yl)-N-hydroxy-1-benzothiophene-5-carboxamide,
N-hydroxy-2-[4-(trifluoromethyl)phenyl]-1-benzothiophene-5-carboxamide,
N-hydroxy-2-[4-(trifluoromethoxy)phenyl]-1-benzothiophene-5-carboxamide,
2-(4-tert-butylphenyl)-N-hydroxy-1-benzothiophene-5-carboxamide,
2-[(E)-2-(4-fluorophenyl)ethenyl]-N-hydroxy-1-benzothiophene-5-carboxamide,
2-(5-fluoro-2-hydroxyphenyl)-N-hydroxy-1-benzothiophene-5-carboxamide,
2-(5-fluoro-2-methoxyphenyl)-N-hydroxy-1-benzothiophene-5-carboxamide,
2-[3-chloro-4-(1-methylethoxy)phenyl]-N-hydroxy-1-benzothiophene-5-carboxamide,
2-[4-(dimethylcarbamoyl)phenyl]-N-hydroxy-1-benzothiophene-5-carboxamide,
N-hydroxy-2-{4-[(methylsulfonyl)amino]phenyl}-1-benzothiophene-5-carboxamide,
N-hydroxy-2-[4-(1-methylethyl)phenyl]thieno[3,2-b]pyridine-6-carboxamide,
N-hydroxy-2-[4-(1-methylethyl)phenyl]-1-benzofuran-5-carboxamide,
N-hydroxy-2-[4-(1-methylethyl)phenyl]-1-benzofuran-6-carboxamide,
N-hydroxy-2-[4-(1-methylethyl)phenyl]furo[2,3-b]pyridine-5-carboxamide,
N-hydroxy-2-[4-(1-methylethyl)phenyl]furo[3,2-b]pyridine-5-carboxamide,
N-hydroxy-2-[4-(1-methylethyl)phenyl]furo[3,2-b]pyridine-6-carboxamide,
N-hydroxy-2-[4-(1-methylethyl)phenyl]furo[2,3-b]pyridine-6-carboxamide,
2-[(diethylamino)methyl]-N-hydroxy-1-benzofuran-6-carboxamide,
N-hydroxy-2-(1-hydroxy-1-methylethyl)-1-benzofuran-6-carboxamide,
N-hydroxy-2-(hydroxymethyl)-1-benzofuran-6-carboxamide,
2-(3,4-dimethoxyphenyl)-N-hydroxy-1-benzothiophene-6-carboxamide,
2-dibenzo [b,d]furan-4-yl-N-hydroxy-1-benzothiophene-6-carboxamide,
2-furan-3-yl-N-hydroxy-1-benzothiophene-6-carboxamide,
N-hydroxy-2-(4-hydroxy-3-methoxyphenyl)-1-benzothiophene-6-carboxamide,
N-hydroxy-2-(hydroxymethyl)-1-benzofuran-5-carboxamide,
N-hydroxy-2-[6-(4-methylpiperidin-1-yl)pyridin-3-yl]-1,3-benzoxazole-5-carboxamide,
N-hydroxy-2-{6-[(1-phenylethyl)amino]pyridin-3-yl}-1,3-benzoxazole-5-carboxamide,
2-{6-[(cis)-2,6-dimethylmorpholin-4-yl]pyridin-3-yl}-N-hydroxy-1,3-benzoxazole-5-carboxamide,
N-hydroxy-2-{6-[(2-methylpropyl)amino]pyridin-3-yl}-1,3-benzoxazole-5-carboxamide,
2-{6-[bis(2-methoxyethyl)amino]pyridin-3-yl}-N-hydroxy-1,3-benzoxazole-5-carboxamide,
N-hydroxy-2-{6-[(pyridin-2-ylmethyl)amino]pyridin-3-yl}-1,3-benzoxazole-5-carboxamide,
2-[6-(cycloheptylamino)pyridin-3-yl]-N-hydroxy-1,3-benzoxazole-5-carboxamide,
N-hydroxy-2-{6-[(2R)-2-(methoxymethyl)pyrrolidin-1-yl]pyridin-3-yl}-1,3-benzoxazole-5-carboxamide,
N-hydroxy-2-{6-[4-(2-methoxyphenyl)piperazin-1-yl]pyridin-3-yl}-1,3-benzoxazole-5-carboxamide,
N-hydroxy-2-(6-phenylpyridin-3-yl)-1,3-benzoxazole-5-carboxamide,
2-[(3-fluorophenoxy)methyl]-N-hydroxy-1-benzofuran-5-carboxamide,
2-[(4-tert-butylphenoxy)methyl]-N-hydroxy-1-benzofuran-5-carboxamide,
N-hydroxy-2-{6-[(1-methylethyl)sulfanyl]pyridin-3-yl}-1,3-benzoxazole-5-carboxamide, 2-(4-bromo-2-fluorophenyl)-N-hydroxy-1,3-benzoxazole-5-carboxamide,
2-[2-fluoro-4-(1-methylethyl)phenyl]-N-hydroxy-1,3-benzoxazole-5-carboxamide,
N-hydroxy-2-[3-(1-methylethyl)phenyl]-1,3-benzoxazole-5-carboxamide,
2-(4-bromo-2-morpholin-4-ylphenyl)-N-hydroxy-1,3-benzoxazole-5-carboxamide,
2-(4-fluorophenyl)-N-hydroxy-1,3-benzoxazole-5-carboxamide,
N-hydroxy-2-[4-(1-methylethyl)-2-pyrrolidin-1-ylphenyl]-1,3-benzoxazole-5-carboxamide,
N-hydroxy-2-[6-(1-methylethyl)pyridin-3-yl]-1,3-benzoxazole-5-carboxamide,
2-(4-bromo-2-ethoxyphenyl)-N-hydroxy-1,3-benzoxazole-5-carboxamide,
2-(3-fluorobiphenyl-4-yl)-N-hydroxy-1,3-benzoxazole-5-carboxamide,
2-(2',3-difluorobiphenyl-4-yl)-N-hydroxy-1,3-benzoxazole-5-carboxamide,
2-(2-fluoro-4-pyridin-3-ylphenyl)-N-hydroxy-1,3-benzoxazole-5-carboxamide,
2-[2-fluoro-4-(6-methoxypyridin-3-yl)phenyl]-N-hydroxy-1,3-benzoxazole-5-carboxamide,
N-hydroxy-2-(2'-methoxybiphenyl-4-yl)-1,3-benzoxazole-5-carboxamide,
2-(2',5'-difluorobiphenyl-4-yl)-N-hydroxy-1,3-benzoxazole-5-carboxamide,
2-(5'-chloro-2'-methoxybiphenyl-4-yl)-N-hydroxy-1,3-benzoxazole-5-carboxamide,
N-hydroxy-2-[4'-(methylsulfonyl)biphenyl-4-yl]-1,3-benzoxazole-5-carboxamide,
2-[4-(3,5-dimethylisoxazol-4-yl)phenyl]-N-hydroxy-1,3-benzoxazole-5-carboxamide,
N-hydroxy-2-(2'-hydroxybiphenyl-4-yl)-1,3-benzoxazole-5-carboxamide,
2-(3'-fluoro-4'-hydroxybiphenyl-4-yl)-N-hydroxy-1,3-benzoxazole-5-carboxamide,
2-(5'-fluoro-2'-hydroxybiphenyl-4-yl)-N-hydroxy-1,3-benzoxazole-5-carboxamide,
N-hydroxy-2-[3'-(methylsulfonyl)biphenyl-4-yl]-1,3-benzoxazole-5-carboxamide,
2-(3-fluoro-3',4'-dimethoxybiphenyl-4-yl)-N-hydroxy-1,3-benzoxazole-5-carboxamide,
2-[3-fluoro-4'-(hydroxymethyl)biphenyl-4-yl]-N-hydroxy-1,3-benzoxazole-5-carboxamide,
2-[3-fluoro-2'-(hydroxymethyl)biphenyl-4-yl]-N-hydroxy-1,3-benzoxazole-5-carboxamide,
2-(3-fluoro-4'-hydroxybiphenyl-4-yl)-N-hydroxy-1,3-benzoxazole-5-carboxamide,
2-[4-(2,3-dihydro-1-benzofuran-5-yl)-2-fluorophenyl]-N-hydroxy-1,3-benzoxazole-5-carboxamide,
2-(3,3'-difluoro-2'-hydroxybiphenyl-4-yl)-N-hydroxy-1,3-benzoxazole-5-carboxamide,
2-[4-(2,3-dihydro-1,4-benzodioxin-6-yl)-2-fluorophenyl]-N-hydroxy-1,3-benzoxazole-5-carboxamide,
2-(3,5'-difluoro-2'-methoxybiphenyl-4-yl)-N-hydroxy-1,3-benzoxazole-5-carboxamide,
N-hydroxy-2-[3-(piperidin-1-ylmethyl)phenyl]-1-benzothiophene-5-carboxamide,
N-hydroxy-2-(3-methoxybiphenyl-4-yl)-1,3-benzoxazole-5-carboxamide,
2-(2'-fluoro-3-methoxybiphenyl-4-yl)-N-hydroxy-1,3-benzoxazole-5-carboxamide,
2-(2'-fluoro-3,3'-dimethoxybiphenyl-4-yl)-N-hydroxy-1,3-benzoxazole-5-carboxamide,
N-hydroxy-2-[3-methoxy-4'-(1-methylethyl)biphenyl-4-yl]-1,3-benzoxazole-5-carboxamide,
2-(4'-fluoro-3-methoxybiphenyl-4-yl)-N-hydroxy-1,3-benzoxazole-5-carboxamide,
2-(4'-amino-3,3'-dimethoxybiphenyl-4-yl)-N-hydroxy-1,3-benzoxazole-5-carboxamide,
N-hydroxy-2-[3-(piperidin-1-ylmethyl)phenyl]-1,3-benzoxazole-5-carboxamide,
2-(3-{[(cis)-2,6-dimethylmorpholin-4-yl]methyl}phenyl)-N-hydroxy-1,3-benzoxazole-5-carboxamide,
2-(3-{[bis(2-methylpropyl)amino]methyl}phenyl)-N-hydroxy-1,3-benzoxazole-5-carboxamide,
2-(3-{[cyclohexyl(methyl)amino]methyl}phenyl)-N-hydroxy-1,3-benzoxazole-5-carboxamide,
N-hydroxy-2-(3-{[(2-methoxyethyl)(methyl)amino]methyl}phenyl)-1,3-benzoxazole-5-carboxamide,
N-hydroxy-2-[4-(piperidin-1-ylmethyl)phenyl]-1,3-benzoxazole-5-carboxamide,
2-(4-{[(2R,6S)-2,6-dimethylmorpholin-4-yl]methyl}phenyl)-N-hydroxy-1,3-benzoxazole-5-carboxamide,
2-(4-{[bis(2-methylpropyl)amino]methyl}phenyl)-N-hydroxy-1,3-benzoxazole-5-carboxamide,
N-hydroxy-2-{4-[(4-pyridin-4-ylpiperazin-1-yl)methyl]phenyl}-1,3-benzoxazole-5-carboxamide,
2-{4-[(tert-butylamino)methyl]phenyl}-N-hydroxy-1,3-benzoxazole-5-carboxamide,
2-[3-fluoro-4-(1-methylethyl)phenyl]-N-hydroxy-1,3-benzoxazole-5-carboxamide,
2-(3,4-dimethylphenyl)-N-hydroxy-1,3-benzoxazole-5-carboxamide,
N-hydroxy-2-(4-propylphenyl)-1,3-benzoxazole-5-carboxamide,
2-(4-bromo-2-chlorophenyl)-N-hydroxy-1,3-benzoxazole-5-carboxamide,
N-hydroxy-2-(6-methoxypyridin-3-yl)-1,3-benzoxazole-5-carboxamide,
N-hydroxy-2-(2-methoxypyridin-3-yl)-1,3-benzoxazole-5-carboxamide,
2-(4-bromo-3-fluorophenyl)-N-hydroxy-1,3-benzoxazole-5-carboxamide,
2-(4-bromo-2-methoxyphenyl)-N-hydroxy-1,3-benzoxazole-5-carboxamide,
2-(2,3-dihydro-1,4-benzodioxin-6-yl)-N-hydroxy-1,3-benzoxazole-5-carboxamide,
N-hydroxy-2-(3-hydroxyphenyl)-1,3-benzoxazole-5-carboxamide,
N-hydroxy-2-(2-hydroxyphenyl)-1,3-benzoxazole-5-carboxamide,
N-hydroxy-2-(2-hydroxynaphthalen-1-yl)-1,3-benzoxazole-5-carboxamide,
N-hydroxy-2-(4-hydroxyphenyl)-1,3-benzoxazole-5-carboxamide,
N-hydroxy-2-(2-phenyl-1H-imidazol-5-yl)-1,3-benzoxazole-5-carboxamide,
N-hydroxy-2-(2-methoxyphenyl)-1,3-benzoxazole-5-carboxamide,
2-(5-chloro-2-hydroxyphenyl)-N-hydroxy-1,3-benzoxazole-5-carboxamide,
N-hydroxy-2-(4-hydroxy-2-methoxyphenyl)-1,3-benzoxazole-5-carboxamide,
N-hydroxy-2-(2-methyl-1H-indol-3-yl)-1,3-benzoxazole-5-carboxamide,
N-hydroxy-2-[(4-propylphenyl)amino]-1,3-benzoxazole-5-carboxamide, 2-(biphenyl-3-ylamino)-N-hydroxy-1,3-benzoxazole-5-carboxamide,
2-[(3-fluorophenyl)amino]-N-hydroxy-1,3-benzoxazole-5-carboxamide,
2-(cyclooctylamino)-N-hydroxy-1,3-benzoxazole-5-carboxamide,
N-hydroxy-2-[(3-methoxyphenyl)amino]-1,3-benzoxazole-5-carboxamide,
2-[(biphenyl-4-ylmethyl)amino]-N-hydroxy-1,3-benzoxazole-5-carboxamide,
N-hydroxy-2-[(4-methoxybenzyl)amino]-1,3-benzoxazole-5-carboxamide,
N-hydroxy-2-[(4-methoxyphenyl)amino]-1,3-benzoxazole-5-carboxamide,
N-hydroxy-2-[(naphthalen-1-ylmethyl)amino]-1,3-benzoxazole-5-carboxamide,
N-hydroxy-2-[(2-methoxyphenyl)amino]-1,3-benzoxazole-5-carboxamide,
2-(benzylamino)-N-hydroxy-1,3-benzoxazole-5-carboxamide,
2-(cyclohexylamino)-N-hydroxy-1,3-benzoxazole-5-carboxamide,
2-[benzyl(phenyl)amino]-N-hydroxy-1,3-benzoxazole-5-carboxamide,
N-hydroxy-2-[(4-methoxybenzyl)(methyl)amino]-1,3-benzoxazole-5-carboxamide,
N-hydroxy-2-{[2-(4-methoxyphenyl)ethyl]amino}-1,3-benzoxazole-5-carboxamide,
2-{(3,4-dimethoxybenzyl)[2-(dimethylamino)ethyl]amino}-N-hydroxy-1,3-benzoxazole-5-carboxamide,
N-hydroxy-2-{[4-(2-morpholin-4-ylethoxy)phenyl]amino}-1,3-benzoxazole-5-carboxamide,
2-{[4-(2-ethoxyethoxy)phenyl]amino}-N-hydroxy-1,3-benzoxazole-5-carboxamide,
N-hydroxy-2-{[3-(2-morpholin-4-ylethoxy)phenyl]amino}-1,3-benzoxazole-5-carboxamide,
2-{[3-(2-ethoxyethoxy)phenyl]amino}-N-hydroxy-1,3-benzoxazole-5-carboxamide,
2-(4-chlorobenzyl)-N-hydroxy-1,3-benzothiazole-5-carboxamide,
N-hydroxy-2-[2-(methylsulfonyl)phenyl]-1,3-benzothiazole-6-carboxamide,
N-hydroxy-2-[3-(hydroxymethyl)phenyl]-1,3-benzothiazole-6-carboxamide,
N-hydroxy-2-[4-(hydroxymethyl)phenyl]-1,3-benzothiazole-6-carboxamide,
N-hydroxy-2-(6-methoxypyridin-3-yl)-1,3-benzothiazole-6-carboxamide,
N-hydroxy-2-(3-hydroxyphenyl)-1,3-benzothiazole-6-carboxamide,
N-hydroxy-2-(4-hydroxyphenyl)-1,3-benzothiazole-6-carboxamide,
N-hydroxy-2-[4-({[(1-methyl-1H-indol-3-yl)methyl]amino}methyl)piperidin-1-yl]-1,3-benzoxazole-5-carboxamide,
2-{4-[(benzylamino)methyl]piperidin-1-yl}-N-hydroxy-1,3-benzoxazole-5-carboxamide,
N-hydroxy-2-{[2-(1-methylethyl)phenyl]amino}-1,3-benzoxazole-5-carboxamide,
N-hydroxy-2-[(2-methylphenyl)amino]-1,3-benzoxazole-5-carboxamide,
N-hydroxy-2-[methyl(4-methylphenyl)amino]-1,3-benzoxazole-5-carboxamide,
N-hydroxy-2-[(4-methoxyphenyl)(methyl)amino]-1,3-benzoxazole-5-carboxamide,
2-{[1-(3-fluorophenyl)cyclohexyl]amino}-N-hydroxy-1,3-benzoxazole-5-carboxamide,
N-hydroxy-2-[(4-methylphenyl)amino]-1,3-benzoxazole-5-carboxamide,
2-(diethylamino)-N-hydroxy-1,3-benzoxazole-5-carboxamide,
2-(2,6-dimethoxypyridin-3-yl)-N-hydroxy-1,3-benzothiazole-6-carboxamide,
N-hydroxy-2-[6-(1-methylethoxy)pyridin-3-yl]-1,3-benzothiazole-6-carboxamide,
N-hydroxy-2-(2-methoxypyridin-4-yl)-1,3-benzothiazole-6-carboxamide,
N-hydroxy-2-(5-methoxypyridin-3-yl)-1,3-benzothiazole-6-carboxamide,
2-{4-[(dimethylamino)methyl]phenyl}-N-hydroxy-1,3-benzothiazole-6-carboxamide,
2-[(benzyloxy)methyl]-N-hydroxy-1,3-benzothiazole-5-carboxamide,
N-hydroxy-2-(hydroxymethyl)-1,3-benzothiazole-5-carboxamide,
N-hydroxy-2-(4-pyridin-4-ylbenzyl)-1,3-benzothiazole-5-carboxamide,
N-hydroxy-2-(piperidin-1-ylmethyl)-1,3-benzothiazole-5-carboxamide,
2-{[bis(2-methylpropyl)amino]methyl}-N-hydroxy-1,3-benzothiazole-5-carboxamide,
N-hydroxy-2-({[4-(1-methylethyl)phenyl]amino}methyl)-1,3-benzothiazole-5-carboxamide,
2-(3-fluorophenyl)-N-hydroxy-1-benzofuran-5-carboxamide,
N-hydroxy-2-(6-methoxypyridin-3-yl)-1-benzofuran-5-carboxamide,
N-hydroxy-2-(4-methoxyphenyl)-1-benzofuran-5-carboxamide,
N-hydroxy-2-pyrimidin-5-yl-1-benzofuran-5-carboxamide,
N-hydroxy-2-[2-(hydroxymethyl)phenyl]-1-benzofuran-5-carboxamide,
2-{4-[(dimethylamino)methyl]phenyl}-N-hydroxy-1-benzofuran-6-carboxamide,
N-hydroxy-2-(3-hydroxyphenyl)-1-benzofuran-6-carboxamide, and
N-hydroxy-2-(3-methoxyphenyl)-1-benzofuran-6-carboxamide,
or a pharmaceutically acceptable salt thereof.

10. A pharmaceutical composition comprising a compound according to claim 1, or a pharmaceutically acceptable salt thereof, and optionally a pharmaceutically acceptable excipient.

11. A combination product comprising a compound according to claim 1, or a pharmaceutically acceptable salt thereof, and a further therapeutic agent.

12. The combination product according to claim 11, wherein the further therapeutic agent is an agent useful in the treatment an autoimmune disorder, a mental disorder, a neurodegenerative disorder, or a hyperproliferative disorder.

13. The combination product according to claim 11, wherein the further therapeutic agent is dexamethasone.

14. A method of treatment of a disorder selected from an autoimmune disorder, a mental disorder, a neurodegenerative disorder, or a hyperproliferative disorder which method comprises administration of a therapeutically effective amount of a compound according to claim 1 or a pharmaceutically acceptable salt thereof, to a mammal having said disorder.

15. The method of claim 14, wherein the compound or pharmaceutically acceptable salt thereof is administered in combination with a further therapeutic agent.

16. The method of claim 15, wherein the further therapeutic agent is dexamethasone.

* * * * *